US010369208B2

(12) United States Patent
Nabel et al.

(10) Patent No.: US 10,369,208 B2
(45) Date of Patent: Aug. 6, 2019

(54) METHODS FOR THE INDUCTION OF IMMUNE RESPONSES IN A SUBJECT COMPROMISING ADMINISTERING VIRUS-LIKE PARTICLES (VLPS) PREPARED FROM CHIKUNGUNYA VIRUS STRUCTURAL PROTEINS

(71) Applicant: The United States of America, as represented by the Secretary, Department of Health and Human Services, Washington, DC (US)

(72) Inventors: Gary J. Nabel, Chestnut Hill, MA (US); Wataru Akahata, Kensington, MD (US); Srinivas Rao, Columbia, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 185 days.

(21) Appl. No.: 15/145,483

(22) Filed: May 3, 2016

(65) Prior Publication Data

US 2016/0303221 A1 Oct. 20, 2016

Related U.S. Application Data

(62) Division of application No. 13/131,287, filed as application No. PCT/EP2009/006294 on Nov. 24, 2009, now Pat. No. 9,353,353.

(60) Provisional application No. 61/201,118, filed on Dec. 5, 2008, provisional application No. 61/118,206, filed on Nov. 26, 2008.

(51) Int. Cl.

| | |
|---|---|
| ***A61K 39/12*** | (2006.01) |
| ***C12N 7/04*** | (2006.01) |
| ***C12N 7/00*** | (2006.01) |
| *A61K 39/00* | (2006.01) |

(52) U.S. Cl.

CPC ................ *A61K 39/12* (2013.01); *C12N 7/00* (2013.01); *C12N 7/045* (2013.01); *A61K 2039/5258* (2013.01); *A61K 2039/55566* (2013.01); *C12N 2740/16043* (2013.01); *C12N 2770/36123* (2013.01); *C12N 2770/36134* (2013.01); *Y02A 50/383* (2018.01); *Y02A 50/51* (2018.01)

(58) Field of Classification Search

CPC ............ A61K 39/12; A61K 2039/5258; C12N 7/045; C12N 2740/16043; C12N 2770/36123; C12N 2770/36134

See application file for complete search history.

(56) References Cited

U.S. PATENT DOCUMENTS

| | | | |
|---|---|---|---|
| 7,947,822 | B2 | 5/2011 | Nabel et al. |
| 9,353,353 | B2 | 5/2016 | Nabel et al. |
| 2006/0216702 | A1 | 9/2006 | Compans et al. |

FOREIGN PATENT DOCUMENTS

| | | |
|---|---|---|
| EP | 1736538 | 12/2006 |
| WO | WO 2008/026225 | 3/2008 |
| WO | WO 2008/030220 | 3/2008 |
| WO | WO 2008/030220 A2 * | 3/2008 |

OTHER PUBLICATIONS

Huang, Y., et al., Nov. 2004, Generation of synthetic severe acute respiratory syndrome coronavirus pseudoparticles: Implications for assembly and vaccine production, J. Virol. 78(22):1255712565.*

Akahata, W., et al., Mar. 2010, A virus-like particle vaccine for epidemic Chikungunya virus protects nonhuman primates against infection, Nat. Med. 16(3):334-339.*

Akahata, W., and G. J. Nabel, Aug. 2012, A Specific Domain of the Chikungunya Virus E2 Protein Regulates Particle Formation in Human Cells: Implications for Alphavirus Vaccine Design, J. Virol. 86(16):8879-8883.*

Akahata et al., "A VLP vaccine for epidemic Chikungunya virus protects nonhuman primates infection," Nature Medicine, 2010, vol. 16, pp. 334-339.

Kim, Medical Molecular Virology, pp. 89-91, Science press, published on Feb. 2001 (evidence 1 in Official Action dated Sep. 28, 2014, English translation of text from p. 90), 1 page.

Muthumani et al., "Immunogenicity of novel consensus-based DNA vaccines against Chikungunya virus," Vaccine, Apr. 14, 2008, vol. 26, pp. 5128-5134.

Pulmanausahakul et al., "Chikungunya in Southeast Asia: understanding the emergence and finding solutions," Internatl. J. Infect. Dis., 2011, vol. 15, pp. e671-e676.

Wei Der, , Science press, published on Jun. 2008, p. 234 (evidence 2 in Official Action dated Sep. 28, 2014, English translation of text from p. 234), 1 page.

Tan, Therapeutic Immunology, Science press, pp. 459-461, Mar. 2007 (evidence 3 in Official Action dated Sep. 28, 2014, English translation of lines 4-5 and 18-22 of p. 460), 1 page.

Thiboutot, M M., et al., "Chikungunya: A potentially emerging epidemic?", PLoS Neglected Tropical Diseases, Apr. 2010, vol. 4(4), pp. e623, 8 pages.

Wang et al., "Chimeric alphavirus vaccine candidates for chikungunya," Vaccine, Aug. 2008, vol. 26, pp. 5030-5039.

(Continued)

*Primary Examiner* — Jeffrey S Parkin

(74) *Attorney, Agent, or Firm* — Sheridan Ross P.C.

(57) ABSTRACT

The invention features compositions and methods for the prevention or treatment of one or more strains of Chikungunya virus, as well as other alphavirus-mediated diseases.

6 Claims, 118 Drawing Sheets

Specification includes a Sequence Listing.

(56) References Cited

OTHER PUBLICATIONS

Wang et al., "Chimeric sindbis/eastern equine encephalitis vaccine candidates are highly attenuated and immunogenic in mice," Vaccine, Aug. 15, 2007, vol. 25, pp. 7573-7581.
International Search Report for International Patent Application No. PCT/US09/06294, dated Oct. 19, 2010.
Official Action for Australian Patent Application No. 2009320287, dated Dec. 11, 2014, 3 pages.
Official Action (with English translation) for Chinese Patent Application No. 200980155476.X, dated May 14, 2014, 20 pages.
Official Action (with English translation) for Chinese Patent Application No. 200980155476.X, dated Sep. 28, 2014, 20 pages.
Official Action for European Patent Application No. 09829477.0, dated Jun. 4, 2012, 6 pages.
Official Action for European Patent Application No. 09829477.0, dated Mar. 9, 2015, 4 pages.
Official Action for Malaysia Patent Application No. PI2011002376, dated May 15, 2015 2 pages.
Official Action for Malaysia Patent Application No. PI 2011002376, dated Mar. 31, 2016 2 pages.
Official Action for Philippines Patent Application No. 1-2011-501012, dated Jul. 25, 2014, 2 pages.
Official Action for Philippines Patent Application No. 1-2011-501012, dated Oct. 10, 2014, 2 pages.
Official Action for Philippines Patent Application No. 1-2011-501012, dated Jan. 22, 2015, 2 pages.
Official Action for Philippines Patent Application No. 1/2011/501012, dated Apr. 14, 2015 2 pages.
Official Action with English Translation for Vietnam Patent Application No. 1-2011-01662, dated Jun. 29, 2015 2 pages.
Official Action for U.S. Appl. No. 13/131,287, dated Jun. 4, 2013 7 pages Restriction Requirement.
Official Action for U.S. Appl. No. 131,287, dated Nov. 4, 2013.
Official Action for U.S. Appl. No. 13/131,287, dated May 8, 2014 6 pages.
Official Action for U.S. Appl. No. 13/131,287, dated May 7, 2015 13 pages.
Official Action for U.S. Appl. No. 13/131,287, dated Nov. 6, 2015 12 pages.
Notice of Reexamination with English Translation for China Patent Application No. 200980155476.X, dated Aug. 4, 2016 15 pages.
Official Action for European Patent Application No. 09829477.0, dated Jul. 22, 2016 5 pages.
Akahata et al. "A Specific Domain of the Chikungunya Virus E2 Protein Regulates Particle Formation in Human Cells: Implications for Alphavirus Vaccine Design," Journal of Virology, Aug. 2012, vol. 86, No. 16, pp. 8879-8883.
Official Action for European Patent Application No. 09829477.0, dated Sep. 28, 2017 5 pages.

* cited by examiner

FIG. 7A

SEQ ID NO: 1

Insert C-E3-E2-6K-E1 (strain 37997)

atggagttcatcccgacgcaaactttctataacagaaggtaccaaccccgaccctgggccccacgccctacaattcaagtaattagacctaga
ccacgtccacagaggcaggctgggcaactcgcccagctgatctccgcagtcaacaaattgaccatgcgcgcggtacctcaacagaagcctc
gcagaaatcggaaaaacaagaagcaaaggcagaagaagcaggcgccgcaaaacgacccaaagcaaaagaagcaaccaccacaa
aagaagccggctcaaaagaagaagaaaccaggccgtagggagagaatgtgcatgaaaattgaaaatgattgcatcttcgaagtcaagcat
gaaggcaaagtgatgggctacgcatgcctggtgggggataaagtaatgaaaccagcacatgtgaagggaactatcgacaatgccgatctg
gctaaactggcctttaagcggtcgtctaaatacgatcttgaatgtgcacagataccggtgcacatgaagtctgatgcctcgaagtttacccacga
gaaacccgaggggtactataactggcatcacggagcagtgcagtattcaggaggccggttcactatcccgacgggtgcaggcaagccggg
agacagcggcagaccgatcttcgacaacaaaggacgggtggtggccatcgtcctaggaggggccaacgaaggtgcccgcacggccctct
ccgtggtgacgtggaacaaagacatcgtcacaaaaattacccctgagggagccgaagagtggagcctcgccctcccggtcttgtgcctgttg
gcaaacactacattcccctgctctcagccgccttgcacaccctgctgctacgaaaaggaaccggaaagcaccttgcgcatgcttgaggacaa
cgtgatgagacccggatactaccagctactaaaagcatcgctgacttgctctccccaccgccaaagacgcagtactaaggacaattttaatgtc
tataaagccacaagaccatatctagctcattgtcctgactgcggagaagggcattcgtgccacagccctatcgcattggagcgcatcagaaat
gaagcaacggacggaacgctgaaaatccaggtctctttgcagatcgggataaagacagatgacagccacgattggaccaagctgcgctat
atggatagccatacgccagcggacgcggagcgagccggattgcttgtaaggacttcagcaccgtgcacgatcaccgggaccatgggacac
tttattctcgcccgatgcccgaaaggagagacgctgacagtgggatttacggacagcagaaagatcagccacacatgcacacacccgttcc
atcatgaaccacctgtgataggtagggagaggttccactctcgaccacaacatggtaaagagttaccttgcagcacgtacgtgcagagcacc
gctgccactgctgaggagatagaggtgcatatgcccccagatactcctgaccgcacgctgatgacgcagcagtctggcaacgtgaagatca
cagttaatgggcagacggtgcggtacaagtgcaactgcggtggctcaaacgagggactgacaaccacagacaaagtgatcaataactgca
aaattgatcagtgccatgctgcagtcactaatcacaagaattggcaatacaactcccctttagtcccgcgcaacgctgaactcggggaccgta
aaggaaagatccacatcccattcccattggcaaacgtgacttgcagagtgccaaaagcaagaaaccctacagtaacttacggaaaaaacc
aagtcaccatgctgctgtatcctgaccatccgacactcttgtcttaccgtaacatgggacaggaaccaaattaccacgaggagtgggtgacac
acaagaaggaggttaccttgaccgtgcctactgagggtctggaggtcacttggggcaacaacgaaccatacaagtactggccgcagatgtct
acgaacggtactgctcatggtcacccacatgagataatcttgtactattatgagctgtaccccactatgactgtagtcattgtgtcggtggcctcgtt
cgtgcttctgtcgatggtgggcacagcagtgggaatgtgtgtgtgcgcacggcgcagatgcattacaccatatgaattaacaccaggagccac
tgttcccttcctgctcagcctgctatgctgcgtcagaacgaccaaggcggccacatattacgaggctgcggcatatctatggaacgaacagcag

FIG. 7A (continued)

cccctgttctggttgcaggctcttatcccgctggccgccttgatcgtcctgtgcaactgtctgaaactcttgccatgctgctgtaagaccctggctttttt
agccgtaatgagcatcggtgcccacactgtgagcgcgtacgaacacgtaacagtgatcccgaacacggtgggagtaccgtataagactcttg
tcaacagaccgggttacagccccatggtgttggagatggagctacaatcagtcaccttggaaccaacactgtcacttgactacatcacgtgcg
agtacaaaactgtcatcccctccccgtacgtgaagtgctgtggtacagcagagtgcaaggacaagagcctaccagactacagctgcaaggt
ctttactggagtctacccatttatgtggggcggcgcctactgcttttgcgacgccgaaaatacgcaattgagcgaggcacatgtagagaaatctg
aatcttgcaaaacagagtttgcatcggcctacagagcccacaccgcatcggcgtcggcgaagctccgcgtcctttaccaaggaaacaacatt
accgtagctgcctacgctaacggtgaccatgccgtcacagtaaaggacgccaagtttgtcgtgggcccaatgtcctccgcctggacaccttttg
acaacaaaatcgtggtgtacaaaggcgacgtctacaacatggactacccaccttttggcgcaggaagaccaggacaatttggtgacattcaa
agtcgtacaccggaaagtaaagacgtttatgccaacactcagttggtactacagaggccagcagcaggcacggtacatgtaccatactctca
ggcaccatctggcttcaagtattggctgaaggaacgaggagcatcgctacagcacacggcaccgttcggttgccagattgcgacaaacccg
gtaagagctgtaaattgcgctgtggggaacataccaatttccatcgacataccggatgcggcctttactagggttgtcgatgcaccctctgtaacg
gacatgtcatgcgaagtaccagcctgcactcactcctccgactttgggggcgtcgccatcatcaaatacacagctagcaagaaaggtaaatgt
gcagtacattcgatgaccaacgccgttaccattcgagaagccgacgtagaagtagaggggaactcccagctgcaaatatccttctcaacagc
cctggcaagcgccgagtttcgcgtgcaagtgtgctccacacaagtacactgcgcagccgcatgccaccctccaaaggaccacatagtcaatt
acccagcatcacacaccacccttggggtccaggatatatccacaacggcaatgtcttgggtgcagaagattacgggaggagtaggattaatt
gttgctgttgctgccttaattttaattgtggtgctatgcgtgtcgtttagcaggcactaa

FIG. 7B

SEQ ID NO: 2
CMV/R 37997 C-E3-E2-6K-E1
tcgcgcgtttcggtgatgacggtgaaaacctctgacacatgcagctcccggagacggtcacagcttgtctgtaagcggatgccgggagcaga
caagcccgtcagggcgcgtcagcgggtgttggcgggtgtcggggctggcttaactatgcggcatcagagcagattgtactgagagtgcacca
tatgcggtgtgaaataccgcacagatgcgtaaggagaaaataccgcatcagattggctattggccattgcatacgttgtatccatatcataatatg
tacatttatattggctcatgtccaacattaccgccatgttgacattgattattgactagttattaatagtaatcaattacggggtcattagttcatagccc
atatatggagttccgcgttacataacttacggtaaatggcccgcctggctgaccgcccaacgacccccgcccattgacgtcaataatgacgtat FIG. 7B (continued)

gttcccatagtaacgccaatagggactttccattgacgtcaatgggtggagtatttacggtaaactgcccacttggcagtacatcaagtgtatcat
atgccaagtacgccccctattgacgtcaatgacggtaaatggcccgcctggcattatgcccagtacatgaccttatgggactttcctacttggcag
tacatctacgtattagtcatcgctattaccatggtgatgcggttttggcagtacatcaatgggcgtggatagcggtttgactcacggggatttccaag
tctccaccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgttttgac
ctccatagaagacaccgggaccgatccagcctccatcggctcgcatctctccttcacgcgcccgccgccctacctgaggccgccatccacgc
cggttgagtcgcgttctgccgcctcccgcctgtggtgcctcctgaactgcgtccgccgtctaggtaagtttaaagctcaggtcgagaccgggcctt
tgtccggcgctcccttggagcctacctagactcagccggctctccacgctttgcctgaccctgcttgctcaactctagttaacggtggagggcagt
gtagtctgagcagtactcgttgctgccgcgcgcgccaccagacataatagctgacagactaacagactgttcctttccatgggtcttttctgcagtc
accgtcgtcgacacgtgtgatcagatatcgcggccgctctagacaccatggagttcatcccgacgcaaactttctataacagaaggtaccaac
cccgaccctgggccccacgccctacaattcaagtaattagacctagaccacgtccacagaggcaggctgggcaactcgcccagctgatctc
cgcagtcaacaaattgaccatgcgcgcggtacctcaacagaagcctcgcagaaatcggaaaaacaagaagcaaaggcagaagaagca
ggcgccgcaaaacgacccaaagcaaaagaagcaaccaccacaaaagaagccggctcaaaagaagaagaaaccaggccgtaggga
gagaatgtgcatgaaaattgaaaatgattgcatcttcgaagtcaagcatgaaggcaaagtgatgggctacgcatgcctggtgggggataaag
taatgaaaccagcacatgtgaagggaactatcgacaatgccgatctggctaaactggcctttaagcggtcgtctaaatacgatcttgaatgtgc
acagataccggtgcacatgaagtctgatgcctcgaagtttacccacgagaaacccgaggggtactataactggcatcacggagcagtgcagt
attcaggaggccggttcactatcccgacgggtgcaggcaagccgggagacagcggcagaccgatcttcgacaacaaaggacgggtggtg
gccatcgtcctaggaggggccaacgaaggtgcccgcacggccctctccgtggtgacgtggaacaaagacatcgtcacaaaaattacccctg
agggagccgaagagtggagcctcgccctcccggtcttgtgcctgttggcaaacactacattcccctgctctcagccgccttgcacaccctgctg
ctacgaaaaggaaccggaaagcaccttgcgcatgcttgaggacaacgtgatgagacccggatactaccagctactaaaagcatcgctgact
tgctctccccaccgccaaagacgcagtactaaggacaattttaatgtctataaagccacaagaccatatctagctcattgtcctgactgcggag
aagggcattcgtgccacagccctatcgcattggagcgcatcagaaatgaagcaacggacggaacgctgaaaatccaggtctctttgcagatc
gggataaagacagatgacagccacgattggaccaagctgcgctatatggatagccatacgccagcggacgcggagcgagccggattgctt
gtaaggacttcagcaccgtgcacgatcaccgggaccatgggacactttattctcgcccgatgcccgaaaggagagacgctgacagtgggatt
tacggacagcagaaagatcagccacacatgcacacacccgttccatcatgaaccacctgtgataggtagggagaggttccactctcgacca
caacatggtaaagagttaccttgcagcacgtacgtgcagagcaccgctgccactgctgaggagatagaggtgcatatgcccccagatactcc FIG. 7B (continued)

tgaccgcacgctgatgacgcagcagtctggcaacgtgaagatcacagttaatgggcagacggtgcggtacaagtgcaactgcggtggctca
aacgagggactgacaaccacagacaaagtgatcaataactgcaaaattgatcagtgccatgctgcagtcactaatcacaagaattggcaat
acaactcccctttagtcccgcgcaacgctgaactcggggaccgtaaaggaaagatccacatcccattcccattggcaaacgtgacttgcaga
gtgccaaaagcaagaaaccctacagtaacttacggaaaaaaccaagtcaccatgctgctgtatcctgaccatccgacactcttgtcttaccgta
acatgggacaggaaccaaattaccacgaggagtgggtgacacacaagaaggaggttaccttgaccgtgcctactgagggtctggaggtca
cttggggcaacaacgaaccatacaagtactggccgcagatgtctacgaacggtactgctcatggtcacccacatgagataatcttgtactattat
gagctgtaccccactatgactgtagtcattgtgtcggtggcctcgttcgtgcttctgtcgatggtgggcacagcagtgggaatgtgtgtgcgcac
ggcgcagatgcattacaccatatgaattaacaccaggagccactgttcccttcctgctcagcctgctatgctgcgtcagaacgaccaaggcgg
ccacatattacgaggctgcggcatatctatggaacgaacagcagcccctgttctggttgcaggctcttatcccgctggccgccttgatcgtcctgt
gcaactgtctgaaactcttgccatgctgctgtaagaccctggctttttagccgtaatgagcatcggtgcccacactgtgagcgcgtacgaacac
gtaacagtgatcccgaacacggtgggagtaccgtataagactcttgtcaacagaccgggttacagccccatggtgttggagatggagctaca
atcagtcaccttggaaccaacactgtcacttgactacatcacgtgcgagtacaaaactgtcatcccctccccgtacgtgaagtgctgtggtacag
cagagtgcaaggacaagagcctaccagactacagctgcaaggtctttactggagtctacccatttatgtggggcggcgcctactgcttttgcga
cgccgaaaatacgcaattgagcgaggcacatgtagagaaatctgaatcttgcaaaacagagtttgcatcggcctacagagcccacaccgca
tcggcgtcggcgaagctccgcgtcctttaccaaggaaacaacattaccgtagctgcctacgctaacggtgaccatgccgtcacagtaaagga
cgccaagtttgtcgtgggcccaatgtcctccgcctggacaccttttgacaacaaaatcgtggtgtacaaaggcgacgtctacaacatggactac
ccaccttttggcgcaggaagaccaggacaatttggtgacattcaaagtcgtacaccggaaagtaaagacgtttatgccaacactcagttggta
ctacagaggccagcagcaggcacggtacatgtaccatactctcaggcaccatctggcttcaagtattggctgaaggaacgaggagcatcgct
acagcacacggcaccgttcggttgccagattgcgacaaacccggtaagagctgtaaattgcgctgtggggaacataccaatttccatcgacat
accggatgcggcctttactagggttgtcgatgcaccctctgtaacggacatgtcatgcgaagtaccagcctgcactcactcctccgactttgggg
gcgtcgccatcatcaaatacacagctagcaagaaaggtaaatgtgcagtacattcgatgaccaacgccgttaccattcgagaagccgacgta
gaagtagaggggaactcccagctgcaaatatccttctcaacagccctggcaagcgccgagtttcgcgtgcaagtgtgctccacacaagtaca
ctgcgcagccgcatgccaccctccaaaggaccacatagtcaattacccagcatcacacaccacccttggggtccaggatatatccacaacg
gcaatgtcttgggtgcagaagattacgggaggagtaggattaattgttgctgttgctgccttaattttaattgtggtgctatgcgtgtcgtttagcaggc
actaatgaggatccagatctgctgtgccttctagttgccagccatctgttgtttgcccctcccccgtgccttccttgaccctggaaggtgccactccc
actgtcctttcctaataaaatgaggaaattgcatcgcattgtctgagtaggtgtcattctattctggggggtggggtggggcaggacagcaaggg FIG. 7B (continued)

ggaggattgggaagacaatagcaggcatgctggggatgcggtgggctctatgggtacccaggtgctgaagaattgacccggttcctcctggg
ccagaaagaagcaggcacatccccttctctgtgacacaccctgtccacgcccctggttcttagttccagccccactcataggacactcatagct
caggagggctccgccttcaatcccacccgctaaagtacttggagcggtctctccctccctcatcagcccaccaaaccaaacctagcctccaag
agtgggaagaaattaaagcaagataggctattaagtgcagagggagagaaaatgcctccaacatgtgaggaagtaatgagagaaatcata
gaattttaaggccatgatttaaggccatcatggccttaatcttccgcttcctcgctcactgactcgctgcgctcggtcgttcggctgcggcgagcggt
atcagctcactcaaaggcggtaatacggttatccacagaatcaggggataacgcaggaaagaacatgtgagcaaaaggccagcaaaag
gccaggaaccgtaaaaaggccgcgttgctggcgtttttccataggctccgcccccctgacgagcatcacaaaaatcgacgctcaagtcagag
gtggcgaaacccgacaggactataaagataccaggcgtttccccctggaagctccctcgtgcgctctcctgttccgaccctgccgcttaccgga
tacctgtccgcctttctcccttcgggaagcgtggcgctttctcatagctcacgctgtaggtatctcagttcggtgtaggtcgttcgctccaagctgggc
tgtgtgcacgaaccccccgttcagcccgaccgctgcgccttatccggtaactatcgtcttgagtccaacccggtaagacacgacttatcgccact
ggcagcagccactggtaacaggattagcagagcgaggtatgtaggcggtgctacagagttcttgaagtggtggcctaactacggctacacta
gaagaacagtatttggtatctgcgctctgctgaagccagttaccttcggaaaaagagttggtagctcttgatccggcaaacaaaccaccgctgg
tagcggtggtttttttgtttgcaagcagcagattacgcgcagaaaaaaaggatctcaagaagatcctttgatcttttctacggggtctgacgctcagt
ggaacgaaaactcacgttaagggattttggtcatgagattatcaaaaaggatcttcacctagatccttttaaattaaaaatgaagttttaaatcaat
ctaaagtatatatgagtaaacttggtctgacagttaccaatgcttaatcagtgaggcacctatctcagcgatctgtctatttcgttcatccatagttgc
ctgactcgggggggggggcgctgaggtctgcctcgtgaagaaggtgttgctgactcataccaggcctgaatcgccccatcatccagccaga
aagtgagggagccacggttgatgagagctttgttgtaggtggaccagttggtgattttgaacttttgctttgccacggaacggtctgcgttgtcggg
aagatgcgtgatctgatccttcaactcagcaaaagttcgatttattcaacaaagccgccgtcccgtcaagtcagcgtaatgctctgccagtgttac
aaccaattaaccaattctgattagaaaaactcatcgagcatcaaatgaaactgcaatttattcatatcaggattatcaataccatatttttgaaaaa
gccgtttctgtaatgaaggagaaaactcaccgaggcagttccataggatggcaagatcctggtatcggtctgcgattccgactcgtccaacatc
aatacaacctattaatttcccctcgtcaaaaataaggttatcaagtgagaaatcaccatgagtgacgactgaatccggtgagaatggcaaaag
cttatgcatttctttccagacttgttcaacaggccagccattacgctcgtcatcaaaatcactcgcatcaaccaaaccgttattcattcgtgattgcgc
ctgagcgagacgaaatacgcgatcgctgttaaaaggacaattacaaacaggaatcgaatgcaaccggcgcaggaacactgccagcgcat
caacaatattttcacctgaatcaggatattcttctaatacctggaatgctgttttcccggggatcgcagtggtgagtaaccatgcatcatcaggagt
acggataaaatgcttgatggtcggaagaggcataaattccgtcagccagtttagtctgaccatctcatctgtaacatcattggcaacgctaccttt
gccatgtttcagaaacaactctggcgcatcgggcttcccatacaatcgatagattgtcgcacctgattgcccgacattatcgcgagcccatttata FIG. 7B (continued)

cccatataaatcagcatccatgttggaatttaatcgcggcctcgagcaagacgtttcccgttgaatatggctcataacaccccttgtattactgtttat
gtaagcagacagttttattgttcatgatgatatatttttatcttgtgcaatgtaacatcagagattttgagacacaacgtggctttcccccccccccatt
attgaagcatttatcagggttattgtctcatgagcggatacatatttgaatgtatttagaaaaataaacaaataggggttccgcgcacatttccccg
aaaagtgccacctgacgtctaagaaaccattattatcatgacattaacctataaaaataggcgtatcacgaggccctttcgtc CMV/R-CHIKV C-E3-E2-6K-E1 (Strain OPY1)

8159 bp

- ApaLI (178)
- NcoI (697)
- NcoI (1317)
- PstI (1334)
- NcoI (1983)
- ClaI (0000)
- ApaLI (1889)
- AvaI (2147)
- AvaI (3335)
- NcoI (3403)
- ApaLI (3531)
- NcoI (3888)
- PstI (4366)
- PstI (4476)
- EcoRI (4855)
- EcoRI (4901)
- AvaI (5000)
- BamHI (5135)
- ApaLI (6163)
- AvaI (6739)
- HindIII (7301)
- AvaI (7547)
- XmaI (7547)
- SmaI (7549)
- ClaI (7730)
- AvaI (7821)

Labels: CMV/R Backbone, CMV IE Enhancer/Promoter, HTLV-1 R Region/Splicing Donor, CMV IE Splicing Acceptor, Capsid, E3, E2, 6K, Envelope, E1, Tbgh, Kan.

FIG. 8B

SEQ ID NO: 3

Insert C-E3-E2-6K-E1 (strain OPY-1)

atggagttcatcccaacccaaactttttacaataggaggtaccagcctcgaccctggactccgcgccctactatccaagtcatcaggcccagac
cgcgccctcagaggcaagctgggcaacttgcccagctgatctcagcagttaataaactgacaatgcgcgcggtaccacaacagaagccac
gcaggaatcggaagaataagaagcaaaagcaaaaacaacaggcgccacaaaacaacacaaatcaaaagaagcagccacctaaaaa
gaaaccggctcaaaagaaaaagaagccgggccgcagagagaggatgtgcatgaaaatcgaaaatgattgtattttcgaagtcaagcacg
aaggtaaggtaacaggttacgcgtgcctggtgggggacaaagtaatgaaaccagcacacgtaaaggggaccatcgataacgcggacctg
gccaaactggcctttaagcggtcatctaagtatgaccttgaatgcgcgcagatacccgtgcacatgaagtccgacgcttcgaagttcacccatg
agaaaccggaggggtactacaactggcaccacggagcagtacagtactcaggaggccggttcaccatccctacaggtgctggcaaacca
ggggacagcggcagaccgatcttcgacaacaagggacgcgtggtggccatagtcttaggaggagctaatgaaggagcccgtacagccctc
tcggtggtgacctggaataaagacattgtcactaaaatcacccccgaggggggccgaagagtggagtcttgccatcccagttatgtgcctgttgg
caaacaccacgttcccctgctcccagccccccttgcacgccctgctgctacgaaaaggaaccggaggaaaccctacgcatgcttgaggacaa
cgtcatgagacctgggtactatcagctgctacaagcatccttaacatgttctccccaccgccagcgacgcagcaccaaggacaacttcaatgt
ctataaagccacaagaccatacttagctcactgtcccgactgtggagaagggcactcgtgccatagtcccgtagcactagaacgcatcagaa
atgaagcgacagacgggacgctgaaaatccaggtctccttgcaaatcggaataaagacggatgacagccacgattggaccaagctgcgtt
atatggacaaccacatgccagcagacgcagagagggcggggctatttgtaagaacatcagcaccgtgtacgattactggaacaatgggac
acttcatcctggcccgatgtccaaaaggggaaactctgacggtgggattcactgacagtaggaagattagtcactcatgtacgcacccatttca
ccacgaccctcctgtgataggtcgggaaaaattccattcccgaccgcagcacggtaaagagctaccttgcagcacgtacgtgcagagcacc
gccgcaactaccgaggagatagaggtacacatgcccccagacacccctgatcgcacattaatgtcacaacagtccggcaacgtaaagatc
acagtcaatggccagacggtgcggtacaagtgtaattgcggtggctcaaatgaaggactaacaactacagacaaagtgattaataactgca
aggttgatcaatgtcatgccgcggtcaccaatcacaaaaagtggcagtataactcccctctggtcccgcgtaatgctgaacttggggaccgaa
aaggaaaaattcacatcccgtttccgctggcaaatgtaacatgcagggtgcctaaagcaaggaaccccaccgtgacgtacgggaaaaacc
aagtcatcatgctactgtatcctgaccacccaacactcctgtcctaccggaatatgggagaagaaccaaactatcaagaagagtgggtgatgc
ataagaaggaagtcgtgctaaccgtgccgactgaagggctcgaggtcacgtggggcaacaacgagccgtataagtattggccgcagttatct
acaaacggtacagcccatggccacccgcatgagataattctgtattattatgagctgtaccccactatgactgtagtagttgtgtcagtggccacg
ttcatactcctgtcgatggtgggtatggcagcggggatgtgcatgtgtgcacgacgcagatgcatcacaccgtatgaactgacaccaggagct

FIG. 8B (continued)

accgtccctttcctgcttagcctaatatgctgcatcagaacagctaaagcggccacataccaagaggctgcgatatacctgtggaacgagcag
caacctttgttttggctacaagcccttattccgctggcagccctgattgttctatgcaactgtctgagactcttaccatgctgctgtaaaacgttggcttt
tttagccgtaatgagcgtcggtgcccacactgtgagcgcgtacgaacacgtaacagtgatcccgaacacggtgggagtaccgtataagactct
agtcaatagacctggctacagccccatggtattggagatggaactactgtcagtcactttggagccaacactatcgcttgattacatcacgtgcg
agtacaaaaccgtcatcccgtctccgtacgtgaagtgctgcggtacagcagagtgcaaggacaaaaacctacctgactacagctgtaaggtc
ttcaccggcgtctacccatttatgtggggcggcgcctactgcttctgcgacgctgaaaacacgcagttgagcgaagcacacgtggagaagtcc
gaatcatgcaaaacagaatttgcatcagcatacagggctcataccgcatctgcatcagctaagctccgcgtcctttaccaaggaaataacatc
actgtaactgcctatgcaaacggcgaccatgccgtcacagttaaggacgccaaattcattgtggggccaatgtcttcagcctggacacctttcg
acaacaaaattgtggtgtacaaaggtgacgtctataacatggactacccgccctttggcgcaggaagaccaggacaatttggcgatatccaa
agtcgcacacctgagagtaaagacgtctatgctaatacacaactggtactgcagagaccggctgtgggtacggtacacgtgccatactctcag
gcaccatctggctttaagtattggctaaaagaacgcggggcgtcgctgcagcacacagcaccatttggctgccaaatagcaacaaacccggt
aagagcggtgaactgcgccgtagggaacatgcccatctccatcgacataccggaagcggccttcactagggtcgtcgacgcgccctctttaa
cggacatgtcgtgcgaggtaccagcctgcacccattcctcagactttgggggcgtcgccattattaaatatgcagccagcaagaaaggcaagt
gtgcggtgcattcgatgactaacgccgtcactattcgggaagctgagatagaagttgaagggaattctcagctgcaaatctctttctcgacggcc
ttagccagcgccgaattccgcgtacaagtctgttctacacaagtacactgtgcagccgagtgccaccccccgaaggaccacatagtcaacta
cccggcgtcacataccaccctcggggtccaggacatctccgctacggcgatgtcatgggtgcagaagatcacgggaggtgtgggactggttg
ttgctgttgccgcactgattctaatcgtggtgctatgcgtgtcgttcagcaggcac

FIG. 8C

SEQ ID NO: 4
CMV/R C-E3-E2-6K-E1 strain OPY-1
tcgcgcgtttcggtgatgacggtgaaaacctctgacacatgcagctcccggagacggtcacagcttgtctgtaagcggatgccgggagcaga
caagcccgtcagggcgcgtcagcgggtgttggcgggtgtcggggctggcttaactatgcggcatcagagcagattgtactgagagtgcacca
tatgcggtgtgaaataccgcacagatgcgtaaggagaaaataccgcatcagattggctattggccattgcatacgttgtatccatatcataatatg
tacatttatattggctcatgtccaacattaccgccatgttgacattgattattgactagttattaatagtaatcaattacggggtcattagttcatagccc
atatatggagttccgcgttacataacttacggtaaatggcccgcctggctgaccgcccaacgacccccgcccattgacgtcaataatgacgtat FIG. 8C (continued)

gttcccatagtaacgccaatagggactttccattgacgtcaatgggtggagtatttacggtaaactgcccacttggcagtacatcaagtgtatcat
atgccaagtacgccccctattgacgtcaatgacggtaaatggcccgcctggcattatgcccagtacatgaccttatgggactttcctacttggcag
tacatctacgtattagtcatcgctattaccatggtgatgcggttttggcagtacatcaatgggcgtggatagcggtttgactcacggggatttccaag
tctccaccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgttttgac
ctccatagaagacaccgggaccgatccagcctccatcggctcgcatctctccttcacgcgcccgccgccctacctgaggccgccatccacgc
cggttgagtcgcgttctgccgcctcccgcctgtggtgcctcctgaactgcgtccgccgtctaggtaagtttaaagctcaggtcgagaccgggcctt
tgtccggcgctcccttggagcctacctagactcagccggctctccacgctttgcctgaccctgcttgctcaactctagttaacggtggagggcagt
gtagtctgagcagtactcgttgctgccgcgcgcgccaccagacataatagctgacagactaacagactgttcctttccatgggtcttttctgcagtc
accgtcgtcgacacgtgtgatcagatatcgcggccgctctagacaccatggagttcatcccaacccaaactttttacaataggaggtaccagcc
tcgaccctggactccgcgccctactatccaagtcatcaggcccagaccgcgccctcagaggcaagctgggcaacttgcccagctgatctcag
cagttaataaactgacaatgcgcgcggtaccacaacagaagccacgcaggaatcggaagaataagaagcaaaagcaaaaacaacagg
cgccacaaaacaacacaaatcaaaagaagcagccacctaaaaagaaaccggctcaaaagaaaaagaagccgggccgcagagaga
ggatgtgcatgaaaatcgaaaatgattgtattttcgaagtcaagcacgaaggtaaggtaacaggttacgcgtgcctggtgggggacaaagta
atgaaaccagcacacgtaaaggggaccatcgataacgcggacctggccaaactggcctttaagcggtcatctaagtatgaccttgaatgcgc
gcagatacccgtgcacatgaagtccgacgcttcgaagttcacccatgagaaaccggaggggtactacaactggcaccacggagcagtaca
gtactcaggaggccggttcaccatccctacaggtgctggcaaaccaggggacagcggcagaccgatcttcgacaacaagggacgcgtggt
ggccatagtcttaggaggagctaatgaaggagcccgtacagccctctcggtggtgacctggaataaagacattgtcactaaaatcacccccg
agggggccgaagagtggagtcttgccatcccagttatgtgcctgttggcaaacaccacgttcccctgctcccagcccccttgcacgccctgctg
ctacgaaaaggaaccggaggaaaccctacgcatgcttgaggacaacgtcatgagacctgggtactatcagctgctacaagcatccttaacat
gttctccccaccgccagcgacgcagcaccaaggacaacttcaatgtctataaagccacaagaccatacttagctcactgtcccgactgtgga
gaagggcactcgtgccatagtcccgtagcactagaacgcatcagaaatgaagcgacagacgggacgctgaaaatccaggtctccttgcaa
atcggaataaagacggatgacagccacgattggaccaagctgcgttatatggacaaccacatgccagcagacgcagagagggcggggct
atttgtaagaacatcagcaccgtgtacgattactggaacaatgggacacttcatcctggcccgatgtccaaaaggggaaactctgacggtggg
attcactgacagtaggaagattagtcactcatgtacgcacccatttcaccacgaccctcctgtgataggtcgggaaaaattccattcccgaccgc
agcacggtaaagagctaccttgcagcacgtacgtgcagagcaccgccgcaactaccgaggagatagaggtacacatgcccccagacacc FIG. 8C (continued)

cctgatcgcacattaatgtcacaacagtccggcaacgtaaagatcacagtcaatggccagacggtgcggtacaagtgtaattgcggtggctca
aatgaaggactaacaactacagacaaagtgattaataactgcaaggttgatcaatgtcatgccgcggtcaccaatcacaaaaagtggcagt
ataactcccctctggtcccgcgtaatgctgaacttggggaccgaaaaggaaaaattcacatcccgtttccgctggcaaatgtaacatgcagggt
gcctaaagcaaggaaccccaccgtgacgtacgggaaaaaccaagtcatcatgctactgtatcctgaccacccaacactcctgtcctaccgg
aatatgggagaagaaccaaactatcaagaagagtgggtgatgcataagaaggaagtcgtgctaaccgtgccgactgaagggctcgaggtc
acgtggggcaacaacgagccgtataagtattggccgcagttatctacaaacggtacagcccatggccacccgcatgagataattctgtattatt
atgagctgtaccccactatgactgtagtagttgtgtcagtggccacgttcatactcctgtcgatggtgggtatggcagcggggatgtgcatgtgtgc
acgacgcagatgcatcacaccgtatgaactgacaccaggagctaccgtccctttcctgcttagcctaatatgctgcatcagaacagctaaagc
ggccacataccaagaggctgcgatatacctgtggaacgagcagcaacctttgttttggctacaagcccttattccgctggcagccctgattgttct
atgcaactgtctgagactcttaccatgctgctgtaaaacgttggctttttttagccgtaatgagcgtcggtgcccacactgtgagcgcgtacgaaca
cgtaacagtgatcccgaacacggtgggagtaccgtataagactctagtcaatagacctggctacagccccatggtattggagatggaactact
gtcagtcactttggagccaacactatcgcttgattacatcacgtgcgagtacaaaaccgtcatcccgtctccgtacgtgaagtgctgcggtacag
cagagtgcaaggacaaaaacctacctgactacagctgtaaggtcttcaccggcgtctacccatttatgtggggcggcgcctactgcttctgcga
cgctgaaaacacgcagttgagcgaagcacacgtggagaagtccgaatcatgcaaaacagaatttgcatcagcatacagggctcataccgc
atctgcatcagctaagctccgcgtcctttaccaaggaaataacatcactgtaactgcctatgcaaacggcgaccatgccgtcacagttaaggac
gccaaattcattgtggggccaatgtcttcagcctggacacctttcgacaacaaaattgtggtgtacaaaggtgacgtctataacatggactaccc
gccctttggcgcaggaagaccaggacaatttggcgatatccaaagtcgcacacctgagagtaaagacgtctatgctaatacacaactggtact
gcagagaccggctgtgggtacggtacacgtgccatactctcaggcaccatctggctttaagtattggctaaaagaacgcggggcgtcgctgca
gcacacagcaccatttggctgccaaatagcaacaaacccggtaagagcggtgaactgcgccgtagggaacatgcccatctccatcgacata
ccggaagcggccttcactagggtcgtcgacgcgccctctttaacggacatgtcgtgcgaggtaccagcctgcacccattcctcagactttgggg
gcgtcgccattattaaatatgcagccagcaagaaaggcaagtgtgcggtgcattcgatgactaacgccgtcactattcgggaagctgagatag
aagttgaagggaattctcagctgcaaatctctttctcgacggccttagccagcgccgaattccgcgtacaagtctgttctacacaagtacactgtg
cagccgagtgccaccccccgaaggaccacatagtcaactacccggcgtcacataccaccctcggggtccaggacatctccgctacggcga
tgtcatgggtgcagaagatcacgggaggtgtgggactggttgttgctgttgccgcactgattctaatcgtggtgctatgcgtgtcgttcagcaggca
ctaatgaggatccagatctgctgtgccttctagttgccagccatctgttgtttgcccctcccccgtgccttccttgaccctggaaggtgccactccca
ctgtcctttcctaataaaatgaggaaattgcatcgcattgtctgagtaggtgtcattctattctggggggtggggtggggcaggacagcaagggg FIG. 8C (continued)

gaggattgggaagacaatagcaggcatgctggggatgcggtgggctctatgggtacccaggtgctgaagaattgacccggttcctcctgggc
cagaaagaagcaggcacatccccttctctgtgacacaccctgtccacgcccctggttcttagttccagccccactcataggacactcatagctc
aggagggctccgccttcaatcccacccgctaaagtacttggagcggtctctccctccctcatcagcccaccaaaccaaacctagcctccaaga
gtgggaagaaattaaagcaagataggctattaagtgcagagggagagaaaatgcctccaacatgtgaggaagtaatgagagaaatcatag
aattttaaggccatgatttaaggccatcatggccttaatcttccgcttcctcgctcactgactcgctgcgctcggtcgttcggctgcggcgagcggta
tcagctcactcaaaggcggtaatacggttatccacagaatcaggggataacgcaggaaagaacatgtgagcaaaaggccagcaaaaggc
caggaaccgtaaaaaggccgcgttgctggcgtttttccataggctccgcccccctgacgagcatcacaaaaatcgacgctcaagtcagaggt
ggcgaaacccgacaggactataaagataccaggcgtttccccctggaagctccctcgtgcgctctcctgttccgaccctgccgcttaccggata
cctgtccgcctttctcccttcgggaagcgtggcgctttctcatagctcacgctgtaggtatctcagttcggtgtaggtcgttcgctccaagctgggctg
tgtgcacgaaccccccgttcagcccgaccgctgcgccttatccggtaactatcgtcttgagtccaacccggtaagacacgacttatcgccactg
gcagcagccactggtaacaggattagcagagcgaggtatgtaggcggtgctacagagttcttgaagtggtggcctaactacggctacactag
aagaacagtatttggtatctgcgctctgctgaagccagttaccttcggaaaaagagttggtagctcttgatccggcaaacaaaccaccgctggt
agcggtggtttttttgtttgcaagcagcagattacgcgcagaaaaaaaggatctcaagaagatcctttgatcttttctacggggtctgacgctcagt
ggaacgaaaactcacgttaagggattttggtcatgagattatcaaaaaggatcttcacctagatccttttaaattaaaaatgaagttttaaatcaat
ctaaagtatatatgagtaaacttggtctgacagttaccaatgcttaatcagtgaggcacctatctcagcgatctgtctatttcgttcatccatagttgc
ctgactcgggggggggggggcgctgaggtctgcctcgtgaagaaggtgttgctgactcataccaggcctgaatcgccccatcatccagccaga
aagtgagggagccacggttgatgagagctttgttgtaggtggaccagttggtgattttgaacttttgctttgccacggaacggtctgcgttgtcggg
aagatgcgtgatctgatccttcaactcagcaaaagttcgatttattcaacaaagccgccgtcccgtcaagtcagcgtaatgctctgccagtgttac
aaccaattaaccaattctgattagaaaaactcatcgagcatcaaatgaaactgcaatttattcatatcaggattatcaataccatatttttgaaaaa
gccgtttctgtaatgaaggagaaaactcaccgaggcagttccataggatggcaagatcctggtatcggtctgcgattccgactcgtccaacatc
aatacaacctattaatttcccctcgtcaaaaataaggttatcaagtgagaaatcaccatgagtgacgactgaatccggtgagaatggcaaaag
cttatgcatttctttccagacttgttcaacaggccagccattacgctcgtcatcaaaatcactcgcatcaaccaaaccgttattcattcgtgattgcgc
ctgagcgagacgaaatacgcgatcgctgttaaaaggacaattacaaacaggaatcgaatgcaaccggcgcaggaacactgccagcgcat
caacaatattttcacctgaatcaggatattcttctaatacctggaatgctgttttcccggggatcgcagtggtgagtaaccatgcatcatcaggagt
acggataaaatgcttgatggtcggaagaggcataaattccgtcagccagtttagtctgaccatctcatctgtaacatcattggcaacgctaccttt
gccatgtttcagaaacaactctggcgcatcgggcttcccatacaatcgatagattgtcgcacctgattgcccgacattatcgcgagcccatttata FIG. 8C (continued)

cccatataaatcagcatccatgttggaatttaatcgcggcctcgagcaagacgtttcccgttgaatatggctcataacacccccttgtattactgtttat
gtaagcagacagttttattgttcatgatgatatatttttatcttgtgcaatgtaacatcagagattttgagacacaacgtggctttccccccccccccatt
attgaagcatttatcagggttattgtctcatgagcggatacatatttgaatgtatttagaaaaataaacaaataggggttccgcgcacatttccccg
aaaagtgccacctgacgtctaagaaaccattattatcatgacattaacctataaaaataggcgtatcacgaggccctttcgtc

*AvaI* (7847)
*ClaI* (7756)
*SmaI* (7575)
*AvaI* (7573)
*XmaI* (7573)
Kan.
*HindIII* (7327)
*AvaI* (6765)

*ApaLI* (6189)

CMV/R Backbone
*ApaLI* (178)
CMV IE Enhancer/Promoter
*NcoI* (697)
HTLV-1 R Region/Splicing Donor
CMV IE Splicing Acceptor
*NcoI* (1317)
*PstI* (1334)

*NcoI* (1960)

CMV/R Middelburg virus VLP
8185 bp

*PstI* (2541)
*NcoI* (2650)
*NcoI* (2658)
*PstI* (3051)
*PstI* (3222)
Structure
*NcoI* (3409)
*ApaLI* (3592)

*ApaLI* (4020)

*HindIII* (4131)

*BamHI* (4394)
*ApaLI* (4502)
*PstI* (5035)
*BamHI* (5161)
Tbgh

FIG. 9B

SEQ ID NO: 5 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcaatgaattacatacctacgcagacgttctacggccgccgatggcgtcctcgcccggcggcccgcccctgggtggc
tccaccacccgtatactatccaccaccgccacccgtgcctgtcgacccgcaagcgcagcaaatgcaacaacttattgctgcggtcaat
acgctggctataaggcagaatggcacccgaacacctggacaacaacgaaggaaacgtcaatcaaacaaaccaaagaggaaacag
acacccccgaagaaacagaacccggcgaaaacaaagaacaagcagaaaccgcaaccacccaagcctaagaaacggaaacccgg
caagagagaaaggaaatgcatgaagatagagaatgattgcatattcgaggtcaagctcgaaggcaaggtcactgggtacgcctgcct
ggtaggagataaagtgatgaaaccagcacacgtgaaaggagtcatagataaccctgaccttgccaagctagcttttaagaaatcgagc
aagtatgaccttgagtgtgcgcaaattccggtccacatgaagtcagatgcctcgcagttcacccacgagaaaccagaaggacactaca
actggcaccatggtgcagtacaatacctgaacggaagatttaccatcccgacaggtgctgggaagccaggggacagcggtaggcct
atctttgacaacaagggtcgcgtagtggccattgtgctgggggggagccaacgagggagcgaggacggctctatcggttgtcacctgg
aacaaagacatggttacgcgcatcaccccagaaggaactgaggagtggactgccctggtgacaactgcttgcatcctgagcaatctg
actttcgattgcagcctgccaccatgtgcgccttgctgctatgaaaaagacgcagagggcaccctgaggatgctggaggacaacgtc
gataaccccggatactacgatctcctggctgcatcaacgcattgtgacgccccgcagcggcgtcgccgcaggggggctaactgagga FIG. 9B (continued)

ctacgaggcttataaactcactaagccgtacatagcctattgctctgactgcgggaacggacagttttgctacagcccgatagctattga
gagagtcagggccgaggcatcggacggaatgctcaagatacagatctctgcgcaaataggcctgcaggtggacggagctcatgcgt
ggacgaaaatcagatacatgaaagggcacgacgtggaggacacagacaggaactcactggaggtgttcaccaccggagagtgtac
ggtccatggcaccatggggcatttcatcgtagctacatgccccgaaggtgactccttgacagtggcgttcgttgacaaacataaggtca
ggcacgcttgcaggatagcatacaagcatcgtgtccccgtattgggcagagagcactttacggtacggccacatcatggagtagaatt
gccatgcaccacgtacgccatgagaacatcagtcactaccgaagaaatagaaatgcacgtggcgcatgacgtgcccgacaacacctt
tctatccaagaccggaaataaagtgaagataacgccaaaaggaaagtctattcgctacaactgcacgtgtgggtctaaggagagcggt
gtcacaaagcaagacaaagaatttgacaactgcgaagtttcgcagtgccacaccatggtgaccgcccacgataagtggcagtttaact
ctccttatgtccctagggcaggctcaggcaagaaaggaaagatccacgtaccctttccactgagcaactctacgtgcagagttccgttg
gcgcctttaccgaacaccatcccggcaaagaatggaatcacactgcagttgcatccggtcgccccgacgctacttacctaccgcaccc
tcggagagaaaccagaacaccacacagaatggatatcagaaagttgcgaacgtacactccccgtacctgaggaggggttggagtac
acatggggcaatcacgcccctgtgagactgtgggcacaactgacgactaagggttcagcccatgggatgccgcacgaaatcttctcat
attactatggattgtaccctgccacgacggttgcagtgtgcgtggggctagcgtgtgtgatcttgctggctctgtccgcgtcctgctgcct
gtgcgtgtcagcgagaaataagtgcttgaccccgtacgcgttgacgccaggagccgtggtgccgtgcactttgagcttattgtgctgcg
cccccagagccaaggccgcaacgtttgcggagacagcggcatatctatgggacgagaaccagacggtgttctggatgcaattcgca
atccccgtagcatgctttatgatagtgacatattgcctgcgccacttgatgctgtgctgtaggaccgcttctttttagtggcagtaagcctg
ggaatgggggcgacccaggcgtatgagcatagtgtaacgctccccaacgcggtcggatttccgtacagagcccatgtagacagacc
agggttctctccattaacgctccatatggaggtagtctccactagcctagagccgacgctcgccctggattacgtcacttgcgagtacaa
aacggtggtgccgtcgcctaaggtcacctgttgcggcatgtcggagtgtgcacaccagcaaaaagcggactttcaatgtaaagtctac
accggcgtctaccccttttgtggggcggtgcctactgcttttgcaattcggaaaacactcagctgagcgaagcttatgttgagcggagc
gaggtgtgcaaacacgatcacgcagcggcgtatcgcgctcatacagccgcattgaaggctaaaatcagagtgacctacggttccacg
aacgggacggctgaggcgtttgtcaacggagagagcaccgcacgaattggagacctgaaaatgatcctaggtcccatatccaccgc
gtggagcccctttgacccaaagatcgtcgtctacaaggacgaagtctacaatcaggattatccaccgtacggatccgggcaaccgggt
agatttggggacttacagagcaggaccaccgagagtaacgatgtgtacgccaatactgcactgaagctggctcgcccatctgccggc
acggtgcacgttccatatacccagacgccgtccgggtttaagtattggctaaaagaaaaggggacgcattgaaccacaaggctccttt
cggctgcatcatcaagacgaaccccgtaagggcagaaaattgtgcagtcggaaacataccagtgtctctagacattcccgacgcggc
ttttacacgcatagtcgacgcaccatcgctaaccggcctgaagtgcgaggtggcgacttgcacgcactcatcggactttggaggcactt
tggtggtggagtacaagaccgacaaagtggggacgtgcgccgtccactcagaatccaacacggctgttatgcaggagacgagtctgt FIG. 9B (continued)

ccgtgacgatggacggccgaggtacgttgcatttctccaccgcctcagcctcaccgtccttcgtactgaaagtgtgcagtagcaaaacc
acttgcacagcaaagtgcgtgccgccgaaggaccacgtcgtccctttcctgccaaccacaacaatgttgtgttcccggacttttccagt
actgcagtgtcttggctcacccacactatgggcggagctactgtggtgattgctattgggatcaccatattcttaatagttacttgcatagct
tttagtaggcactaggcggccgctctagaccaggccctggatccagatctgctgtgccttctagttgccagccatctgttgtttgcccctc
ccccgtgccttccttgaccctggaaggtgccactcccactgtcctttcctaataaaatgaggaaattgcatcgcattgtctgagtaggtgt
cattctattctggggggtggggtggggcaggacagcaagggggaggattgggaagacaatagcaggcatgctggggatgcggtgg
gctctatgggtacccaggtgctgaagaattgacccggttcctcctgggccagaaagaagcaggcacatccccttctctgtgacacacc
ctgtccacgcccctggttcttagttccagccccactcataggacactcatagctcaggagggctccgccttcaatcccacccgctaaagt
acttggagcggtctctccctccctcatcagcccaccaaaccaaacctagcctccaagagtgggaagaaattaaagcaagataggctat
taagtgcagagggagagaaaatgcctccaacatgtgaggaagtaatgagagaaatcatagaattttaaggccatgatttaaggccatc
atggccttaatcttccgcttcctcgctcactgactcgctgcgctcggtcgttcggctgcggcgagcggtatcagctcactcaaaggcggt
aatacggttatccacagaatcaggggataacgcaggaaagaacatgtgagcaaaaggccagcaaaaggccaggaaccgtaaaaag
gccgcgttgctggcgtttttccataggctccgcccccctgacgagcatcacaaaaatcgacgctcaagtcagaggtggcgaaacccg
acaggactataaagataccaggcgtttccccctggaagctccctcgtgcgctctcctgttccgaccctgccgcttaccggatacctgtcc
gcctttctcccttcgggaagcgtggcgctttctcatagctcacgctgtaggtatctcagttcggtgtaggtcgttcgctccaagctgggct
gtgtgcacgaaccccccgttcagcccgaccgctgcgccttatccggtaactatcgtcttgagtccaacccggtaagacacgacttatcg
ccactggcagcagccactggtaacaggattagcagagcgaggtatgtaggcggtgctacagagttcttgaagtggtggcctaactac
ggctacactagaagaacagtatttggtatctgcgctctgctgaagccagttaccttcggaaaaagagttggtagctcttgatccggcaaa
caaaccaccgctggtagcggtggtttttttgtttgcaagcagcagattacgcgcagaaaaaaaggatctcaagaagatcctttgatctttt
ctacggggtctgacgctcagtggaacgaaaactcacgttaagggattttggtcatgagattatcaaaaaggatcttcacctagatcctttt
aaattaaaaatgaagttttaaatcaatctaaagtatatatgagtaaacttggtctgacagttaccaatgcttaatcagtgaggcacctatctc
agcgatctgtctatttcgttcatccatagttgcctgactcggggggggggggcgctgaggtctgcctcgtgaagaaggtgttgctgactc
ataccaggcctgaatcgccccatcatccagccagaaagtgagggagccacggttgatgagagctttgttgtaggtggaccagttggtg
attttgaacttttgctttgccacggaacggtctgcgttgtcgggaagatgcgtgatctgatccttcaactcagcaaaagttcgatttattcaa
caaagccgccgtcccgtcaagtcagcgtaatgctctgccagtgttacaaccaattaaccaattctgattagaaaaactcatcgagcatca
aatgaaactgcaatttattcatatcaggattatcaataccatatttttgaaaaagccgtttctgtaatgaaggagaaaactcaccgaggcag
ttccataggatggcaagatcctggtatcggtctgcgattccgactcgtccaacatcaatacaacctattaatttcccctcgtcaaaaataag
gttatcaagtgagaaatcaccatgagtgacgactgaatccggtgagaatggcaaaagcttatgcatttctttccagacttgttcaacaggc FIG. 9B (continued)

cagccattacgctcgtcatcaaaatcactcgcatcaaccaaaccgttattcattcgtgattgcgcctgagcgagacgaaatacgcgatcg
ctgttaaaaggacaattacaaacaggaatcgaatgcaaccggcgcaggaacactgccagcgcatcaacaatattttcacctgaatcag
gatattcttctaatacctggaatgctgttttcccggggatcgcagtggtgagtaaccatgcatcatcaggagtacggataaaatgcttgat
ggtcggaagaggcataaattccgtcagccagtttagtctgaccatctcatctgtaacatcattggcaacgctacctttgccatgtttcagaa
acaactctggcgcatcgggcttcccatacaatcgatagattgtcgcacctgattgcccgacattatcgcgagcccatttatacccatataa
atcagcatccatgttggaatttaatcgcggcctcgagcaagacgtttcccgttgaatatggctcataacaccccttgtattactgtttatgta
agcagacagttttattgttcatgatgatatatttttatcttgtgcaatgtaacatcagagattttgagacacaacgtggctttcccccccccc
cattattgaagcatttatcagggttattgtctcatgagcggatacatatttgaatgtatttagaaaaataaacaaataggggttccgcgcaca
tttccccgaaaagtgccacctgacgtctaagaaaccattattatcatgacattaacctataaaaataggcgtatcacgaggccctttcgtc

FIG. 10B (continued)

SEQ ID NO: 6 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgccaccatgtttcccatgcaattcaccaactcagcctatcgccagatggagcccatgttcgcac
cggcttctcgaggacaagtacagccgtatcggccgcgcacaaagcgccgccaagagccgcaagtcggcaacgctgctattgctgcc
ctcgcgaaccagatgagcgcgctccagctgcaggtggctggacttgccggccaggcaagggtggaccgtcgtggaccgagacgtg
ttcagaaaaacaagcagaagaagaagaactcttccaacggagaaaaacccaaggagaagaagaagaagcaaaaacaacaggaga
agaaagggagcggcggtgaaaaagccaagaagccgcggaaccggcccgggaaggaggtaaggatctccgtaaagcgtgcccg
acagagcaccttccccgtgtaccatgacggtgccatatccggctatgcggtgctgattggctcccgcgtgtttaagccagcgcacgtga
agggtaagttcgaccaccccgaactggcggacatcaagttccaggtcgccgaggtcatggacctcgaagcagccgcataccctaag
tgcatgcgagaccaggcggctgaaccagcaaccatgatggatggagtgtacaatggggagtacggcaatattcaggagtggaggac
aattttgtattcgatgcgagcggcagaggcaagccggggtgacagtggcaggccattcaccgacaactcaggaaaggttgtcggtat
cgtcctcggaggaggacccgatggtaggcgcacacgtctctccgtgataggtttcgacaagaagctgaaggccagagagatcgcct
acagcgaggccatcccttggacacgcgcaccagctctcctgctgctgcctatggtcatcgcctgcacctacaactccaatacctttgatt
gctccaaaccgtcctgccaggattgttgcattactgctgaaccaaagaaggccatgactatgctgaaggacaacctgaatgacccgaa FIG. 10B (continued)

ctactgggacctgctcattgccgtcaccacctgcagttccgcccgaaaaagagggctgtgtctacgtcgcctgtcgccgtttacgaca
cacaaattctcgccgcccacgcagctgcctccccgtatagggcgtactgccccgattgtgacggaactgcctgcatctcgccgatagc
tatcgacgaggtggtaagtagcggtagtgaccacgtccttcgcatccgggtcggttctcaatcgggagtgaccgctaaaggcggtgc
ggcgggtgaaacctctctgcgatacctgggaagggacggtaaggtttacgccgcggacaacacgcggctcgtggtgcgcaccactg
caaagtgtgacgtgctgcaggccactggccactacattctggccaactgcccagtggggcagagtctcactgttgcggccacactgg
acggtacccggcatcaatgcaccacggttttcgaacatcaagtaacggagaagttcacaagagaacgcagcaagggccaccacctg
tccgatctgaccaagaaatgcaccaggttctccaccaccccgaagaagtccgcgctctatctcgttgatgtgtatgatgctctgccgact
tctgtagagatcagcaccgtggtgacatgcaacgaaagacagtgcacagtgagggtgccacccggtaccacagtgaaattcgataag
aggtgcaagaacgctgccaaagagaccgtcaccttcaccagcgactcccagacgtttacgtgcgaggagccggtcctaacggccgc
cagcatcacccagggcaagccgcacctcagatcgtcaatgttgcccagcggaggcaaagaggtgaaagcgaggattccattcccgt
tcccgccagagactgcgacttgcagagtgagcatcgccccactgccatcgattacctatgaggaaagcgatgttctgctggccggcac
tgcgaaataccccgtgctgctaactacacggaaccttggtttccatagcaacgccacatctgaatggatccagggtaagtacctgcgcc
gcatcccggtcacgccccaagggattgaactaatgttgggaaacaacgcaccgctgcacttctggtcatctgtcaggtacgcatctgg
agacgccgacgcgtacccctgggaacttctggtgcaccacatcaagcaccatccggagtacgcgtgggcgtttgtaggagttgcatgt
ggcctgctggccgttgcagcatgcatgttcgcgtgcgcatgcaacagggtgcggtactctctgctcgccaacacgttcaacccgaacc
caccaccattgaccgcactgactgcagcattgtgctgcatacctggggctcgcgcggatcaaccctacctggacatcattgcctacttgt
ggaccaacagcaaagtggccttcgggctgcaatgcgcggcgcccgtggcttgcatgctcatcgttacatacgcccttagacattgcag
attgtgctgcaattctttttaggggtaagagggtggtcggctctgctggtcatccttgcgtatgtacagagctgcaaggcgtacgaacac
accgtggtggtcccaatggatccaagagccccgtcgtacgaggcggtgataaaccggaatgggtatgacccccctgaagcttaccatc
gcagtgaactttaccgtcatctcaccaactacggctctggaatactggacctgtgcaggagtccctgtcgtcgagccgccccatgtggg
ctgctgcacgtcagtgtcctgcccctccgacctctccacgctgcacgcgttcaccggcaaagccgtctccgacgtgcactgcgatgtg
cacacgaacgtgtaccccttgttgtggggtgcggctcactgcttctgttccactgaaaacacgcaggtcagcgctgtggccgccaccgt
ttctgagttctgtgctcaggactcagagcgcgccgaggcgttcagcgttcacagcagctcagtcactgcagagattctggtgacgcttg
gtgaagtggtgacggcggtccacgtttacgtggacggggtaacatcagccaggggtaccgacctcaagatcgtggctggcccaata
acaactgactactccccgtttgaccgcaaagtagtccgtatcggcgaagaggtctataattacgactggcctccttacggggctggtcg
accaggcacattcggagacattcaagctaggtcaaccaactatgtcaaacccaatgatctgtacggggacatcggaattgaagtactg
cagccgactaatgaccacgtgcacgtggcttacacgtatacgacctctgggttgctgcgttggttgcaggacgctccgaaaccactca
gtgtcacagcaccgcacggttgtaagatcagtgctaacccgctcctggccctcgattgtggggttggtgccgtccccatgtccatcaac
attccggacgcgaagttcacccgcaaactaaaggacccgaaaccttcggccctgaaatgcgtggtggacagttgcgagtacggggt FIG. 10B (continued)

ggactacgggggcgccgccacgatcacctacgagggccacgaggctgggaagtgcgggatccattccctgacaccaggagtccct
ctgagaacatcagtggttgaagtagttgccggcgctaataccgtcaaaacgaccttctcctcacccacgcccgaggttacactcgaggt
agagatctgttcggcaatagtgaagtgcgccagtgagtgcactccaccgaaggaacacgtagtcgcagccaggcctcgccatggca
gcgacactggaggctacatctccgggcccgcaatgcgctgggccggaaggattgtagggaaccctagtggtcctgtttcctcatcctt
ggccgtcacctactgcgtggtgaagaagtgccgctctaaaagaatccggatagtcaagagctaatctagaccaggccctggatccag
atctgctgtgccttctagttgccagccatctgttgtttgcccctcccccgtgccttccttgaccctggaaggtgccactcccactgtcctttc
ctaataaaatgaggaaattgcatcgcattgtctgagtaggtgtcattctattctggggggtggggtggggcaggacagcaagggggag
gattgggaagacaatagcaggcatgctggggatgcggtgggctctatgggtacccaggtgctgaagaattgacccggttcctcctgg
gccagaaagaagcaggcacatccccttctctgtgacacaccctgtccacgcccctggttcttagttccagccccactcataggacactc
atagctcaggagggctccgccttcaatcccacccgctaaagtacttggagcggtctctccctccctcatcagcccaccaaaccaaacct
agcctccaagagtgggaagaaattaaagcaagataggctattaagtgcagagggagagaaaatgcctccaacatgtgaggaagtaat
gagagaaatcatagaattttaaggccatgatttaaggccatcatggccttaatcttccgcttcctcgctcactgactcgctgcgctcggtc
gttcggctgcggcgagcggtatcagctcactcaaaggcggtaatacggttatccacagaatcaggggataacgcaggaaagaacat
gtgagcaaaaggccagcaaaaggccaggaaccgtaaaaaggccgcgttgctggcgtttttccataggctccgcccccctgacgagc
atcacaaaaatcgacgctcaagtcagaggtggcgaaacccgacaggactataaagataccaggcgtttccccctggaagctccctcg
tgcgctctcctgttccgaccctgccgcttaccggatacctgtccgcctttctcccttcgggaagcgtggcgctttctcatagctcacgctgt
aggtatctcagttcggtgtaggtcgttcgctccaagctgggctgtgtgcacgaaccccccgttcagcccgaccgctgcgccttatccgg
taactatcgtcttgagtccaacccggtaagacacgacttatcgccactggcagcagccactggtaacaggattagcagagcgaggtat
gtaggcggtgctacagagttcttgaagtggtggcctaactacggctacactagaagaacagtatttggtatctgcgctctgctgaagcca
gttaccttcggaaaaagagttggtagctcttgatccggcaaacaaaccaccgctggtagcggtggtttttttgtttgcaagcagcagatta
cgcgcagaaaaaaaggatctcaagaagatcctttgatcttttctacggggtctgacgctcagtggaacgaaaactcacgttaagggattt
tggtcatgagattatcaaaaaggatcttcacctagatccttttaaattaaaaatgaagttttaaatcaatctaaagtatatatgagtaaacttg
gtctgacagttaccaatgcttaatcagtgaggcacctatctcagcgatctgtctatttcgttcatccatagttgcctgactcggggggggg
gggcgctgaggtctgcctcgtgaagaaggtgttgctgactcataccaggcctgaatcgccccatcatccagccagaaagtgagggag
ccacggttgatgagagctttgttgtaggtggaccagttggtgattttgaacttttgctttgccacggaacggtctgcgttgtcgggaagatg
cgtgatctgatccttcaactcagcaaaagttcgatttattcaacaaagccgccgtcccgtcaagtcagcgtaatgctctgccagtgttaca
accaattaaccaattctgattagaaaaactcatcgagcatcaaatgaaactgcaatttattcatatcaggattatcaataccatatttttgaaa
aagccgtttctgtaatgaaggagaaaactcaccgaggcagttccataggatggcaagatcctggtatcggtctgcgattccgactcgtc
caacatcaatacaacctattaatttcccctcgtcaaaaataaggttatcaagtgagaaatcaccatgagtgacgactgaatccggtgaga FIG. 10B (continued)

atggcaaaagcttatgcatttctttccagacttgttcaacaggccagccattacgctcgtcatcaaaatcactcgcatcaaccaaaccgtta
ttcattcgtgattgcgcctgagcgagacgaaatacgcgatcgctgttaaaaggacaattacaaacaggaatcgaatgcaaccggcgca
ggaacactgccagcgcatcaacaatattttcacctgaatcaggatattcttctaatacctggaatgctgttttcccggggatcgcagtggt
gagtaaccatgcatcatcaggagtacggataaaatgcttgatggtcggaagaggcataaattccgtcagccagtttagtctgaccatctc
atctgtaacatcattggcaacgctacctttgccatgtttcagaaacaactctggcgcatcgggcttcccatacaatcgatagattgtcgca
cctgattgcccgacattatcgcgagcccatttatacccatataaatcagcatccatgttggaatttaatcgcggcctcgagcaagacgttt
cccgttgaatatggctcataacaccccttgtattactgtttatgtaagcagacagttttattgttcatgatgatatatttttatcttgtgcaatgta
acatcagagattttgagacacaacgtggctttcccccccccccattattgaagcatttatcagggttattgtctcatgagcggatacatatt
tgaatgtatttagaaaaataaacaaataggggttccgcgcacatttccccgaaaagtgccacctgacgtctaagaaaccattattatcatg
acattaacctataaaaataggcgtatcacgaggccctttcgtc

FIG. 11B

SEQ ID NO: 7 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcacaccatgaattacattccaactcaaacctttacggacgccgttggcgaccacgcccggcgtaccgtccatggcg
ggtgccgatgcagccggccccacccatggtgattcctgagctgcaaactccgatcgtccaggcccaacagatgcagcagctaatcag
tgcagtttctgccctgacgaccaagcaaaatggcaaagcaccgaagaagccgaagaaaaagccgcaaaaagcgaaggctaagaaa
aacgaacagcaaaagaagaacgagaacaagaaaccaccgcctaagcagaagaatccggctaagaagaagaaaccaggaaaaag
ggaacgcatgtgcatgaagatagagaatgattgcatcttcgaggtcaagcttgacggtaaggtcacgggatacgcctgcctagtcggg
gataaagtgatgaagccggcacacgtcaaaggtgtgatcgacaaccccgacctagcgaagcttacctacaagaaatcgagcaagtat
gacctggagtgcgcccagataccagtgcacatgaagtcagatgcttcaaagtacacccatgaaaaaccagaagggcactacaattgg
catcacggtgcagtgcagtacagcggtggcaggttcacaatcccgacaggcgcaggtaaaccaggagacagcggccggccgatct
tcgacaacaaaggacgcgtggtggccattgtcctgggaggggccaacgaaggagccaggactgccctatccgtcgtgacctggac
caaagacatggtcacacggtacaccccagaaggaacagaagaatggtccgccgccttgatgatgtgcgtcttagccaacgttacattc
ccatgctcagagcccgcgtgtgcaccctgttgctatgaaaaacaaccagaacagacactgaggatgttagaggacaacgtggaccgc
ccgggctactacgacctgctcgaggccacgatgacgtgtaacaatagtgcacgccaccgtcgcagtgtgacgaaacacttcaacgtc FIG. 11B (continued)

tacaaggccacgaaaccgtatctagcgtattgcgcggactgcggagacgggcagttctgttacagcccggtggctatagaaaaaatta
gggatgaggcttccgatggcatgataaaaatccaggtcgcagcgcaaattggcatcaacaaaggaggaacacacgaacacaacaaa
atcaggtacatcgccgggcatgacatgaaagaggcaaaccgggactctttacaagtgcatacttccggtgtgtgcgctattcgaggca
cgatgggccacttcatcgtggcctactgccctccaggggacgaactaaaggtccagttccaagatgcagaatcgcacacccaggcct
gcaaagtgcagtacaaacacgcaccggccccagtaggcagagaaaaattcaccgtcaggccccacttcggtatcgaagtgccatgc
acaacgtaccagctgactaccgcaccgacggaggaagagatcgacatgcataccccaccggatatcccagacataacgttgctgtcg
cagcagtcaggtaatgtaaagatcacagcaggaggaaaaaccatcagatacaactgcacgtgtggtagtggcaacgtgggcaccac
cagtagcgacaagactatcaattcgtgcaaaatagcacagtgccacgctgcggtgactaaccacgataagtggcagtacacctcctcg
tttgtccctagagccgaccagttgtctcgcaaaggtaaagtgcacgtacctttccctctgaccaactccacatgcagggtgcctgttgca
cgtgcaccaggtgtcacatacggaaagagagaactgacagtgaaactgcacccagatcatcccacgctgttgacgtaccggagtcta
ggagcagatccgcgcccgtatgaggagtggatagaccgatacgtcgaacggaccataccggtgaccgaagatgggatcgagtaca
gatggggaaacaacccacccgtgcgcttgtgggcccagctgacaactgaaggcaaaccccatgggtggccgcacgagatcatactc
tattactatgggctatacccagcagccaccatcgccgccgtctcagccgcgggtctcgcagtcgtactatcgctgctggcgtcatgttac
atgttcgccactgcacgccgcaagtgcctgaccccatacgccctgacccccggagctgtcgtcccggtaacactaggagtactatgct
gcgcaccacgagcgcatgccgcgtcatttgcggaatctatggcgtatctatgggatgagaatcaaaccctgttttggctggagcttgca
acgccgctcgctgccataatcatacttgtatgctgcctgaagaacctgctttgctgctgcaaaccgctttctttttagtgctggtgagcctg
ggaactcccgtcgtaaaatcttacgaacacaccgcaacgatcccgaatgtggtgggattcccgtataaggctcacattgagaggaacg
gcttctccccgatgaccctacagcttgaagtacttggaaccagcttggaacccacgctaaacttagagtacataacctgtgaatacaaga
cagtcgtgccatcaccttatatcaagtgctgcgggacatcagaatgcagatccatggagcgccccgactatcaatgccaggtctacac
aggagtgtacccatttatgtggggcggcgcatactgcttctgcgacactgagaacacccagctgagtgaagcatacgttgatagatcg
gacgtatgcaagcacgaccatgccgccgcctacaaggcgcatactgcggcaatgaaagccaccatccgaataagctacgggaacct
caatcagacaacaacggcgttcgtcaacggggagcacacagtgaccgtcggaggcagcaggtttacttttggtccaatctccactgcc
tggacgcctttcgacaacaagatcgtcgtctacaagaacgacgtctacaaccaggacttcccaccctacgggtcaggacaaccaggg
aggtttggagacatccagagcaggacggtagagagcaaggacctgtatgccaacaccgccctcaagttgtcaagaccttcgtccggt
actgttcacgtgccttacacacagacccccttctggctttaagtactggataaaagagagaggcacgtcgctgaatgacaaggctcccttt
ggatgcgtaatcaagaccaacccagtcagagcagaaaattgcgccgttggcaacatcccagtctccatggacatcccggacaccgc
gtttacgcgcgtgattgatgcacctgccgtcacaaacctggagtgccaagtggcggtctgcacgcactcatcggacttcggcgggatc
gcgactctgactttcaaaactgacaaacccggaaaatgtgctgtccattctcattcgaacgtagccaccatacaggaggcagctgtgga FIG. 11 B (continued)

catcaaaacagatggcaagataaccctgcatttctctacagcatcagcatccccggcattcaaggtatctgtgtgcagtgccaaaacga
catgcatggcagcgtgtgagccgccgaaggaccacatcgtcccttatggggcgagccataacaaccaagtttttcctgacatgtctgg
cacggcaatgacatgggtgcagcgggtagccggcggactcggcgggctaacactcgccgcagtggcagtacttatactggtgacgt
gtgtgactatgcgccgctaatctagaccaggccctggatccagatctgctgtgccttctagttgccagccatctgttgtttgcccctcccc
cgtgccttccttgaccctggaaggtgccactcccactgtcctttcctaataaaatgaggaaattgcatcgcattgtctgagtaggtgtcatt
ctattctggggggtggggtggggcaggacagcaagggggaggattgggaagacaatagcaggcatgctggggatgcggtgggct
ctatgggtacccaggtgctgaagaattgacccggttcctcctgggccagaaagaagcaggcacatccccttctctgtgacacaccctgt
ccacgcccctggttcttagttccagccccactcataggacactcatagctcaggagggctccgccttcaatcccacccgctaaagtactt
ggagcggtctctccctccctcatcagcccaccaaaccaaacctagcctccaagagtgggaagaaattaaagcaagataggctattaag
tgcagagggagagaaaatgcctccaacatgtgaggaagtaatgagagaaatcatagaatttaaggccatgatttaaggccatcatgg
ccttaatcttccgcttcctcgctcactgactcgctgcgctcggtcgttcggctgcggcgagcggtatcagctcactcaaaggcggtaata
cggttatccacagaatcaggggataacgcaggaaagaacatgtgagcaaaaggccagcaaaaggccaggaaccgtaaaaaggcc
gcgttgctggcgtttttccataggctccgcccccctgacgagcatcacaaaaatcgacgctcaagtcagaggtggcgaaacccgaca
ggactataaagataccaggcgtttccccctggaagctccctcgtgcgctctcctgttccgaccctgccgcttaccggatacctgtccgcc
tttctcccttcgggaagcgtggcgctttctcatagctcacgctgtaggtatctcagttcggtgtaggtcgttcgctccaagctgggctgtgt
gcacgaaccccccgttcagcccgaccgctgcgccttatccggtaactatcgtcttgagtccaacccggtaagacacgacttatcgcca
ctggcagcagccactggtaacaggattagcagagcgaggtatgtaggcggtgctacagagttcttgaagtggtggcctaactacggct
acactagaagaacagtatttggtatctgcgctctgctgaagccagttaccttcggaaaaagagttggtagctcttgatccggcaaacaaa
ccaccgctggtagcggtggtttttttgtttgcaagcagcagattacgcgcagaaaaaaaggatctcaagaagatcctttgatcttttctacg
gggtctgacgctcagtggaacgaaaactcacgttaagggattttggtcatgagattatcaaaaaggatcttcacctagatccttttaaatta
aaaatgaagttttaaatcaatctaaagtatatatgagtaaacttggtctgacagttaccaatgcttaatcagtgaggcacctatctcagcgat
ctgtctatttcgttcatccatagttgcctgactcgggggggggggcgctgaggtctgcctcgtgaagaaggtgttgctgactcatacca
ggcctgaatcgccccatcatccagccagaaagtgagggagccacggttgatgagagctttgttgtaggtggaccagttggtgattttga
acttttgctttgccacggaacggtctgcgttgtcgggaagatgcgtgatctgatccttcaactcagcaaaagttcgatttattcaacaaagc
cgccgtcccgtcaagtcagcgtaatgctctgccagtgttacaaccaattaaccaattctgattagaaaaactcatcgagcatcaaatgaa
actgcaatttattcatatcaggattatcaataccatatttttgaaaaagccgtttctgtaatgaaggagaaaactcaccgaggcagttccata
ggatggcaagatcctggtatcggtctgcgattccgactcgtccaacatcaatacaacctattaatttcccctcgtcaaaaataaggttatca
agtgagaaatcaccatgagtgacgactgaatccggtgagaatggcaaaagcttatgcatttctttccagacttgttcaacaggccagcc FIG. 11B (continued)

attacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatatt
cttctaatacctggaatgctgttttcccggggatcgcagtggtgagtaaccatgcatcatcaggagtacggataaaatgcttgatggtcg
gaagaggcataaattccgtcagccagtttagtctgaccatctcatctgtaacatcattggcaacgctacctttgccatgtttcagaaacaac
tctggcgcatcgggcttcccatacaatcgatagattgtcgcacctgattgcccgacattatcgcgagcccatttatacccatataaatcag
catccatgttggaatttaatcgcggcctcgagcaagacgtttcccgttgaatatggctcataacaccccttgtattactgtttatgtaagcag
acagttttattgttcatgatgatatatttttatcttgtgcaatgtaacatcagagattttgagacacaacgtggctttcccccccccccccattatt
gaagcatttatcagggttattgtctcatgagcggatacatatttgaatgtatttagaaaaataaacaaataggggttccgcgcacatttccc
cgaaaagtgccacctgacgtctaagaaaccattattatcatgacattaacctataaaaataggcgtatcacgaggccctttcgtc

FIG. 12B

SEQ ID NO: 8 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgccaccatgttcccgttccaaccaatgtatccgatgcagccaatgccctatcgtaacccgttcg
cggccccgcgcaggccctggttccccagaaccgacccttttctggcgatgcaggtgcaggaattaacccgctcgatggctaacctga
cgttcaagcaacgccgggacgcgccacctgaggggccacctgctaagaaacctaagagggaggccccgcaaaagcaaaaaggg
ggaggccaagggaagaagaagaagaaccaggggaagaagaaggccaagacggggccgcctaatccgaaggcacagagtgga
aacaagaagaagcccaacaagaaaccaggcaagagacagcgcatggtcatgaaattggaatctgacaagacattcccaattatgctg
gaagggaagattaacggctacgcttgcgtggtcggagggaagttattcaggccgatgcacgtggaaggcaagatcgacaacgacgt
tctggccgcacttaagacgaagaaagcatccaaatatgatcttgagtatgcagatgtgccacagaacatgcgggccgatacattcaagt
acacccatgagaagccccaaggctattacagctggcatcatggagcagtccaatatgaaaatgggcgtttcacggtgccaaaaggag
ttggggccaagggagacagcggaagacccattctggataatcagggacgggtggtcgctattgtgctgggaggtgtgaatgaaggat
ctaggacagccctttcagtcgtcatgtggaacgagaagggagtaactgtgaagtatactccggagaactgcgagcaatggtcactagt
gaccactatgtgcctgctcgccaatgtgacgttcccatgtgccgaaccaccaatttgctacgacagaaaaccagcagagactttggcca FIG. 12 B (continued)

tgctcagcgttaacgttgacaacccgggctacgatgagctgctggaagcagctgttaagtgccccggaagaaaaaggagatctaccg
aggagctgtttaaggagtataagctaacgcgcccttacatggccagatgcatcagatgtgccgttgggagctgccatagtccaatagca
attgaggcagtgaagagcgacgggcacgacggctatgttagacttcagacttcctcgcagtatggcctggattcctctggcaacttaaa
gggaaggactatgcggtatgatatgcacgggaccattgaagagataccactacatcaagtgtcactccacacatctcgcccgtgtcac
attgtggatgggcatggttattttctgcttgctaggtgcccggcaggggactccatcaccatggaatttaagaaaggttcagtcacacact
cctgctcagtgccgtatgaagtgaaatttaatcctgtaggcagagaactctacactcatccaccagaacacggagcagagcaagcgtg
ccaagtctacgcgcacgatgcacagaacagaggagcttatgtcgagatgcacctcccgggctcagaagtggacagcagtttgatttcc
ttgagcggcagttcagtcaccgtgacacctcctgtcgggactagcgccttggtgaaatgcaagtgcggcggcacaaagatctccgaa
accatcaacaaggcaaaacagttcagccagtgcacaaagaaggagcagtgcagagcatatcgactgcagaatgacaagtgggtgta
taattctgacaaactgcccaaagcagcgggagccaccctaaaggaaaactacacgtcccgttcttgctggcagacggcaaatgcac
cgtgcctctagcaccggaacctatgataaccttcggtttccgatcagtgtcactgaaactgcaccctaagaatcccacatatctgaccact
cgccaacttgctgatgagcctcattacacgcacgagctcatatctgaaccagctgttaggaattttaccgtcactgaaaaggggtggga
gtttgtatggggaaaccatccgccgaaaaggttttgggcacaggaaacagcacccggaaatccacatgggctgccacatgaggtgat
aactcattattaccacagataccctatgtccaccatcctgggtttgtcaatttgcgccgccattgtaaccgtttccgttgcagcgtccacctg
gctgttttgcaaatccagagtttcgtgcctaactccttaccggctaacacctaacgccaggatgccgctttgcctggccgtgctttgctgc
gcccgcactgcccgggccgagaccacctgggagtccttggatcacctatggaacaataaccaacagatgttctggattcaattgctgat
ccctctggccgccttgattgtagtgactcgcctgctcaagtgcgtgtgctgtgtagtgcctttttttagtcgtggccggcgccgcaggcgc
cggcgcctacgagcacgcgaccacgatgccgagccaagcgggaatctcgtataacaccatagtcaacagagcaggctacgcgcca
ctccctatcagcataacaccaacaaagatcaagctgatacccacagtgaacttggagtacgtcacctgccactacaaaacaggaatgg
attcaccagccatcaaatgctgcggatctcaggaatgtactccaactaacaggcctgatgaacagtgcaaagtcttcacaggggtttac
ccgttcatgtggggaggtgcatattgcttttgcgacactgagaatactcaggtcagcaaggcctacgtaatgaaatctgacgactgcctt
gcggatcatgctgaagcatacaaagcgcacacagcctcagtgcaggcgttcctcaacatcacagtgggggaacactctattgtgacc
accgtgtatgtgaatggagaaactcctgtgaacttcaatggggtcaaactaactgcaggtccactttccacagcttggacaccctttgac
agaaaaatcgtgcagtatgccggggagatctataattacgattttcctgagtatggggcaggacaaccaggagcatttggagacataca
atccagaacagtctcaagctcagatctgtatgccaataccaacctagtgctgcagagacccaaagcaggagcgatccatgtgccatac
actcaggcaccatcgggttttgagcaatggaagaaagataaagctccgtcattgaaattcaccgcccctttcggatgcgaaatatataca
aaccccattcgcgccgaaaattgtgctgtagggtcaattccattagcctttgacattcccgacgccttgttcaccagggtgtcagaaaca FIG. 12 B (continued)

ccgacactttcagcggccgaatgcactcttaacgagtgcgtgtattcatccgactttggcgggatcgccacggtcaagtattcggccag
caagtcaggcaagtgcgcagtccatgtgccatcagggactgctaccctaaaagaagcagcagtcgagctaaccgagcaagggtcg
gcgaccattcatttctcgaccgcaaatatccacccggagttcaggctccaaatatgcacatcatatgtcacgtgcaaaggtgattgtcac
cccccgaaagaccacattgtgacacacccccagtatcacgcccaaacatttacagccgcggtgtcaaaaaccgcgtggacgtggtta
acatccctgctgggaggatcggccgtaattattataattggcttagtgctggctactattgtggccatgtacgtgctgaccaaccagaaac
ataattgatctagaccaggccctggatccagatctgctgtgccttctagttgccagccatctgttgtttgcccctcccccgtgccttccttga
ccctggaaggtgccactcccactgtcctttcctaataaaatgaggaaattgcatcgcattgtctgagtaggtgtcattctattctggggggt
ggggtggggcaggacagcaagggggaggattgggaagacaatagcaggcatgctggggatgcggtgggctctatgggtacccag
gtgctgaagaattgacccggttcctcctgggccagaaagaagcaggcacatccccttctctgtgacacaccctgtccacgcccctggtt
cttagttccagccccactcataggacactcatagctcaggagggctccgccttcaatcccacccgctaaagtacttggagcggtctctc
cctccctcatcagcccaccaaaccaaacctagcctccaagagtgggaagaaattaaagcaagataggctattaagtgcagagggaga
gaaaatgcctccaacatgtgaggaagtaatgagagaaatcatagaattttaaggccatgatttaaggccatcatggccttaatcttccgct
tcctcgctcactgactcgctgcgctcggtcgttcggctgcggcgagcggtatcagctcactcaaaggcggtaatacggttatccacaga
atcaggggataacgcaggaaagaacatgtgagcaaaaggccagcaaaaggccaggaaccgtaaaaaggccgcgttgctggcgttt
ttccataggctccgcccccctgacgagcatcacaaaaatcgacgctcaagtcagaggtggcgaaacccgacaggactataaagatac
caggcgtttccccctggaagctccctcgtgcgctctcctgttccgaccctgccgcttaccggatacctgtccgcctttctcccttcgggaa
gcgtggcgctttctcatagctcacgctgtaggtatctcagttcggtgtaggtcgttcgctccaagctgggctgtgtgcacgaaccccccg
ttcagcccgaccgctgcgccttatccggtaactatcgtcttgagtccaacccggtaagacacgacttatcgccactggcagcagccact
ggtaacaggattagcagagcgaggtatgtaggcggtgctacagagttcttgaagtggtggcctaactacggctacactagaagaaca
gtatttggtatctgcgctctgctgaagccagttaccttcggaaaaagagttggtagctcttgatccggcaaacaaaccaccgctggtagc
ggtggtttttttgtttgcaagcagcagattacgcgcagaaaaaaaggatctcaagaagatcctttgatcttttctacggggtctgacgctca
gtggaacgaaaactcacgttaagggattttggtcatgagattatcaaaaaggatcttcacctagatccttttaaattaaaaatgaagttttaa
atcaatctaaagtatatatgagtaaacttggtctgacagttaccaatgcttaatcagtgaggcacctatctcagcgatctgtctatttcgttca
tccatagttgcctgactcgggggggggggcgctgaggtctgcctcgtgaagaaggtgttgctgactcataccaggcctgaatcgcc
ccatcatccagccagaaagtgagggagccacggttgatgagagctttgttgtaggtggaccagttggtgattttgaacttttgctttgcca
cggaacggtctgcgttgtcgggaagatgcgtgatctgatccttcaactcagcaaaagttcgatttattcaacaaagccgccgtcccgtca
agtcagcgtaatgctctgccagtgttacaaccaattaaccaattctgattagaaaaactcatcgagcatcaaatgaaactgcaatttattca FIG. 12 B (continued)

tatcaggattatcaataccatatttttgaaaaagccgtttctgtaatgaaggagaaaactcaccgaggcagttccataggatggcaagatc
ctggtatcggtctgcgattccgactcgtccaacatcaatacaacctattaatttcccctcgtcaaaaataaggttatcaagtgagaaatcac
catgagtgacgactgaatccggtgagaatggcaaaagcttatgcatttctttccagacttgttcaacaggccagccattacgctcgtcatc
aaaatcactcgcatcaaccaaaccgttattcattcgtgattgcgcctgagcgagacgaaatacgcgatcgctgttaaaaggacaattaca
aacaggaatcgaatgcaaccggcgcaggaacactgccagcgcatcaacaatattttcacctgaatcaggatattcttctaatacctgga
atgctgttttcccggggatcgcagtggtgagtaaccatgcatcatcaggagtacggataaaatgcttgatggtcggaagaggcataaat
tccgtcagccagtttagtctgaccatctcatctgtaacatcattggcaacgctacctttgccatgtttcagaaacaactctggcgcatcggg
cttcccatacaatcgatagattgtcgcacctgattgcccgacattatcgcgagcccatttatacccatataaatcagcatccatgttggaatt
taatcgcggcctcgagcaagacgtttcccgttgaatatggctcataacaccccttgtattactgtttatgtaagcagacagttttattgttcat
gatgatatatttttatcttgtgcaatgtaacatcagagattttgagacacaacgtggctttcccccccccccattattgaagcatttatcagg
gttattgtctcatgagcggatacatatttgaatgtatttagaaaaataaacaaataggggttccgcgcacatttccccgaaaagtgccacct
gacgtctaagaaaccattattatcatgacattaacctataaaaataggcgtatcacgaggccctttcgtc

FIG. 13B

SEQ ID NO: 9 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgccaccatgtttccatacctcagctgaactttccaccagtttaccctacaaatccgatggcttac
cgagatccaaaccctcctaggcgccgctggaggccgtttcggcccccgctggctgctcaaatcgaagatcttaggaggtcgatagtc
aacttgactttcaaacaacgatcacctaatccgccgccaggtccaccgccaaagaagaagaagagtgctcctaagccaaaacctactc
agcctaaaaagaagaagcagcaagccaagaggacgaaacgcaagcctaaaccagggaaacgacaacgtatgtgtatgaagttgga
gtcggacaagacatttccgatcatgctgaacggccaagtgaatggatatgcctgcgttgtcggaggaaggctgatgaaaccactccac
gttgaaggaaaaattgataatgagcaattagcggccgtgaaattgaagaaggctagcatgtacgacttggagtacggcgacgttcccc
agaacatgaaatcagacacgctgcagtacaccagcgacaaaccaccgggcttctacaactggcaccacggcgcagtccagtatgag
aatgggagatttaccgtaccgagaggagtgggcgggaaaggcgacagcggaagaccgatcctggacaacagaggcagagttgtg
gctattgttctaggaggtgcaaatgagggcacgcgtacggcgctttcagtggtcacttggaaccagaaaggggtgaccattagggata
cccccgaaggttctgaaccgtggtcactagttacagcgctatgcgtgctttcgaatgtcacgttcccatgcgacaaaccacccgtgtgct
attcactgacgccagaacgaacactcgacgtgctcgaagagaacgtcgacaatccaaattacgacacgctgctggagaacgtcttga FIG. 13 B (continued)

aatgtccatcacgccggcccaaacgaagcattaccgatgacttcacactgaccagtccctacctggggttctgcccgtattgcagacac
tcaacgccgtgtttcagcccaataaaaattgagaacgtgtgggacgaatctgatgatggatcgattagaatccaggtctcggcacaattc
ggctacaatcaggcaggcactgcggatgtcaccaaattccgttacatgtctttcgaccacgaccatgacatcaaggaagacagtatgg
agaaaatagctatcagcacatctggaccctgccgtcgtcttggccacaaagggtacttcctgttagctcaatgtcctccaggtgacagtg
taaccgtcagtatcacgagcggagcatctgagaattcatgcaccgtggagaaaaagatcaggaggaagtttgtcggtagagaggagt
acttgttcccacccgtccatggaaagctggtaaagtgccacgtttacgatcacttgaaggagacgtctgccgggtacataaccatgcac
aggccaggcccacacgcgtataagtcctatctggaggaagcgtcaggcgaagtgtacattaaaccaccttctggcaagaacgtcacc
tacgaatgtaagtgtggcgactacagcacaggtatcgtgagcacgcgaacgaagatgaacggctgcactaaagcaaaacagtgcatt
gcctacaagagcgaccaaacgaaatgggtcttcaactcgccggatcttattaggcacacagaccactcagtgcaaggtaaattgcaca
ttccattccgcttgacaccgacagtctgcccggttccgttagctcacacgcctacagtcacgaagtggttcaaaggcatcaccctccacc
tgactgcaatgcgaccaacattgctgacaacgagaaaattggggctgcgagcagacgcaacagcagaatggattacagggtctacat
ccaggaatttttctgtggggcgagaagggctggagtacgtatggggtaaccatgaaccagtcagagtctgggcccaggagtcggcac
caggcgacccacatggatggccgcatgagatcatcatccactattatcatcggcatccagtctacactgtcattgtgctgtgtggtgtcg
ctcttgctatcctggtaggcactgcatcatcagcagcttgcatcgccaaagcaagaagagactgcctgacgccatacgcgcttgcacc
gaacgcaacggtacccacagcattagcggttttgtgctgcattcggccaaccaacgctgaaacatttggagaaactttgaaccatctgt
ggtttaacaaccaaccgtttctctgggcacagttgtgcattcctctggcagcgcttgttattctgttccgctgcttttcatgctgcatgccttttt
tattggttgcaggcgtctgcctggggaaggtagacgccttcgaacatgcgaccactgtgccaaatgttccggggatcccgtataaggc
gttggtcgaacgcgcaggttacgcgccacttaacctggagatcacggtcgtctcatcggaattaacaccttcaactaacaaggagtacg
tgacctgcaaattccacacagtcattccttcaccacaagttaaatgctgcgggtccctcgagtgcaaggcatcctcaaaggcggattac
acatgccgcgtttttggcggtgtgtaccctttcatgtggggaggcgcacaatgcttctgtgacagtgagaacacacaactgagtgaggc
gtacgtcgagttcgctccagactgcactatagatcacgcagtcgcactaaaagttcacacagctgctctgaaagtcggcctgcgtatag
tatacggcaacaccaccgcgcacctggatacgtttgtcaatggcgtcacgccaggttcctcacgggacctgaaggtcatagcagggc
cgatatcagccgctttttcaccctttgaccataaggtcgtcatcagaaaggggcttgtttacaactacgacttccctgagtatggagctatg
aaaccaggagcgttcggcgatattcaagcatcctcgcttgatgctacagacatagtagcccgcactgacatacggctgctgaagccttc
tgtcaagaacatccacgtcccctacacccaagcagtatcagggtatgaaatgtggaagaacaactcaggacgacccctgcaagaaac
agcaccatttggatgtaaaattgaagtggagcctctgcgagcgtctaactgtgcttacgggcacatccctatctcgattgacatccctgat
gcagcttttgtgagatcatcagaatcaccaacaattttagaagttagctgcacagtagcagactgcatttattctgcagactttggtggttct FIG. 13 B (continued)

ctaacattacagtacaaagctgacagggagggacattgtccagttcactcccactccacgacagctgttttgaaggaagcgaccacac
atgtgactgccgtaggcagcataacactacattttagcacatcgagcccacaagcaaattttatagtttcgctatgcggcaagaagtcca
cctgcaatgctgaatgtaaaccaccggccgaccacataattggagaaccacataaagtcgaccaagaattccaggcggcagtttccaa
aacatcttggaactggctgcttgcactgtttgggggagcatcatccctcattgttgtaggacttatagtgttggtctgcagctctatgcttata
aacacacgtagatgatctagaccaggccctggatccagatctgctgtgccttctagttgccagccatctgttgtttgcccctcccccgtgc
cttccttgaccctggaaggtgccactcccactgtcctttcctaataaaatgaggaaattgcatcgcattgtctgagtaggtgtcattctattct
ggggggtggggtggggcaggacagcaagggggaggattgggaagacaatagcaggcatgctggggatgcggtgggctctatgg
gtacccaggtgctgaagaattgacccggttcctcctgggccagaaagaagcaggcacatccccttctctgtgacacaccctgtccacg
cccctggttcttagttccagccccactcataggacactcatagctcaggagggctccgccttcaatcccacccgctaaagtacttggag
cggtctctccctccctcatcagcccaccaaaccaaacctagcctccaagagtgggaagaaattaaagcaagataggctattaagtgca
gagggagagaaaatgcctccaacatgtgaggaagtaatgagagaaatcatagaattttaaggccatgatttaaggccatcatggcctta
atcttccgcttcctcgctcactgactcgctgcgctcggtcgttcggctgcggcgagcggtatcagctcactcaaaggcggtaatacggtt
atccacagaatcaggggataacgcaggaaagaacatgtgagcaaaaggccagcaaaaggccaggaaccgtaaaaaggccgcgtt
gctggcgtttttccataggctccgcccccctgacgagcatcacaaaaatcgacgctcaagtcagaggtggcgaaacccgacaggact
ataaagataccaggcgtttccccctggaagctccctcgtgcgctctcctgttccgaccctgccgcttaccggatacctgtccgcctttctc
ccttcgggaagcgtggcgctttctcatagctcacgctgtaggtatctcagttcggtgtaggtcgttcgctccaagctgggctgtgtgcac
gaaccccccgttcagcccgaccgctgcgccttatccggtaactatcgtcttgagtccaacccggtaagacacgacttatcgccactggc
agcagccactggtaacaggattagcagagcgaggtatgtaggcggtgctacagagttcttgaagtggtggcctaactacggctacact
agaagaacagtatttggtatctgcgctctgctgaagccagttaccttcggaaaaagagttggtagctcttgatccggcaaacaaaccac
cgctggtagcggtggtttttttgtttgcaagcagcagattacgcgcagaaaaaaaggatctcaagaagatcctttgatcttttctacggggt
ctgacgctcagtggaacgaaaactcacgttaagggattttggtcatgagattatcaaaaaggatcttcacctagatccttttaaattaaaaa
tgaagttttaaatcaatctaaagtatatatgagtaaacttggtctgacagttaccaatgcttaatcagtgaggcacctatctcagcgatctgt
ctatttcgttcatccatagttgcctgactcggggggggggggcgctgaggtctgcctcgtgaagaaggtgttgctgactcataccaggc
ctgaatcgccccatcatccagccagaaagtgagggagccacggttgatgagagctttgttgtaggtggaccagttggtgattttgaactt
ttgctttgccacggaacggtctgcgttgtcgggaagatgcgtgatctgatccttcaactcagcaaaagttcgatttattcaacaaagccgc FIG. 13B (continued)

cgtcccgtcaagtcagcgtaatgctctgccagtgttacaaccaattaaccaattctgattagaaaaactcatcgagcatcaaatgaaactg
caatttattcatatcaggattatcaataccatatttttgaaaaagccgtttctgtaatgaaggagaaaactcaccgaggcagttccataggat
ggcaagatcctggtatcggtctgcgattccgactcgtccaacatcaatacaacctattaatttcccctcgtcaaaaataaggttatcaagtg
agaaatcaccatgagtgacgactgaatccggtgagaatggcaaaagcttatgcatttctttccagacttgttcaacaggccagccattac
gctcgtcatcaaaatcactcgcatcaaccaaaccgttattcattcgtgattgcgcctgagcgagacgaaatacgcgatcgctgttaaaag
gacaattacaaacaggaatcgaatgcaaccggcgcaggaacactgccagcgcatcaacaatattttcacctgaatcaggatattcttct
aatacctggaatgctgttttcccggggatcgcagtggtgagtaaccatgcatcatcaggagtacggataaaatgcttgatggtcggaag
aggcataaattccgtcagccagtttagtctgaccatctcatctgtaacatcattggcaacgctacctttgccatgtttcagaaacaactctg
gcgcatcgggcttcccatacaatcgatagattgtcgcacctgattgcccgacattatcgcgagcccatttatacccatataaatcagcatc
catgttggaatttaatcgcggcctcgagcaagacgtttcccgttgaatatggctcataacaccccttgtattactgtttatgtaagcagaca
gttttattgttcatgatgatatatttttatcttgtgcaatgtaacatcagagattttgagacacaacgtggctttccccccccccccattattgaa
gcatttatcagggttattgtctcatgagcggatacatatttgaatgtatttagaaaaataaacaaataggggttccgcgcacatttccccga
aaagtgccacctgacgtctaagaaaccattattatcatgacattaacctataaaaataggcgtatcacgaggccctttcgtc

FIG. 14B

SEQ ID NO: 10 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgccaccatgttcccataccctacacttaactacccgcctatggcgccgattaacccgatggctta
ccgggatcctaatccgcctaggcgcaggtggcggccctttaggccaccacttgcagctcaaattgaggacctgagacgttccatcgct
aacctgactttgaaacaacgagcacctaaccctccagcaggaccgcccgccaaacgcaagaagcctgcgccaagcctaagcctgc
gcaggaaaaagaagcgaccaccaccacctgccaagaaacaaaaacgtaaacctaaaccaggcaaacgacagcgaatgtgtatgaa
gctagagtcagataaaacgtttccaatcatgttgaacggacaggtgaatggttacgcgtgcgtcgtgggtggacgagtgttcaaaccgc
tgcacgtagaaggcagaatagacaatgagcaactggccgccatcaagctgaagaaggccagcatatatgaccttgagtatggtgatg
tgccacaatgcatgaaatcagataccctccagtacaccagtgacaagcctcctggcttttataactggcaccatggagctgtacagtatg
agaacaataggttcaccgtaccacggggggtcggtggaaagggtgacagcgggagacctattcttgacaacaaaggtagagtcgtc
gcaattgtcctgggtggagtcaacgaaggatccaggacggctctatcagtggtgacatggaaccaaaaaggggttacagtcaaagat
acaccagaggggtcagagccatggtcgcttgccactgtcatgtgcgtcctggccaatatcacgtttccatgtgatcaaccaccctgcat
gccatgctgttatgaaaagaatccacacgaaacactcaccatgttggaacagaattacgacagccgagcctatgatcagctgctcgatg FIG. 14 B (continued)

ccgctgtgaaatgtaatgctaggagaaccaggagagatttggacactcatttcacccagtataagctggcacgcccgtatattgctgatt
gccctaactgtgggcatagtcggtgcgacagccctatagctatagaagaagtcagaggggatgcgcacgcaggagtcatccgcatc
cagacatcagctatgttcggtctgaagacggatggagttgatttggcctacatgagtttcatgaacggcaaaacgcagaaatcaataaa
gatcgacaacctgcatgtgcgcacctcagccccttgttccctcgtgtcgcaccacggctattacatcctggctcaatgcccaccagggg
acacggttacagttgggtttcacgacgggcctaaccgccatacgtgcacagttgcccataaggtagaattcaggccagtgggtagaga
gaaataccgtcacccacctgaacatggagttgaattaccatgcaaccgttacacccacaagcgtgcagaccaaggacactacgttgag
atgcatcaacccgggctagttgccgaccactctctccttagcatccacagtgccaaggtgaaaattacggtaccgagcggcgcccaag
tgaaatactactgcaagtgcccagacgtacgagagggaactaccagcagcgactatacaaccacctgcacggatgtcaaacaatgca
gggcttacctgattgacaacaaaaaatgggtgtacaactctggaagactgcctcgaggagagggcgacactttaaaggaaaacttca
tgtgccctttgtgcctgttaaggccaagtgcatcgccacgctggcaccagagcctctagttgagcacaaacaccgcaccctgatttaca
cctgtacccggaccacccgaccttgctgacgaccaggtcacttggaagtgatgcaaatccaactcgacaatggattgagcgaccaac
aactgtcaatttcacagtcaccggagaagggttggagtatacctggggaaaccatccaccaaaaagagtatgggctcaagagtcagg
agaagggaatccacatggatggccgcacgaagtggtagtctattactacaacagatacccattaaccacaattatcgggttatgcacct
gtgtggctatcatcatggtctcttgtgtcacatccgtgtggctcctttgcaggactcgcaatctttgcataaccccgtataaactagccccg
aacgctcaagtcccaatactcctggcgttactttgctgcattaagccgacgagggcagatgacaccttgcaagtgctgaattacctgtgg
aacaacaatcaaaactttttctggatgcagacgcttatcccacttgcagcgcttattgtatgcatgcgcatgctgcgctgcttattttgctgt
gggccggctttttacttgtctgcggcgccttgggcgccgcagcgtacgaacacacagcagtgatgccgaacaaggtggggatcccg
tacaaagctttagtcgaacgcccaggttatgcacccgttcacctacagatacagctggttaataccaggataattccatcaactaacctg
gagtacatcacctgcaagtataagacaaaagtgccttctccagtagtgaaatgctgcggtgccactcaatgtacctccaaaccccatcct
gactatcagtgtcaggtgtttacaggtgtttacccattcatgtggggaggagcctactgcttctgcgacactgaaaacacccagatgagc
gaggcgtatgtagagcgctcggaagagtgctctattgaccacgcaaaagcttataaagtacacacaggcactgttcaggcaatggtga
acataacttatgggagcgtcagctggagatctgcagatgtttacgtcaatggtgaaactcccgcgaaaataggagatgccaaactcatc
ataggtccactgtcatctgcgtggtccccattcgataacaaggtggtggttcatgggcatgaagtgtataattacgactttcctgagtacg
gcaccggcaaagcaggctcttttggagacctgcaatcacgcacatcaaccagcaacgatctgtacgcaaacaccaacttgaagctac
aacgaccccaggctggtatcgtgcacacacctttcacccaggcgccctccggcttcgaacgatggaaaagggacaaggggcacc
gttgaacgacgtagccccgtttggctgttcgattgccctggagccgctccgtgcagaaaattgtgcagtgggaagcatccctatatctat
agatatacccgatgcggcttttaccagaatatctgaaacaccgacagtctcagacctggaatgcaaaattacggagtgtacttatgcctc FIG. 14 B (continued)

Figure 14:
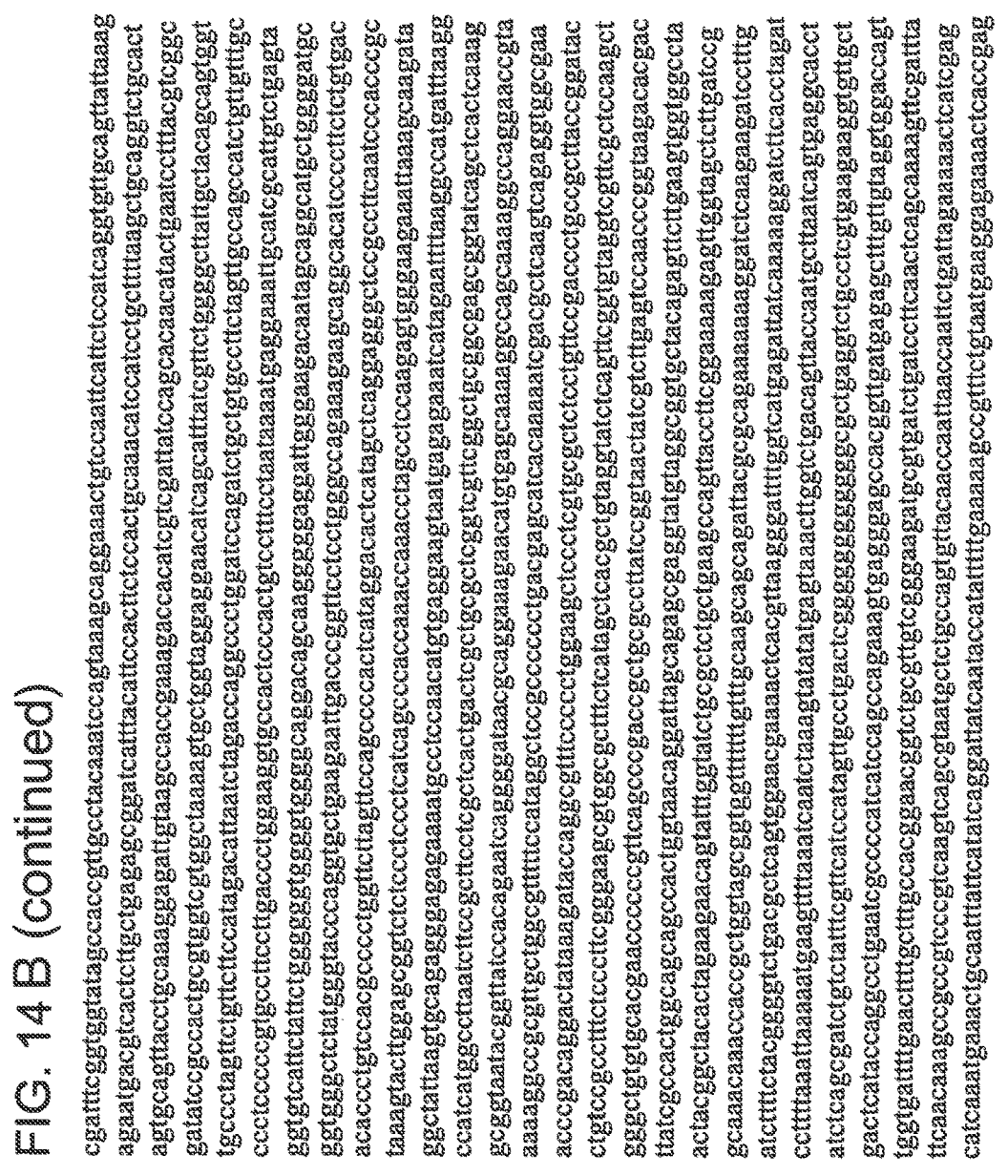

cgatttcggtggtatagccaccgttgcctacaaatccagtaaagcaggaaactgtccaattcattctccatcaggtgttgcagttattaaag
agaatgacgtcactcttgctgagagcggatcatttacattccacttctccactgcaaacatccatcctgcttttaagctgcaggtctgcact
agtgcagttacctgcaaaggagattgtaagccaccgaaagaccacatcgtcgattatccagcacaacatactgaatcctttacgtcggc
gatatccgccactgcgtggtcgtggctaaaagtgctggtaggaggaacatcagcatttatcgttctggggcttattgctacagcagtggt
tgccctagttctgttcttccatagacattaatctagaccaggccctggatccagatctgctgtgccttctagttgccagccatctgttgtttgc
ccctcccccgtgccttccttgaccctggaaggtgccactcccactgtcctttcctaataaaatgaggaaattgcatcgcattgtctgagta
ggtgtcattctattctggggggtggggtggggcaggacagcaagggggaggattgggaagacaatagcaggcatgctggggatgc
ggtgggctctatgggtacccaggtgctgaagaattgacccggttcctcctgggccagaaagaagcaggcacatccccttctctgtgac
acaccctgtccacgcccctggttcttagttccagccccactcataggacactcatagctcaggagggctccgccttcaatcccacccgc
taaagtacttggagcggtctctccctccctcatcagcccaccaaaccaaacctagcctccaagagtgggaagaaattaaagcaagata
ggctattaagtgcagagggagagaaaatgcctccaacatgtgaggaagtaatgagagaaatcatagaattttaaggccatgatttaagg
ccatcatggccttaatcttccgcttcctcgctcactgactcgctgcgctcggtcgttcggctgcggcgagcggtatcagctcactcaaag
gcggtaatacggttatccacagaatcaggggataacgcaggaaagaacatgtgagcaaaaggccagcaaaaggccaggaaccgta
aaaaggccgcgttgctggcgtttttccataggctccgcccccctgacgagcatcacaaaaatcgacgctcaagtcagaggtggcgaa
acccgacaggactataaagataccaggcgtttccccctggaagctccctcgtgcgctctcctgttccgaccctgccgcttaccggatac
ctgtccgcctttctcccttcgggaagcgtggcgctttctcatagctcacgctgtaggtatctcagttcggtgtaggtcgttcgctccaagct
gggctgtgtgcacgaaccccccgttcagcccgaccgctgcgccttatccggtaactatcgtcttgagtccaacccggtaagacacgac
ttatcgccactggcagcagccactggtaacaggattagcagagcgaggtatgtaggcggtgctacagagttcttgaagtggtggccta
actacggctacactagaagaacagtatttggtatctgcgctctgctgaagccagttaccttcggaaaaagagttggtagctcttgatccg
gcaaacaaaccaccgctggtagcggtggtttttttgtttgcaagcagcagattacgcgcagaaaaaaaggatctcaagaagatcctttg
atcttttctacggggtctgacgctcagtggaacgaaaactcacgttaagggattttggtcatgagattatcaaaaaggatcttcacctagat
ccttttaaattaaaaatgaagttttaaatcaatctaaagtatatatgagtaaacttggtctgacagttaccaatgcttaatcagtgaggcacct
atctcagcgatctgtctatttcgttcatccatagttgcctgactcggggggggggggcgctgaggtctgcctcgtgaagaaggtgttgct
gactcataccaggcctgaatcgccccatcatccagccagaaagtgagggagccacggttgatgagagctttgttgtaggtggaccagt
tggtgattttgaacttttgctttgccacggaacggtctgcgttgtcgggaagatgcgtgatctgatccttcaactcagcaaaagttcgattta
ttcaacaaagccgccgtcccgtcaagtcagcgtaatgctctgccagtgttacaaccaattaaccaattctgattagaaaaactcatcgag
catcaaatgaaactgcaatttattcatatcaggattatcaataccatatttttgaaaaagccgtttctgtaatgaaggagaaaactcaccgag FIG. 14 B (continued)

gcagttccataggatggcaagatcctggtatcggtctgcgattccgactcgtccaacatcaatacaacctattaatttcccctcgtcaaaa
ataaggttatcaagtgagaaatcaccatgagtgacgactgaatccggtgagaatggcaaaagcttatgcatttctttccagacttgttcaa
caggccagccattacgctcgtcatcaaaatcactcgcatcaaccaaaccgttattcattcgtgattgcgcctgagcgagacgaaatacg
cgatcgctgttaaaaggacaattacaaacaggaatcgaatgcaaccggcgcaggaacactgccagcgcatcaacaatattttcacctg
aatcaggatattcttctaatacctggaatgctgttttcccggggatcgcagtggtgagtaaccatgcatcatcaggagtacggataaaatg
cttgatggtcggaagaggcataaattccgtcagccagtttagtctgaccatctcatctgtaacatcattggcaacgctacctttgccatgttt
cagaaacaactctggcgcatcgggcttcccatacaatcgatagattgtcgcacctgattgcccgacattatcgcgagcccatttataccc
atataaatcagcatccatgttggaatttaatcgcggcctcgagcaagacgtttcccgttgaatatggctcataacaccccttgtattactgtt
tatgtaagcagacagttttattgttcatgatgatatatttttatcttgtgcaatgtaacatcagagattttgagacacaacgtggctttcccccc
ccccccattattgaagcatttatcagggttattgtctcatgagcggatacatatttgaatgtatttagaaaaataaacaaataggggttccgc
gcacatttccccgaaaagtgccacctgacgtctaagaaaccattattatcatgacattaacctataaaaataggcgtatcacgaggccctt
tcgtc

FIG. 15B

SEQ ID NO: 11 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgccaccatgaatagaggattctttaacatgctcggccgccgccccttcccggcccccactgcc
atgtggaggccgcggagaaggaggcaggcggccccgatgcctgcccgcaacgggctggcttctcaaatccagcaactgaccaca
gccgtcagtgccctagtcattggacaggcaactagacctcaacccccacgtccacgcccgccaccgcgccagaagaagcaggcgc
ccaagcaaccaccgaagccgaagaaaccaaaaacgcaggagaagaagaagaagcaacctgcaaaacccaaacccggaaagag
acagcgcatggcacttaagttggaggccgacagattgttcgacgtcaagaacgaggacggagatgtcatcgggcacgcactggcca
tggaaggaaaggtaatgaaacctctgcacgtgaaaggaaccatcgaccaccctgtgctatcaaagctcaaatttaccaagtcgtcagc
atacgacatggagttcgcacagttgccagtcaacatgagaagtgaggcattcacctacaccagtgaacaccccgaaggattctataact
ggcaccacggagcggtgcagtatagtggaggtagatttaccatccctcgcggagtaggaggcagaggagacagcggtcgtccgat
catggataactccggtcgggttgtcgcgatagtcctcggtggcgctgatgaaggaacacgaactgccctttcggtcgtcacctggaata
gtaaagggaagacaattaagacgaccccggaagggacagaagagtggtccgcagcaccactggtcacggcaatgtgtttgctcgga
aatgtgagcttcccatgcgaccgcccgcccacatgctatacccgcgaaccttccagagccctcgacatccttgaagagaacgtgaacc FIG. 15 B (continued)

atgaggcctacgataccctgctcaatgccatattgcggtgcggatcgtctggcagaagcaaaagaagcgtcattgacgactttaccctg
accagcccctacttgggcacatgctcgtactgccaccatactgtaccgtgcttcagccctgttaagatcgagcaggtctgggacgaagc
ggacgataacaccatacgcatacagacttccgcccagtttggatacgaccaaagcggagcagcaagcgcaaacaagtaccgctaca
tgtcgcttaagcaggatcacaccgttaaagaaggcaccatggatgacatcaagattagcacctcaggaccgtgtagaaggcttagcta
caaaggatactttctcctcgcaaaatgccctccaggggacagcgtaacggttagcatagtgagtagcaactcagcaacgtcatgtaca
ctggcccgcaagataaaaccaaaattcgtgggacgggaaaaatatgatctacctcccgttcacggtaaaaaaattccttgcacagtgta
cgaccgtctgaaagaaacaactgcaggctacatcactatgcacaggccgagaccgcacgcttatacatcctacctggaagaatcatca
gggaaagtttacgcaaagccgccatctgggaagaacattacgtatgagtgcaagtgcggcgactacaagaccggaaccgtttcgacc
cgcaccgaaatcactggttgcaccgccatcaagcagtgcgtcgcctataagagcgaccaaacgaagtgggtcttcaactcaccggac
ttgatcagacatgacgaccacacggcccaagggaaattgcatttgcctttcaagttgatcccgagtacctgcatggtccctgttgcccac
gcgccgaatgtaatacatggctttaaacacatcagcctccaattagatacagaccacttgacattgctcaccaccaggagactaggggc
aaacccggaaccaaccactgaatggatcgtcggaaagacggtcagaaacttcaccgtcgaccgagatggcctggaatacatatggg
gaaatcatgagccagtgagggtctatgcccaagagtcagcaccaggagaccctcacggatggccacacgaaatagtacagcattact
accatcgccatcctgtgtacaccatcttagccgtcgcatcagctaccgtggcgatgatgattggcgtaactgttgcagtgttatgtgcctg
taaagcgcgccgtgagtgcctgacgccatacgccctggccccaaacgccgtaatcccaacttcgctggcactcttgtgctgcgttagg
tcggccaatgctgaaacgttcaccgagaccatgagttacttgtggtcgaacagtcagccgttcttctgggtccagttgtgcataccttgg
ccgctttcatcgttctaatgcgctgctgctcctgctgcctgcctttttagtggttgccggcgcctacctggcgaaggtagacgcctacga
acatgcgaccactgttccaaatgtgccacagataccgtataaggcacttgttgaaagggcagggtatgccccgctcaatttggagatca
ctgtcatgtcctcggaggttttgccttccaccaaccaagagtacattacctgcaaattcaccactgtggtcccctccccaaaaatcaaatg
ctgcggctccttggaatgtcagccggccgctcatgcagactatacctgcaaggtcttcggaggggtctacccctttatgtggggagga
gcgcaatgtttttgcgacagtgagaacagccagatgagtgaggcgtacgtcgaattgtcagcagattgcgcgtctgaccacgcgcag
gcgattaaggtgcacactgccgcgatgaaagtaggactgcgtattgtgtacgggaacactaccagtttcctagatgtgtacgtgaacgg
agtcacaccaggaacgtctaaagacttgaaagtcatagctggaccaatttcagcatcgtttacgccattcgatcataaggtcgttatccat
cgcggcctggtgtacaactatgacttcccggaatatggagcgatgaaaccaggagcgtttggagacattcaagctacctccttgactag
caaggatctcatcgccagcacagacattaggctactcaagccttccgccaagaacgtgcatgtcccgtacacgcaggcctcatcagg
atttgagatgtggaaaaacaactcaggccgcccactgcaggaaaccgcacctttcgggtgtaagattgcagtaaatccgctccgagcg
gtggactgttcatacgggaacattcccatttctattgacatcccgaacgctgcctttatcaggacatcagatgcaccactggtctcaacag FIG. 15 B (continued)

tcaaatgtgaagtcagtgagtgcacttattcagcagacttcggcgggatggccaccctgcagtatgtatccgaccgcgaaggtcaatgc
cccgtacattcgcattcgagcacagcaactctccaagagtcgacagtacatgtcctggagaaaggagcggtgacagtacactttagca
ccgcgagtccacaggcgaactttatcgtatcgctgtgtgggaagaagacaacatgcaatgcagaatgtaaaccaccagctgaccatat
cgtgagcaccccgcacaaaaatgaccaagaatttcaagccgccatctcaaaaacatcatggagttggctgtttgcccttttcggcggcg
cctcgtcgctattaattataggacttatgattttgcttgcagcatgatgctgactagcacacgaagatgatctagaccaggccctggatcc
agatctgctgtgccttctagttgccagccatctgttgtttgcccctcccccgtgccttccttgaccctggaaggtgccactcccactgtcctt
tcctaataaaatgaggaaattgcatcgcattgtctgagtaggtgtcattctattctggggggtggggtggggcaggacagcaaggggg
aggattgggaagacaatagcaggcatgctggggatgcggtgggctctatgggtacccaggtgctgaagaattgacccggttcctcct
gggccagaaagaagcaggcacatccccttctctgtgacacaccctgtccacgcccctggttcttagttccagccccactcataggaca
ctcatagctcaggagggctccgccttcaatcccacccgctaaagtacttggagcggtctctccctccctcatcagcccaccaaaccaaa
cctagcctccaagagtgggaagaaattaaagcaagataggctattaagtgcagagggagagaaaatgcctccaacatgtgaggaagt
aatgagagaaatcatagaatttaaggccatgatttaaggccatcatggccttaatcttccgcttcctcgctcactgactcgctgcgctcgg
tcgttcggctgcggcgagcggtatcagctcactcaaaggcggtaatacggttatccacagaatcaggggataacgcaggaaagaaca
tgtgagcaaaaggccagcaaaaggccaggaaccgtaaaaaggccgcgttgctggcgtttttccataggctccgcccccctgacgag
catcacaaaaatcgacgctcaagtcagaggtggcgaaacccgacaggactataaagataccaggcgtttccccctggaagctccctc
gtgcgctctcctgttccgaccctgccgcttaccggatacctgtccgcctttctcccttcgggaagcgtggcgctttctcatagctcacgct
gtaggtatctcagttcggtgtaggtcgttcgctccaagctgggctgtgtgcacgaaccccccgttcagcccgaccgctgcgccttatcc
ggtaactatcgtcttgagtccaacccggtaagacacgacttatcgccactggcagcagccactggtaacaggattagcagagcgaggt
atgtaggcggtgctacagagttcttgaagtggtggcctaactacggctacactagaagaacagtatttggtatctgcgctctgctgaagc
cagttaccttcggaaaaagagttggtagctcttgatccggcaaacaaaccaccgctggtagcggtggtttttttgtttgcaagcagcagat
tacgcgcagaaaaaaaggatctcaagaagatcctttgatcttttctacggggtctgacgctcagtggaacgaaaactcacgttaaggga
ttttggtcatgagattatcaaaaaggatcttcacctagatccttttaaattaaaaatgaagttttaaatcaatctaaagtatatatgagtaaactt
ggtctgacagttaccaatgcttaatcagtgaggcacctatctcagcgatctgtctatttcgttcatccatagttgcctgactcgggggggg
ggggcgctgaggtctgcctcgtgaagaaggtgttgctgactcataccaggcctgaatcgccccatcatccagccagaaagtgaggga FIG. 15B (continued)

gccacggttgatgagagctttgttgtaggtggaccagttggtgattttgaacttttgctttgccacggaacggtctgcgttgtcgggaagat
gcgtgatctgatccttcaactcagcaaaagttcgatttattcaacaaagccgccgtcccgtcaagtcagcgtaatgctctgccagtgttac
aaccaattaaccaattctgattagaaaaactcatcgagcatcaaatgaaactgcaatttattcatatcaggattatcaataccatatttttgaa
aaagccgtttctgtaatgaaggagaaaactcaccgaggcagttccataggatggcaagatcctggtatcggtctgcgattccgactcgt
ccaacatcaatacaacctattaatttcccctcgtcaaaaataaggttatcaagtgagaaatcaccatgagtgacgactgaatccggtgag
aatggcaaaagcttatgcatttctttccagacttgttcaacaggccagccattacgctcgtcatcaaaatcactcgcatcaaccaaaccgtt
attcattcgtgattgcgcctgagcgagacgaaatacgcgatcgctgttaaaaggacaattacaaacaggaatcgaatgcaaccggcgc
aggaacactgccagcgcatcaacaatattttcacctgaatcaggatattcttctaatacctggaatgctgttttcccggggatcgcagtgg
tgagtaaccatgcatcatcaggagtacggataaaatgcttgatggtcggaagaggcataaattccgtcagccagtttagtctgaccatct
catctgtaacatcattggcaacgctacctttgccatgtttcagaaacaactctggcgcatcgggcttcccatacaatcgatagattgtcgc
acctgattgcccgacattatcgcgagcccatttatacccatataaatcagcatccatgttggaatttaatcgcggcctcgagcaagacgtt
tcccgttgaatatggctcataacaccccttgtattactgtttatgtaagcagacagttttattgttcatgatgatatatttttatcttgtgcaatgta
acatcagagattttgagacacaacgtggctttcccccccccccccattattgaagcatttatcagggttattgtctcatgagcggatacatatt
tgaatgtatttagaaaaataaacaaataggggttccgcgcacatttccccgaaaagtgccacctgacgtctaagaaaccattattatcatg
acattaacctataaaaataggcgtatcacgaggccctttcgtc

FIG. 16 B

SEQ ID NO: 12 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgccaccatgaattacatccctacgcaaacgttttacggccgccggtggcgcccgcgcccggc
ggcccgtccttggccgttgcaggccactccggtggctcccgtcgtccccgacttccaggcccagcagatgcagcaactcatcagcgc
cgtaaatgcgctgacaatgagacagaacgcaattgctcctgctaggcctcccaaaccaaagaagaagaagacaaccaaaccaaagc
cgaaaacgcagcccaagaagatcaacggaaaaacgcagcagcaaaagaagaaagacaagcaagccgacaagaagaagaagaa
acccggaaaaagagaaagaatgtgcatgaagattgaaaatgactgtatcttcgaagtcaaacacgaaggaaaggtcactgggtacgc
ctgcctggtgggcgacaaagtcatgaaacctgcccacgtgaaaggagtcatcgacaacgcggacctggcaaagctagctttcaaga
aatcgagcaagtatgaccttgagtgtgcccagataccagttcacatgaggtcggatgcctcaaagtacacgcatgagaagcccgagg
gacactataactggcaccacggggctgttcagtacagcggaggtaggttcactataccgacaggagcgggcaaaccgggagacagt
ggccggcccatctttgacaacaaggggagggtagtcgctatcgtcctgggcggggccaacgagggctcacgcacagcactgtcggt
ggtcacctggaacaaagatatggtgactagagtgacccccgaggggtccgaagagtggtccgccccgctgattactgccatgtgtgt
ccttgccaatgctaccttcccgtgcttccagcccccgtgtgtaccttgctgctatgaaaacaacgcagaggccacactacggatgctcg FIG. 16 B (continued)

aggataacgtggataggccagggtactacgacctccttcaggcagccttgacgtgccgaaacggaacaagacaccggcgcagcgt
gtcgcaacacttcaacgtgtataaggctacacgcccttacatcgcgtactgcgccgactgcggagcagggcactcgtgtcatagcccc
gtagcaattgaagcggtcaggtccgaagctaccgacgggatgctgaagattcagttctcggcacaaattggcatagataagagtgaca
atcatgactacacgaagataaggtacgcagacgggcacgccattgagaatgccgtccggtcatctttgaaggtagccacctccggag
actgtttcgtccatggcacaatgggacatttcatactggcaaagtgcccaccgggtgaattcctgcaggtctcgatccaggacaccaga
aacgcggtccgtgcctgcagaatacaatatcatcatgaccctcaaccggtgggtagagaaaaatttacaattagaccacactatggaaa
agagatcccttgcaccacttatcaacagaccacagcggagaccgtggaggaaatcgacatgcatatgccgccagatacgccggaca
ggacgttgctatcacagcaatctggcaatgtaaagatcacagtcggaggaaagaaggtgaaatacaactgcacctgtggaaccggaa
acgttggcactactaattcggacatgacgatcaacacgtgtctaatagagcagtgccacgtctcagtgacggaccataagaaatggca
gttcaactcacctttcgtcccgagagccgacgaaccggctagaaaaggcaaagtccatatcccattcccgttggacaacatcacatgc
agagttccaatggcgcgcgaaccaaccgtcatccacggcaaaagagaagtgacactgcaccttcacccagatcatcccacgctctttt
cctaccgcacactgggtgaggacccgcagtatcacgaggaatgggtgacagcggcggtggaacggaccatacccgtaccagtgga
cgggatggagtaccactggggaaacaacgacccagtgaggctttggtctcaactcaccactgaagggaaaccgcacggctggccg
catcagatcgtacagtactactatgggctttacccggccgctacagtatccgcggtcgtcgggatgagcttactggcgttgatatcgatct
tcgcgtcgtgctacatgctggttgcggcccgcagtaagtgcttgaccccttatgctttaacaccaggagctgcagttccgtggacgctg
gggatactctgctgcgccccgcgggcgcacgcagctagtgtggcagagactatggcctacttgtgggaccaaaaccaagcgttgttc
tggttggagtttgcggcccctgttgcctgcatcctcatcatcacgtattgcctcagaaacgtgctgtgttgctgtaagagcctttctttttag
tgctactgagcctcggggcaaccgccagagcttacgaacattcgacagtaatgccgaacgtggtggggttcccgtataaggctcacat
tgaaaggccaggatatagcccccctcactttgcagatgcaggttgttgaaaccagcctcgaaccaacccttaatttggaatacataacctg
tgagtacaagacggtcgtcccgtcgccgtacgtgaagtgctgcggcgcctcagagtgctccactaaagagaagcctgactaccaatg
caaggtttacacaggcgtgtacccgttcatgtggggaggggcatattgcttctgcgactcagaaaacacgcaactcagcgaggcgtac
gtcgatcgatcggacgtatgcaggcatgatcacgcatctgcttacaaagcccatacagcatcgctgaaggccaaagtgagggttatgt
acggcaacgtaaaccagactgtggatgtttacgtgaacggagaccatgccgtcacgataggggtactcagttcatattcgggccgct
gtcatcggcctggaccccgttcgacaacaagatagtcgtgtacaaagacgaagtgttcaatcaggacttcccgccgtacggatctggg
caaccagggcgcttcggcgacatccaaagcagaacagtggagagtaacgacctgtacgcgaacacggcactgaagctggcacgc
ccttcacccggcatggtccatgtaccgtacacacagacaccttcagggttcaaatattggctaaaggaaaaagggacagccctaaata
cgaaggctcctttggctgccaaatcaaaacgaaccctgtcagggccatgaactgcgccgtgggaaacatccctgtctccatgaatttg FIG. 16 B (continued)

cctgacagcgcctttacccgcattgtcgaggcgccgaccatcattgacctgacttgcacagtggctacctgtacgcactcctcggatttc
ggcggcgtcttgacactgacgtacaagaccaacaagaacggggactgctctgtacactcgcactctaacgtagctactctacaggag
gccacagcaaaagtgaagacagcaggtaaggtgaccttacacttctccacggcaagcgcatcaccttctttgtggtgtcgctatgcag
tgctagggccacctgttcagcgtcgtgtgagcccccgaaagaccacatagtcccatatgcggctagccacagtaacgtagtgtttcca
gacatgtcgggcaccgcactatcatgggtgcagaaaatctcgggtggtctgggggccttcgcaatcggcgctatcctggtgctggttgt
ggtcacttgcattgggctccgcagataatctagaccaggccctggatccagatctgctgtgccttctagttgccagccatctgttgtttgc
ccctcccccgtgccttccttgaccctggaaggtgccactcccactgtcctttcctaataaaatgaggaaattgcatcgcattgtctgagta
ggtgtcattctattctggggggtggggtggggcaggacagcaagggggaggattgggaagacaatagcaggcatgctggggatgc
ggtgggctctatgggtacccaggtgctgaagaattgacccggttcctcctgggccagaaagaagcaggcacatccccttctctgtgac
acaccctgtccacgcccctggttcttagttccagccccactcataggacactcatagctcaggagggctccgccttcaatcccacccgc
taaagtacttggagcggtctctccctccctcatcagcccaccaaaccaaacctagcctccaagagtgggaagaaattaaagcaagata
ggctattaagtgcagagggagagaaaatgcctccaacatgtgaggaagtaatgagagaaatcatagaattttaaggccatgatttaagg
ccatcatggccttaatcttccgcttcctcgctcactgactcgctgcgctcggtcgttcggctgcggcgagcggtatcagctcactcaaag
gcggtaatacggttatccacagaatcaggggataacgcaggaaagaacatgtgagcaaaaggccagcaaaaggccaggaaccgta
aaaaggccgcgttgctggcgtttttccataggctccgcccccctgacgagcatcacaaaaatcgacgctcaagtcagaggtggcgaa
acccgacaggactataaagataccaggcgtttccccctggaagctccctcgtgcgctctcctgttccgaccctgccgcttaccggatac
ctgtccgcctttctcccttcgggaagcgtggcgctttctcatagctcacgctgtaggtatctcagttcggtgtaggtcgttcgctccaagct
gggctgtgtgcacgaaccccccgttcagcccgaccgctgcgccttatccggtaactatcgtcttgagtccaacccggtaagacacgac
ttatcgccactggcagcagccactggtaacaggattagcagagcgaggtatgtaggcggtgctacagagttcttgaagtggtggccta
actacggctacactagaagaacagtatttggtatctgcgctctgctgaagccagttaccttcggaaaaagagttggtagctcttgatccg
gcaaacaaaccaccgctggtagcggtggtttttttgtttgcaagcagcagattacgcgcagaaaaaaaggatctcaagaagatcctttg
atcttttctacggggtctgacgctcagtggaacgaaaactcacgttaagggattttggtcatgagattatcaaaaaggatcttcacctagat
ccttttaaattaaaaatgaagttttaaatcaatctaaagtatatatgagtaaacttggtctgacagttaccaatgcttaatcagtgaggcacct
atctcagcgatctgtctatttcgttcatccatagttgcctgactcgggggggggggggcgctgaggtctgcctcgtgaagaaggtgttgct
gactcataccaggcctgaatcgccccatcatccagccagaaagtgagggagccacggttgatgagagctttgttgtaggtggaccagt
tggtgattttgaacttttgctttgccacggaacggtctgcgttgtcgggaagatgcgtgatctgatccttcaactcagcaaaagttcgattta
ttcaacaaagccgccgtcccgtcaagtcagcgtaatgctctgccagtgttacaaccaattaaccaattctgattagaaaaactcatcgag FIG. 16B (continued)

catcaaatgaaactgcaatttattcatatcaggattatcaataccatatttttgaaaaagccgtttctgtaatgaaggagaaaactcaccgag
gcagttccataggatggcaagatcctggtatcggtctgcgattccgactcgtccaacatcaatacaacctattaatttcccctcgtcaaaa
ataaggttatcaagtgagaaatcaccatgagtgacgactgaatccggtgagaatggcaaaagcttatgcatttctttccagacttgttcaa
caggccagccattacgctcgtcatcaaaatcactcgcatcaaccaaaccgttattcattcgtgattgcgcctgagcgagacgaaatacg
cgatcgctgttaaaaggacaattacaaacaggaatcgaatgcaaccggcgcaggaacactgccagcgcatcaacaatattttcacctg
aatcaggatattcttctaatacctggaatgctgttttcccggggatcgcagtggtgagtaaccatgcatcatcaggagtacggataaaatg
cttgatggtcggaagaggcataaattccgtcagccagtttagtctgaccatctcatctgtaacatcattggcaacgctacctttgccatgttt
cagaaacaactctggcgcatcgggcttcccatacaatcgatagattgtcgcacctgattgcccgacattatcgcgagcccatttataccc
atataaatcagcatccatgttggaatttaatcgcggcctcgagcaagacgtttcccgttgaatatggctcataacaccccttgtattactgtt
tatgtaagcagacagttttattgttcatgatgatatatttttatcttgtgcaatgtaacatcagagattttgagacacaacgtggctttcccccc
ccccccattattgaagcatttatcagggttattgtctcatgagcggatacatatttgaatgtatttagaaaaataaacaaataggggttccgc
gcacatttccccgaaaagtgccacctgacgtctaagaaaccattattatcatgacattaacctataaaaataggcgtatcacgaggccctt
tcgtc

FIG. 17B

SEQ ID NO: 13 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgcatgtttcccatgcaattcaccaactcagcctatcgccagatggagcccatgtttgcaccggg
ttcccgaggacaagtacagccgtaccggccgcgcactaagcgccgccaggagccgcaagtcggcaacgccgccattactgccctc
gcgaaccagatgagtgcgctccagttgcaggtagctggacttgccggccaggcaagggtggaccgccgtgggccaagacgtgttc
agaagaacaagcagaagaagaagaactcttccaacggagaaaaacccaaagagaagaagaagaagcaaaaacaacaggagaag
aagggaagcggtggcgaaaaagtcaagaagactaggaaccgacccgggaaggaggtaaggatctccgtaaagtgtgcccgacag
agcaccttccccgtgtaccacgaaggtgctatatccggctacgctgtgctgattggatctcgcgtattcaagccggcacacgtgaaggg
taagatcgaccaccctgaactggcagacatcaagttccaggtcgccgaggacatggacctcgaagcagctgcgtacccgaagagca
tgcgagaccaagcggctgaaccagcgaccatgatggacagagtgtacaactgggagtatggcactatcagagtggaggataatgtc
ataatcgacgcaagcggtaggggcaagccgggtgacagtggcagggccatcaccgacaactcgggaaaggttgttggtattgtcct
cggaggaggacccgatggcaggcgcacacgcctctccgtgataggtttcgacaagaagatgaaggctagggagatcgcctacagt
gatgccataccttggacacgcgctccggccctcctgctgctgcctatggttattgtctgcacctacaattccaacaccttcgattgctcca FIG. 17B (continued)

aaccgtcctgccaggactgctgcattactgctgaaccagagaaggccatgaccatgctgaaggacaatctgaacgacccgaactact
gggacctactcattgctgtcaccacctgtggctccgcccggagaaagagggctgtgtctacgtcgcctgccgccttttacgacacaca
gatcctcgccgcccacgcagctgcctccccatacagggcgtactgccccgattgtgacggaacagcgtgtatctcgccgatagccat
cgacgaggtggtgagcagtggcagcgaccacgtcctccgcatgcgggttggttctcaatcgggagtgaccgctaagggtggtgcgg
cgggtgaaacctctctgcgatacctgggaagggacgggaaggttcacgccgcagacaacacgcgactcgtggtgcgcacgactgc
aaagtgcgacgtgctgcaggccactggccactacatcctggccaactgcccagtggggcagagcctaaccgttgcggccacactgg
atggcacccggcatcaatgcaccacggttttcgaacaccaagtaacggagaagttcaccagagaacgcagcaagggccaccatctg
tccgacatgaccaagaaatgcaccagattttccactacaccaaaaaagtccgccctctacctcgttgatgtgtatgacgctctgccgattt
ctgtagagattagcaccgtcgtaacatgcagcgacagccagtgcacagtgagggtgccacctggtaccacagtgaaattcgacaaga
aatgcaagagcgctgactcggcaaccgtcactttcaccagcgactcccagacgtttacgtgtgaggagccagtcctaacggctgcca
gtatcacccagggcaagccacacctcagatcggcaatgttgcctagcggaggcaaggaagtgaaagcaaggatcccgttcccgttc
ccgccggaaaccgcaacttgcagagtgagtgtagccccactgccgtcgatcacctacgaggaaagcgatgtcctgctagccggtac
cgcaaaataccctgtgctgctaaccacacggaaccttggtttccatagcaacgccacatccgaatggatccagggcaagtacctgcgc
cgcatcccggtcacgcctcaagggatcgagctaacatggggaaacaacgcgccgatgcacttttggtcatccgtcaggtacgcatcc
ggggacgctgatgcgtaccctgggaacttctggtgtaccacaccaagcaccatccagagtacgcgtgggcgtttgtaggagttgcat
gcggcctgctggctatcgcagcgtgcatgtttgcgtgcgcatgcagcagggtgcggtactctctggtcgccaacacgttcaactcgaa
cccaccaccattgaccgcactgactgcagcactgtgttgcataccaggggctcgcgcggaccaaccctacttggacatcattgcctact
tgtggaccaacagcaaagtggccttcgggctacaatttgcggcgcccgtggcctgtgtgctcatcattacatacgcccttaggcactgc
agattgtgctgcaagtctttttaggggtaagagggtggtcagccctgctggtcatccttgcgtatgtacagagctgcaagagctacgaa
cacaccgtggtggtcccaatggatccaagagccccgtcgtacgaagcagtgataaaccggaatgggtatgatccattgaagctgacc
atctcagtgaatttcaccgtcatctcaccaactacggctctggaatattggacctgcgcaggagtccccatcgtcgagccgccccatgtg
ggctgctgcacgtcggtgtcctgcccctctgacctctctacgctgcatgcgtttactggcaaagctgtctccgacgtgcactgcgatgtg
cacacaaacgtgtaccccttgttgtggggcgcggctcactgcttctgttccaccgagaatacacaggtcagcgctgtggcagccaccg
tttctgagttctgtgcccaggactcagagcgtgccgaagcgttcagcgtacacagcagctcagtcaccgctgaggtcctggtgacgctt
ggtgaagtggtgacggcagtccacgtttacgtggacggggtaacatcagccaggggcactgacctcaagatcgtggctggaccaat
aacaaccgactactccccattcgatcgcaaagtagtccgcatcggcgaagaggtctataactatgactggcctccttacggggctggc
cgaccaggcacattcggagacattcaagctaggtcaaccaactatgtcaaacccaacgatctgtatggggacatcggaattgaagtac FIG. 17B (continued)

tgcagccgactaacgaccacgtacatgtggcttacacgtatacgacctctgggttactgcgttggctgcaggacgctccgaaaccactc
agtgtcacagcaccgcacggttgtaagatcagtgccaatccgctcctggccctcgattgtggggttggtgccgtccccatgtccatcaa
cattccggacgcgaagtttacccgcaaattaaaggatccgaaaccatcggccctgaaatgcgtggtggacagctgcgagtacggggt
ggactacgggggcgccgccacgatcacctacgagggccacgaggccgggaagtgcgggattcattccctgacaccaggagtccc
cctgagaacatcggtggttgaagtggttgctggcgccaataccgtcaaaacgaccttctcctcacccacgcccgaggttgcactcgag
gtagagatctgttcggcaatagtgaagtgcgctggtgagtgcactccaccgaaggaacatgtggtcgcaaccaggcctcgccatggc
agcgaccctggaggctacatctccgggcccgcaatgcgctgggccggagggattgtagggaccctagtggtcctgttccttatccttg
ccgtcatctactgcgtggtgaagaagtgccgctccaaaagaatccggatagtcaagagctaatctagaccaggccctggatccagatc
tgctgtgccttctagttgccagccatctgttgtttgcccctcccccgtgccttccttgaccctggaaggtgccactcccactgtcctttccta
ataaaatgaggaaattgcatcgcattgtctgagtaggtgtcattctattctggggggtggggtggggcaggacagcaagggggaggat
tgggaagacaatagcaggcatgctggggatgcggtgggctctatgggtacccaggtgctgaagaattgacccggttcctcctgggcc
agaaagaagcaggcacatccccttctctgtgacacaccctgtccacgcccctggttcttagttccagccccactcataggacactcata
gctcaggagggctccgccttcaatcccacccgctaaagtacttggagcggtctctccctccctcatcagcccaccaaaccaaacctag
cctccaagagtgggaagaaattaaagcaagataggctattaagtgcagagggagagaaaatgcctccaacatgtgaggaagtaatga
gagaaatcatagaattttaaggccatgatttaaggccatcatggccttaatcttccgcttcctcgctcactgactcgctgcgctcggtcgtt
cggctgcggcgagcggtatcagctcactcaaaggcggtaatacggttatccacagaatcaggggataacgcaggaaagaacatgtg
agcaaaaggccagcaaaaggccaggaaccgtaaaaaggccgcgttgctggcgtttttccataggctccgcccccctgacgagcatc
acaaaaatcgacgctcaagtcagaggtggcgaaacccgacaggactataaagataccaggcgtttccccctggaagctccctcgtgc
gctctcctgttccgaccctgccgcttaccggatacctgtccgcctttctcccttcgggaagcgtggcgctttctcatagctcacgctgtag
gtatctcagttcggtgtaggtcgttcgctccaagctgggctgtgtgcacgaaccccccgttcagcccgaccgctgcgccttatccggta
actatcgtcttgagtccaacccggtaagacacgacttatcgccactggcagcagccactggtaacaggattagcagagcgaggtatgt
aggcggtgctacagagttcttgaagtggtggcctaactacggctacactagaagaacagtatttggtatctgcgctctgctgaagccagt
taccttcggaaaaagagttggtagctcttgatccggcaaacaaaccaccgctggtagcggtggtttttttgtttgcaagcagcagattacg
cgcagaaaaaaaggatctcaagaagatcctttgatcttttctacggggtctgacgctcagtggaacgaaaactcacgttaagggattttg
gtcatgagattatcaaaaaggatcttcacctagatccttttaaattaaaaatgaagttttaaatcaatctaaagtatatatgagtaaacttggtc
tgacagttaccaatgcttaatcagtgaggcacctatctcagcgatctgtctatttcgttcatccatagttgcctgactcggggggggggg
cgctgaggtctgcctcgtgaagaaggtgttgctgactcataccaggcctgaatcgccccatcatccagccagaaagtgagggagcca FIG. 17B (continued)

cggttgatgagagctttgttgtaggtggaccagttggtgattttgaacttttgctttgccacggaacggtctgcgttgtcgggaagatgcgt
gatctgatccttcaactcagcaaaagttcgatttattcaacaaagccgccgtcccgtcaagtcagcgtaatgctctgccagtgttacaacc
aattaaccaattctgattagaaaaactcatcgagcatcaaatgaaactgcaatttattcatatcaggattatcaataccatatttttgaaaaag
ccgtttctgtaatgaaggagaaaactcaccgaggcagttccataggatggcaagatcctggtatcggtctgcgattccgactcgtccaa
catcaatacaacctattaatttcccctcgtcaaaaataaggttatcaagtgagaaatcaccatgagtgacgactgaatccggtgagaatg
gcaaaagcttatgcatttctttccagacttgttcaacaggccagccattacgctcgtcatcaaaatcactcgcatcaaccaaaccgttattc
attcgtgattgcgcctgagcgagacgaaatacgcgatcgctgttaaaaggacaattacaaacaggaatcgaatgcaaccggcgcagg
aacactgccagcgcatcaacaatattttcacctgaatcaggatattcttctaatacctggaatgctgttttcccggggatcgcagtggtga
gtaaccatgcatcatcaggagtacggataaaatgcttgatggtcggaagaggcataaattccgtcagccagtttagtctgaccatctcat
ctgtaacatcattggcaacgctacctttgccatgtttcagaaacaactctggcgcatcgggcttcccatacaatcgatagattgtcgcacc
tgattgcccgacattatcgcgagcccatttatacccatataaatcagcatccatgttggaatttaatcgcggcctcgagcaagacgtttcc
cgttgaatatggctcataacaccccttgtattactgtttatgtaagcagacagttttattgttcatgatgatatatttttatcttgtgcaatgtaac
atcagagattttgagacacaacgtggctttcccccccccccccattattgaagcatttatcagggttattgtctcatgagcggatacatatttg
aatgtatttagaaaaataaacaaataggggttccgcgcacatttccccgaaaagtgccacctgacgtctaagaaaccattattatcatgac
attaacctataaaaataggcgtatcacgaggccctttcgtc CMV/R Ross River virus VLP
8179 bp

- AvaI (7841)
- ClaI (7750)
- SmaI (7569)
- AvaI (7567)
- XmaI (7567)
- Kan.
- HindIII (7321)
- AvaI (6759)
- ApaLI (6183)
- BamHI (5155)
- ApaLI (4947)
- ApaLI (4882)
- SmaI (4500)
- AvaI (4498)
- XmaI (4498)
- HindIII (3930)
- PstI (3911)
- HindIII (3818)
- NcoI (3417)
- AvaI (2153)
- NcoI (1971)
- ApaLI (1906)
- NcoI (1438)
- PstI (1334)
- NcoI (1317)
- NcoI (697)
- ApaLI (178)
- CMV/R Backbone
- CMV IE Enhancer/Promoter
- HTLV-1 R Region/Splicing Donor
- CMV IE Splicing Acceptor
- structure
- Tbgh

FIG. 18B

SEQ ID NO: 14 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgcatgaattacataccaacccagacttttacggacgccgttggcggcctcgcccggcgttcc
gtccatggcaggtgccgatgcagccgacacctactatggttacacccatgctgcaagcaccggacctacaggctcaacagatgcaac
aactgatcagcgcagtctctgcactaaccaccaaacagaatgtaaaagcaccaaaagggcaacggaaacagaaacagcagaaacc
aaaggaaaagaaggaaaaacagaagaaaaagccgacgcnnaagaagaagcagcagcagaaaccaaaaccacaggctaagaag
aagaaaccagggagaagagaaagaatgtgcatgaagatcgagaatgactgcatattcgaggtcaaactggacggcaaggttaccgg
ctatgcgtgcctagtcggagataaggtcatgaagccggctcacgttaaaggcacaattgataacccagaccttgcgaagttgacttaca
agaaatccagtaagtatgacctcgaatgcgcccagatcccagtgcacatgaagtccgacgcctccaagtacacacatgaaaagcccg
aaggtcattacaattggcaccatggagcagtgcagtacagcgnnggaaggtttaccatccccacaggcgccggcaaaccaggagat
agcggtaggcctatttttgacaacaaagggcgagtngtggccatcgtgttaggcggggccaacgaaggtgcccgcactgcgctgtct
gtggtgacgtggacaaaagacatggtcactcgggtaacgccagaaggaaccgaagagtggtctgccgcgctgatgatgtgtatcctt
gccaacacctctttcccatgctcgtcacctccctgctacccctgctgctacgaaaaacagccagaacagacactgcggatgctggaag FIG. 18 B (continued)

acaacgtgaatagacctgggtactatgagttactggaagcgtccatgacatgcagaaacagatcacgccaccgccgcagtgtaatag
agcacttcaatgtgtataaggctactagaccgtacttagcnnactgcgctgactgcggggacgggtacttctgctatagcccggttgcta
tcgagaagatccgagatgaggcgtctgatggcatgctcaagatccaagtctccgcccaaataggtctggacaaggcaggtacccacg
cccacacgaagatgcgatatatggctggtcatgatgttcaggaatctaagagagattccttgagggtgtatacgtccgcagcgtgctcta
tacatgggacgatgggacacttcatcgtcgcacactgtccaccaggcgactacctcaaggnttcgttcgaggacgcaaattcacacgt
gaaggcatgtaaggtccaatacaagcacgacccattgccggtgggtagagagaagtttgtggttagaccacactttggcgtagagctg
ccatgcacctcataccagctgacaacggctcccaccgacgaggagattgacatgcatacaccgccagatataccggatcgcaccctg
ctatcacagacggcgggcaacgtcaaaataacagcaggcggcaggactatcaggtacaattgtacctgcggccgtgacaacgtagg
cactaccagtactgacaagaccatcaacacatgcaagatagaccaatgccatgctgccgttaccagccatgacaaatggnaatttacct
ctccatttgttcccagggctgatcagacagccaggaaaggcaaagtgcatgttccattccctttgactaacgtcacctgccgagtgccgt
tggcacgagcgccggatgtcacctatggtaagaaggaggtgaccctaagattacacccagatcatccgacgcncttctcctataggag
tttaggagccgtaccgcacccgtacgaggaatgggttgacaagttctctgagcgcatcatcccagtgacggaagaagggattgagtac
cagtggggtaacaacccgccggtccgcctgtgggcgcaactgacgactgagggtaaaccccatggctggccacatgaaatcattca
gtactattatggactataccccgccgccactattgccgcagtatccggggcgagtctgatggccctcctaactctagcggccacatgct
gcatgctggccaccgcgaggagaaagtgcctaacaccgtacgctttgacgccaggagcggtggtaccgttgacattggggctgcttn
nntgcgcaccgagggcgaacgcagcatcatttgctgagactatggcctatctgtgggacgagaacaaaaccctcttttggatggaatn
nnnnnnnnnnnnnnnngcgcttgctttgctggcatgctgtatcaaaagcctgatctgctgttgtaagccatttttcttttttagtgttactga
gcctgggagcctccgcaaaagcttatgagcacacagccacaattccgaacgtggtggggttcccgtataaggctcacattgaaagga
atnnnttctcgcccatgactctgcagcttgaagtggtgganncaagcttggaacccacacttaacctggagtacattacctgcgaatac
aagacggtggtcccttcgccatttatcaaatgttgcggaacatcagaatgctcatctaaagagcagccagactaccaatgcaaggtgta
cacgggtgtataccctttcatgtggggtggagcttactgtttctgcgactccgagaacacgcagcttagcgaggcctatgtcgacaggt
cagacgtttgcaaacatgatcatgcattggcctacaaggcacacacggcctctctaaaagcaacaatcaggatcagctacggcaccat
caaccagaccaccgaggccttcgtcaatggagaacacgcggtcaacgtgggcggaagcaagttcatctttggaccgatctcaacagc
ttggtcaccgttcgacaataaaattgtcgtgtataaagatgatgtctacaaccaggacttcccaccctacggatcaggccagccgggna
gattcggagacatccagagcaggacagtggagagcaaagacttgtatgctaatacggccctaaaactctcaagaccatcacccgggg
ttgtgcatgtgccatacacgcagacaccatccggatttaagtattggctgaaggagaaaggatcttcattgaatacaaaggcccctttg
gctgcaagataaagaccaatccagtcagagctatggattgtgcagttggcagtatacctgtgtcgatggacatacctgacagtgcattca FIG. 18B (continued)

cacgagtggtagatgccccggctgtaacagacctgagctgccaggtagctgtctgtacacactcctccgatttcggannngttgccac
attgtcttacaagacggacaaacccggcaagtgcgccgttcactcacattccaacgtcgcaacgttgcaagaggcgacggtggatgtc
aaggaggatggcaaggtcacagtgcacttttctnnnnngtccgcctccccggcattcaaagtgtccgtctgtgacgcaaaaacaacgt
gcacggcggcgtgcgagcctccgaaagaccacatcgtcccttatggggcgagccataacaaccaggtctttccggacatgtcagga
actgcgatgacgtgggtacagaggatggccagtgggttaggtgggctggccctcatcgcggtggttgtgctggtcttggtaacctgca
taacaatgcgtcggtaatctagaccaggccctggatccagatctgctgtgccttctagttgccagccatctgttgtttgcccctcccccgt
gccttccttgaccctggaaggtgccactcccactgtcctttcctaataaaatgaggaaattgcatcgcattgtctgagtaggtgtcattctat
tctggggggtggggtggggcaggacagcaagggggaggattgggaagacaatagcaggcatgctggggatgcggtgggctctat
gggtacccaggtgctgaagaattgacccggttcctcctgggccagaaagaagcaggcacatccccttctctgtgacacaccctgtcca
cgcccctggttcttagttccagccccactcataggacactcatagctcaggagggctccgccttcaatcccacccgctaaagtacttgg
agcggtctctccctccctcatcagcccaccaaaccaaacctagcctccaagagtgggaagaaattaaagcaagataggctattaagtg
cagagggagagaaaatgcctccaacatgtgaggaagtaatgagagaaatcatagaatttaaggccatgatttaaggccatcatggcc
ttaatcttccgcttcctcgctcactgactcgctgcgctcggtcgttcggctgcggcgagcggtatcagctcactcaaaggcggtaatacg
gttatccacagaatcaggggataacgcaggaaagaacatgtgagcaaaaggccagcaaaaggccaggaaccgtaaaaaggccgc
gttgctggcgtttttccataggctccgcccccctgacgagcatcacaaaaatcgacgctcaagtcagaggtggcgaaacccgacagg
actataaagataccaggcgtttccccctggaagctccctcgtgcgctctcctgttccgaccctgccgcttaccggatacctgtccgccttt
ctcccttcgggaagcgtggcgctttctcatagctcacgctgtaggtatctcagttcggtgtaggtcgttcgctccaagctgggctgtgtgc
acgaaccccccgttcagcccgaccgctgcgccttatccggtaactatcgtcttgagtccaacccggtaagacacgacttatcgccactg
gcagcagccactggtaacaggattagcagagcgaggtatgtaggcggtgctacagagttcttgaagtggtggcctaactacggctac
actagaagaacagtatttggtatctgcgctctgctgaagccagttaccttcggaaaaagagttggtagctcttgatccggcaaacaaacc
accgctggtagcggtggtttttttgtttgcaagcagcagattacgcgcagaaaaaaaggatctcaagaagatcctttgatcttttctacgg
ggtctgacgctcagtggaacgaaaactcacgttaagggattttggtcatgagattatcaaaaaggatcttcacctagatccttttaaattaa
aaatgaagttttaaatcaatctaaagtatatatgagtaaacttggtctgacagttaccaatgcttaatcagtgaggcacctatctcagcgatc
tgtctatttcgttcatccatagttgcctgactcgggggggggggcgctgaggtctgcctcgtgaagaaggtgttgctgactcataccag
gcctgaatcgccccatcatccagccagaaagtgagggagccacggttgatgagagctttgttgtaggtggaccagttggtgattttgaa
cttttgctttgccacggaacggtctgcgttgtcgggaagatgcgtgatctgatccttcaactcagcaaaagttcgatttattcaacaaagcc
gccgtcccgtcaagtcagcgtaatgctctgccagtgttacaaccaattaaccaattctgattagaaaaactcatcgagcatcaaatgaaa FIG. 18B (continued)

ctgcaatttattcatatcaggattatcaataccatatttttgaaaaagccgtttctgtaatgaaggagaaaactcaccgaggcagttccatag
gatggcaagatcctggtatcggtctgcgattccgactcgtccaacatcaatacaacctattaatttcccctcgtcaaaaataaggttatcaa
gtgagaaatcaccatgagtgacgactgaatccggtgagaatggcaaaagcttatgcatttctttccagacttgttcaacaggccagccat
tacgctcgtcatcaaaatcactcgcatcaaccaaaccgttattcattcgtgattgcgcctgagcgagacgaaatacgcgatcgctgttaa
aaggacaattacaaacaggaatcgaatgcaaccggcgcaggaacactgccagcgcatcaacaatattttcacctgaatcaggatattc
ttctaatacctggaatgctgttttcccggggatcgcagtggtgagtaaccatgcatcatcaggagtacggataaaatgcttgatggtcgg
aagaggcataaattccgtcagccagtttagtctgaccatctcatctgtaacatcattggcaacgctacctttgccatgtttcagaaacaact
ctggcgcatcgggcttcccatacaatcgatagattgtcgcacctgattgcccgacattatcgcgagcccatttatacccatataaatcagc
atccatgttggaatttaatcgcggcctcgagcaagacgtttcccgttgaatatggctcataacaccccttgtattactgtttatgtaagcaga
cagttttattgttcatgatgatatatttttatcttgtgcaatgtaacatcagagattttgagacacaacgtggctttcccccccccccccattattg
aagcatttatcagggttattgtctcatgagcggatacatatttgaatgtatttagaaaaataaacaaataggggttccgcgcacatttcccc
gaaaagtgccacctgacgtctaagaaaccattattatcatgacattaacctataaaaataggcgtatcacgaggccctttcgtc Plasmid map: CMV/R O'nyong-nyong virus 8145 bp Labels (clockwise):
- CMV/R Backbone
- ApaLI (178)
- CMV IE Enhancer/Promoter
- NcoI (697)
- HTLV-1 R Region/Splicing Donor
- CMV IE Splicing Acceptor
- NcoI (1317)
- PstI (1334)
- NcoI (1352)
- PstI (1467)
- ApaLI (1855)
- ApaLI (2595)
- PstI (3124)
- NcoI (3221)
- BamHI (3230) structure
- CMV/R O'nyong-nyong virus VLP 8145 bp
- ApaLI (4765)
- EcoRI (4867)
- BamHI (5121)
- Tbgh
- ApaLI (6149)
- AvaI (6725)
- HindIII (7287)
- Kan.
- XmaI (7533)
- AvaI (7533)
- SmaI (7535)
- ClaI (7716)
- AvaI (7807)

FIG. 19B

SEQ ID NO: 15 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
accaccatggagttcataccagcacaaacttactacaatagaagataccagcctagaccctggactcaacgccctactatccaggtgat
caggccaaaaccacgccgaagaaggcctgcaggacaactcgcacaactgatatccgcagtcagcagactagcactgcgtacagttc
cccagaaaccacgccggacccgaaaaattaagaagcaaaagcaagtaaagcaagaacaacagagtactacgaaccagaagaaaa
aggcgccgaaacaaaagcagacccaaaagaaaaagagaccaggacgaagggaaaggatgtgcatgaagattgaaaatgactgca
tcttcgaagtcagacatgaaggaaaagtaacggggtatgcatgcctagtaggtgataaggtaatgaaaccagcacacgtgaaaggaa
ctattgacaacgcagacctagcgaagttggcgttcaaaagatcatccaaatatgatctagagtgcgcacagataccagtgcacatgaaa
tcggacgcctcaaagttcacccatgaaaaaccagaaggctattacaactggcatcacggagcagtacagtattctggagggaggttca
cgatccctacaggcgcaggaaagcctggggacagcggaagaccaatctttgacaacaaggggcgtgtcgtggctattgttctaggcg
gagcaaacgaaggaaccaggacagcactatctgtagtgacttggaataaagacatagtcacaaaaatcacaccagaggggtcagttg
aatggagccttgccctccctgtcatgtgcctgttggcaaatacaaccttcccatgttcccaaccgccttgcgcgccgtgctgctacgaaa
agaaaccggaagaaaccttgagaatgctggaggacaacgtcatgcaaccaggatattaccagttactcgattcagcattggcctgctc FIG. 19B (continued)

acaacgtcgtcaaaaacgtaatgcaagagaaaacttcaatgtctacaaagtcactaggccgtacttagcccactgtcctgactgcgggg
agggacactcatgccacagcccaatagcattagaacggatcagaagtgaggcaacagatggtaccttgaaaatccaggtatctctgca
aatcggaataaagacagacgacagccacgattggacgaagctacggtatatggatagccatacacctgtggatgcagaccgatccg
ggttgtttgtcagaacgtcagcaccgtgcaccatcacgggaacgatgggacatttcatactagcacgctgtccgaaaggagagacgct
gacggtaggatttgtagacagtagaaggatcagtcacacgtgcatgcacccgttccgccacgagccaccgctgatagggagagaga
agtttcactcccgcccgcagcatggcaaagaactaccttgcagtacatacgtccataccacagcggcaactgctgaggaaatagaagt
gcatatgccgccagataccccctgactacacgctgatgacacagcaagcgggaaacgttaagatcacagttgacggccagacggtac
gatacaagtgcaaatgtgacggctccaatgaaggattaataaccgctgacaaagtcataaataactgcaaagtagaccaatgccacac
agcggttacaaaccacaagaaatggcaatacaattcaccgctgaccccgcggaactccgaacaaggagatagaaaaggtaagatcc
atatcccatttccactggtgaacacaacctgcagggtaccaaaagcaagaaatccgactgtcacatacggtaaaaacagagtcactctg
ctgttacatccagaccacccaacactcctttcgtaccgcgccatgggaaggatcccggattaccatgaagagtggataacaaacaaga
aggaaataagtatcacagtaccagcagaaggcttagaggttacgtggggtaataatgacccatacaaatattggccccaactgtctaca
aatggtactgcgcacgggcacccacatgaaataatcctctattactatgagctgtacccaactaccacaattgctgtactagctgctgctt
ctatcgtaataacatctttggtaggtctatcattaggcatgtgcatatgcgcgagacgcaggtgcatcacgccatatgagctgactccag
gagctaccatcccattcctcctaggtgtactatgctgtgccaggactgcaaaagcagcatcgtactacgaagctgcaacatacctctgg
aatgagcaacaaccattattttggttacagcttctaatccctctgtcagctgcaattgttgtgtgtaattgcctaaaacttttaccatgctgctg
caaaacattgactttttagccgtcatgagcatcggtgcccgcactgtgaccgcgtacgagcacgcaacagtgatcccgaacacggtg
ggagtaccgtgtaagactcttgttagcagaccagggtacagccctatggtcttagaaatggagctacagtcggtcactctggaaccagc
attatccttggattacattacgtgtgagtataaaacaatcacaccgtccccgtacgtaaaatgctgtggtacagctgaatgtaaggccaag
aacctgccagattataactgcaaagtattcacaggcgtctacccatttatgtggggaggagcatactgcttctgtgacgcagagaacac
acagctcagcgaggcacacgttgagaaatcagaatcatgcaaaactgagtttgcatcagcctacagagcccacacagcttcagtatca
gctaaactacgtgtcttttaccaagggaataatatcaccgtgtctgcatacgccaatggtgatcatgcagttacggtggaagacgcgaag
tttgtcatcggtccactatcgtccgcctggtcaccatttgataataagatcgtggtgtacaaaggcgaagtctacaatatggactatccacc
tttcggcgcagggaggccaggacagttcggtgacatccagagccgcacgccagacagcaaggacgtctatgcgaatacgcagttaa
tactgcaaagaccagcggcaggagcaatacacgtgccttactcccaggcaccttcgggctttaagtactggctcaaggaaaaagggg
catcattgcagcatactgcaccatttggctgtcagatagcaacaaacccggtaagagcagtgaactgtgcagtgggcaacataccagt
ctccattgacatcccagatgcagctttcaccagggtcactgacgctccttccatcacagacatgtcctgcgaagtagcttcgtgtaccat FIG. 19B (continued)

tcatctgattttggaggtgccgcagtcataaagtacacagctagtaaaaaggaaaatgcgccgtgcactctgtaacaaatgcggtcac
tatccgcgaacctaacgtagatgtcaagggaacagcacaattgcaaattgccttctcgaccgcactagctagtgcggaattcaaggtgc
agatctgctccacactggtacactgctcagcgacgtgccatcctcctaaagaccatatagtcaattacccgtcacctcacaccacactag
gagtgcaggacatttcaacgacagctatgtcttgggtccagaagattacaggaggagtgggactcgtggttgctatagctgctttgatct
taattatagttctctgcgtatcatttagcagacactaagcggccgctctagaccaggccctggatccagatctgctgtgccttctagttgcc
agccatctgttgtttgcccctcccccgtgccttccttgaccctggaaggtgccactcccactgtcctttcctaataaaatgaggaaattgca
tcgcattgtctgagtaggtgtcattctattctggggggtggggtggggcaggacagcaagggggaggattgggaagacaatagcagg
catgctggggatgcggtgggctctatgggtacccaggtgctgaagaattgacccggttcctcctgggccagaaagaagcaggcacat
ccccttctctgtgacacaccctgtccacgcccctggttcttagttccagccccactcataggacactcatagctcaggagggctccgcct
tcaatcccacccgctaaagtacttggagcggtctctccctccctcatcagcccaccaaaccaaacctagcctccaagagtgggaagaa
attaaagcaagataggctattaagtgcagagggagagaaaatgcctccaacatgtgaggaagtaatgagagaaatcatagaatttaa
ggccatgatttaaggccatcatggccttaatcttccgcttcctcgctcactgactcgctgcgctcggtcgttcggctgcggcgagcggta
tcagctcactcaaaggcggtaatacggttatccacagaatcaggggataacgcaggaaagaacatgtgagcaaaaggccagcaaaa
ggccaggaaccgtaaaaaggccgcgttgctggcgtttttccataggctccgcccccctgacgagcatcacaaaaatcgacgctcaag
tcagaggtggcgaaacccgacaggactataaagataccaggcgtttccccctggaagctccctcgtgcgctctcctgttccgaccctg
ccgcttaccggatacctgtccgcctttctcccttcgggaagcgtggcgctttctcatagctcacgctgtaggtatctcagttcggtgtaggt
cgttcgctccaagctgggctgtgtgcacgaaccccccgttcagcccgaccgctgcgccttatccggtaactatcgtcttgagtccaacc
cggtaagacacgacttatcgccactggcagcagccactggtaacaggattagcagagcgaggtatgtaggcggtgctacagagttctt
gaagtggtggcctaactacggctacactagaagaacagtatttggtatctgcgctctgctgaagccagttaccttcggaaaaagagttg
gtagctcttgatccggcaaacaaaccaccgctggtagcggtggtttttttgtttgcaagcagcagattacgcgcagaaaaaaaggatctc
aagaagatcctttgatcttttctacggggtctgacgctcagtggaacgaaaactcacgttaagggattttggtcatgagattatcaaaaag
gatcttcacctagatccttttaaattaaaaatgaagttttaaatcaatctaaagtatatatgagtaaacttggtctgacagttaccaatgcttaa
tcagtgaggcacctatctcagcgatctgtctatttcgttcatccatagttgcctgactcgggggggggggggcgctgaggtctgcctcgtg
aagaaggtgttgctgactcataccaggcctgaatcgccccatcatccagccagaaagtgagggagccacggttgatgagagctttgtt
gtaggtggaccagttggtgattttgaactttttgctttgccacggaacggtctgcgttgtcgggaagatgcgtgatctgatccttcaactcag FIG. 19B (continued)

caaaagttcgatttattcaacaaagccgccgtcccgtcaagtcagcgtaatgctctgccagtgttacaaccaattaaccaattctgattag
aaaaactcatcgagcatcaaatgaaactgcaatttattcatatcaggattatcaataccatatttttgaaaaagccgtttctgtaatgaagga
gaaaactcaccgaggcagttccataggatggcaagatcctggtatcggtctgcgattccgactcgtccaacatcaatacaacctattaat
ttcccctcgtcaaaaataaggttatcaagtgagaaatcaccatgagtgacgactgaatccggtgagaatggcaaaagcttatgcatttctt
tccagacttgttcaacaggccagccattacgctcgtcatcaaaatcactcgcatcaaccaaaccgttattcattcgtgattgcgcctgagc
gagacgaaatacgcgatcgctgttaaaaggacaattacaaacaggaatcgaatgcaaccggcgcaggaacactgccagcgcatcaa
caatattttcacctgaatcaggatattcttctaatacctggaatgctgttttcccggggatcgcagtggtgagtaaccatgcatcatcagga
gtacggataaaatgcttgatggtcggaagaggcataaattccgtcagccagtttagtctgaccatctcatctgtaacatcattggcaacgc
tacctttgccatgtttcagaaacaactctggcgcatcgggcttcccatacaatcgatagattgtcgcacctgattgcccgacattatcgcg
agcccatttatacccatataaatcagcatccatgttggaatttaatcgcggcctcgagcaagacgtttcccgttgaatatggctcataacac
cccttgtattactgtttatgtaagcagacagttttattgttcatgatgatatatttttatcttgtgcaatgtaacatcagagattttgagacacaac
gtggctttccccccccccccattattgaagcatttatcagggttattgtctcatgagcggatacatatttgaatgtatttagaaaaataaaca
aataggggttccgcgcacatttccccgaaaagtgccacctgacgtctaagaaaccattattatcatgacattaacctataaaaataggcg
tatcacgaggccctttcgtc CMV/R Mayaro virus VLP 8132 bp

- ApaLI (178) — CMV/R Backbone
- CMV IE Enhancer/Promoter
- NcoI (697)
- HTLV-1 R Region/Splicing Donor
- CMV IE Splicing Acceptor
- NcoI (1317)
- PstI (1334)
- NcoI (1377)
- AvaI (1604)
- XmaI (1790)
- AvaI (1790)
- SmaI (1792)
- ApaLI (1860)
- AvaI (1916)
- ApaLI (2220)
- ApaLI (2620)
- AvaI (3161)
- structure
- PstI (3885)
- ApaLI (4696)
- ApaLI (4915)
- BamHI (5108)
- Tbgh
- ApaLI (6136)
- AvaI (6712)
- HindIII (7274)
- Kan.
- XmaI (7520)
- AvaI (7520)
- SmaI (7522)
- ClaI (7703)
- AvaI (7794)

FIG. 20B

SEQ ID NO: 16 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgccaccatggacttcctaccaactcaagtgttctatggcagacgctggagaccacgaatgccg
ccacgcccttggagaccacgcatgcctacaatgcagagaccagaccaacaggcccgacaaatgcagcaattgattgcagcggttag
cacgcttgccctgaggcagaatgcagccgcccctcagcgtggaaagaagaagcagccacgcagaaagaaaccaaaaccgcagcc
cgagaaaccaaagaagcaagaacagaagccgaagcaaaagaaggcccctaaacgaaagccagggagaagagaacgcatgtgc
atgaagattgagcatgattgcatcttcgaggttaagcacgaaggtaaagtcacgggttacgcctgccttgtcggtgacaaggtaatgaa
gccagcacacgttcccggggtgatagacaatgcagatcttgcacgcctgtcgtacaagaaatccagtaagtacgatctggaatgtgca
caaatacccgtggctatgaagtcagatgcttcgaagtacacccatgagaaacccgagggtcattacaactggcactacggcgccgtcc
agtacacgggaggaagattcacggtgcccacaggagtgggtaagcctggcgacagcggtcggcccatctttgacaacaaagggcc
ggttgtcgcaatagtgctgggaggagccaacgaaggtaccagaaccgccctttccgttgtgacatggaataaagacatggtcacgaa
gattacacctgaaggcactgtggagtgggcagcctcgacagtgacagccatgtgtcttttgacaaatatatccttcccatgtttccaaccg
agctgtgcaccgtgctgctatgaaaaggggcctgagccgacgctgaggatgctggaggagaacgtaaattcagaaggatattacgac FIG. 20 B (continued)

ctgctgcacgctgccgtgtactgtagaaacagttcaaggtcgaagagaagcactgcaaatcattttaatgcgtataagttgacccgtcca
tatgtggcttactgcgcagactgcggtatgggtcattcttgccacagcccagccatgatcgaaaatattcaggcggatgcaacagatgg
cacgctaaaaattcagtttgcttcccaaattggcctgaccaaaacggacacgcacgatcacacaaagattagatatgctgaaggacac
gacattgcagaggctgccagatcaacccttaaggtacacagtagcagtgagtgcacggtaaccggcacaatgggacactttatcctgg
ccaaatgtccacctggcgaacgaatcagtgtctcatttgttgattcgaaaaacgaacaccggacctgccggatagcctaccaccatgaa
cagaggttaatagggcgagaaagattcacggtgcgaccgcatcatggaattgagctaccttgcaccacttatcaattgactaccgccga
aacctctgaagaaattgatatgcacatgccgccggacattccggatagaactatcctttcccaacaatcaggaaatgttaagataacggt
gaatggacgaaccgtcaggtacagctcttcttgcggttcccaagccgtcgggacaacaaccacagacaagaccattaatagctgtacc
gttgacaaatgtcaggcttacgtcacgagccacacaaaatggcaattcaattcaccttttgtcccacgtcggatgcaagcagagcgcaa
gggcaaagtgcatatccccttttcccttattaacaccacctgccgtgtaccgctggctcccgaggccccttgttaggagcggtaaacgcg
aagctacactttcattgcaccctatccaccccacattgctaagttacagaacatttggagcggagcgggtctttgacgagcagtggatca
ccgcccagacggaggtaacgatcccggtacctgtggagggagtggagtaccagtggggcaaccataaacctcaacgttttgtggtcg
cactgacgactgaaggcaaagcacatggatggcctcatgaaattattgaatactactacggactgcatcctacgacaaccattgtcgtg
gtgattcgtgtctcagtggtggtgcttctgtcattcgccgcctcggtctacatgtgcgtggtagcacgaaccaaatgtctgacaccatatg
cactcacgccgggagctgttgttcctgttaccattggggtgctgtgttgcgcaccgaaagcacatgcagccagtttcgcagaaggtatg
gcctatctgtgggataacaatcagtcgatgttctggatggagctgaccggaccattggccctccttattctggctacatgctgcgcccgat
cactgctttcctgctgcaaggggtctttttagtcgcaatgagcatcgggagtgccgttgccagtgcttacgagcacacggcaattattcc
gaaccaagtgggattcccgtataaggctcatgttgcgcgtgaaggttacagtcctttgaccctgcagatgcaggtgatagagaccagc
cttgagccaacactcaacctggagtatatcacttgcgattacaaaacaaaagttccatcaccatacgtaaagtgctgcggcacggcaga
atgccgcacacaggacaagcctgagtacaaatgtgcagtgttcacaggtgtgtatcctttatgtggggaggtgcatactgtttttgtgatt
cggagaacacacagatgagcgaagcctacgtggagcgcgctgacgtgtgtaaacacgaccacgcagctgcctaccgtgcccacac
cgcatcccttagagcaaaaattaaggtgacatacggtactgtgaaccagacagttgaggcgtatgtgaacggtgaccatgccgtaacg
attgccggaacaaaatttattttgggccagtgtcaacgccttggacaccgttcgatacaaaaattctggtttacaaaggggagttataca
atcaggacttcccacggtatggtgccgggcagcctggaagatttggggacattcagagccggacgctggatagtcgagacctatatg
ccaacacgggcctcaagctggcacgaccggcagccggcaacattcacgtcccctatacccagactccatctggctttaaaacatggc
aaaaagacagggactcaccgcttaacgccaaggcgccttttggatgcataatccagacaaatccggtccgagccatgaactgcgccg
tcggcaacatacccgtttcgatggatatcgccgacagcgccttcacaagattgaccgacgcgcctgtaatctctgagttgacgtgcact FIG. 20 B (continued)

gtgtctacatgcacgcactcatcggattttggcgggatcgctgtactttcctacaaggtggaaaaatcaggcaggtgcgacatccattca
cattcaaacgtcgcggtactccaggaagtttccatcgagacagaaggtcgatcagtgatccacttctcaaccgcatcagcctccccttcc
ttcgtagtttctgtttgtagttcgcgtgctacgtgcacagcgaaatgtgaaccaccgaaagaccacgttgttacatatccagcaaatcataa
cggggtaactttgccagacttatctagcactgccatgacgtgggcacaacatcttgccggcggagttgggttgctgatagctctggccg
tgctaattctggtaatagttacttgtgtgactttgagaaggtaaggatccagatctgctgtgccttctagttgccagccatctgttgtttgccc
ctcccccgtgccttccttgaccctggaaggtgccactcccactgtcctttcctaataaaatgaggaaattgcatcgcattgtctgagtaggt
gtcattctattctggggggtggggtggggcaggacagcaagggggaggattgggaagacaatagcaggcatgctggggatgcggt
gggctctatgggtacccaggtgctgaagaattgacccggttcctcctgggccagaaagaagcaggcacatccccttctctgtgacaca
ccctgtccacgcccctggttcttagttccagccccactcataggacactcatagctcaggagggctccgccttcaatcccacccgctaa
agtacttggagcggtctctccctccctcatcagcccaccaaaccaaacctagcctccaagagtgggaagaaattaaagcaagataggc
tattaagtgcagagggagagaaaatgcctccaacatgtgaggaagtaatgagagaaatcatagaattttaaggccatgatttaaggcca
tcatggccttaatcttccgcttcctcgctcactgactcgctgcgctcggtcgttcggctgcggcgagcggtatcagctcactcaaaggcg
gtaatacggttatccacagaatcaggggataacgcaggaaagaacatgtgagcaaaaggccagcaaaaggccaggaaccgtaaaa
aggccgcgttgctggcgtttttccataggctccgcccccctgacgagcatcacaaaaatcgacgctcaagtcagaggtggcgaaacc
cgacaggactataaagataccaggcgtttccccctggaagctccctcgtgcgctctcctgttccgaccctgccgcttaccggatacctgt
ccgcctttctcccttcgggaagcgtggcgctttctcatagctcacgctgtaggtatctcagttcggtgtaggtcgttcgctccaagctggg
ctgtgtgcacgaaccccccgttcagcccgaccgctgcgccttatccggtaactatcgtcttgagtccaacccggtaagacacgacttat
cgccactggcagcagccactggtaacaggattagcagagcgaggtatgtaggcggtgctacagagttcttgaagtggtggcctaact
acggctacactagaagaacagtatttggtatctgcgctctgctgaagccagttaccttcggaaaaagagttggtagctcttgatccggca
aacaaaccaccgctggtagcggtggtttttttgtttgcaagcagcagattacgcgcagaaaaaaaggatctcaagaagatcctttgatctt
ttctacggggtctgacgctcagtggaacgaaaactcacgttaagggattttggtcatgagattatcaaaaaggatcttcacctagatccttt
taaattaaaaatgaagttttaaatcaatctaaagtatatatgagtaaacttggtctgacagttaccaatgcttaatcagtgaggcacctatctc
agcgatctgtctatttcgttcatccatagttgcctgactcggggggggggggcgctgaggtctgcctcgtgaagaaggtgttgctgactc
ataccaggcctgaatcgccccatcatccagccagaaagtgagggagccacggttgatgagagctttgttgtaggtggaccagttggtg
attttgaacttttgctttgccacggaacggtctgcgttgtcgggaagatgcgtgatctgatccttcaactcagcaaaagttcgatttattcaa
caaagccgccgtcccgtcaagtcagcgtaatgctctgccagtgttacaaccaattaaccaattctgattagaaaaactcatcgagcatca
aatgaaactgcaatttattcatatcaggattatcaataccatatttttgaaaaagccgtttctgtaatgaaggagaaaactcaccgaggcag FIG. 20 B (continued)

ttccataggatggcaagatcctggtatcggtctgcgattccgactcgtccaacatcaatacaacctattaatttcccctcgtcaaaaataag
gttatcaagtgagaaatcaccatgagtgacgactgaatccggtgagaatggcaaaagcttatgcatttctttccagacttgttcaacaggc
cagccattacgctcgtcatcaaaatcactcgcatcaaccaaaccgttattcattcgtgattgcgcctgagcgagacgaaatacgcgatcg
ctgttaaaaggacaattacaaacaggaatcgaatgcaaccggcgcaggaacactgccagcgcatcaacaatattttcacctgaatcag
gatattcttctaatacctggaatgctgttttcccggggatcgcagtggtgagtaaccatgcatcatcaggagtacggataaaatgcttgat
ggtcggaagaggcataaattccgtcagccagtttagtctgaccatctcatctgtaacatcattggcaacgctacctttgccatgtttcagaa
acaactctggcgcatcgggcttcccatacaatcgatagattgtcgcacctgattgcccgacattatcgcgagcccatttatacccatataa
atcagcatccatgttggaatttaatcgcggcctcgagcaagacgtttcccgttgaatatggctcataacaccccttgtattactgtttatgta
agcagacagttttattgttcatgatgatatatttttatcttgtgcaatgtaacatcagagattttgagacacaacgtggctttcccccccccc
cattattgaagcatttatcagggttattgtctcatgagcggatacatatttgaatgtatttagaaaaataaacaaataggggttccgcgcaca
tttccccgaaaagtgccacctgacgtctaagaaaccattattatcatgacattaacctataaaaataggcgtatcacgaggccctttcgtc

FIG. 21 B

SEQ ID NO: 17 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgctctagaccaggccctggatccatggatttcatccccacccaaaccttctatggtagacgatg
gagaccagcaccagtccagagatacataccccaaccccaaccaccagcgcctccacgccgtaggagaggaccatctcaactccaa
cagcttgtggctgcattgggcgcactagctctacaacccaagcagaaacaaaaaagagcacagaagaagcccaagaagacaccac
caccaaaaccaaaaaagacccagaagcctaagaaaccaacccaaaagaagaagtccaaacccggcaaacgtatgcgtaactgcat
gaagatcgagaatgactgcatctttccggtgatgctcgatggaaaggttaacggctacgcttgcttagtgggggataaagtcatgaaac
cagctcatgtgaagggcacgatcgacaatccagaactagccaaattgacattcaagaaatctagcaagtatgatctagaatgtgctcaa
gtgccggtatgcatgaaatcagacgcatccaagttcacccatgagaaaccagaaggacattacaactggcaccatggggcagtgcaa
tttagcaatggtaggtttaccattccgacgggctctggcaaacctggagacagtggtaggcctatttttgacaataccggcaaggtagta
gccatagtgctgggaggtgcaaatgaaggggcccggacagccctatccgtggtcacctggaataaggatatggtgacccgcataac
acctgaagaatcagtggagtggtcggcggccgcactgnatataacagcactatgtgtcctccagaacttatcgttcccgtgtgatgcac
caccatgtgcaccatgctgttacgaaaaagaccctgcagggaccctaagattgctgtctgaccactactaccaccccaagtattatgaat FIG. 21 B (continued)

tacttgactcgacgatgcactgcccacaaggaaggagacctaagaggtctgttgcgcatttcgaagcctacaaggctacgagaccgta
tatagggtggtgcgcagattgtggactggcaggatcatgcccatcccctgtgagcatcgagcacgtctggagtgatgccgacgacgg
cgtactgaagatccaagtgtccatgcagatcggtatagctaaaagcaatactattaaccacgctaagatacgttacatgggtgccaatgg
agtacaggaggctgaacgctctaccctaagtgtatccacaacagcaccatgtgacatcttggcgaccatgggccatttcatcttggccc
gctgccgacccggcagtcaagttgaagtatcactaagcaccgatccaaagctgctatgccgtacaccattctcccacaagcccaggttt
attggcaatgaaaagtccccagcacccaccgggcacaagacccgaattccctgcaaaacttactcccatcagacagacttaacgaga
gaagagattacaatgcatgtaccgccggatgtccccatccaagggctagtgtccaatacaggtaagtcgtactcattagacccaaaga
cgaagaccatcaagtacaaatgcacttgcggcgagactgtaaaagaaggtactgctacgaacaaaatcacactgttcaattgtgacac
cgccccaaagtgtattacatatgcagtggataacacagtgtggcagtacaactcccaatacgtgcccaggtccgaagttacggaggtg
aaaggaaagatccatgtgcctttccctctgaccgacagcacgtgtgcagtcagcgtagcacctgaaccgcaagtgacatacagactg
gggaagtggagttccacttccaccctatgtaccccaccctcttctccattaggagcctcggaaaggatccgagccacagtcaagaat
ggatagatacacccatgagcaagacaatccaagttggggcagaaggcgtggagtatgtctggggaaacaacaacccggtacgacta
tgggcacagaagagctcatcgagcagcgcgcatggtaaccctattagcatagtctcacattactatgacctgtacccttactggaccatc
acagtactagcgagtctaggcttgctaatagtgattagttccggtttttcatgctttttgtgttcagtcgctcgaaccaaatgccttacaccct
atcaattagcaccaggcgcccaattacccacatttatagcactcctttgctgcgctaagtctgcacgcgcagacactttagatgatttttcc
tacctgtggaccaacaaccaagccatgttttggctccaactggcatctccggttgcagcgttcttgtgcttatcctattgctgtagaaatcta
gcatgctgtatgaagattttttagggataagcggcctgtgtgtaattgccacgcaggcctacgagcactcaaccacgatgccgaatca
ggtgggaataccgtttaaagccttgatagagcgaccaggttacgcaggcctcccgctatctttagtagtgattaagtcagaattagtccc
ctcattagttcaggattatattacctgcaactacaagactgtggtcccgtctccgtacattaaatgttgcggaggcgctgagtgttcacaca
aaaatgaagcggactataagtgctcggtgttcacaggcgtgtacccgtttatgtggggaggcgcctactgcttctgtgacaccgaaaac
agtcagatgagtgaagtatacgtaaccagaggagaatcatgcgaggctgaccatgccatcgcttatcaggtacacacagcatcgctta
aggcacaagtaatgatatcgattggagaactgaaccaaaccgtcgacgtgtttgtcaacggagacagtccagccagaatccaacaatc
aaagttcatacttgggccgatatccagtgcctggtctcctttgatcacaaggtgatcgtatacagggatgaggtgtacaatgaagactac
gcaccgtacggatccggccaagcaggcaggttcggagacatccaaagtagaactgttaacagcactgatgtctatgccaacaccaatt
tgaagcttaaaagaccggcttcaggcaatgttcatgtaccatacacgcaaacccccttcgggtttctcgtactggaaaaaagagaaggga
gtaccattgaatcgaaacgccccttttggctgtatcatcaaagtcaatccagtacgtgctgaaaactgcgtatatggcaacataccgatca
gtatggatattgcggacgcgcacttcacaaggatcgatgaatccccgtctgtgtccttgaaggcgtgtgaagtgcagtcctgcacttatt FIG. 21B (continued)

catcggattttggcggagtagcgagcatttcctacacatctaataaggtaggtaagtgtgccatccacagccactcgaactccgcaacg
atgaaggattctgtgcaggatgtccaggaaagcggcgccttgtcgctttttctttgcgacttcctctgtcgagccgaacttcgtggtccaag
tgtgtaacgcgcggatcacttgccatggtaagtgtgaaccaccgaaagaccacatcgtaccatacgcagccaaacacaacgacgccg
agtttccatccatctctactacagcttggcaatggttggcacacaccacctcagggccactcaccatacttgtggtagctattatagtcgtt
gttgtagtatccattgtagtatgtgcaagacactagagatctgctgtgccttctagttgccagccatctgttgtttgcccctcccccgtgcctt
ccttgaccctggaaggtgccactcccactgtcctttcctaataaaatgaggaaattgcatcgcattgtctgagtaggtgtcattctattctgg
ggggtggggtggggcaggacagcaagggggaggattgggaagacaatagcaggcatgctggggatgcggtgggctctatgggta
cccaggtgctgaagaattgacccggttcctcctgggccagaaagaagcaggcacatccccttctctgtgacacaccctgtccacgccc
ctggttcttagttccagccccactcataggacactcatagctcaggagggctccgccttcaatcccacccgctaaagtacttggagcggt
ctctccctccctcatcagcccaccaaaccaaacctagcctccaagagtgggaagaaattaaagcaagataggctattaagtgcagagg
gagagaaaatgcctccaacatgtgaggaagtaatgagagaaatcatagaatttaaggccatgatttaaggccatcatggccttaatctt
ccgcttcctcgctcactgactcgctgcgctcggtcgttcggctgcggcgagcggtatcagctcactcaaaggcggtaatacggttatcc
acagaatcaggggataacgcaggaaagaacatgtgagcaaaaggccagcaaaaggccaggaaccgtaaaaaggccgcgttgctg
gcgtttttccataggctccgcccccctgacgagcatcacaaaaatcgacgctcaagtcagaggtggcgaaacccgacaggactataa
agataccaggcgtttccccctggaagctccctcgtgcgctctcctgttccgaccctgccgcttaccggatacctgtccgcctttctccctt
cgggaagcgtggcgctttctcatagctcacgctgtaggtatctcagttcggtgtaggtcgttcgctccaagctgggctgtgtgcacgaac
cccccgttcagcccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtggcctaactacggctacactagaa
gaacagtatttggtatctgcgctctgctgaagccagttaccttcggaaaaagagttggtagctcttgatccggcaaacaaaccaccgctg
gtagcggtggtttttttgtttgcaagcagcagattacgcgcagaaaaaaaggatctcaagaagatcctttgatcttttctacggggtctgac
gctcagtggaacgaaaactcacgttaagggattttggtcatgagattatcaaaaaggatcttcacctagatccttttaaattaaaaatgaag
ttttaaatcaatctaaagtatatatgagtaaacttggtctgacagttaccaatgcttaatcagtgaggcacctatctcagcgatctgtctatttc
gttcatccatagttgcctgactcggggggggggggcgctgaggtctgcctcgtgaagaaggtgttgctgactcataccaggcctgaat
cgccccatcatccagccagaaagtgagggagccacggttgatgagagctttgttgtaggtggaccagttggtgattttgaacttttgcttt
gccacggaacggtctgcgttgtcgggaagatgcgtgatctgatccttcaactcagcaaaagttcgatttattcaacaaagccgccgtcc
cgtcaagtcagcgtaatgctctgccagtgttacaaccaattaaccaattctgattagaaaaactcatcgagcatcaaatgaaactgcaatt
tattcatatcaggattatcaataccatatttttgaaaaagccgtttctgtaatgaaggagaaaactcaccgaggcagttccataggatggca FIG. 21 B (continued)

agatcctggtatcggtctgcgattccgactcgtccaacatcaatacaacctattaatttcccctcgtcaaaaataaggttatcaagtgagaa
atcaccatgagtgacgactgaatccggtgagaatggcaaaagcttatgcatttctttccagacttgttcaacaggccagccattacgctc
gtcatcaaaatcactcgcatcaaccaaaccgttattcattcgtgattgcgcctgagcgagacgaaatacgcgatcgctgttaaaaggac
aattacaaacaggaatcgaatgcaaccggcgcaggaacactgccagcgcatcaacaatattttcacctgaatcaggatattcttctaata
cctggaatgctgttttcccggggatcgcagtggtgagtaaccatgcatcatcaggagtacggataaaatgcttgatggtcggaagagg
cataaattccgtcagccagtttagtctgaccatctcatctgtaacatcattggcaacgctacctttgccatgtttcagaaacaactctggcg
catcgggcttcccatacaatcgatagattgtcgcacctgattgcccgacattatcgcgagcccatttatacccatataaatcagcatccat
gttggaatttaatcgcggcctcgagcaagacgtttcccgttgaatatggctcataacaccccttgtattactgtttatgtaagcagacagttt
tattgttcatgatgatatatttttatcttgtgcaatgtaacatcagagattttgagacacaacgtggctttcccccccccccattattgaagca
tttatcagggttattgtctcatgagcggatacatatttgaatgtatttagaaaaataaacaaataggggttccgcgcacatttccccgaaaa
gtgccacctgacgtctaagaaaccattattatcatgacattaacctataaaaataggcgtatcacgaggccctttcgtc

FIG. 22 B

SEQ ID NO: 18 tcgcgcgtttcggtgatgacggtgaaaacctctgacacatgcagctcccggagacggtcacagcttgtctgtaagcggatgccggga
gcagacaagcccgtcagggcgcgtcagcgggtgttggcgggtgtcggggctggcttaactatgcggcatcagagcagattgtactg
agagtgcaccatatgcggtgtgaaataccgcacagatgcgtaaggagaaaataccgcatcagattggctattggccattgcatacgttg
tatccatatcataatatgtacatttatattggctcatgtccaacattaccgccatgttgacattgattattgactagttattaatagtaatcaatta
cggggtcattagttcatagcccatatatggagttccgcgttacataacttacggtaaatggcccgcctggctgaccgcccaacgacccc
cgcccattgacgtcaataatgacgtatgttcccatagtaacgccaatagggactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctcc
atcggctcgcatctctccttcacgcgcccgccgccctacctgaggccgccatccacgccggttgagtcgcgttctgccgcctcccgcc
tgtggtgcctcctgaactgcgtccgccgtctaggtaagtttaaagctcaggtcgagaccgggcctttgtccggcgctcccttggagcct
acctagactcagccggctctccacgctttgcctgaccctgcttgctcaactctagttaacggtggagggcagtgtagtctgagcagtact
cgttgctgccgcgcgcgccaccagacataatagctgacagactaacagactgttcctttccatgggtcttttctgcagtcaccgtcgtcg
acacgtgtgatcagatatcgcggccgccaccatgaactctgtctttacaatccgtttggccgaggtgcctacgctcaacctccaatagc
atggaggccaagacgtagggctgcacctgcgcctcgaccatccgggttgactacccagatccaacagctcactagggctgttagagc
tttggtgctggacaatgctacacgtcgccagcgcccggctcctcgcacgcgcccgaggaagccgaagactcaaaaacctaagccga
agaagcaaaaccagaaaccaccacaacagcagaagaaagggaaaaatcagccccaacaaccgaagaaaccgaagcccggtaaa
cgacagcgtaccgccctgaaatttgaagccgaccgcacatttgtcgggaagaatgaagacggcaagattatgggatacgccgttgcc
atggaagggaaagtgataaaaccactacatgtaaaaggaaccattgaccacccggccctagcgaaacttaaattcactaaatcttcttct
tacgacatggagtttgctaaactaccgaccgaaatgaaaagcgacgcattcgggtatacaacggaacaccccgaagtattttacaactg
gcatcacggagctgtccaattttccggcggaaggttcaccatccctacaggagtcggaggccccggagatagcggaaggcctatact
ggataactccggaaaagtggtagccatagtcctaggaggagctaatgaagtgccaggaacggcactttctgttgtcacctggaataag
aagggagccgctattaaaaccacccacgaagatactgtagagtggtcgcgggctattaccgctatgtgcatcctgcagaacgtcacatt
cccatgtgaccgaccgccaacttgctataatcgtaatcctgacttgaccctaaccatgttggaaacaaatgtcaatcacccttcgtacgac FIG. 22 B (continued)

gttctgctggacgctgctctgaggtgccccacgagacggcacgtcagatcaacgcccaccgatgacttcactctcacagcaccgtacc
tcggcttgtgtcacagatgtaagacgatggaaccatgctacagccctataaaaatcgaaaaagtgtgggatgatgccgatgacggagtt
ctccgtatacaagtaagtgcccagttagggtacaacagggcgggcactgcagctagcgcccgactccggttcatgggcggaggagt
gcctccggaaatccaggagggagcaattgcagattttaaggtcttcacgtccaaaccatgtttacacctatcacataaaggatactttgtc
attgtcaagtgccctcctggtgatagtattacaacatcattgaaagtgcatggctcggatcaaacctgcacaattccaatgcgagtaggtt
acaagttcgtaggcagggaaaaatatactctgccaccaatgcatgggacacaaataccttgccttacctacgaaaggacacgagaga
aaagtgcaggatacgtgaccatgcatcgtcccggacaacaatccataaccatgctgatggaagagagcggaggggaggtgtacgta
caaccgaccagtgggcgaaacgtcacctacgagtgtaaatgcggagactttaaaactgggactgtcactgcgcgcactaaaatagac
ggctgtacagaaaggaaacaatgcattgcgatttctgccgaccacgtcaaatgggtgtttaactcccctgacttgatcaggcataccga
ccacacagcccaagggaagttgcatataccattcccgctacagcaggctcaatgtacagtaccactggcgcaccttccaggcgttaag
catgcttatcgcagtatgtctctgacactgcacgctgagcatcctacattgcttactacccgccatcttggagaaaatcctcagcccactg
cagaatggattgtcgggagtgtaactcgaaacttctccataaccatacaagggttcgagtatacttggggaaatcagaaaccggtccga
gtgtacgcgcaggaatcggcacctggcaatcctcatggctggccacatgaaatcgtacgccattactaccacctctatcccttctacacc
gttacagtgctgagcggcatgggactggccatatgcgctggcttagtgatcagtattttatgctgctgcaaagcaagaagggattgccta
acaccttaccaactggccccgaacgctaccgtaccatttctggtaacattgtgttgctgtttccaacggacttcagcggatgaatttaccg
ataccatggggtacctatggcaacacagtcaaacaatgttctggatacaattggtcatacctttagcagcagtgataactttggttagatgt
tgctcctgctgtctacctttttattggttgccagtcctcctaacaaagcggacgcctacgaacatacgatcactgtcccaaatgcgccgtt
gaactcgtataaagcactagtggaacggcctgggtatgccccctttgaatcttgaagtcatggtcatgaacacccagatcataccatcgg
ttaaacgtgaatacattacctgcaggtaccacaccgttgttccttcaccgcagattaaatgttgcggaactgtcgaatgcccgaaaggtg
aaaaagcagactatacctgcaaggtgttcactggtgtgtacccatttctgtggggaggagcacagtgtttttgcgactccgaaaacagtc
agcttagcgacaagtacgtcgaactgtcaacagattgcgccacagaccatgccgaggcggtcagagtacacacggcttcggtgaaat
cacagctccgaataacctacgggaactccacagcacaagtagacgtatttgtcaacggtgtgactccagccaggagcaaagacatga
aattgatagccggcccattatctactacattttccccgtttgataataaggtcattatatatcatgggaaagtctataactatgacttcccgga
atttggggccggaacacctggagctttcggagatgtccaagcgtcatccaccaccggatcagatctattagcaaacacagcaattcattt
gcagaggccggaagccagaaacatacacgtcccgtacacccaagctccaagcgggttcgaattctggaagaataacagcggtcag
cctttatctgacactgcccctttcggatgcaaagtcaatgtcaacccgctacgtgcagacaagtgtgccgtgggatcactcccgatatcc
gtggatataccggacgctgcatttacacgcgtatccgagcccctgccatcactgcttaagtgcaccgttactagttgcacatactctaca

FIG. 22 B (continued)

gactatggcggagtgctcgtgttgacatacgagtcggatcgcgcggggcaatgcgctgtacactcgcattcatcaacagcggtactgc
gagacccatcggtatacgtcgagcaaaaaggggagactacacttaaatttagtacgcgttccttgcaggcagacttcgaggtatcgatg
tgcggaacgagaaccacttgccatgcccaatgtcaaccaccaacggaacacgtaatgaacagaccccagaagtcgactccagacttc
tcctcagcgatatccaaaacatcatggaactggattacagcgcttatgggggggaatttccagtatagctgctatagccgcaattgtgctg
gtcatagcattagtatttacagcacaacacagatgatctagaccaggccctggatccagatctgctgtgccttctagttgccagccatctg
ttgtttgcccctcccccgtgccttccttgaccctggaaggtgccactcccactgtcctttcctaataaaatgaggaaattgcatcgcattgtc
tgagtaggtgtcattctattctggggggtggggtggggcaggacagcaagggggaggattgggaagacaatagcaggcatgctggg
gatgcggtgggctctatgggtacccaggtgctgaagaattgacccggttcctcctgggccagaaagaagcaggcacatccccttctct
gtgacacaccctgtccacgcccctggttcttagttccagccccactcataggacactcatagctcaggagggctccgccttcaatccca
cccgctaaagtacttggagcggtctctccctccctcatcagcccaccaaaccaaacctagcctccaagagtgggaagaaattaaagca
agataggctattaagtgcagagggagagaaaatgcctccaacatgtgaggaagtaatgagagaaatcatagaattttaaggccatgatt
taaggccatcatggccttaatcttccgcttcctcgctcactgactcgctgcgctcggtcgttcggctgcggcgagcggtatcagctcact
caaaggcggtaatacggttatccacagaatcaggggataacgcaggaaagaacatgtgagcaaaaggccagcaaaaggccagga
accgtaaaaaggccgcgttgctggcgtttttccataggctccgcccccctgacgagcatcacaaaaatcgacgctcaagtcagaggtg
gcgaaacccgacaggactataaagataccaggcgtttccccctggaagctccctcgtgcgctctcctgttccgaccctgccgcttacc
ggatacctgtccgcctttctcccttcgggaagcgtggcgctttctcatagctcacgctgtaggtatctcagttcggtgtaggtcgttcgctc
caagctgggctgtgtgcacgaaccccccgttcagcccgaccgctgcgccttatccggtaactatcgtcttgagtccaacccggtaaga
cacgacttatcgccactggcagcagccactggtaacaggattagcagagcgaggtatgtaggcggtgctacagagttcttgaagtggt
ggcctaactacggctacactagaagaacagtatttggtatctgcgctctgctgaagccagttaccttcggaaaaagagttggtagctctt
gatccggcaaacaaaccaccgctggtagcggtggtttttttgtttgcaagcagcagattacgcgcagaaaaaaaggatctcaagaaga
tcctttgatcttttctacggggtctgacgctcagtggaacgaaaactcacgttaagggattttggtcatgagattatcaaaaaggatcttca
cctagatccttttaaattaaaaatgaagttttaaatcaatctaaagtatatatgagtaaacttggtctgacagttaccaatgcttaatcagtga
ggcacctatctcagcgatctgtctatttcgttcatccatagttgcctgactcggggggggggggcgctgaggtctgcctcgtgaagaag
gtgttgctgactcataccaggcctgaatcgccccatcatccagccagaaagtgagggagccacggttgatgagagctttgttgtaggtg
gaccagttggtgattttgaacttttgctttgccacggaacggtctgcgttgtcgggaagatgcgtgatctgatccttcaactcagcaaaagt
tcgatttattcaacaaagccgccgtcccgtcaagtcagcgtaatgctctgccagtgttacaaccaattaaccaattctgattagaaaaact
catcgagcatcaaatgaaactgcaatttattcatatcaggattatcaataccatatttttgaaaaagccgtttctgtaatgaaggagaaaact FIG. 22B (continued)

caccgaggcagttccataggatggcaagatcctggtatcggtctgcgattccgactcgtccaacatcaatacaacctattaatttcccctc
gtcaaaaataaggttatcaagtgagaaatcaccatgagtgacgactgaatccggtgagaatggcaaaagcttatgcatttctttccagac
ttgttcaacaggccagccattacgctcgtcatcaaaatcactcgcatcaaccaaaccgttattcattcgtgattgcgcctgagcgagacg
aaatacgcgatcgctgttaaaaggacaattacaaacaggaatcgaatgcaaccggcgcaggaacactgccagcgcatcaacaatattt
tcacctgaatcaggatattcttctaatacctggaatgctgttttcccggggatcgcagtggtgagtaaccatgcatcatcaggagtacgga
taaaatgcttgatggtcggaagaggcataaattccgtcagccagtttagtctgaccatctcatctgtaacatcattggcaacgctacctttg
ccatgtttcagaaacaactctggcgcatcgggcttcccatacaatcgatagattgtcgcacctgattgcccgacattatcgcgagcccatt
tatacccatataaatcagcatccatgttggaatttaatcgcggcctcgagcaagacgtttcccgttgaatatggctcataacaccccttgta
ttactgtttatgtaagcagacagttttattgttcatgatgatatatttttatcttgtgcaatgtaacatcagagattttgagacacaacgtggcttt
cccccccccccccattattgaagcatttatcagggttattgtctcatgagcggatacatatttgaatgtatttagaaaaataaacaaataggg
gttccgcgcacatttccccgaaaagtgccacctgacgtctaagaaaccattattatcatgacattaacctataaaaataggcgtatcacga
ggccctttcgtc

FIG. 23B (continued)

SEQ ID NO:19 atgagcctcgccctcccggtcttgtgcctgttggcaaacactacattcccctgctctcagccgccttgcacaccctgctgctacgaaaaggaacc
ggaaagcaccttgcgcatgcttgaggacaacgtgatgagacccggatactaccagctactaaaagcatcgctgacttgctctccccaccgcc
aaagacgcagtactaaggacaattttaatgtctataaagccacaagaccatatctagctcattgtcctgactgcggagaagggcattcgtgcca
cagccctatcgcattggagcgcatcagaaatgaagcaacggacggaacgctgaaaatccaggtctctttgcagatcgggataaagacagat
gacagccacgattggaccaagctgcgctatatggatagccatacgccagcggacgcggagcgagccggattgcttgtaaggacttcagcac
cgtgcacgatcaccgggaccatgggacactttattctcgcccgatgcccgaaaggagagacgctgacagtgggatttacggacagcagaaa
gatcagccacacatgcacacacccgttccatcatgaaccacctgtgataggtagggagaggttccactctcgaccacaacatggtaaagagt
taccttgcagcacgtacgtgcagagcaccgctgccactgctgaggagatagaggtgcatatgcccccagatactcctgaccgcacgctgatg
acgcagcagtctggcaacgtgaagatcacagttaatgggcagacggtgcggtacaagtgcaactgcggtggctcaaacgagggactgaca
accacagacaaagtgatcaataactgcaaaattgatcagtgccatgctgcagtcactaatcacaagaattggcaatacaactcccctttagtcc
cgcgcaacgctgaactcggggaccgtaaaggaaagatccacatcccattcccattggcaaacgtgacttgcagagtgccaaaagcaagaa
accctacagtaacttacggaaaaaaccaagtcaccatgctgctgtatcctgaccatccgacactcttgtcttaccgtaacatgggacaggaacc
aaattaccacgaggagtgggtgacacacaagaaggaggttaccttgaccgtgcctactgagggtctggaggtcacttggggcaacaacgaa
ccatacaagtactggccgcagatgtctacgaacggtactgctcatggtcacccacatgagataatcttgtactattatgagctgtaccccactatg
actgtagtcattgtgtcggtggcctcgttcgtgcttctgtcgatggtgggcacagcagtgggaatgtgtgtgtgcgcacggcgcagatgcattaca
ccatatgaattaacaccaggagccactgttcccttcctgctcagcctgctatgctgcgtcagaacgaccaaggcggccacatattacgaggctg
cggcatatctatggaacgaacagcagcccctgttctggttgcaggctcttatcccgctggccgccttgatcgtcctgtgcaactgtctgaaactctt
gccatgctgctgtaagaccctggctttttttagccgtaatgagcatcggtgcccacactgtgagcgcgtacgaacacgtaacagtgatcccgaac
acggtgggagtaccgtataagactcttgtcaacagaccgggttacagccccatggtgttggagatggagctacaatcagtcaccttggaacca
acactgtcacttgactacatcacgtgcgagtacaaaactgtcatcccctccccgtacgtgaagtgctgtggtacagcagagtgcaaggacaag
agcctaccagactacagctgcaaggtctttactggagtctacccatttatgtggggcggcgcctactgcttttgcgacgccgaaaatacgcaatt
gagcgaggcacatgtagagaaatctgaatcttgcaaaacagagtttgcatcggcctacagagcccacaccgcatcggcgtcggcgaagctc
cgcgtcctttaccaaggaaacaacattaccgtagctgcctacgctaacggtgaccatgccgtcacagtaaaggacgccaagtttgtcgtgggc
ccaatgtcctccgcctggacaccttttgacaacaaaatcgtggtgtacaaaggcgacgtctacaacatggactacccaccttttggcgcaggaa
gaccaggacaatttggtgacattcaaagtcgtacaccggaaagtaaagacgtttatgccaacactcagttggtactacagaggccagcagca
ggcacggtacatgtaccatactctcaggcaccatctggcttcaagtattggctgaaggaacgaggagcatcgctacagcacacggcaccgtt FIG. 23B (continued)

cggttgccagattgcgacaaacccggtaagagctgtaaattgcgctgtggggaacataccaatttccatcgacataccggatgcggcctttact
agggttgtcgatgcaccctctgtaacggacatgtcatgcgaagtaccagcctgcactcactcctccgactttgggggcgtcgccatcatcaaata
cacagctagcaagaaaggtaaatgtgcagtacattcgatgaccaacgccgttaccattcgagaagccgacgtagaagtagaggggaactc
ccagctgcaaatatccttctcaacagccctggcaagcgccgagtttcgcgtgcaagtgtgctccacacaagtacactgcgcagccgcatgcca
ccctccaaaggaccacatagtcaattacccagcatcacacaccacccttggggtccaggatatatccacaacggcaatgtcttgggtgcaga
agattacgggaggagtaggattaattgttgctgttgctgccttaattttaattgtggtgctatgcgtgtcgtttagcaggcac

SEQ ID NO: 20 atgagtcttgccatcccagttatgtgcctgttggcaaacaccacgttcccctgctcccagccccttgcacgccctgctgctacgaaaaggaacc
ggaggaaaccctacgcatgcttgaggacaacgtcatgagacctgggtactatcagctgctacaagcatccttaacatgttctccccaccgcca
gcgacgcagcaccaaggacaacttcaatgtctataaagccacaagaccatacttagctcactgtcccgactgtggagaagggcactcgtgcc
atagtcccgtagcactagaacgcatcagaaatgaagcgacagacgggacgctgaaaatccaggtctccttgcaaatcggaataaagacgg
atgacagccacgattggaccaagctgcgttatatggacaaccacatgccagcagacgcagagagggcggggctatttgtaagaacatcag
caccgtgtacgattactggaacaatgggacacttcatcctggcccgatgtccaaaaggggaaactctgacggtgggattcactgacagtagg
aagattagtcactcatgtacgcacccatttcaccacgaccctcctgtgataggtcgggaaaaattccattcccgaccgcagcacggtaaagag
ctaccttgcagcacgtacgtgcagagcaccgccgcaactaccgaggagatagaggtacacatgcccccagacacccctgatcgcacatta
atgtcacaacagtccggcaacgtaaagatcacagtcaatggccagacggtgcggtacaagtgtaattgcggtggctcaaatgaaggactaa
caactacagacaaagtgattaataactgcaaggttgatcaatgtcatgccgcggtcaccaatcacaaaaagtggcagtataactcccctctggt
cccgcgtaatgctgaacttggggaccgaaaaggaaaaattcacatcccgtttccgctggcaaatgtaacatgcagggtgcctaaagcaagg
aaccccaccgtgacgtacgggaaaaaccaagtcatcatgctactgtatcctgaccacccaacactcctgtcctaccggaatatgggagaaga
accaaactatcaagaagagtgggtgatgcataagaaggaagtcgtgctaaccgtgccgactgaagggctcgaggtcacgtggggcaaca
acgagccgtataagtattggccgcagttatctacaaacggtacagcccatggccacccgcatgagataattctgtattattatgagctgtacccc
actatgactgtagtagttgtgtcagtggccacgttcatactcctgtcgatggtgggtatggcagcggggatgtgcatgtgtgcacgacgcagatgc
atcacaccgtatgaactgacaccaggagctaccgtccctttcctgcttagcctaatatgctgcatcagaacagctaaagcggccacataccaa
gaggctgcgatatacctgtggaacgagcagcaacctttgttttggctacaagcccttattccgctggcagccctgattgttctatgcaactgtctga
gactcttaccatgctgctgtaaaacgttggctttttagccgtaatgagcgtcggtgcccacactgtgagcgcgtacgaacacgtaacagtgatcc
cgaacacggtgggagtaccgtataagactctagtcaatagacctggctacagccccatggtattggagatggaactactgtcagtcactttgga FIG. 23B (continued)

gccaacactatcgcttgattacatcacgtgcgagtacaaaaccgtcatcccgtctccgtacgtgaagtgctgcggtacagcagagtgcaagga
caaaaacctacctgactacagctgtaaggtcttcaccggcgtctacccatttatgtggggcggcgcctactgcttctgcgacgctgaaaacacg
cagttgagcgaagcacacgtggagaagtccgaatcatgcaaaacagaatttgcatcagcatacagggctcataccgcatctgcatcagctaa
gctccgcgtcctttaccaaggaaataacatcactgtaactgcctatgcaaacggcgaccatgccgtcacagttaaggacgccaaattcattgtg
gggccaatgtcttcagcctggacacctttcgacaacaaaattgtggtgtacaaaggtgacgtctataacatggactacccgccctttggcgcag
gaagaccaggacaatttggcgatatccaaagtcgcacacctgagagtaaagacgtctatgctaatacacaactggtactgcagagaccggc
tgtgggtacggtacacgtgccatactctcaggcaccatctggctttaagtattggctaaaagaacgcggggcgtcgctgcagcacacagcacc
atttggctgccaaatagcaacaaacccggtaagagcggtgaactgcgccgtagggaacatgcccatctccatcgacataccggaagcggc
cttcactagggtcgtcgacgcgccctctttaacggacatgtcgtgcgaggtaccagcctgcacccattcctcagactttgggggcgtcgccattat
taaatatgcagccagcaagaaaggcaagtgtgcggtgcattcgatgactaacgccgtcactattcgggaagctgagatagaagttgaaggg
aattctcagctgcaaatctctttctcgacggccttagccagcgccgaattccgcgtacaagtctgttctacacaagtacactgtgcagccgagtgc
caccccccgaaggaccacatagtcaactacccggcgtcacataccaccctcggggtccaggacatctccgctacggcgatgtcatgggtgc
agaagatcacgggaggtgtgggactggttgttgctgttgccgcactgattctaatcgtggtgctatgcgtgtcgttcagcaggcac

SEQ ID NO: 21

Atggagttcatcccgacgcaaactttctataacagaaggtaccaaccccgaccctgggccccacgccctacaattcaagtaattagacctagacca
cgtccacagaggcaggctgggcaactcgcccagctgatctccgcagtcaacaaattgaccatgcgcgcggtacctcaacagaagcctcgcagaa
atcggaaaaacaagaagcaaaggcagaagaagcaggcgccgcaaaacgacccaaagcaaaagaagcaaccaccacaaaagaagccggctc
aaaagaagaagaaaccaggccgtagggagagaatgtgcatgaaaattgaaaatgattgcatcttcgaagtcaagcatgaaggcaaagtgatggg
ctacgcatgcctggtgggggataaagtaatgaaaccagcacatgtgaagggaactatcgacaatgccgatctggctaaactggcctttaagcggtc
gtctaaatacgatcttgaatgtgcacagataccggtgcacatgaagtctgatgcctcgaagtttacccacgagaaacccgaggggtactataactgg
catcacggagcagtgcagtattcaggaggccggttcactatcccgacgggtgcaggcaagccgggagacagcggcagaccgatcttcgacaac
aaaggacgggtggtggccatcgtcctaggaggggccaacgaaggtgcccgcacggccctctccgtggtgacgtggaacaaagacatcgtcaca
aaaattacccctgagggagccgaagagtgg

FIG. 23B (continued)

SEQ ID NO: 22

Atggagttcatcccaacccaaactttttacaataggaggtaccagcctcgaccctggactccgcgccctactatccaagtcatcaggcccagaccg
cgccctcagaggcaagctgggcaacttgcccagctgatctcagcagttaataaactgacaatgcgcgcggtaccacaacagaagccacgcagga
atcggaagaataagaagcaaaagcaaaaacaacaggcgccacaaaacaacacaaatcaaaagaagcagccacctaaaaagaaaccggctcaa
aagaaaaagaagccgggccgcagagagaggatgtgcatgaaaatcgaaaatgattgtattttcgaagtcaagcacgaaggtaaggtaacaggtta
cgcgtgcctggtgggggacaaagtaatgaaaccagcacacgtaaaggggaccatcgataacgcggacctggccaaactggcctttaagcggtca
tctaagtatgaccttgaatgcgcgcagatacccgtgcacatgaagtccgacgcttcgaagttcacccatgagaaaccggaggggtactacaactgg
caccacggagcagtacagtactcaggaggccggttcaccatccctacaggtgctggcaaaccaggggacagcggcagaccgatcttcgacaac
aagggacgcgtggtggccatagtcttaggaggagctaatgaaggagcccgtacagccctctcggtggtgacctggaataaagacattgtcactaa
aatcacccccgagggggccgaagagtgg

FIG. 24

Seq ID NO: 23

```
   1 atggctgcgt gagacacacg tagcctacca gtttcttact gctctactct gcaaagcaag
  61 agattaataa cccatcatgg atcctgtgta cgtggacata gacgctgaca gcgccttttt
 121 gaaggccctg caacgtgcgt accccatgtt tgaggtggaa ccaaggcagg tcacaccgaa
 181 tgaccatgct aatgctagag cgttctcgca tctagctata aaactaatag agcaggaaat
 241 tgaccccgac tcaaccatcc tggatatcgg cagtgcgcca gcaaggagga tgatgtcgga
 301 caggaagtac cactgcgtct gcccgatgcg cagtgcggaa gatcccgaga gactcgccaa
 361 ttatgcgaga aagctagcat ctgccgcagg aaaagtcctg gacagaaaca tctctggaaa
 421 gatcggggac ttacaagcag taatggccgt gccagacacg gagacgccaa cattctgctt
 481 acacacagac gtctcatgta gacagagagc agacgtcgct atataccaag acgtctatgc
 541 tgtacacgca cccacgtcgc tataccacca ggcgattaaa ggggtccgag tggcgtactg
 601 ggttgggttc gacacaaccc cgttcatgta caatgccatg gcgggtgcct acccctcata
 661 ctcgacaaac tgggcagatg agcaggtact gaaggctaag aacataggat tatgttcaac
 721 agacctgacg gaaggtagac gaggcaagtt gtctattatg agagggaaaa agctaaaacc
 781 gtgcgaccgt gtgctgttct cagtagggtc aacgctctac ccggaaagcc gcaagctact
 841 taagagctgg cacctgccat cggtgttcca tttaaagggc aaactcagct tcacatgccg
 901 ctgtgataca gtggtttcgt gtgagggcta cgtcgttaag agaataacga tgagcccagg
 961 cctttatgga aaaaccacag ggtatgcggt aacccaccac gcagacggat tcctgatgtg
1021 caagactacc gacacggttg acggcgaaag aatgtcattc tcggtgtgca catacgtgcc
1081 ggcgaccatt tgtgatcaaa tgaccggcat ccttgctaca gaagtcacgc cggaggatgc
1141 acagaagctg ttggtggggc tgaaccagag aatagtggtt aacggcagaa cgcaacggaa
1201 tacgaacacc atgaaaaatt atctgcttcc cgtggtcgcc caagccttca gtaagtgggc
1261 aaaggagtgc cggaaagaca tggaagatga aaaactcctg gggtcagag aaagaacact
1321 gacctgctgc tgtctatggg cattcaagaa gcagaaaaca cacacggtct acaagaggcc
1381 tgatacccag tcaattcaga aggttcaggc cgagtttgac agctttgtgg taccgagtct
1441 gtggtcgtcc gggttgtcaa tccctttgag gactagaatc aaatggttgt taagcaaggt
1501 gccaaaaacc gacctgatcc catacagcgg agacgcccga gaagcccggg acgcagaaaa
1561 agaagcagag gaagaacgag aagcagaact gactcgcgaa gccctaccac ctctacaggc
```

FIG. 24 (continued)

```
1621 agcacaggaa gatgttcagg tcgaaatcga cgtggaacag cttgaggaca gagcgggcgc
1681 aggaataata gagactccga gaggagctat caaagttact gcccaaccaa cagaccacgt
1741 cgtgggagag tacctggtac tctccccgca gaccgtacta cgtagccaga agctcagtct
1801 gattcacgct ttggcggagc aagtgaagac gtgcacgcac aacggacgag cagggaggta
1861 tgcggtcgaa gcgtacgacg gccgagtcct agtgccctca ggctatgcaa tctcgcctga
1921 agacttccag agtctaagcg aaagcgcaac gatggtgtat aacgaaagag agttcgtaaa
1981 cagaaagcta caccatattg cgatgcacgg accagccctg aacaccgacg aagagtcgta
2041 tgagctggtg agggcagaga ggacagaaca cgagtacgtc tacgacgtgg atcagagaag
2101 atgctgtaag aaggaagaag ccgcaggact ggtactggtg ggcgacttga ctaatccgcc
2161 ctaccacgaa ttcgcatatg aagggctaaa aatccgccct gcctgcccat acaaaattgc
2221 agtcatagga gtcttcggag taccgggatc tggcaagtca gctattatca agaacctagt
2281 taccaggcag gacctggtga ctagcggaaa gaaagaaaac tgccaagaaa tcaccaccga
2341 cgtgatgaga cagagaggtc tagagatatc tgcacgtacg gttgactcgc tgctcttgaa
2401 tggatgcaac agaccagtcg acgtgttgta cgtagacgag gcgtttgcgt gccactctgg
2461 aacgctactt gctttgatcg ccttggtgag accaaggcag aaagttgtac tttgtggtga
2521 cccgaagcag tgcggcttct tcaatatgat gcagatgaaa gtcaactata atcacaacat
2581 ctgcacccaa gtgtaccaca aaagtatctc caggcggtgt acactgcctg tgaccgccat
2641 tgtgtcatcg ttgcattacg aaggcaaaat gcgcactacg aatgagtaca acaagccgat
2701 tgtagtggac actacaggct caacaaaacc tgaccctgga gacctcgtgt taacgtgctt
2761 cagagggtgg gttaaacaac tgcaaattga ctatcgtgga tacgaggtca tgacagcagc
2821 cgcatcccaa gggttaacca gaaaaggagt ttacgcagtt agacaaaaag ttaatgaaaa
2881 cccgctctat gcatcaacgt cagagcacgt caacgtactc ctaacgcgta cggaaggtaa
2941 actggtatgg aagacacttt ccggcgaccc gtggataaag acgctgcaga acccaccgaa
3001 aggaaacttc aaagcaacta ttaaggagtg ggaggtggag catgcatcaa taatggcggg
3061 catctgcagt caccaaatga ccttcgatac attccaaaat aaagccaacg tttgttgggc
3121 taagagcttg gtccctatcc tcgaaacagc ggggataaaa ctaaatgata ggcagtggtc
3181 tcagataatt caagccttca aagaagacaa agcatactca cctgaagtag ccctgaatga
3241 aatatgtacg cgcatgtatg ggtggatct agacagcggg ctattttcta aaccgttggt
3301 gtctgtgtat tacgcggata accactggga taataggcct ggagggaaaa tgttcggatt
```

FIG. 24 (continued)

```
3361 taaccccgag gcagcatcca ttctagaaag aaagtatcca ttcacaaaag ggaagtggaa
3421 catcaacaag cagatctgcg tgactaccag gaggatagaa gactttaacc ctaccaccaa
3481 catcataccg gccaacagga gactaccaca ctcattagtg gccgaacacc gcccagtaaa
3541 aggggaaaga atggaatggc tggttaacaa gataaacggc caccacgtgc tcctggtcag
3601 tggctataac cttgcactgc ctactaagag agtcacttgg gtagcgccgt taggtgtccg
3661 cggagcggac tacacataca acctagagtt gggtctgcca gcaacgcttg gtaggtatga
3721 cctagtggtc ataaacatcc acacaccttt tcgcatacac cattaccaac agtgcgtcga
3781 ccacgcaatg aaactgcaaa tgctcggggg tgactcattg agactgctca aaccgggcgg
3841 ctctctattg atcagagcat atggttacgc agatagaacc agtgaacgag tcatctgcgt
3901 attgggacgc aagtttagat cgtctagagc gttgaaacca ccatgtgtca ccagcaacac
3961 tgagatgttt ttcctattca gcaactttga caatggcaga aggaatttca caactcatgt
4021 catgaacaat caactgaatg cagccttcgt aggacaggtc acccgagcag gatgtgcacc
4081 gtcgtaccgg gtaaaacgca tggacatcgc gaagaacgat gaagagtgcg tagtcaacgc
4141 cgctaaccct cgcgggttac cgggtggcgg tgtttgcaag gcagtataca aaaaatggcc
4201 ggagtccttt aagaacagtg caacaccagt gggaaccgca aaaacagtta tgtgcggtac
4261 gtatccagta atccacgctg ttggaccaaa cttctctaat tattcggagt ctgaagggga
4321 ccgggaattg gcagctgcct atcgagaagt cgcaaaggaa gtaactaggc tgggagtaaa
4381 tagtgtagct atacctctcc tctccacagg tgtatactca ggagggaaag acaggctgac
4441 ccagtcactg aaccacctct ttacagccat ggactcgacg gatgcagacg tggtcatcta
4501 ctgccgcgac aaagaatggg agaagaaaat atctgaggcc atacagatgc ggacccaagt
4561 agagctgctg gatgagcaca tctccataga ctgcgatatt gttcgcgtgc accctgacag
4621 cagcttggca ggcagaaaag gatacagcac cacggaaggc gcactgtact catatctaga
4681 agggacccgt tttcatcaga cggctgtgga tatggcggag atacatacta tgtggccaaa
4741 gcaaacagag gccaatgagc aagtctgcct atatgccctg gggaaagta ttgaatcgat
4801 caggcagaaa tgcccggtgg atgatgcaga cgcatcatct cccccaaaa ctgtcccgtg
4861 cctttgccgt tacgctatga ctccagaacg cgtcacccgg cttcgcatga accacgtcac
4921 aagcataatt gtgtgttctt cgtttcccct cccaaagtac aaaatagaag gagtgcaaaa
4981 agtcaaatgc tctaaggtaa tgctatttga ccacaacgtg ccatcgcgcg taagtccaag
5041 ggaatataga tcttcccagg agtctgcaca ggaggcgagt acaatcacgt cactgacgca
```

FIG. 24 (continued)

```
5101 tagtcaattc gacctaagcg ttgatggcga gatactgccc gtcccgtcag acctggatgc
5161 tgacgcccca gccctagaac cagcactaga cgacggggcg acacacacgc tgccatccac
5221 aaccggaaac cttgcggccg tgtctgattg ggtaatgagc accgtacctg tcgcgccgcc
5281 cagaagaagg cgagggagaa acctgactgt gacatgtgac gagagagaag ggaatataac
5341 acccatggct agcgtccgat tctttagggc agagctgtgt ccggtcgtac aagaaacagc
5401 ggagacgcgt gacacagcaa tgtctcttca ggcaccaccg agtaccgcca cggaaccgaa
5461 tcatccgccg atctccttcg gagcatcaag cgagacgttc cccattacat ttggggactt
5521 caacgaagga gaaatcgaaa gcttgtcttc tgagctacta actttcggag acttcttacc
5581 aggagaagtg gatgacttga cagacagcga ctggtccacg tgctcagaca cggacgacga
5641 gttaagacta gacagggcag gtgggtatat attctcgtcg gacaccggtc caggtcattt
5701 acaacagaag tcagtacgcc agtcagtgct gccggtgaac accctggagg aagtccacga
5761 ggagaagtgt tacccaccta agctggatga agcaaaggag caactattac ttaagaaact
5821 ccaggagagt gcatccatgg ccaacagaag caggtatcag tcgcgcaaag tagaaaacat
5881 gaaagcagca atcatccaga gactaaagag aggctgtaga ctatacttaa tgtcagagac
5941 cccaaaagtc cctacttacc ggactacata tccggcgcct gtgtactcgc ctccgatcaa
6001 cgtccgattg tccaatcccg agtccgcagt ggcagcatgc aatgagttct tagctagaaa
6061 ctatccaact gtctcatcat accaaattac cgacgagtat gatgcatatc tagacatggt
6121 ggacgggtcg gagagttgcc tggaccgagc gacattcaat ccgtcaaaac tcaggagcta
6181 cccgaaacag cacgcttacc acgcgccctc catcagaagc gctgtaccgt ccccattcca
6241 gaacacacta cagaatgtac tggcagcagc cacgaaaaga aactgcaacg tcacacagat
6301 gagggaatta cccactttgg actcagcagt attcaacgtg gagtgtttca aaaaattcgc
6361 atgcaaccaa gaatactggg aagaatttgc tgccagccct attaggataa caactgagaa
6421 tttagcaacc tatgttacta aactaaaagg gccaaaagca gcagcgctat tcgcaaaaac
6481 ccataatcta ctgccactac aggaagtacc aatggatagg ttcacagtag atatgaaaag
6541 ggacgtaaag gtgactcctg gtacaaagca tacagaggaa agacctaagg tgcaggttat
6601 acaggcggct gaacccttgg cgacagcata cctatgtggg attcacagag agctggttag
6661 gaggctgaac gccgtcctcc tacccaatgt acatacacta tttgacatgt ctgccgagga
6721 tttcgatgcc atcatagccg cacactttaa gccaggagac actgttttgg aaacggacat
6781 agcctccttt gataagagcc aagatgattc acttgcgctt actgctttga tgctgttaga
```

FIG. 24 (continued)

```
6841 ggatttaggg gtggatcact ccctgctgga cttgatagag gctgctttcg gagagatttc
6901 cagctgtcac ctaccgacag gtacgcgctt caagttcggc gccatgatga aatcaggtat
6961 gttcctaact ctgttcgtca acacattgtt aaacatcacc atcgccagcc gagtgctgga
7021 agatcgtctg acaaaatccg cgtgcgcggc cttcatcggc gacgacaaca taatacatgg
7081 agtcgtctcc gatgaattga tggcagccag atgtgccact tggatgaaca tggaagtgaa
7141 gatcatagat gcagttgtat ccttgaaagc cccttacttt tgtggagggt ttatactgca
7201 cgatactgtg acaggaacag cttgcagagt ggcagacccg ctaaaaaggc tttttaaact
7261 gggcaaaccg ctagcggcag gtgacgaaca agatgaagat agaagacgag cgctggctga
7321 cgaagtgatc agatggcaac gaacagggct aattgatgag ctggagaaag cggtatactc
7381 taggtacgaa gtgcagggta tatcagttgt ggtaatgtcc atggccacct ttgcaagctc
7441 cagatccaac ttcgagaagc tcagaggacc cgtcataact ttgtacggcg gtcctaaata
7501 ggtacgcact acagctacct atttgcaga agccgacagc aagtatctaa acactaatca
7561 gctacaatgg agttcatccc aacccaaact ttttacaata ggaggtacca gcctcgaccc
7621 tggactccgc gccctactat ccaagtcatc aggcccagac cgcgccctca gaggcaagct
7681 gggcaacttg cccagctgat ctcagcagtt aataaactga caatgcgcgc ggtaccacaa
7741 cagaagccac gcaggaatcg gaagaataag aagcaaaagc aaaaacaaca ggcgccacaa
7801 aacaacacaa atcaaaagaa gcagccacct aaaaagaaac cggctcaaaa gaaaaagaag
7861 ccgggccgca gagagaggat gtgcatgaaa atcgaaaatg attgtatttt cgaagtcaag
7921 cacgaaggta aggtaacagg ttacgcgtgc ctggtggggg acaaagtaat gaaaccagca
7981 cacgtaaagg ggaccatcga taacgcggac ctggccaaac tggcctttaa gcggtcatct
8041 aagtatgacc ttgaatgcgc gcagataccc gtgcacatga agtccgacgc ttcgaagttc
8101 acccatgaga aaccggaggg gtactacaac tggcaccacg gagcagtaca gtactcagga
8161 ggccggttca ccatccctac aggtgctggc aaaccagggg acagcggcag accgatcttc
8221 gacaacaagg gacgcgtggt ggccatagtc ttaggaggag ctaatgaagg agcccgtaca
8281 gccctctcgg tggtgacctg gaataaagac attgtcacta aaatcacccc cgaggggcc
8341 gaagagtgga gtcttgccat cccagttatg tgcctgttgg caaacaccac gttcccctgc
8401 tcccagcccc cttgcacgcc ctgctgctac gaaaaggaac cggaggaaac cctacgcatg
8461 cttgaggaca acgtcatgag acctgggtac tatcagctgc tacaagcatc cttaacatgt
8521 tctccccacc gccagcgacg cagcaccaag gacaacttca atgtctataa agccacaaga
```

FIG. 24 (continued)

```
 8581 ccatacttag ctcactgtcc cgactgtgga gaagggcact cgtgccatag tcccgtagca
 8641 ctagaacgca tcagaaatga agcgacagac gggacgctga aaatccaggt ctccttgcaa
 8701 atcggaataa agacggatga cagccacgat tggaccaagc tgcgttatat ggacaaccac
 8761 atgccagcag acgcagagag ggcggggcta tttgtaagaa catcagcacc gtgtacgatt
 8821 actggaacaa tgggacactt catcctggcc cgatgtccaa aaggggaaac tctgacggtg
 8881 ggattcactg acagtaggaa gattagtcac tcatgtacgc acccatttca ccacgaccct
 8941 cctgtgatag gtcgggaaaa attccattcc cgaccgcagc acggtaaaga gctaccttgc
 9001 agcacgtacg tgcagagcac cgccgcaact accgaggaga tagaggtaca catgccccca
 9061 gacacccctg atcgcacatt aatgtcacaa cagtccggca acgtaaagat cacagtcaat
 9121 ggccagacgg tgcggtacaa gtgtaattgc ggtggctcaa atgaaggact aacaactaca
 9181 gacaaagtga ttaataactg caaggttgat caatgtcatg ccgcggtcac caatcacaaa
 9241 aagtggcagt ataactcccc tctggtcccg cgtaatgctg aacttgggga ccgaaaagga
 9301 aaaattcaca tcccgtttcc gctggcaaat gtaacatgca gggtgcctaa agcaaggaac
 9361 cccaccgtga cgtacgggaa aaaccaagtc atcatgctac tgtatcctga ccacccaaca
 9421 ctcctgtcct accggaatat gggagaagaa ccaaactatc aagaagagtg ggtgatgcat
 9481 aagaaggaag tcgtgctaac cgtgccgact gaagggctcg aggtcacgtg gggcaacaac
 9541 gagccgtata agtattggcc gcagttatct acaaacggta cagcccatgg ccacccgcat
 9601 gagataattc tgtattatta tgagctgtac cccactatga ctgtagtagt tgtgtcagtg
 9661 gccacgttca tactcctgtc gatggtgggt atggcagcgg ggatgtgcat gtgtgcacga
 9721 cgcagatgca tcacaccgta tgaactgaca ccaggagcta ccgtcccttt cctgcttagc
 9781 ctaatatgct gcatcagaac agctaaagcg gccacatacc aagaggctgc gatatacctg
 9841 tggaacgagc agcaaccttt gttttggcta caagccctta ttccgctggc agccctgatt
 9901 gttctatgca actgtctgag actcttacca tgctgctgta aaacgttggc ttttttagcc
 9961 gtaatgagcg tcggtgccca cactgtgagc gcgtacgaac acgtaacagt gatcccgaac
10021 acggtgggag taccgtataa gactctagtc aatagacctg gctacagccc catggtattg
10081 gagatggaac tactgtcagt cactttggag ccaacactat cgcttgatta catcacgtgc
10141 gagtacaaaa ccgtcatccc gtctccgtac gtgaagtgct gcggtacagc agagtgcaag
10201 gacaaaaacc tacctgacta cagctgtaag gtcttcaccg gcgtctaccc atttatgtgg
```

FIG. 24 (continued)

```
10261 ggcggcgcct actgcttctg cgacgctgaa aacacgcagt tgagcgaagc acacgtggag
10321 aagtccgaat catgcaaaac agaatttgca tcagcataca gggctcatac cgcatctgca
10381 tcagctaagc tccgcgtcct ttaccaagga aataacatca ctgtaactgc ctatgcaaac
10441 ggcgaccatg ccgtcacagt taaggacgcc aaattcattg tggggccaat gtcttcagcc
10501 tggacacctt tcgacaacaa aattgtggtg tacaaaggtg acgtctataa catggactac
10561 ccgccctttg gcgcaggaag accaggacaa tttggcgata tccaaagtcg cacacctgag
10621 agtaaagacg tctatgctaa tacacaactg gtactgcaga gaccggctgt gggtacggta
10681 cacgtgccat actctcaggc accatctggc tttaagtatt ggctaaaaga acgcggggcg
10741 tcgctgcagc acacagcacc atttggctgc caaatagcaa caaacccggt aagagcggtg
10801 aactgcgccg tagggaacat gcccatctcc atcgacatac cggaagcggc cttcactagg
10861 gtcgtcgacg cgccctcttt aacggacatg tcgtgcgagg taccagcctg cacccattcc
10921 tcagactttg ggggcgtcgc cattattaaa tatgcagcca gcaagaaagg caagtgtgcg
10981 gtgcattcga tgactaacgc cgtcactatt cgggaagctg agatagaagt tgaagggaat
11041 tctcagctgc aaatctcttt ctcgacggcc ttagccagcg ccgaattccg cgtacaagtc
11101 tgttctacac aagtacactg tgcagccgag tgccaccccc cgaaggacca catagtcaac
11161 tacccggcgt cacataccac cctcggggtc caggacatct ccgctacggc gatgtcatgg
11221 gtgcagaaga tcacgggagg tgtgggactg gttgttgctg ttgccgcact gattctaatc
11281 gtggtgctat gcgtgtcgtt cagcaggcac taacttgaca attaagtatg aaggtatatg
11341 tgtcccctaa gagacacact gtacatagca aataatctat agatcaaagg gctacgcaac
11401 ccctgaatag taacaaaata caaaatcact aaaaattata aaaacagaaa aatacataaa
11461 taggtatacg tgtcccctaa gagacacatt gtatgtaggt gataagtata gatcaaaggg
11521 ccgaataacc cctgaatagt aacaaaatat gaaaatcaat aaaaatcata aaatagaaaa
11581 accataaaca gaagtagttc aaagggctat aaaacccctg aatagtaaca aaacataaaa
11641 ttaataaaaa tcaaatgaat accataattg gcaaacggaa gagatgtagg tacttaagct
11701 tcctaaaagc agccgaactc actttgagaa gtaggcatag cataccgaac tcttccacga
11761 ttctccgaac ccacagggac gtaggagatg ttattttgtt tttaatattt caaaaaaaaa
11821 aaaaaaaaaa aaaaaaaaaa aaaaaaaaaa agcggccgct taattaatcg aggggaatta
11881 attcttgaag acgaaagggc caggtggcac ttttcgggga aatgtgcgcg gaacccctat
11941 ttgtttattt ttctaaatac attcaaatat gtatccgctc atgagacaat aaccctgata
```

FIG. 24 (continued)

```
12001 aatgcttcaa taatattgaa aaaggaagag tatgagtatt caacatttcc gtgtcgccct
12061 tattcccttt tttgcggcat tttgccttcc tgtttttgct cacccagaaa cgctggtgaa
12121 agtaaaagat gctgaagatc agttgggtgc acgagtgggt tacatcgaac tggatctcaa
12181 cagcggtaag atccttgaga gttttcgccc cgaagaacgt tttccaatga tgagcacttt
12241 taaagttctg ctatgtggcg cggtattatc ccgtgttgac gccgggcaag agcaactcgg
12301 tcgccgcata cactattctc agaatgactt ggttgagtac tcaccagtca cagaaaagca
12361 tcttacggat ggcatgacag taagagaatt atgcagtgct gccataacca tgagtgataa
12421 cactgcggcc aacttacttc tgacaacgat cggaggaccg aaggagctaa ccgctttttt
12481 gcacaacatg ggggatcatg taactcgcct tgatcgttgg gaaccggagc tgaatgaagc
12541 cataccaaac gacgagcgtg acaccacgat gcctgtagca atggcaacaa cgttgcgcaa
12601 actattaact ggcgaactac ttactctagc ttcccggcaa caattaatag actggatgga
12661 ggcggataaa gttgcaggac cacttctgcg ctcggccctt ccggctggct ggtttattgc
12721 tgataaatct ggagccggtg agcgtgggtc tcgcggtatc attgcagcac tggggccaga
12781 tggtaagccc tcccgtatcg tagttatcta cacgacgggg agtcaggcaa ctatggatga
12841 acgaaataga cagatcgctg agataggtgc ctcactgatt aagcattggt aactgtcaga
12901 ccaagtttac tcatatatac tttagattga tttaaaactt catttttaat ttaaaaggat
12961 ctaggtgaag atcctttttg ataatctcat gaccaaaatc ccttaacgtg agttttcgtt
13021 ccactgagcg tcagaccccg tagaaaagat caaaggatct tcttgagatc ctttttttct
13081 gcgcgtaatc tgctgcttgc aaacaaaaaa accaccgcta ccagcggtgg tttgtttgcc
13141 ggatcaagag ctaccaactc tttttccgaa ggtaactggc ttcagcagag cgcagatacc
13201 aaatactgtc cttctagtgt agccgtagtt aggccaccac ttcaagaact ctgtagcacc
13261 gcctacatac ctcgctctgc taatcctgtt accagtggct gctgccagtg gcgataagtc
13321 gtgtcttacc gggttggact caagacgata gttaccggat aaggcgcagc ggtcgggctg
13381 aacggggggt tcgtgcacac agcccagctt ggagcgaacg acctacaccg aactgagata
13441 cctacagcgt gagcattgag aaagcgccac gcttcccgaa gggagaaagg cggacaggta
13501 tccggtaagc ggcagggtcg gaacaggaga gcgcacgagg gagcttccag ggggaaacgc
13561 ctggtatctt tatagtcctg tcgggtttcg ccacctctga cttgagcgtc gatttttgtg
13621 atgctcgtca ggggggcgga gcctatggaa aaacgccagc aacgcgagct cgtatggaca
13681 tattgtcgtt agaacgcggc tacaattaat acataacctt atgtatcata cacaatcgat
13741 ttaggtgaca ctatag
```

FIG. 25

Seq ID NO: 33

```
   1 atggctgcgt gagacacacg tagcctacca gtttcttact gctctactct gcttagcaag
  61 agacttgaga acccatcatg gatcccgtgt acgtggacat agacgccgac agcgcctttt
 121 taaaggccct gcagcgtgcg taccccatgt ttgaggtgga accaaggcag gtcacaccga
 181 atgaccatgc caatgctaga gcattctcgc atctagctat aaaactaata gagcaggaaa
 241 ttgatcccga ctcaaccatc ctggacatag gcagcgcgcc agcaaggagg atgatgtcgg
 301 ataggaagta ccactgcgtt tgccctatgc gcagcgcaga agaccctgag agactcgcca
 361 actacgcgag aaaactagca tctgccgcag gaaaagtctt ggacagaaac atctccgaaa
 421 aaattggaga tctacaagca gtaatggctg taccagacgc agaaacgccc acattctgct
 481 tgcacactga cgtctcatgt agacaaaggg cggacgtcgc tatataccag gatgtctacg
 541 ccgtgcatgc accaacatcg ctgtaccacc aggcgattaa aggagtccgt gtagcatact
 601 ggatagggtt tgatacaacc ccgttcatgt ataatgccat ggcaggtgca tacccctcgt
 661 actcgacaaa ctgggcagat gagcaggtgc tgaaggcaaa gaacatagga ttatgttcaa
 721 cagacctgac ggaaggtaga cgaggtaaat tgtctatcat gagaggaaaa aagatgaagc
 781 catgtgaccg cgtactgttc tcagtcgggt caacgcttta cccggagagc cgtaagcttc
 841 ttaagagttg gcacttacct tcagtgttcc atctaaaagg gaagctcagc ttcacgtgcc
 901 gctgtgatac agtggtttcg tgtgaaggct atgtcgttaa gagaataacg attagcccgg
 961 gcctctacgg taaaaccaca gggtacgcag taacccacca tgcagacgga ttcctaatgt
1021 gcaaaacaac cgatacggta gatggcgaga gagtgtcatt ttcggtatgc acgtacgtac
1081 ccgcaaccat ttgtgatcaa atgacaggta ttcttgccac ggaggttaca ccggaggatg
1141 cacagaagct gctggtggga ctgaaccaga ggatagtggt caatggcaga acgcagagga
1201 acacgaacac aatgaagaat tacttgcttc ctgtagttgc ccaagccctc agtaagtggg
1261 caaaggaatg ccggaaagat atggaagatg aaaaactttt gggcatcaga gaaaggacac
1321 tgacatgctg ctgcctttgg gcgttcaaga agcagaagac acacacggtc tacaagaggc
1381 ctgacactca gtcaattcag aaagtcccag ccgaatttga cagctttgtg gtaccaagtc
1441 tgtggtcatc tggactgtcg atcccgctac ggaccagaat caagtggctg ctaagcaaag
```

FIG. 25 (continued)

```
1501 tgccaaagac tgatttgatc ccttacagcg gtgacgccaa agaagcccgc gacgctgaaa
1561 aagaagcaga agaagaacga gaagcggagc taactcgcga ggcactacca ccactacagg
1621 cggcacagga cgacgtccag gtcgaaattg acgtggaaca gctcgaagac agagctgggg
1681 caggaataat tgaaactcca agaggagcta tcaaagtcac tgcccaacca acagaccacg
1741 tcgtgggaga gtacttggta ctttccccgc agaccgtgtt acgaagccag aagctcagcc
1801 tgatccacgc attggcggaa caagtgaaga catgcacaca cagcggacgg gcaggaaggt
1861 acgcggtcga agcatatgac ggcagaatcc ttgtgccctc aggctatgca atatcacctg
1921 aagacttcca gagcctgagc gaaagtgcga cgatggtgta caacgaaagg gagttcgtaa
1981 ataggaaatt acaccatatc gcgttgcacg gaccagccct gaacactgac gaggagtcgt
2041 acgagctggt aagggcagaa aggacagagc atgagtacgt ctatgatgtg gaccaaagaa
2101 ggtgctgcaa gaaagaggag gcagccgggc tggtactggt cggcgacttg accaacccgc
2161 cctaccatga gttcgcatat gaagggctga gaatccgccc cgcctgccca tacaagaccg
2221 cagtaatagg ggtctttgga gtgccaggat ccggcaaatc agcaatcatt aagaacctag
2281 ttaccaggca agacctagtg accagtggaa agaaagaaaa ctgccaagaa atctccaccg
2341 acgtgatgcg acagaggaac ctggagatat ctgcacgcac ggtcgactca ctgctcttga
2401 acggatgcaa tagaccagtc gacgtgttgt acgtcgacga agcttttgcg tgccattctg
2461 gcacgctact tgctctgata gccttggtga gaccgaggca gaaagtcgtg ctatgcggtg
2521 atccgaaaca gtgcggcttc ttcaatatga tgcagatgaa agttaactac aaccataaca
2581 tctgcaccca agtgtaccat aaaagtattt ccaggcggtg tacactgcct gtgactgcca
2641 ttgtgtcctc gttgcattac gaaggcaaaa tgcgcacaac aaatgagtac aacaagccaa
2701 ttgtagtgga tactacaggc tcgacaaaac ccgaccccgg agaccttgtg ctaacatgtt
2761 tcagagggtg ggttaagcaa ctgcaaattg actatcgtgg acacgaggtc atgacagcag
2821 ctgcatctca ggggctaacc agaaaagggg tctatgccgt caggcaaaaa gttaatgaaa
2881 acccccttta cgcatcaaca tcagagcacg tgaacgtgct actgacgcgt acggaaggca
2941 aactagtatg gaagacactt tctggagacc catggataaa gacactgcag aacccgccga
```

FIG. 25 (continued)

```
3001 aaggaaattt taaagcaaca attaaggaat gggaagtgga acatgcttca ataatggcgg
3061 gtatctgtaa ccaccaagtg acctttgaca cgttccagaa taaagccaat gtctgctggg
3121 cgaagagctt agtccccatc ctagaaacag cagggataaa attaaacgac aggcagtggt
3181 cccagataat ccaggctttt aaagaagaca gagcatactc acccgaggtg gccctgaatg
3241 agatatgcac gcgcatgtac ggggtagacc tggacagcgg actgttctct aaaccactgg
3301 tgtccgtgca tcatgcggat aatcactggg acaacaggcc gggagggaag atgttcggat
3361 tcaaccccga agcggcgtcc atactggaga ggaaataccc gtttacaaaa gggaagtgga
3421 ataccaacaa gcaaatctgt gtgactacta ggaggattga agattttaac ccgaacacca
3481 acattatacc tgccaacagg agattaccgc attcattggt ggccgaacat cgcccggtaa
3541 aaggggagag gatggaatgg ttggtcaaca aaataaatgg ccaccatgtg ctcctggtca
3601 gcggctacaa cctcgttctg cccactaaga gagtcacctg ggtggcgccg ctgggcattc
3661 ggggagctga ctacacatac aacctagagt taggcctacc agcaacgctc ggtagatatg
3721 acctagtgat tataaacatc cacacaccct ttcgcataca tcattaccaa cagtgcgtgg
3781 atcacgcaat gaagctgcag atgctcggag gagactccct gagactgctc aagccgggtg
3841 gttcattact gatcagggca tacggctacg cagacagaac aagcgaacga gtagtctgcg
3901 tattgggacg caagtttcga tcatccagag cgttgaaacc gccgtgcgtc actagcaaca
3961 ccgagatgtt tttcttgttc agcaactttg ataacggcag aaggaacttt acgacgcacg
4021 taatgaacaa ccagctgaat gctgcttttg ttggtcaggc cacccgagca gggtgcgcac
4081 cgtcgtaccg ggttaaacgc atggacatcg caaagaacga tgaagagtgt gtagtcaacg
4141 ccgccaaccc tcgtgggcta ccaggcgatg gcgtctgtaa agcagtatac aaaaaatggc
4201 cggagtcctt caagaacagt gcaacaccag tgggaaccgc aaagacagtc atgtgcggta
4261 catacccggt aatccatgca gtaggaccta atttctcaaa ttactctgag tccgaaggag
4321 accgggaatt ggcagctgct taccgagaag tcgctaagga ggtgactaga ctaggagtaa
4381 acagcgtagc tataccgctc ctttccaccg gtgtgtactc tggagggaaa gacaggctga
4441 ctcagtcact aaaccacctt tttacagcat tagactcaac tgatgcagat gtggttatct
```

FIG. 25 (continued)

```
4501 actgccgcga caaggagtgg gagaagaaaa tagctgaggc catacaaatg aggacccaag
4561 tggaattact agacgaacac atctctgtag actgcgatat catccgagtg caccctgaca
4621 gcagtttggc aggtagaaaa gggtacagca ctacagaagg ttcactgtac tcctacttgg
4681 aagggacacg gttccatcag acggcagtgg acatggcaga agtatacacc atgtggccaa
4741 agcagacgga ggctaatgaa caagtttgct tgtacgcatt gggggaaagt atagaatcaa
4801 tcaggcaaaa gtgcccagtg gatgacgcag atgcatcgtc gcccccaaaa accgtcccgt
4861 gcctctgccg ttatgccatg acacccgaac gagtcaccag gcttcgtatg aaccatgtca
4921 caagcataat agtatgctca tcattccccc ttccaaagta taaaatagaa ggagtgcaga
4981 aagtcaagtg ttctaaagtg atgctgttcg accataacgt gccatcacgc gttagtccaa
5041 gggaatataa atcgcctcag gagaccgcac aagaagtaag ttcgaccacg tcactgacgc
5101 acagccaatt cgaccttagc gttgacggtg aggaactgcc cgctccgtct gacttggaag
5161 ctgacgctcc gattccggaa ccaacaccag acgacagagc ggtacttact ttgcctccca
5221 cgattgataa tttttcggct gtgtcagact gggtaatgaa taccgcgcca gtcgcaccac
5281 ccagaagaag acgtgggaaa aacttgaatg tcacctgcga cgagagagaa gggaacgtac
5341 ttcccatggc tagcgttcgg ttcttcagag cggatctgca ctccatcgta caggaaacgg
5401 cagagatacg cgatacggcc gcgtccctcc aggcgcccct gagtgtcgct acagaaccga
5461 atcaactgcc gatctcattt ggagcaccaa acgagacttt ccccataacg ttcggggatt
5521 ttgatgaagg ggagattgaa agcttgtcct ctgagttact gacctttggg gacttctcgc
5581 cgggcgaagt ggatgacctg acagacagcg actggtccac gtgttcagac acggacgacg
5641 aattatgact agatagggca ggtgggtaca tattctcatc tgacaccggc cccggccacc
5701 tgcaacagag gtctgtccgt cagacagtac tgccggtaaa taccttggag gaagttcagg
5761 aggagaaatg ttacccacct aagttggatg aagtgaaaga gcagttgtta cttaagaaac
5821 tccaggaaag tgcgtccatg gctaacagaa gcaggtacca atcccgcaaa gtagagaaca
5881 tgaaagcaac aatagtccaa aggctgaagg gtggttgcaa actttattta atgtcggaga
5941 ccccgaaagt tcctacctac cgaactacat atccggcacc agtgtactca cccccaatca
```

FIG. 25 (continued)

```
6001 atatccgact gtccaacccc gagtctgctg tggcagcgtg caatgagttc ctagcaagga
6061 actatccgac agttgcgtcg taccaaatca ccgatgagta cgatgcatac ctagacatgg
6121 tggacgggtc ggaaagttgc cttgaccggg cgacgttcaa cccatcaaag cttagaagtt
6181 atccaaaaca gcactcctac catgcaccca caatcagaag tgccgtacct tccccgttcc
6241 agaacacgct gcagaacgta ctggctgctg ccacgaaaag aaattgcaac gtcacacaga
6301 tgagagaact gcctactttg gattcagcgg tatttaatgt tgagtgcttt aaaaaatttg
6361 cgtgcaatca agaatactgg aaggaatttg ccgccagccc tattaggata acgactgaga
6421 acttgacaac ttatgtcaca aaactaaaag gaccaaaagc agcagcactg tttgccaaga
6481 cacataacct gctaccactg caggaggtgc cgatggacag gtttactgta gacatgaaaa
6541 gggacgtgaa ggtgactccg gggacgaagc acactgagga aagacctaaa gtgcaggtca
6601 tacaggcagc cgaacctttg gcaacagcat atctgtgtgg gatccacaga gagttggtca
6661 gaaggctgaa tgcagtcctt ctacctaatg tacacacgct gtttgacatg tctgccgagg
6721 actttgacgc cattattgcc gcgcacttca agccggggga cgccgtattg gaaaccgata
6781 tagcctcctt tgacaagagc caagacgact cattggcgct cactgctcta atgttgctag
6841 aggatttggg ggtggatcat cccctgttgg acttgataga ggctgccttc ggggagatct
6901 ccagctgcca cctaccgacg ggcacccgtt ttaagttcgg cgccatgatg aagtctggta
6961 tgttcctaac cctgttcgtc aacacactgc taaacatcac catagccagc cgagtgctgg
7021 aggaccgctt gacaaggtct gcgtgcgcgg ccttcatcgg cgacgacaat ataatacatg
7081 gggttgtctc tgacgaactg atggcagcaa ggtgtgctac atggatgaac atggaagtga
7141 agatcataga tgcggtcgtg tctcagaaag ccccgtactt ctgcggaggg tttatactgt
7201 atgacacagt agcaggcacg gcctgcagag tggcagaccc gctaaagcgg ctgttcaagc
7261 tgggcaaacc gctggcagcg ggagatgaac aagacgacga cagaagacgt gcactggctg
7321 acgaagtggt tagatggcaa cgaacaggac taactgatga gctagaaaaa gcggtacact
7381 ccaggtatga agtgcagggc atatctgtcg tggtaatgtc tatggccacc tttgcaagct
7441 ctagatctaa ctttgagaag ctcagaggac ccgtcgtaac cctgtacggt ggtcctaaat
```

FIG. 25 (continued)

```
7501 aggtacgcac tacagctacc tatttcgtca gaaaccaatc gcagctactt gcatacctac
7561 cagctacaat ggagttcatc ccgacgcaaa ctttctataa cagaaggtac caaccccgac
7621 cctgggcccc acgccctaca attcaagtaa ttagacctag accacgtcca cagaggcagg
7681 ctgggcaact cgcccagctg atctccgcag tcaacaaatt gaccatgcgc gcggtacctc
7741 aacagaagcc tcgcagaaat cggaaaaaca agaagcaaag gcagaagaag caggcgccgc
7801 aaaacgaccc aaagcaaaag aagcaaccac cacaaaagaa gccggctcaa aagaagaaga
7861 aaccaggccg tagggagaga atgtgcatga aaattgaaaa tgattgcatc ttcgaagtca
7921 agcatgaagg caaagtgatg ggctacgcat gcctggtggg ggataaagta atgaaaccag
7981 cacatgtgaa gggaactatc gacaatgccg atctggctaa actggccttt aagcggtcgt
8041 ctaaatacga tcttgaatgt gcacagatac cggtgcacat gaagtctgat gcctcgaagt
8101 ttacccacga gaaacccgag gggtactata actggcatca cggagcagtg cagtattcag
8161 gaggccggtt cactatcccg acgggtgcag gcaagccggg agacagcggc agaccgatct
8221 tcgacaacaa aggacgggtg gtggccatcg tcctaggagg ggccaacgaa ggtgcccgca
8281 cggccctctc cgtggtgacg tggaacaaag acatcgtcac aaaaattacc cctgagggag
8341 ccgaagagtg gagcctcgcc ctcccggtct tgtgcctgtt ggcaaacact acattcccct
8401 gctctcagcc gccttgcaca ccctgctgct acgaaaagga accggaaagc accttgcgca
8461 tgcttgagga caacgtgatg agacccggat actaccagct actaaaagca tcgctgactt
8521 gctctcccca ccgccaaaga cgcagtacta aggacaattt taatgtctat aaagccacaa
8581 gaccatatct agctcattgt cctgactgcg gagaagggca ttcgtgccac agccctatcg
8641 cattggagcg catcagaaat gaagcaacgg acggaacgct gaaaatccag gtctctttgc
8701 agatcgggat aaagacagat gacagccacg attggaccaa gctgcgctat atggatagcc
8761 atacgccagc ggacgcggag cgagccggat tgcttgtaag gacttcagca ccgtgcacga
8821 tcaccgggac catgggacac tttattctcg cccgatgccc gaaaggagag acgctgacag
8881 tgggatttac ggacagcaga aagatcagcc acacatgcac acacccgttc catcatgaac
8941 cacctgtgat aggtagggag aggttccact ctcgaccaca acatggtaaa gagttacctt
```

FIG. 25 (continued)

```
 9001 gcagcacgta cgtgcagagc accgctgcca ctgctgagga gatagaggtg catatgcccc
 9061 cagatactcc tgaccgcacg ctgatgacgc agcagtctgg caacgtgaag atcacagtta
 9121 atgggcagac ggtgcggtac aagtgcaact gcggtggctc aaacgaggga ctgacaacca
 9181 cagacaaagt gatcaataac tgcaaaattg atcagtgcca tgctgcagtc actaatcaca
 9241 agaattggca atacaactcc cctttagtcc cgcgcaacgc tgaactcggg gaccgtaaag
 9301 gaaagatcca catcccattc ccattggcaa acgtgacttg cagagtgcca aaagcaagaa
 9361 accctacagt aacttacgga aaaaaccaag tcaccatgct gctgtatcct gaccatccga
 9421 cactcttgtc ttaccgtaac atgggacagg aaccaaatta ccacgaggag tgggtgacac
 9481 acaagaagga ggttaccttg accgtgccta ctgagggtct ggaggtcact tggggcaaca
 9541 acgaaccata caagtactgg ccgcagatgt ctacgaacgg tactgctcat ggtcacccac
 9601 atgagataat cttgtactat tatgagctgt accccactat gactgtagtc attgtgtcgg
 9661 tggcctcgtt cgtgcttctg tcgatggtgg gcacagcagt gggaatgtgt gtgtgcgcac
 9721 ggcgcagatg cattacacca tatgaattaa caccaggagc cactgttccc ttcctgctca
 9781 gcctgctatg ctgcgtcaga acgaccaagg cggccacata ttacgaggct gcggcatatc
 9841 tatggaacga acagcagccc ctgttctggt tgcaggctct tatcccgctg gccgccttga
 9901 tcgtcctgtg caactgtctg aaactcttgc catgctgctg taagaccctg gcttttttag
 9961 ccgtaatgag catcggtgcc cacactgtga gcgcgtacga acacgtaaca gtgatcccga
10021 acacggtggg agtaccgtat aagactcttg tcaacagacc gggttacagc cccatggtgt
10081 tggagatgga gctacaatca gtcaccttgg aaccaacact gtcacttgac tacatcacgt
10141 gcgagtacaa aactgtcatc ccctccccgt acgtgaagtg ctgtggtaca gcagagtgca
10201 aggacaagag cctaccagac tacagctgca aggtctttac tggagtctac ccatttatgt
10261 ggggcggcgc ctactgcttt tgcgacgccg aaaatacgca attgagcgag gcacatgtag
10321 agaaatctga atcttgcaaa acagagtttg catcggccta cagagcccac accgcatcgg
10381 cgtcggcgaa gctccgcgtc ctttaccaag gaaacaacat taccgtagct gcctacgcta
10441 acggtgacca tgccgtcaca gtaaaggacg ccaagtttgt cgtgggccca atgtcctccg
```

FIG. 25 (continued)

```
10501 cctggacacc ttttgacaac aaaatcgtgg tgtacaaagg cgacgtctac aacatggact
10561 acccaccttt tggcgcagga agaccaggac aatttggtga cattcaaagt cgtacaccgg
10621 aaagtaaaga cgtttatgcc aacactcagt tggtactaca gaggccagca gcaggcacgg
10681 tacatgtacc atactctcag gcaccatctg gcttcaagta ttggctgaag gaacgaggag
10741 catcgctaca gcacacggca ccgttcggtt gccagattgc gacaaacccg gtaagagctg
10801 taaattgcgc tgtggggaac ataccaattt ccatcgacat accggatgcg gcctttacta
10861 gggttgtcga tgcaccctct gtaacggaca tgtcatgcga agtaccagcc tgcactcact
10921 cctccgactt tgggggcgtc gccatcatca aatacacagc tagcaagaaa ggtaaatgtg
10981 cagtacattc gatgaccaac gccgttacca ttcgagaagc cgacgtagaa gtagagggga
11041 actcccagct gcaaatatcc ttctcaacag ccctggcaag cgccgagttt cgcgtgcaag
11101 tgtgctccac acaagtacac tgcgcagccg catgccaccc tccaaaggac cacatagtca
11161 attacccagc atcacacacc acccttgggg tccaggatat atccacaacg gcaatgtctt
11221 gggtgcagaa gattacggga ggagtaggat taattgttgc tgttgctgcc ttaattttaa
11281 ttgtggtgct atgcgtgtcg tttagcaggc actaaaccga tgataaggca cgaaataact
11341 aaatagcaaa agtagaaagt acataaccag gtatatgtgc cccttaagag gcacaatata
11401 tatagctaag cactattaga tcaaagggct atacaacccc tgaatagtaa caaaacacaa
11461 aaaccaataa aaatcataaa aagaaaaatc tcataaacag gtataagtgt cccctaagag
11521 acacattgta tgtaggtagt aagtatagat caaagggcta tattaacccc tgaatagtaa
11581 caaaacacaa aaacaataaa aactacaaaa tagaaaatct ataaacaaaa gtagttcaaa
11641 gggctacaaa acccctgaat agtaacaaaa cataaaatgt aataaaaatt aagtgtgtac
11701 ccaaaagagg tacagtaaga atcagtgaat atcacaattg gcaacgagaa gagacgtagg
11761 tatttaagct tcctaaaagc agccgaactc actttgagac gtaggcatag cataccgaac
11821 tcttccacta ttctccgaac ccacagggac gtaggagatg ttattttgtt tttaatattt
11881 caaaaaaaaa aaaaaaaaaa aaaaaaaaaa aaaaaaaaaa agcggccgct taattaatcg
11941 aggggaatta attcttgaag acgaaagggc caggtggcac ttttcgggga aatgtgcgcg
```

FIG. 25 (continued)

```
12001 gaacccctat ttgtttattt ttctaaatac attcaaatat gtatccgctc atgagacaat
12061 aaccctgata aatgcttcaa taatattgaa aaaggaagag tatgagtatt caacatttcc
12121 gtgtcgccct tattcccttt tttgcggcat tttgccttcc tgtttttgct cacccagaaa
12181 cgctggtgaa agtaaaagat gctgaagatc agttgggtgc acgagtgggt tacatcgaac
12241 tggatctcaa cagcggtaag atccttgaga gttttcgccc cgaagaacgt tttccaatga
12301 tgagcacttt taaagttctg ctatgtggcg cggtattatc ccgtgttgac gccgggcaag
12361 agcaactcgg tcgccgcata cactattctc agaatgactt ggttgagtac tcaccagtca
12421 cagaaaagca tcttacggat ggcatgacag taagagaatt atgcagtgct gccataacca
12481 tgagtgataa cactgcggcc aacttacttc tgacaacgat cggaggaccg aaggagctaa
12541 ccgctttttt gcacaacatg ggggatcatg taactcgcct tgatcgttgg gaaccggagc
12601 tgaatgaagc cataccaaac gacgagcgtg acaccacgat gcctgtagca atggcaacaa
12661 cgttgcgcaa actattaact ggcgaactac ttactctagc ttcccggcaa caattaatag
12721 actggatgga ggcggataaa gttgcaggac cacttctgcg ctcggccctt ccggctggct
12781 ggtttattgc tgataaatct ggagccggtg agcgtgggtc tcgcggtatc attgcagcac
12841 tggggccaga tggtaagccc tcccgtatcg tagttatcta cacgacgggg agtcaggcaa
12901 ctatggatga acgaaataga cagatcgctg agataggtgc ctcactgatt aagcattggt
12961 aactgtcaga ccaagtttac tcatatatac tttagattga tttaaaactt catttttaat
13021 ttaaaaggat ctaggtgaag atcctttttg ataatctcat gaccaaaatc ccttaacgtg
13081 agttttcgtt ccactgagcg tcagaccccg tagaaaagat caaaggatct tcttgagatc
13141 cttttttttct gcgcgtaatc tgctgcttgc aaacaaaaaa accaccgcta ccagcggtgg
13201 tttgtttgcc ggatcaagag ctaccaactc tttttccgaa ggtaactggc ttcagcagag
13261 cgcagatacc aaatactgtc cttctagtgt agccgtagtt aggccaccac ttcaagaact
13321 ctgtagcacc gcctacatac ctcgctctgc taatcctgtt accagtggct gctgccagtg
13381 gcgataagtc gtgtcttacc gggttggact caagacgata gttaccggat aaggcgcagc
13441 ggtcgggctg aacggggggt tcgtgcacac agcccagctt ggagcgaacg acctacaccg
```

FIG. 25 (continued)

```
13501 aactgagata cctacagcgt gagcattgag aaagcgccac gcttcccgaa gggagaaagg
13561 cggacaggta tccggtaagc ggcagggtcg gaacaggaga gcgcacgagg gagcttccag
13621 ggggaaacgc ctggtatctt tatagtcctg tcgggtttcg ccacctctga cttgagcgtc
13681 gatttttgtg atgctcgtca ggggggcgga gcctatggaa aaacgccagc aacgcgagct
13741 cgtatggaca tattgtcgtt agaacgcggc tacaattaat acataacctt atgtatcata
13801 cacaatcgat ttaggtgaca ctatag
```

METHODS FOR THE INDUCTION OF IMMUNE RESPONSES IN A SUBJECT COMPROMISING ADMINISTERING VIRUS-LIKE PARTICLES (VLPS) PREPARED FROM CHIKUNGUNYA VIRUS STRUCTURAL PROTEINS

CROSS-REFERENCE TO RELATED APPLICATION

This application is a divisional of U.S. patent application Ser. No. 13/131,287, filed Sep. 19, 2011; which claims the benefit and priority to, and is a 35 U.S.C. § 371 U.S. National Phase entry of International Patent Application No. PCT/US09/06294, filed on Nov. 24, 2009, designating the United States of America and published in the English language; which is an International application of and claims the benefit of the following U.S. Provisional Application Nos. 61/118,206 and 61/201,118, filed on Nov. 26, 2008 and Dec. 5, 2008, respectively, the entire contents of each of which are incorporated herein by reference.

STATEMENT OF RIGHTS TO INVENTIONS MADE UNDER FEDERALLY SPONSORED RESEARCH

Research supporting this application was carried out by the United States of America as represented by the Secretary, Department of Health and Human Services. This research was supported by the Intramural Research Program, Vaccine Research Center, NIAID of the National Institute of Health. The Government has certain rights in this invention.

BACKGROUND OF THE INVENTION

Chikungunya virus (CHIKV), a mosquito-borne alphavirus in the family Togaviridae, was first isolated in Tanzania in 1952. Infection by this virus causes human disease that is characterized by rash, high fever and, its hallmark feature, severe arthritis that can persist for years. Chikungunya virus (CHIKV) has infected millions of people in Africa, Europe, and Asia since its re-emergence in Kenya in 2004. The evolution and spread of the virus into new geographic areas, and the disease severity present a serious public health in the absence of a vaccines or anti-viral therapies. Therefore, the development of anti-viral therapies for CHIKV and vaccine development remains a high priority. Phylogenetic analysis of CHIKV showed that there are three genotypes: Asian, East/Central/South African and West African. The Asian and East/Central/South African genotypes are most similar, whereas the West African strains are more divergent. Therapeutic and/or prophylactic methods for treating or preventing Chikungunya viral disease are urgently required.

SUMMARY OF THE INVENTION

As described below, the present invention features compositions and methods for the prevention or treatment of one or more strains of Chikungunya virus, as well as other alphavirus-mediated diseases.

In one aspect, the invention provides a virus-like particle (VLP) containing one or more (e.g., one, two, three, four, five) Chikungunya virus structural polypeptides. In one embodiment, the structural polypeptides are any one or more of capsid and envelope proteins E3, E2, 6K and E1.

In another aspect, the invention provides an isolated polynucleotide encoding a virus-like particle of the previous aspect or any other VLP delineated herein. In one embodiment, the polynucleotide encodes a Chikungunya virus polyprotein containing C-E3-E2-6K-E1.

In a related aspect, the invention provides an expression vector containing a polynucleotide encoding one or more Chikungunya virus structural polypeptides.

In another aspect, the invention provides a prokaryotic or eukaryotic cell (e.g., mammalian, human, insect) containing the expression vector of any previous aspect or any other expression vector delineated herein. In one embodiment, the cell is in vitro.

In another aspect, the invention provides an immunogenic composition containing an effective amount of a virus-like particle of any previous aspect or any other VLP delineated herein.

In a related aspect, the invention provides an immunogenic composition containing an effective amount of a VLP containing a Chikungunya structural polyprotein containing C-E3-E2-6K-E1 and an adjuvant.

In another aspect, the invention provides an immunogenic composition containing an effective amount of an expression vector of any previous aspect or otherwise delineated herein (e.g., a DNA vaccine).

In another aspect, the invention provides a vaccine containing an effective amount of one or more Chikungunya virus structural polypeptides that is any one or more of capsid (C) and envelope proteins E1, E2, E3 and 6K.

In another aspect, the invention provides a vaccine containing an effective amount of a virus-like particle of any previous aspect or containing a polyprotein containing C-E3-E2-6K-E1.

In another aspect, the invention provides a vaccine containing a polynucleotide encoding a Chikungunya structural polyprotein or fragment thereof. In one embodiment, the Chikungunya structural polyprotein is encoded by an expression vector of any previous aspect. In one embodiment, the expression vector comprises a CMV/R promoter. In another embodiment, the vaccine is a DNA vaccine.

In another aspect, the invention provides a method of inducing an immune response against Chikungunya in a subject (e.g. human), the method involving administering to the subject an effective amount of an immunogenic composition of any previous aspect or any other immunogenic composition delineated herein. In one embodiment, the immunogenic composition contains one or more Chikungunya virus structural polypeptides that is any one or more of capsid (C) and envelope proteins E1, E2, E3 and 6K. In another embodiment, the immunogenic composition comprises a polyprotein containing C-E3-E2-6K-E1. In another embodiment, the method induces neutralizing antibodies in a subject.

In another aspect, the invention provides a method for treating or preventing a Chikungunya infection in a subject, the method involving administering to the subject an effective amount of a vaccine of any previous aspect or an immunogenic composition of any previous aspect. In one embodiment, wherein the vaccine or immunogenic composition is administered in one or more doses.

In another aspect, the invention provides a method for producing a virus-like particle, the method involves expressing in a cell one or more Chikungunya structural protein capable of self-assembly to form a virus-like particle. In one embodiment, the method further involves isolating the virus-like particle.

In another aspect, the invention provides a virus-like particle (VLP) containing one or more alphavirus structural polypeptides (e.g., capsid or envelope polypeptide). In one embodiment, the alphavirus is any one or more of Chikungunya virus, Sindbis virus, Eastern equine encephalitis (EEE) virus, Western equine encephalitis (WEE) virus, and Venezuelan equine encephalitis (VEE) virus.

In another aspect, the invention provides an isolated polynucleotide encoding a virus-like particle of the previous aspect or otherwise delineated herein.

In another aspect, the invention provides an expression vector containing a polynucleotide encoding one or more alphavirus structural polypeptides wherein the alphavirus is selected from the group consisting of Chikungunya virus, Sindbis virus, Eastern equine encephalitis (EEE) virus, Western equine encephalitis (WEE) virus, and Venezuelan equine encephalitis (VEE) virus.

In another aspect, the invention provides an immunogenic composition containing an effective amount of a virus-like particle of any previous aspect or otherwise delineated herein.

In another aspect, the invention provides a vaccine containing an effective amount of one or more alphavirus structural polypeptides or a polynucleotide encoding one or more alphavirus structural proteins, wherein the alphavirus is selected from the group consisting of Chikungunya virus, Sindbis virus, Eastern equine encephalitis (EEE) virus, Western equine encephalitis (WEE) virus, and Venezuelan equine encephalitis (VEE) virus.

In another aspect, the invention provides a method of inducing an immune response against an alphavirus in a subject, the method involving administering to the subject an effective amount of an immunogenic composition of a previous aspect. In one embodiment, the immunogenic composition contains one or more alphavirus structural polypeptides (e.g. envelope or capsid).

In another aspect, the invention provides a method for treating or preventing an alphavirus infection in a subject, the method involving administering to the subject an effective amount of a vaccine or an immunogenic composition of any previous aspect.

In another aspect, the invention provides a kit containing a VLP of any previous aspect, and instructions for use.

In another aspect, the invention provides a kit containing an immunogenic composition of any previous aspect, and instructions for use in a subject. In one embodiment, the immunogenic composition is provided in a first container and a second immunogenic composition is provided in a second container, and instructions for use in a prime boost immunization. In another embodiment, the immunogenic composition in the second container contains a VLP, viral polypeptide, or viral polynucleotide.

In another aspect, the invention provides a method for identifying inhibitors of Chikungunya virus entry into a eukaryotic cell, the method involving contacting a cell that expresses a Chikungunya virus receptor with a Chikungunya polypeptide selected from the group consisting of C, E3, E2, 6K, and E1 and a candidate compound, and assaying for viral entry, wherein a candidate compound that reduces viral entry in the cell relative to a control cell is identified as an inhibitor of Chikungunya virus entry. In one embodiment, the candidate inhibitor is an antibody, or fragment thereof or small molecule.

In another aspect, the invention provides a method for identifying inhibitors of Chikungunya viral entry involving contacting a cell that expresses a Chikungunya virus receptor with a candidate inhibitor and a pseudotyped virus containing a reporter gene; and measuring expression of the reporter gene in the cell, wherein a compound that reduces expression of the reporter gene relative to a control cell is identified as inhibiting viral entry. In one embodiment, the pseudotyped virus (e.g., lentivirus) contains one or more Chikungunya virus envelope proteins (e.g., E3, E2, 6K and E1). In one embodiment, the candidate inhibitor is an antibody, or fragment thereof or small molecule.

In another aspect, the invention provides a virus-like particle (VLP) containing one or more Chikungunya virus structural polypeptides for use in treating or preventing a Chikungunya infection.

In another aspect, the invention provides a method for treating or preventing a Chikungunya infection, the method involving administering a virus-like particle (VLP) containing one or more Chikungunya virus structural polypeptides prior to, subsequent to, concurrent with, or in any other sequence with the administration of one or more of another immunogenic composition, antiviral, or antibiotic agent.

In another aspect, the invention provides methods for treating or preventing a Chikungunya infection by administering neutralizing antibodies (e.g., mammalian, human) generated against a VLP of the invention to a subject (e.g., human).

In various embodiments of the above aspects or any other aspect of the invention delineated herein, the VLP contains one or more (1, 2, 3, 4) envelop proteins E3, E2, 6K and E1. In other embodiments, the VLP contains a polyprotein containing C-E3-E2-6K-E1 or a fragment thereof. In other embodiments of the above aspects or any other aspect of the invention delineated herein, a polynucleotide encodes one or more structural polypeptides that is any one or more of a alphavirus or Chikungunya virus capsid (C) and envelope proteins E3, E2, 6K and E1. In other embodiments, the polynucleotide encodes envelop proteins E3, E2, 6K and E1. In other embodiments, the polynucleotide encodes a Chikungunya virus polyprotein containing C-E3-E2-6K-E1. In still other embodiments, the expression vector is capable of expression in a prokaryotic or eukaryotic cell (e.g., mammal, human). In other embodiments, the structural polyprotein is derived from Chikungunya strain 37997 or LR2006. In other embodiments, the vector comprises the CMV/R promoter. In other embodiments, the expression vector is C-E37997 or C-EOPY-1. In other embodiments, the VLP induces an immune response (e.g., a protective immune response) in a subject. In other embodiments, the immune response treats or prevents a Chikungunya infection in a subject. In other embodiments of the above aspects, the VLP induces antibodies against homologous or heterologous strains of Chikungunya. In embodiments of the above aspects, the adjuvant is an immunostimulating agent (e.g., Ribi, aluminum salts, muramyl peptides, bacterial cell wall components, saponin adjuvants).

In other embodiments of the above aspects, the vaccine or immunogenic composition is administered in one or more priming immunizations and one or more boosting immunizations. In still another embodiment, the priming immunizations are administered at one, two, three, four, five, six, seven or eight week intervals. In still another embodiment, the boosting immunizations are administered two weeks, one month, two months or three months after the priming immunization. In other embodiments of the above aspects or any other aspect of the invention delineated herein, the immunization protects the subject against viremia or the inflammatory consequences of infection. In other embodiments, the method protects a subject from lethality. In other embodiments, the method induces neutralizing antibodies in the subject.

The invention provides immunogenic compositions featuring virus-like particles comprising Chikungunya polypeptides for the prevention or treatment of Chikungunya viral disease. Compositions and articles defined by the invention were isolated or otherwise manufactured in connection with the examples provided below. Other features and advantages of the invention will be apparent from the detailed description, and from the claims.

Definitions

By "alphavirus structural protein" is meant a polypeptide or fragment thereof having at least about 40% amino acid sequence identity to a naturally occurring viral capsid or envelope protein and having immunogenic activity in a mammal. In one embodiment, the alphavirus structural protein has at least about 85%, 90%, 95% or greater amino acid sequence identity with a Chikunguna virus structural protein or immunogenic fragment thereof. In one embodiment, the protein Exemplary alphaviruses include, but are not limited to, Western, Eastern, and Venezuelan equine encephalitis viruses, o'nyong-nyong virus, Ross River virus and Sindbis virus.

By "Chikungunya virus structural protein" is meant a polypeptide or fragment thereof having at least about 85% amino acid sequence identity to a naturally occurring Chikungunya virus capsid or envelope protein. In other embodiments, the amino acid sequence identity is at least about 90%, 95%, or more.

By "agent" is meant any small molecule chemical compound, antibody, nucleic acid molecule, or polypeptide, or fragments thereof.

As used herein, the term "adjuvant" is meant to refer to a compound that, when used in combination with a specific immunogen in a formulation, will augment, alter or modify the resultant immune response. In certain embodiments, the adjuvant is used in combination with a VLP. In other embodiments, the adjuvant is used in combination with a DNA vaccine. Modification of the immune response includes intensification or broadening the specificity of either or both antibody and cellular immune responses. Modification of the immune response can also mean decreasing or suppressing certain antigen-specific immune responses. In one embodiment, the adjuvant is Ribi adjuvant.

As used herein "alphavirus" is meant to refer to RNA-containing viruses that belong to the group IV Togaviridae family of viruses. Exemplary alphaviruses include but are not limited to Western, Eastern, and Venezuelan equine encephalitis viruses, o'nyong-nyong virus, Ross River virus and Sindbis virus.

As used herein "inducing immunity" is meant to refer to any immune response generated against an antigen. In one embodiment, immunity is mediated by antibodies against an infectious agent, which is exhibited by a vertebrate (e.g., a human), that prevents or ameliorates an infection or reduces at least one symptom thereof. VLPs or DNA vaccines of the invention can stimulate the production of antibodies that, for example, neutralize infectious agents, block infectious agents from entering cells, block replication of infectious agents, and/or protect host cells from infection and destruction. The term can also refer to an immune response that is mediated by T-lymphocytes and/or other white blood cells against an infectious agent, exhibited by a vertebrate (e.g., a human), that prevents or ameliorates an infection, for example CHIKV infection, or reduces at least one symptom thereof.

By "ameliorate" is meant decrease, suppress, attenuate, diminish, arrest, or stabilize the development or progression of a disease or a symptom thereof.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include viral infections including but not limited to Western, Eastern, and Venezuelan equine encephalitis viruses, o'nyong-nyong virus, Ross River virus and Sindbis virus.

By "effective amount" is meant the amount of an agent required to ameliorate the symptoms of a disease relative to an untreated patient. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or prevent a diseases delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid molecule (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "structural polyprotein" is meant a composite amino acid molecule comprising at least two separable polypeptides that contribute to a viral capsid or envelope. In one embodiment, the polypeptides are susceptible to cleavage with a viral enzyme (e.g., capsid autoproteinase and signalases).

An exemplary structural polyprotein sequence is provided at Genbank Accession No. ABX40006.1, which is reproduced below.

(SEQ ID NO: 24)

MEFIPTQTFYNRRYQPRPWTPRPTIQVIRPRPRPQRQAGQLAQLISAV

NKLTMRAVPQQKPRRNRKNKKQKQKQQAPQNNTNQKKQPPKKKPAQKK

KKPGRRERMCMKIENDCIFEVKHEGKVTGYACLVGDKVMKPAHVKGTI

DNADLAKLAFKRSSKYDLECAQIPVHMKSDASKFTHEKPEGYYNWHHG

AVQYSGGRFTIPTGAGKPGDSGRPIFDNKGRVVAIVLGGANEGARTAL

SVVTWNKDIVTKITPEGAEEWSLAIPVMCLLANTTFPCSQPPCTPCCY

EKEPEETLRMLEDNVMRPGYYQLLQASLTCSPHRQRRSTKDNFNVYKA

TRPYLAHCPDCGEGHSCHSPVALERIRNEATDGTLKIQVSLQIGIKTD

DSHDWTKLRYMDNHMPADAERAGLFVRTSAPCTITGTMGHFILARCPK

GETLTVGFTDSRKISHSCTHPFHHDPPVIGREKFHSRPQHGKELPCST

YVQSTAATTEEIEVHMPPDTPDRTLMSQQSGNVKITVNGQTVRYKCNC

GGSNEGLTTTDKVINNCKVDQCHAAVTNHKKWQYNSPLVPRNAELGDR

KGKIHIPFPLANVTCRVPKARNPTVTYGKNQVIMLLYPDHPTLLSYRN

-continued

MGEEPNYQEEWVMHKKEVVLTVPTEGLEVTWGNNEPYKYWPQLSTNGT

AHGHPHEIILYYYELYPTMTVVVVSVATFILLSMVGMAAGMCMCARRR

CITPYELTPGATVPFLLSLICCIRTAKAATYQEAAIYLWNEQQPLFWL

QALIPLAALIVLCNCLRLLPCCCKTLAFLAVMSVGAHTVSAYEHVTVI

PNTVGVPYKTLVNRPGYSPMVLEMELLSVTLEPTLSLDYITCEYKTVI

PSPYVKCCGTAECKDKNLPDYSCKVFTGVYPFMWGGAYCFCDAENTQL

SEAHVEKSESCKTEFASAYRAHTASASAKLRVLYQGNNITVTAYANGD

HAVTVKDAKFIVGPMSSAWTPFDNKIVVYKGDVYNMDYPPFGAGRPGQ

FGDIQSRTPESKDVYANTQLVLQRPAVGTVHVPYSQAPSGFKYWLKER

GASLQHTAPFGCQIATNPVRAVNCAVGNMPISIDIPEAAFTRVVDAPS

LTDMSCEVPACTHSSDFGGVAIIKYAASKKGKCAVHSMTNAVTIREAE

IEVEGNSQLQISFSTALASAEFRVQVCSTQVHCAAECHPPKDHIVNYP

ASHTTLGVQDISATAMSWVQKITGGVGLVVAVAALILIVVLCVSFSR

H"

An exemplary expression vector encoding the structural polyprotein shown above is provided at Genbank Accession No. EU224268 (FIG. 24).

A second exemplary structural polyprotein sequence is provided at Genbank Accession No. ABX40011.1", which is reproduced below:

(SEQ ID NO: 25)

MEFIPTQTFYNRRYQPRPWAPRPTIQVIRPRPRPQRQAGQLAQLISAV

NKLTMRAVPQQKPRRNRKNKKQRQKKQAPQNDPKQKKQPPQKKPAQKK

KKPGRRERMCMKIENDCIFEVKHEGKVMGYACLVGDKVMKPAHVKGTI

DNADLAKLAFKRSSKYDLECAQIPVHMKSDASKFTHEKPEGYYNWHHG

AVQYSGGRFTIPTGAGKPGDSGRPIFDNKGRVVAIVLGGANEGARTAL

SVVTWNKDIVTKITPEGAEEWSLALPVLCLLANTTFPCSQPPCTPCCY

EKEPESTLRMLEDNVMRPGYYQLLKASLTCSPHRQRRSTKDNFNVYKA

TRPYLAHCPDCGEGHSCHSPIALERIRNEATDGTLKIQVSLQIGIKTD

DSHDWTKLRYMDSHTPADAERAGLLVRTSAPCTITGTMGHFILARCPK

GETLTVGFTDSRKISHTCTHPFHHEPPVIGRERFHSRPQHGKELPCST

YVQSTAATAEEIEVHMPPDTPDRTLMTQQSGNVKITVNGQTVRYKCNC

GGSNEGLTTTDKVINNCKIDQCHAAVTNHKNWQYNSPLVPRNAELGDR

KGKIHIPFPLANVTCRVPKARNPTVTYGKNQVTMLLYPDHPTLLSYRN

MGQEPNYHEEWVTHKKEVTLTVPTEGLEVTWGNNEPYKYWPQMSTNGT

AHGHPHEIILYYYELYPTMTVVIVSVASFVLLSMVGTAVGMCVCARRR

CITPYELTPGATVPFLLSLLCCVRTTKAATYYEAAAYLWNEQQPLFWL

QALIPLAALIVLCNCLKLLPCCCKTLAFLAVMSIGAHTVSAYEHVTVI

PNTVGVPYKTLVNRPGYSPMVLEMELQSVTLEPTLSLDYITCEYKTVI

PSPYVKCCGTAECKDKSLPDYSCKVFTGVYPFMWGGAYCFCDAENTQL

SEAHVEKSESCKTEFASAYRAHTASASAKLRVLYQGNNITVAAYANGD

HAVTVKDAKFVVGPMSSAWTPFDNKIVVYKGDVYNMDYPPFGAGRPGQ

-continued

```
FGDIQSRTPESKDVYANTQLVLQRPAAGTVHVPYSQAPSGFKYWLKER

GASLQHTAPFGCQIATNPVRAVNCAVGNIPISIDIPDAAFTRVVDAPS

VTDMSCEVPACTHSSDFGGVAIIKYTASKKGKCAVHSMTNAVTIREAD

VEVEGNSQLQISFSTALASAEFRVQVCSTQVHCAAACHPPKDHIVNYP

ASHTTLGVQDISTTAMSWVQKITGGVGLIVAVAALILIVVLCVSFSRH
```

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the term "vaccine" refers to a formulation which contains VLPs or DNAs, or other gene-based vaccine vectors, of the present invention, which is in a form that is capable of being administered to a vertebrate and which induces a protective immune response sufficient to induce immunity to prevent and/or ameliorate an infection and/or to reduce at least one symptom of an infection and/or to enhance the efficacy of another dose of VLPs or DNA vaccines. Typically, the vaccine comprises a conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses. In certain embodiments, a vaccine can also be a protein. For example, recombinant proteins have been produced by genetically engineering cells to produce one or more foreign genes, which in turn produce proteins that serve as the immunogen.

As used herein, the term "virus-like particle" (VLP) refers to a structure that in at least one attribute resembles a virus but which has not been demonstrated to be infectious. Virus-like particles in accordance with the invention do not carry genetic information encoding for the proteins of the virus-like particles. In general, virus-like particles lack a viral genome and, therefore, are noninfectious. In addition, virus-like particles can often be produced in large quantities by heterologous expression and can be easily purified.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a schematic representation of the CHIKV genome and CHIKV E expression vector used for incorporation of CHIKV E from strains 37997 and LR2006 OPY-1 into pseudotyped lentiviral vectors. The CHIKV genome consists of nonstructural polyproteins NS1, NS2, NS3 and NS4 and structural polyproteins capsid (C) and envelope (E: E3, E2, 6K and E1) (top). The polypeptide E genes from strains 37997 and LR2006 OPY-1 were inserted into an expression vector (bottom). FIG. 1B includes two graphs. The graph on the left shows the infectivity of the indicated pseudotyped lentiviral vectors in several CHIKV-permissive cell lines, including 293A human renal epithelial, HeLa cervical epithelial, Vero renal epithelial, A549 squamous epithelial and baby hamster kidney (BHK) cells. The pseudotyped vectors were standardized by HIV-1 Gag p24 (left) or the indicated concentration of p24 and used to infect 293A cells (right). After incubation with pseudotyped vectors for 24 hours, cells were lysed and luciferase activity was measured. The experiment was performed in triplicate. FIG. 1C includes two graphs that show the pH-dependent entry of CHIKV pseudotyped lentiviral vectors. Pseudotyped lentiviral vectors were incubated in the presence of the indicated amounts of ammonium chloride (left) and chloroquine (right). The experiment was performed in triplicate. Data are presented as the percentage of activity at the indicated dose relative to activity with no treatment. FIG. 1D is a graph showing neutralization measured with pseudotyped lentiviral vectors in sera from mice injected with CHIKV (strain S-27). Sera were incubated at the indicated dilutions with VSV-G, CHIKV strain 37997 or LR2006 OPY-1 E-pseudotyped lentiviral vectors and the mixture infected to 293A cells. Luciferase activity was analyzed 24 hours after infection. The experiment was performed in triplicate. No inhibition was observed with control non-immune antisera.

FIG. 2A provides a schematic representation of CHIKV C-E or E expression vectors used for DNA vaccine and VLP production. The CHIKV structural polyproteins capsid plus envelope (C-E) or E alone from strains 37997 and LR2006 OPY-1 were inserted into an expression vector. 293T cells were transfected with each of the indicated plasmids. Expression was measured 48 h after transfection by Western blotting as described previously (29) with antisera reactive with CHIKV. FIG. 2B includes a graph, Western blot, and electron micrograph. VLPs were purified from the supernatants of 293F cells transfected with C-E expression vector $_{(C\text{-}E37997)}$ (left). The supernatants were harvested 72 hours after transfection followed by OptiPrep density gradient centrifugation. Each fraction was characterized for its buoyant density (left upper panel) and protein content (left lower panel) by Western blot analysis with antisera to CHIKV. The fractionated VLPs were observed by transmission electron microscopy with magnification 20,000× (left, bar 100 nm) (right). FIG. 2C provides a comparison of cryo-EM reconstructions of CHIKV VLP with Sindbis virus showing that CHIKV VLP is structurally similar to alphaviruses. Shaded-surface representation of the 3D density map of CHIKV VLP (left upper panel) and Sindbis virus (right upper panel) viewed along an icosahedral 2-fold axis. The white triangle marks the boundary of an icosahedral asymmetric unit. The numbers show the positions of the icosahedral 2-, 3-, and 5-fold axes limiting an asymmetric unit. The central cross-section through the cryo-EM maps of CHIKV VLP (left lower panel) and Sindbis virus (right lower panel). The orientations of the icosahedral (2-, 3-, and 5-fold) axes as well as the quasi-threefold (q3) axis are shown with white lines. Maps are calculated to 1 8 Å resolution.

FIG. 3C shows results from monkeys immunized with $_{VLP37997}$ or PBS (control) at 0, 4, and 24 weeks. A neutralizing assay was performed with CHIKV strain 37997 (left panel) or LR2006 OPY-1 (right panel) E pseudotyped lentiviral vectors in sera collected from immunized monkeys at 10 days after each immunization. The symbols show the average of the six monkeys and bars show the standard error of the mean. FIG. 3D shows the neutralizing activity against CHIKV LR2006 OPY-1 in immunized monkeys' sera after the 2nd and 3rd immunizations was confirmed by a standard plaque reduction neutralization test (PRNT). The symbols show the average of the six monkeys and bars show the standard error of the mean.

FIG. 4A quantitates results obtained in monkeys injected with PBS (Control) or immunized with $_{VLP37997}$. Monkeys were challenged with $10^{10}$ PFU of the CHIKV strain LR2006 OPY-1 15 weeks after the final boost. The peak viremia at 24 hours after challenge was measured by plaque assay. The serum dilutions started from 1:200 (limit of detection=1000 PFU/ml). Error bars represent the standard error of the mean. FIG. 4B is a graph showing the percentage of monocytes in the monkeys' white blood cells. Monocyte percentage was measured using a hematology analyzer before and 7 days after challenge with CHIKV. Error bars represent the standard error of the mean. A non-parametric two t-test was used for statistical analysis (Control vs. VLPs at 7 days, P=0.0036; Control at 0 days vs. 7 days, P=0.0015; VLPs at 0 days vs. 7 days, P>0.5). FIG. 4C shows the number of viral RNA copies present following passive transfer of purified IgG from a monkey immunized with VLPs (Immune) or a control monkey (Control IgG) into mice (2 mg of total IgG per mouse, n=5 per group). Recipient mice were challenged 24 hours after IgG transfer with a lethal LR2006 OPY-1 challenge (30 PFU) by intradermal injection. The viremia in the mice after challenge was measured by quantitative RT-PCR (limit of detection=40 RNA copies/ml). Error bars represent the standard error of the mean. FIG. 4D shows a survival curve of mice passively transferred with control IgG or CHIKV immunized IgG against lethal LR2006 OPY-1 challenge.

FIG. 7A shows the sequence of the insert (SEQ ID NO:1). FIG. 7B shows the sequence of the entire plasmid sequence (SEQ ID NO: 2).

FIG. 8B shows the sequence of the insert (SEQ ID NO:3). FIG. 8C shows the entire plasmid sequence (SEQ ID NO: 4).

FIG. 9B shows the entire plasmid sequence (SEQ ID NO: 5).

FIG. 10B shows the entire plasmid sequence (SEQ ID NO: 6).

FIG. 12B shows the entire plasmid sequence (SEQ ID NO: 8).

FIG. 13B shows the entire plasmid sequence (SEQ ID NO: 9).

FIG. 14B shows the entire plasmid sequence (SEQ ID NO: 10).

FIG. 15B shows the entire plasmid sequence (SEQ ID NO: 11).

FIG. 16B shows the entire plasmid sequence (SEQ ID NO: 12).

FIG. 18B shows the entire plasmid sequence (SEQ ID NO: 14).

FIG. 19B shows the entire plasmid sequence (SEQ ID NO: 15).

FIG. 20B shows the entire plasmid sequence (SEQ ID NO: 16).

FIG. 21B shows the entire plasmid sequence (SEQ ID NO: 17).

FIG. 24 shows the sequence of Genbank Accession No. EU224268, which is a Cloning vector pCHIKV-LR ic, complete sequence. See, Tsetsarkin, K., Higgs, S., McGee, C. E., De Lamballerie, X., Charrel, R. N. and Vanlandingham, D. L. Infectious clones of Chikungunya virus (La Reunion isolate) for vector competence studies, Vector Borne Zoonotic Dis. 6 (4), 325-337 (2006).

FIG. 25 shows the sequence of Genbank Accession No. EU224270, which is the complete sequence of the Cloning vector pCHIK-37997ic.

DETAILED DESCRIPTION OF THE INVENTION

Figure 1A:
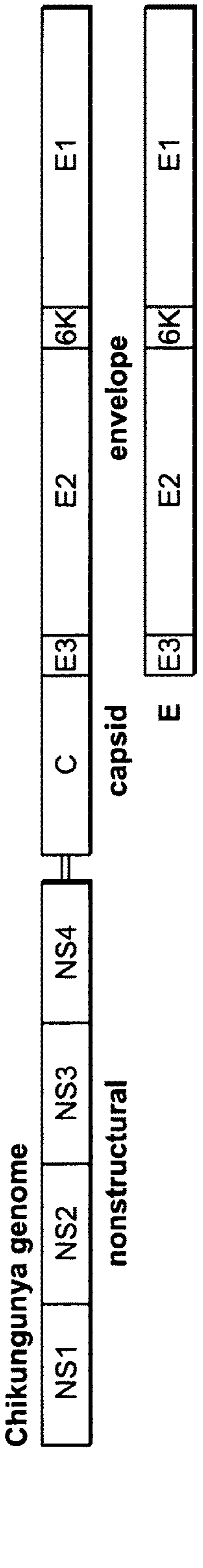
FIGS. 1A-1D show the characterization of CHIKV E pseudotyped lentiviral vectors.

Chikungunya virus (CHIKV) has infected millions of people in Africa, Europe, and Asia since its re-emergence in Kenya in 2004. The evolution and spread of the virus into new geographic areas, and the severity of the disease, present a serious public health threat in the absence of a vaccines or anti-viral therapies. The invention provides compositions and methods for inducing protective immunity. The invention is based, at least in part, on the discovery that a recombinant virus-like particle (VLP) vaccine protects against CHIKV infection in non-human primates. VLPs were generated by expression of viral structural proteins. These had similar buoyant density and morphology to replication-competent virus. Immunization with VLPs elicited neutralizing antibodies against homologous and heterologous envelope. Monkeys immunized with VLPs produced high titer cross-reactive neutralizing antibodies that protected against high dose challenge with emerging epidemic CHIKV. Furthermore, passive transfer of these antibodies from immune monkeys protected against lethal CHIKV challenge in immunodeficient mice, demonstrating that protection is mediated by the humoral immune response. Immunization with the VLP vaccine is a strategy that would prevent the infection and spread of CHIKV and related pathogenic viruses in humans.

Accordingly, the invention provides immunogenic compositions containing one or more alphavirus (e.g., Chikungunya virus) structural polypeptides. In particular, the immunogenic composition (e.g., vaccine) contains envelope or capsid polypeptides sufficient to form a virus-like particle. The invention further provides nucleic acid molecules encoding alphavirus (Chikungunya) structural polypeptides, expression vectors comprising these coding sequences, and methods of using these nucleic acid molecules for the preparation of virus-like particles. In other embodiments, the invention provides DNA vaccines that provide for the expression of one or more viral polypeptides in the cell of a subject.

Immunogenic Compositions

The invention provides compositions and methods for inducing an immunological response in a subject, particularly a human, which involves inoculating the subject with a VLP comprising one or more alphavirus or CHIKV polypeptides, or fragments thereof, in a suitable carrier for the purpose of inducing or enhancing an immune response. In one embodiment, an immune response protects the subject from a CHIKV infection, or inflammatory consequences thereof (e.g., arthritis). The administration of this immunological composition may be used either therapeutically in subjects already experiencing a CHIKV infection, or may be used prophylactically to prevent a CHIKV infection.

In certain embodiments, CHIKV candidate vaccines were developed by comparing the immunogenicity of gene products derived from two disparate strains, the 37997 strain from West Africa and the latest outbreak strain, OPY-1, of the East/Central/South African genotype, to develop CHIKV candidate vaccines. These strains share ~95% amino acid sequence similarity but have distinct biological differences, particularly related to their host range.

VLPs of the invention are useful for preparing vaccines and immunogenic compositions. One important feature of VLPs is the ability to express surface proteins so that the immune system of a vertebrate induces an immune response against said protein. However, not all proteins can be expressed on the surface of VLPs. There may be many reasons why certain proteins are not expressed, or be poorly expressed, on the surface of VLPs. One reason is that said protein is not directed to the membrane of a host cell or that said protein does not have a transmembrane domain.

The preparation of immunogenic compositions and vaccines is known to one skilled in the art. The vaccine includes a VLP comprising one or more CHIKV polypeptides, or fragments thereof. The invention also provides expression vectors encoding one or more CHIKV polypeptides or fragments thereof or variants thereof. Such an immunogenic composition is delivered in vivo in order to induce or enhance an immunological response in a subject, such as a humoral response.

For example, a VLP comprising one or more CHIKV polypeptides, or fragments or variants thereof are delivered in vivo in order to induce an immune response.

Typically vaccines are prepared in an injectable form, either as a liquid solution or as a suspension. Solid forms suitable for injection may also be prepared as emulsions, or with the polypeptides encapsulated in liposomes. Vaccine antigens are usually combined with a pharmaceutically acceptable carrier, which includes any carrier that does not induce the production of antibodies harmful to the subject receiving the carrier. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

The VLP comprising one or more CHIKV polypeptides, or fragments or variants thereof may be administered in combination with an adjuvant (e.g., Ribi). Adjuvants are immunostimulating agents that enhance vaccine effectiveness. If desired, the VLP comprising one or more CHIKV polypeptides or fragments or variants thereof are administered in combination with an adjuvant that enhances the effectiveness of the immune response generated against the antigen of interest. Effective adjuvants include, but are not limited to, aluminum salts such as aluminum hydroxide and aluminum phosphate, muramyl peptides, bacterial cell wall components, saponin adjuvants, and other substances that act as immunostimulating agents to enhance the effectiveness of the composition.

Immunogenic compositions, i.e. the VLP comprising one or more CHIKV polypeptides, pharmaceutically acceptable carrier and adjuvant, also typically contain diluents, such as water, saline, glycerol, ethanol. Auxiliary substances may also be present, such as wetting or emulsifying agents, pH buffering substances, and the like. Proteins may be formulated into the vaccine as neutral or salt forms. The immunogenic compositions are typically administered parenterally, by injection; such injection may be either subcutaneously or intramuscularly. Additional formulations are suitable for other forms of administration, such as by suppository or orally. Oral compositions may be administered as a solution, suspension, tablet, pill, capsule, or sustained release formulation.

Immunogenic compositions are administered in a manner compatible with the dose formulation. The immunogenic composition comprises an immunologically effective amount of the VLP and other previously mentioned components. By an immunologically effective amount is meant a single dose, or a composition administered in a multiple dose schedule, that is effective for the treatment or prevention of an infection. The dose administered will vary, depending on the subject to be treated, the subject's health and physical condition, the capacity of the subject's immune system to produce antibodies, the degree of protection desired, and other relevant factors. Precise amounts of the active ingredient required will depend on the judgement of the practitioner, but typically range between 5 μg to 250 μg of antigen per dose.

The invention provides a VLP for use in treating or preventing an alphavirus infection (e.g., Chikungunya infection).

Polypeptide Expression

In general, VLPs comprising one or more CHIKV polypeptides of the invention may be produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, COS cells). Such cells are available from a wide range of sources (e.g., the American Type Culture Collection, Rockland, Md.; also, see, e.g., Ausubel et al., supra). Non limiting examples of insect cells are, *Spodoptera frugiperda* (Sf) cells, e.g. Sf9, Sf21, *Trichoplusia ni* cells, e.g. High Five cells, and *Drosophila* S2 cells. Examples of fungi (including yeast) host cells are *S. cerevisiae, Kluyveromyces lactis* (*K lactis*), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO) cells, human embryonic kidney (HEK) cells, African green monkey cells, CV1 cells, HeLa cells, MDCK cells, Vero and Hep-2 cells. *Xenopus laevis* oocytes, or other cells of amphibian origin, may also be used. Prokaryotic host cells include bacterial cells, for example, *E. coli, B. subtilis*, and mycobacteria.

Methods of cloning said proteins are known in the art. For example, the gene encoding a specific CHIKV or any alphavirus protein can be isolated by RT-PCR from polyadenylated mRNA extracted from cells which had been infected with said virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

The invention further provides nucleotides that encode proteins, including chimeric molecules, cloned into an expression vector that can be expressed in a cell that provides for the formation of VLPs. An "expression vector" is a vector, such as a plasmid, that is capable of promoting expression, as well as replication of a nucleic acid incorporated therein. Typically, the nucleic acid molecule to be expressed is "operably linked" to a promoter and/or enhancer, and is subject to transcription regulatory control by the promoter and/or enhancer. In one embodiment, the VLP comprises one or more alphavirus envelope proteins, and in particular CHIKV virus envelope proteins. In another embodiment, the one or more envelope proteins are any one or more of E3, E2, 6K and E1. In another embodiment, the VLP further comprises a CHIKV virus capsid protein. In related embodiments, the Chikungunya virus capsid protein is used. In still another embodiment, the VLPs are comprised of capsid, E3, E2, 6K and E1. In another embodiment, the expression vector is a mammalian expression vector or baculovirus vector.

The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Constructs and/or vectors provided herein comprise CHIKV polynucleotides that encode structural polypeptides, including envelope proteins or capsid proteins or portions thereof as described herein. The vector may be, for example, a phage, plasmid, viral, or retroviral vector. The constructs and/or vectors that comprise the nucleotides should be operatively linked to an appropriate promoter, such as the CMV promoter, phage lambda PL promoter, the *E. coli* lac, phoA and tac promoters, the SV40 early and late promoters, and promoters of retroviral LTRs are non-limiting examples.

Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan.

Recombinant constructs can be prepared and used to transfect, infect, or transform and can express viral proteins, including those described herein, into eukaryotic cells and/or prokaryotic cells. Thus, the invention provides for host cells which comprise a vector (or vectors) that contain nucleic acids which code for CHIKV structural genes, including capsid, E3, E2, 6K, and E1 or portions thereof, and/or any chimeric molecule described above, and permit the expression of CHIKV structural genes, including capsid E3, E2, 6K, and E1, or portions thereof, and/or any chimeric molecule described above in said host cell under conditions which allow the formation of VLPs.

In one embodiment, said vector is a recombinant baculovirus. In another embodiment, said recombinant baculovirus is transfected into an insect cell. In a preferred embodiment, said cell is an insect cell. In another embodiment, said insect cell is a Sf9 cell.

In another embodiment, said vector and/or host cell comprise nucleotides that encode CHIKV genes, including capsid, E3, E2, 6K, and E1, or portions thereof as described herein. In another embodiment, said vector and/or host cell consists essentially of CHIKV capsid E3, E2, 6K, and E1, or portions thereof as described herein. In a further embodiment, said vector and/or host cell consists of CHIKV protein comprising capsid, E3, E2, 6K, and E1, or portions thereof, as described herein. These vector and/or host cell contain CHIKV core E3, E2, 6K, and E1, or portions thereof, as described herein, and may contain additional cellular constituents such as cellular proteins, baculovirus proteins, lipids, carbohydrates etc.

One particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, a recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Once a recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

CHIKV Polypeptides and Analogs

The invention provides VLPs comprising one or more CHIKV polypeptides. Also included in the invention are VLPs comprising one or more CHIKV polypeptides or fragments thereof that are modified in ways that enhance or do not inhibit their ability to modulate an immune response. In one embodiment, the invention provides methods for optimizing a CHIKV amino acid sequence or nucleic acid sequence by producing an alteration. Such alterations may include certain mutations, deletions, insertions, or post-translational modifications. The invention further includes analogs of any naturally-occurring polypeptide of the invention. Analogs can differ from the naturally-occurring the polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino, acid sequence of the invention. The length of sequence comparison is at least 10, 13, 15 amino acid residues, preferably at least 25 amino acid residues, and more preferably more than 35 amino acid residues.

Alterations of a alphavirus or CHIKV polypeptide include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

In one embodiment, the invention provides polypeptide variants that differ from a reference polypeptide. The term "variant" refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software. Desirably, variants show substantial biological activity. In one embodiment, a protein variant forms a VLP and elicits an antibody response when administered to a subject.

Natural variants can occur due to mutations in the proteins. These mutations may lead to antigenic variability within individual groups of infectious agents, for example CHIKV. Thus, a person infected with a particular strain develops antibody against that virus, as newer virus strains appear, the antibodies against the older strains no longer recognize the newer virus and reinfection can occur. The invention encompasses all antigenic and genetic variability of proteins from infectious agents for making VLPs.

Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., .beta. or .gamma. amino acids.

In addition to full-length polypeptides, the invention also includes fragments of any one of the polypeptides of the invention. As used herein, the term "a fragment" means at least 5, 10, 13, or 15. In other embodiments a fragment is at least 20 contiguous amino acids, at least 30 contiguous amino acids, or at least 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs having a chemical structure designed to mimic CHIKV VLPs or one or more CHIKV polypeptides functional activity can be administered according to methods of the invention. CHIKV analogs may exceed the physiological activity of native CHIKV. Methods of analog design are well known in the art, and synthesis of analogs can be carried out according to such methods by modifying the chemical structures such that the resultant analogs exhibit the immunomodulatory activity of a native CHIKV polypeptide. These chemical modifications include, but are not limited to, substituting alternative R groups and varying the degree of saturation at specific carbon atoms of the native CHIKV molecule. Preferably, the analogs are relatively resistant to in vivo degradation, resulting in a more prolonged therapeutic effect upon administration. Assays for measuring functional activity include, but are not limited to, those described in the Examples below.

CHIKV Polynucleotides

In general, the invention includes any nucleic acid sequence encoding a VLP comprising one or more CHIKV polypeptides or a fragment thereof, where the fragment induces an immune response. An isolated nucleic acid molecule is can be manipulated by recombinant DNA techniques well known in the art. Thus, a nucleotide sequence contained in a vector in which 5' and 3' restriction sites are known, or for which polymerase chain reaction (PCR) primer sequences have been disclosed, is considered isolated, but a nucleic acid sequence existing in its native state in its natural host is not. In certain exemplary embodiments, the vector comprises Chikungunya$_{37997}$ or Chikungunya$_{OPY\text{-}1}$ nucleic acid segments, or fragments thereof. The vector may further comprise a CMV/R promoter. The vector may also comprise the capsid protein, or a fragment thereof.

In other exemplary embodiments, the vector comprises an envelope protein selected from the group consisting of E3, E2, 6K, and E1. In certain examples, the vaccine may comprise capsid, E3, E2, 6K and E1. In other examples, the vaccine may comprise E3, E2, 6K and E1.

According to certain preferred embodiments of the invention, C-Env$_{37997}$ is set forth as SEQ ID NO:1; Env$_{37997}$ is set forth as SEQ ID NO:19; C-Env$_{OPY\text{-}1}$ is set forth as SEQ ID NO:3; Env$_{OPY\text{-}1}$ is set forth as SEQ ID NO: 20.

Shown below is the nucleotide sequence corresponding to the capsid (SEQ ID NO: 21) and E3, E2, 6K and E1 (SEQ ID NO: 19) of the CMV/R-CHIKV C-E3-E2-6K-E1 plasmid (Strain 37997). The CMV/R expression vector is described, for example, in U.S. Pat. No. 7,094,598, which is incorporated herein in its entirety.

```
E3-E2-6K-E1
                                         SEQ ID NO: 19
Atgagcctcgccctcccggtcttgtgcctgttggcaaacactacattc

ccctgctctcagccgccttgcacaccctgctgctacgaaaaggaaccg

gaaagcaccttgcgcatgatgaggacaacgtgatgagacccggatact

accagctactaaaagcatcgctgacttgctctccccaccgccaaagac

gcagtactaaggacaattttaatgtctataaagccacaagaccatatc

tagctcattgtcctgactgcggagaagggcattcgtgccacagcccta
```

-continued tcgcattggagcgcatcagaaatgaagcaacggacggaacgctgaaaa tccaggtctctttgcagatcgggataaagacagatgacagccacgatt ggaccaagctgcgctatatggatagccatacgccagcggacgcggagc gagccggattgcttgtaaggacttcagcaccgtgcacgatcaccggga ccatgggacactttattctcgcccgatgcccgaaaggagagacgctga cagtgggatttacggacagcagaaagatcagccacacatgcacacacc cgttccatcatgaaccacctgtgataggtagggagaggttccactctc gaccacaacatggtaaagagttaccttgcagcacgtacgtgcagagca ccgctgccactgctgaggagatagaggtgcatatgcccccagatactc ctgaccgcacgctgatgacgcagcagtctggcaacgtgaagatcacag ttaatgggcagacggtgcggtacaagtgcaactgcggtggctcaaacg agggactgacaaccacagacaaagtgatcaataactgcaaaattgatc agtgccatgctgcagtcactaatcacaagaattggcaatacaactccc ctttagtcccgcgcaacgctgaactcggggaccgtaaaggaaagatcc acatcccattcccattggcaaacgtgacttgcagagtgccaaaagcaa gaaaccctacagtaacttacggaaaaaaccaagtcaccatgctgctgt atcctgaccatccgacactcttgtcttaccgtaacatgggacaggaac caaattaccacgaggagtgggtgacacacaagaaggaggttaccttga ccgtgcctactgagggtctggaggtcacttggggcaacaacgaaccat acaagtactggccgcagatgtctacgaacggtactgctcatggtcacc cacatgagataatcttgtactattatgagctgtaccccactatgactg tagtcattgtgtcggtggcctcgttcgtgcttctgtcgatggtgggca cagcagtgggaatgtgtgtgtgcgcacggcgcagatgcattacaccat atgaattaacaccaggagccactgttcccttcctgctcagcctgctat gctgcgtcagaacgaccaaggcggccacatattacgaggctgcggcat atctatggaacgaacagcagcccctgttctggttgcaggctcttatcc cgctggccgccttgatcgtcctgtgcaactgtctgaaactcttgccat gctgctgtaagaccctggctttttagccgtaatgagcatcggtgccc acactgtgagcgcgtacgaacacgtaacagtgatcccgaacacggtgg gagtaccgtataagactcttgtcaacagaccgggttacagccccatgg tgttggagatggagctacaatcagtcaccttggaaccaacactgtcac ttgactacatcacgtgcgagtacaaaactgtcatcccctccccgtacg tgaagtgctgtggtacagcagagtgcaaggacaagagcctaccagact acagctgcaaggtctttactggagtctacccatttatgtggggcggcg cctactgcttttgcgacgccgaaaatacgcaattgagcgaggcacatg tagagaaatctgaatcttgcaaaacagagtttgcatcggcctacagag cccacaccgcatcggcgtcggcgaagctccgcgtcctttaccaaggaa acaacattaccgtagctgcctacgctaacggtgaccatgccgtcacag taaaggacgccaagtttgtcgtgggcccaatgtcctccgcctggacac cttttgacaacaaaatcgtggtgtacaaaggcgacgtctacaacatgg -continued actacccaccttttggcgcaggaagaccaggacaatttggtgacattc aaagtcgtacaccggaaagtaaagacgtttatgccaacactcagttgg tactacagaggccagcagcaggcacggtacatgtaccatactctcagg caccatctggcttcaagtattggctgaaggaacgaggagcatcgctac agcacacggcaccgttcggttgccagattgcgacaaacccggtaagag ctgtaaattgcgctgtggggaacataccaatttccatcgacataccgg atgcggcctttactagggttgtcgatgcaccctctgtaacggacatgt catgcgaagtaccagcctgcactcactcctccgactttgggggcgtcg ccatcatcaaatacacagctagcaagaaaggtaaatgtgcagtacatt cgatgaccaacgccgttaccattcgagaagccgacgtagaagtagagg ggaactcccagctgcaaatatccttctcaacagccctggcaagcgccg agtttcgcgtgcaagtgtgctccacacaagtacactgcgcagccgcat gccaccctccaaaggaccacatagtcaattacccagcatcacacacca cccttggggtccaggatatatccacaacggcaatgtcttgggtgcaga agattacgggaggagtaggattaattgttgctgttgctgccttaattt taattgtggtgctatgcgtgtcgtttagcaggcac Core

SEQ ID NO: 21

Atggagttcatcccgacgcaaactttctataacagaaggtaccaaccc cgaccctgggccccacgccctacaattcaagtaattagacctagacca cgtccacagaggcaggctgggcaactcgcccagctgatctccgcagtc aacaaattgaccatgcgcgcggtacctcaacagaagcctcgcagaaat cggaaaaacaagaagcaaaggcagaagaagcaggcgccgcaaaacgac ccaaagcaaaagaagcaaccaccacaaaagaagccggctcaaaagaag aagaaaccaggccgtagggagagaatgtgcatgaaaattgaaaatgat tgcatcttcgaagtcaagcatgaaggcaaagtgatgggctacgcatgc ctggtgggggataaagtaatgaaaccagcacatgtgaagggaactatc gacaatgccgatctggctaaactggcctttaagcggtcgtctaaatac gatcttgaatgtgcacagataccggtgcacatgaagtctgatgcctcg aagtttacccacgagaaacccgaggggtactataactggcatcacgga gcagtgcagtattcaggaggccggttcactatcccgacgggtgcaggc aagccgggagacagcggcagaccgatcttcgacaacaaaggacgggtg gtggccatcgtcctaggaggggccaacgaaggtgcccgcacggccctc tccgtggtgacgtggaacaaagacatcgtcacaaaaattacccctgag ggagccgaagagtgg Shown below is the nucleotide sequence corresponding to the capsid (SEQ ID NO: 22) and E3, E2, 6K and E1 (SEQ ID NO: 20) of the CMV/R-CHIKV C-E3-E2-6K-E1 plasmid (Strain OPY-1).

E3-E2-6K-E1

SEQ ID NO: 20

Atgagtcttgccatcccagttatgtgcctgttggcaaacaccacgttc ccctgctcccagccccccttgcacgccctgctgctacgaaaaggaaccg -continued

```
gaggaaaccctacgcatgcrtgaggacaacgtcatgagacctgggtac
tatcagctgctacaagcatccttaacatgttctccccaccgccagcga
cgcagcaccaaggacaacttcaatgtctataaagccacaagaccatac
ttagctcactgtcccgactgtggagaagggcactcgtgccatagtccc
gtagcactagaacgcatcagaaatgaagcgacagacgggacgctgaaa
atccaggtctccttgcaaatcggaataaagacggatgacagccacgat
tggaccaagctgcgttatatggacaaccacatgccagcagacgcagag
agggcggggctatttgtaagaacatcagcaccgtgtacgattactgga
caatgggacacttcatcctggcccgatgtccaaaaggggaaactctga
cggtgggattcactgacagtaggaagattagtcactcatgtacgcacc
catttcaccacgaccctcctgtgataggtcgggaaaaattccattccc
gaccgcagcacggtaaagagctaccttgcagcacgtacgtgcagagca
ccgccgcaactaccgaggagatagaggtacacatgcccccagacaccc
ctgatcgcacattaatgtcacaacagtccggcaacgtaaagatcacag
tcaatggccagacggtgcggtacaagtgtaattgcggtggctcaaatg
aaggactaacaactacagacaaagtgattaataactgcaaggttgatc
aatgtcatgccgcggtcaccaatcacaaaaagtggcagtataactccc
ctctggtcccgcgtaatgctgaacttggggaccgaaaaggaaaaattc
acatcccgtttccgctggcaaatgtaacatgcagggtgcctaaagcaa
ggaaccccaccgtgacgtacgggaaaaaccaagtcatcatgctactgt
atcctgaccacccaacactcctgtcctaccggaatatgggagaagaac
caaactatcaagaagagtgggtgatgcataagaaggaagtcgtgctaa
ccgtgccgactgaagggctcgaggtcacgtggggcaacaacgagccgt
ataagtattggccgcagttatctacaaacggtacagcccatggccacc
cgcatgagataattctgtattattatgagctgtaccccactatgactg
tagtagttgtgtcagtggccacgttcatactcctgtcgatggtgggta
tggcagcggggatgtgcatgtgtgcacgacgcagatgcatcacaccgt
atgaactgacaccaggagctaccgtccctttcctgcttagcctaatat
gctgcatcagaacagctaaagcggccacataccaagaggctgcgatat
acctgtggaacgagcagcaacctttgttttggctacaagcccttattc
cgctggcagccctgattgttctatgcaactgtctgagactcttaccat
gctgctgtaaaacgttggctttttttagccgtaatgagcgtcggtgccc
acactgtgagcgcgtacgaacacgtaacagtgatcccgaacacggtgg
gagtaccgtataagactctagtcaatagacctggctacagccccatgg
tattggagatggaactactgtcagtcactttggagccaacactatcgc
ttgattacatcacgtgcgagtacaaaaccgtcatcccgtctccgtacg
tgaagtgctgcggtacagcagagtgcaaggacaaaaacctacctgact
acagctgtaaggtcttcaccggcgtctacccatttatgtggggcggcg
cctactgcttctgcgacgctgaaaacacgcagttgagcgaagcacacg
tggagaagtccgaatcatgcaaaacagaatttgcatcagcatacaggg
ctcataccgcatctgcatcagctaagctccgcgtcctttaccaaggaa
```

-continued

```
ataacatcactgtaactgcctatgcaaacggcgaccatgccgtcacag
ttaaggacgccaaattcattgtggggccaatgtcttcagcctggacac
ctttcgacaacaaaattgtggtgtacaaaggtgacgtctataacatgg
actacccgccctttggcgcaggaagaccaggacaatttggcgatatcc
aaagtcgcacacctgagagtaaagacgtctatgctaatacacaactgg
tactgcagagaccggctgtgggtacggtacacgtgccatactctcagg
caccatctggctttaagtattggctaaaagaacgcggggcgtcgctgc
agcacacagcaccatttggctgccaaatagcaacaaacccggtaagag
cggtgaactgcgccgtagggaacatgcccatctccatcgacataccgg
aagcggccttcactagggtcgtcgacgcgccctctttaacggacatgt
cgtgcgaggtaccagcctgcacccattcctcagactttgggggcgtcg
ccattattaaatatgcagccagcaagaaaggcaagtgtgcggtgcatt
cgatgactaacgccgtcactattcgggaagctgagatagaagttgaag
ggaattctcagctgcaaatctctttctcgacggccttagccagcgccg
aattccgcgtacaagtctgttctacacaagtacactgtgcagccgagt
gccacccccccgaaggaccacatagtcaactacccggcgtcacatacca
ccctcggggtccaggacatctccgctacggcgatgtcatgggtgcaga
agatcacgggaggtgtgggactggttgttgctgttgccgcactgattc
taatcgtggtgctatgcgtgtcgttcagcaggcac
```

Core

SEQ ID NO: 22

```
Atggagttcatcccaacccaaactttttacaataggaggtaccagcct
cgaccctggactccgcgccctactatccaagtcatcaggcccagaccg
cgccctcagaggcaagctgggcaacttgcccagctgatctcagcagtt
aataaactgacaatgcgcgcggtaccacaacagaagccacgcaggaat
cggaagaataagaagcaaaagcaaaaacaacaggcgccacaaaacaac
acaaatcaaaagaagcagccacctaaaaagaaaccggctcaaaagaaa
aagaagccgggccgcagagagaggatgtgcatgaaaatcgaaaatgat
tgtattttcgaagtcaagcacgaaggtaaggtaacaggttacgcgtgc
ctggtgggggacaaagtaatgaaaccagcacacgtaaaggggaccatc
gataacgcggacctggccaaactggcctttaagcggtcatctaagtat
gaccttgaatgcgcgcagatacccgtgcacatgaagtccgacgcttcg
aagttcacccatgagaaaccggaggggtactacaactggcaccacgga
gcagtacagtactcaggaggccggttcaccatccctacaggtgctggc
aaaccaggggacagcggcagaccgatcttcgacaacaagggacgcgtg
gtggccatagtcttaggaggagctaatgaaggagcccgtacagccctc
tcggtggtgacctggaataaagacattgtcactaaaatcacccccgag
gggccgaagagtgg
```

In a particular embodiment, a nucleic acid molecule set forth as SEQ ID NO: 1, 19, 3 or 20 includes a nucleotide sequence encoding a polypeptide having at least about 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or more identity (e.g., when compared to the overall length of the amino acid sequence) to a polypeptide encoding an envelope protein selected from capsid, E3, E2, 6K and E1 or E3, E2, 6K and E1.

In some embodiments of the invention proteins may comprise mutations containing alterations which produce silent substitutions, additions, or deletions, but do not alter the properties or activities of the encoded protein or how the proteins are made. Nucleotide variants can be produced for a variety of reasons, e.g., to optimize codon expression for a particular host See U.S. patent publication 2005/0118191, herein incorporated by reference in its entirety for all purposes.

In addition, the nucleotides can be sequenced to ensure that the correct coding regions were cloned and do not contain any unwanted mutations. The nucleotides can be subcloned into an expression vector (e.g. baculovirus) for expression in any cell. A person with skill in the art understands that various subcloning methods are available and are possible.

An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, as the term is used herein, because it is readily manipulatable by standard techniques known to those of ordinary skill in the art.

CHIKV VLP Production

The invention also provides constructs and methods for producing a VLP comprising CHIKV polypeptides, or fragments thereof, as well as compositions and methods that increase the efficiency of VLP production. For example, the addition of leader sequences to the CHIKV capsid, E3, E2, 6K, and E1 or portions thereof, that can improve the efficiency of protein transporting within the cell. In another example, a heterologous signal sequence can be fused to the CHIKV capsid, E3, E2, 6K, and E1 or portions thereof. In one embodiment, the signal sequence can be derived from the gene of an insect cell. Another method to increase efficiency of VLP production is to codon optimize the nucleotides that encode CHIKV capsid, E3, E2, 6K, and E1 or portions thereof, for a specific cell type.

Methods of cloning said proteins are known in the art. For example, the gene encoding a specific CHIKV or any alphavirus protein can be isolated by RT-PCR from polyadenylated mRNA extracted from cells which had been infected with said virus. The resulting gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode proteins, including chimeric molecules, cloned into an expression vector that can be expressed in a cell that induces the formation of VLPs of the invention. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, the VLP comprises one or more alphavirus envelope proteins, and in particular CHIKV virus envelope proteins. In another embodiment, the one or more envelope proteins are selected from the group consisting of E3, E2, 6K and E1. In another embodiment, the VLP comprises a CHIKV virus capsid protein. In related embodiments, the Chikungunya virus capsid protein is used. In another embodiment, the VLPs are comprised of E3, E2, 6K and E1. In still another embodiment, the VLPs are comprised of capsid, E3, E2, 6K and E1. In another embodiment, the expression vector is a baculovirus vector.

The invention also provides methods of producing a VLP comprising CHIKV polypeptides, or fragments thereof. In one example, the method involves expressing in a cell a polynucleotide encoding a CHIKV polypeptide and culturing said cell, thereby producing VLPs. In one embodiment, a cell (e.g., human cell) is infected with a DNA vaccine, where the DNA vaccine is a DNA vector, comprising a nucleic acid segment encoding an alphavirus capsid protein or one or more alphavirus envelope proteins, or fragments thereof to produce an alphavirus VLP. In particular, the alphavirus is CHIKV.

Depending on the expression system and host cell selected, the VLPs are produced by growing host cells transformed by an expression vector under conditions whereby the recombinant proteins are expressed and VLPs are formed. In one embodiment, the invention comprises a method of producing a VLP, that involves transfecting vectors encoding at least one alphavirus protein into a suitable host cell and expressing said alphavirus protein under conditions that allow VLP formation. In another embodiment, the eukaryotic cell is selected from the group consisting of, yeast, insect, amphibian, avian or mammalian cells. The selection of the appropriate growth conditions is within the skill or a person with skill of one of ordinary skill in the art.

Methods to grow cells that produce VLPs of the invention include, but are not limited to, batch, batch-fed, continuous and perfusion cell culture techniques. In one embodiment, a cell comprising a CHIKV or alphavirus polynucleotide is grown in a bioreactor or fermentation chamber where cells propagate and express protein (e.g. recombinant proteins) for purification and isolation. Typically, cell culture is performed under sterile, controlled temperature and atmospheric conditions. A bioreactor is a chamber used to culture cells in which environmental conditions such as temperature, atmosphere, agitation and/or pH can be monitored. In one embodiment, the bioreactor is a stainless steel chamber. In another embodiment, said bioreactor is a pre-sterilized plastic bag (e.g. Cellbag®, Wave Biotech, Bridgewater, N.J.). In other embodiment, said pre-sterilized plastic bags are about 50 L to 1000 L bags.

The VLPs are isolated using methods that preserve the integrity thereof, such as by gradient centrifugation, e.g., cesium chloride, sucrose and iodixanol, as well as standard purification techniques including, e.g., ion exchange and gel filtration chromatography.

The following is an example of how VLPs of the invention can be made, isolated and purified. A person of skill in the art appreciates that there are additional methods that can be used to make and purify VLPs. Accordingly, the invention is not limited to the methods described herein.

In general, production of VLPs of the invention is accomplished by seeding a mammalian cell (e.g., human embryonic kidney (293T) cells) or Sf9 cells (non-infected) into shaker flasks, allowing the cells to expand and scaling up as the cells grow and multiply (for example from a 125-ml flask to a 50 L Wave bag). The medium used to grow the cells is formulated for the appropriate cell line (preferably serum free media, e.g. insect medium ExCell-420, JRH). Next, the cells are transfected or infected with an appropriate vector (e.g., mammalian expression vector or for SF (cells recombinant baculovirus at the most efficient multiplicity of infection (e.g. from about 1 to about 3 plaque forming units per cell). The polynucleotides, or portions thereof, are expressed in the cells where they self assemble into VLPs and are secreted from the cells approximately 24 to 72 hours post infection. Usually, transfection or infection is most efficient when the cells are in mid-log phase of growth ($4\text{-}8.\times10^6$ cells/ml) and are at least about 90% viable.

VLPs of the invention are harvested approximately 48 to 120 hours post infection, when the levels of VLPs in the cell culture medium are near the maximum but before extensive cell lysis. The cell density and viability at the time of harvest can be about $0.5\times10^6$ cells/ml to about $1.5\times10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid VLP aggregation. The removal of cell and cellular debris from the cell culture medium containing VLPs of the invention can be accomplished by tangential flow filtration (TFF) with a single use, pre-sterilized hollow fiber 0.5 or 1.00 μm filter cartridge or a similar device.

Next, VLPs in the clarified culture medium are concentrated by ultrafiltration using a disposable, pre-sterilized 500,000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltered VLPs can be furthered purified on a 20% to 60% discontinuous sucrose gradient in pH 7.2 PBS buffer with 0.5 M NaCl by centrifugation at 6,500×g for 18 hours at about 4 C to about 10 C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluded via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or .beta.-propiolactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25 C to about 27 C. The baculovirus can also be inactivated by incubating the sample containing the VLPs at 0.05% BPL at 4 C for 3 days, then at 37 C for one hour.

After the inactivation/removal step, the product comprising VLPs can be run through another diafiltration step to remove any reagent from the inactivation step and/or any residual sucrose, and to place the VLPs into the desired buffer (e.g. PBS). The solution comprising VLPs can be sterilized by methods known in the art (e.g. sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

In certain embodiments, a DNA vaccine or VLP comprises agents, such as nucleic acid molecules, siRNA, microRNA, chemotherapeutic agents, imaging agents, and/or other agents that need to be delivered to a patient.

Accordingly, the present invention provides methods of treating viral diseases and/or disorders or symptoms thereof which comprise administering a therapeutically effective amount of a pharmaceutical composition comprising a VLP or DNA of the formulae herein to a subject (e.g., a mammal such as a human). Thus, one embodiment is a method of treating a subject suffering from or susceptible to a viral infection, viral disease or disorder or symptom thereof. The method includes the step of administering to the mammal a therapeutic or prophylactic amount of an amount of a compound herein sufficient to treat the disease or disorder or symptom thereof, under conditions such that the disease or disorder is prevented or treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the agents herein, such as a VLP or DNA of a formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk"

can be made by any objective or subjective determination by a diagnostic test or opinion of a subject or health care provider (e.g., genetic test, enzyme or protein marker, Marker (as defined herein), family history, and the like). The agents herein may be also used in the treatment of any other disorders in which an alphavirus may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with an alphavirus, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Pharmaceutical Compositions and Administration

The invention features pharmaceutical compositions that comprise VLPs of an alphavirus as described herein. The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and a VLP of the invention. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful as a vaccine and/or antigenic compositions for inducing a protective immune response in a vertebrate.

In particular embodiments, the invention encompasses an antigenic formulation comprising VLPs which comprises at least one viral protein, for example one alphavirus protein. The alphavirus may be selected from the group consisting of, but not limited to, Chikungunya virus, Sindbis virus, Eastern equine encephalitis (EEE) virus, Western equine encephalitis (WEE) virus, and Venezuelan equine encephalitis (VEE) virus.

In certain preferred embodiments, the pharmaceutical composition comprises VLPs of Chikungunya virus, and a pharmaceutically acceptable carrier. In other certain preferred embodiments, the pharmaceutical composition comprises VLPs of Chikungunya virus, an adjuvant, and a pharmaceutically acceptable carrier.

In one embodiment, the VLPs are comprised of Chikungunya virus envelope proteins, for example, the envelope proteins can be selected from the group consisting of E3, E2, 6K and E1. In another embodiment, the pharmaceutical composition further comprises a Chikungunya virus capsid protein. The Chikungunya virus capsid protein is, in certain examples, a capsid protein. In certain examples, the VLPs are comprised of E3, E2, 6K and E1. In other examples, the VLPs are comprised of capsid, E3, E2, 6K and E1.

The invention also encompasses a vaccine formulation comprising VLPs that comprise at least one viral protein, for example one alphavirus protein. The alphavirus may be selected from the group consisting of, but not limited to, Chikungunya virus, Sindbis virus, Eastern equine encephalitis (EEE) virus, Western equine encephalitis (WEE) virus, and Venezuelan equine encephalitis (VEE) virus.

In certain preferred embodiments, the vaccine composition comprises VLPs of Chikungunya virus, and a pharmaceutically acceptable carrier. In other certain preferred embodiments, the vaccine composition comprises VLPs of Chikungunya virus, an adjuvant, and a pharmaceutically acceptable carrier. In one embodiment, the vaccine composition comprises VLPs of Chikungunya virus envelope proteins, for example, the envelope proteins can be selected from the group consisting of E3, E2, 6K and E1. In another embodiment, the vaccine composition further comprises a Chikungunya virus capsid protein and a pharmaceutically acceptable carrier or excipient. The Chikungunya virus capsid protein is, in certain examples, a capsid protein. In certain examples, the VLPs are comprised of E3, E2, 6K and E1. In other examples, the VLPs are comprised of capsid, E3, E2, 6K and E1.

Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

In certain embodiments, the VLP composition is supplied in liquid form, for example in a sealed container indicating the quantity and concentration of the VLP composition. Preferably, the liquid form of the VLP composition is supplied in a hermetically sealed container at least about 50 μg/ml, more preferably at least about 100 μg/ml, at least about 200 μg/ml, at least 500 μg/ml, or at least 1 mg/ml.

Generally, VLPs or DNA vaccines of the invention are administered in an effective amount or quantity (as described herein) sufficient to stimulate an immune response against one or more strains of a virus a described here, for example an alphavirus, e.g. CHIKV. Preferably, administration of the VLP of the invention elicits immunity against a virus, for example an alphavirus, in particular example CHIKV. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract or small particle aerosol (less than 10 microns) or spray into the lower respiratory tract. While any of the above routes of delivery results in an immune response, intranasal administration confers the added benefit of eliciting mucosal immunity at the site of entry of many viruses, including alphaviruses, for example CHIKV.

Thus, the invention also comprises a method of formulating a vaccine or antigenic composition that induces immunity to an infection or at least one symptom thereof to a mammal, comprising adding to said formulation an effective dose of VLPs, e.g. CHIKV VLP. In one embodiment, the infection is an alphavirus infection, for example, but not limited to, Chikungunya virus, Sindbis virus, Eastern equine encephalitis (EEE) virus, Western equine encephalitis (WEE) virus, and Venezuelan equine encephalitis (VEE) virus.

In certain cases, stimulation of immunity with a single dose is preferred, however additional dosages can be also be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against infections. Similarly, adults who are particularly susceptible to repeated or serious infections, such as, for example, health care workers, day care workers, family members of young children, the elderly, and individuals with compromised cardiopulmonary function or immune systems may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Prime Boost

The present methods also include a variety of prime-boost regimens. In these methods, one or more priming immunizations is followed by one or more boosting immunizations. The actual immunogenic composition can be the same or different for each immunization and the type of immunogenic composition (e.g., containing protein or expression vector), the route, and formulation of the immunogens can also be varied.

For example, in one embodiment, the prime comprises administering a DNA or gene-based vaccine as described herein and the boost comprises administering a VLP as described herein. In another embodiment, the prime comprises administering a VLP as described herein and the boost comprises administering a DNA or other gene-based vaccine as described herein.

One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

Methods of administering a composition comprising VLPs and/or DNA vaccines (vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present invention are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition comprising VLPs of the invention may induce an antibody or other immune response that is substantially higher than other routes of administration. In another embodiment, intranasal or other mucosal routes of administration of a composition comprising VLPs of the invention may induce an antibody or other immune response that will induce cross protection against other strains of the virus. Administration can be intramuscular, subdermal, intraperitoneal. In one preferred embodiment, the administration is intramuscular.

In yet another embodiment, the vaccine and/or antigenic formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccines and/or antigenic formulations of the invention may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration. In another embodiment, said VLPs of the invention can be administered as part of a combination therapy. For example, VLPs of the invention can be formulated with other immunogenic compositions, antivirals and/or antibiotics. A VLP may be administered concurrently, subsequent to, or sequentially with another immunogenic composition, antiviral, antibiotic, or any other agent that prevents or treats an alphavirus (e.g., Chikungunya infection).

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study the efficacy of vaccines include the guinea pig, hamster, ferrets, chinchilla, mouse and cotton rat, and non-human primates. Most animals are not natural hosts to infectious agents but can still serve in studies of various aspects of the disease. For example, any of the above animals can be dosed with a vaccine candidate, e.g. VLPs of the invention, to partially characterize the immune response induced, and/or to determine if any neutralizing antibodies have been produced. For example, many studies have been conducted in the mouse model because mice are small size and their low cost allows researchers to conduct studies on a larger scale.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients (2nd Edition)," herein incorporated by reference in its entirety for all purposes, is envisioned within the scope of this invention.

Exemplary adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween-80 emulsion also is contemplated. MF-59, Novasomes®, MHC antigens may also be used.

The VLPs of the invention can also be formulated with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the VLPs, or can be administered separately. Either the protein or an expression vector encoding the protein can be administered to produce an immunostimulatory effect. Thus in one embodiment, the invention comprises antigenic and vaccine formulations comprising an adjuvant and/or an immune stimulator.

Methods of Delivery

The VLPs of the invention are useful for preparing compositions that stimulate an immune response. Such compositions are useful for the treatment or prevention or a viral infection (e.g., a CHIKV or other alphavirus infection). Both mucosal and cellular immunity may contribute to immunity to infectious agents and disease. In one embodiment, the invention encompasses a method of inducing immunity to a viral infection, for example Chikungunya virus infection in a subject, by administering to the subject a Chikungunya virus VLP or a DNA vaccine.

The invention also provides a method to induce immunity to viral infection or at least one symptom thereof in a subject, comprising administering at least one effective dose of a VLP or DNA vaccine as described herein, for example a VLP comprising one or more viral proteins, for example one or more CHIKV virus envelope proteins or a DNA vaccine comprising a nucleic acid segment encoding an alphavirus capsid protein or one or more alphavirus envelope proteins, or fragments thereof. In certain cases, the VLP further comprises a virus capsid protein. In another embodiment, the method comprises inducing immunity to a viral infection, e.g. CHIKV infection or at least one symptom thereof by administering said formulation in multiple doses.

VLPs of the invention can induce substantial immunity in a vertebrate (e.g. a human) when administered to said vertebrate. The substantial immunity results from an immune response against VLPs of the invention that protects or ameliorates infection or at least reduces a symptom of infection in said vertebrate. In some instances, if the said vertebrate is infected, said infection will be asymptomatic. The response may be not a fully protective response. In this case, if said vertebrate is infected with an infectious agent, the vertebrate will experience reduced symptoms or a shorter duration of symptoms compared to a non-immunized vertebrate.

In one embodiment, the invention comprises a method of inducing substantial immunity to alphavirus infection or at least one symptom thereof in a subject, comprising administering at least one effective dose of a VLP and/or a DNA vaccine comprising a nucleic acid segment encoding an alphavirus capsid protein or one or more alphavirus envelope proteins, or fragments thereof. In particular embodiments, the infection is CHIKV and the VLP comprises one or more CHIKV envelope protein as described herein. In another embodiment, the invention comprises a method of vaccinating a mammal against an alphavirus comprising administering to said mammal a protection-inducing amount of VLPs or DNA vaccines comprising at least one alphavirus protein. In one embodiment, said method comprises administering DNA vaccines comprising capsid, E3, E2, 6K and E1. In another embodiment, said method comprises administering DNA vaccines comprising E3, E2, 6K and E1. In another embodiment, said method comprises administering DNA vaccines comprising C-$Env_{37997}$ as set forth as SEQ ID NO:1. In another embodiment, said method comprises administering DNA vaccines comprising $Env_{37997}$ as set forth as SEQ ID NO:19. In another embodiment, said method comprises administering DNA vaccines comprising C-$Env_{OPY\text{-}1}$ as set forth as SEQ ID NO:3. In another embodiment, said method comprises administering DNA vaccines comprising $Env_{OPY\text{-}1}$ as set forth as SEQ ID NO:20. In one embodiment, said method comprises administering VLPs comprising capsid, E3, E2, 6K and E1. In another embodiment, said method comprises administering VLPs comprising E3, E2, 6K and E1. In one embodiment, said method comprises administering VLPs comprised of Chikungunya virus envelope proteins.

In another embodiment, the invention comprises a method of inducing a protective cellular response to a viral infection or at least one symptom thereof in a subject, comprising administering at least one effective dose of a DNA vaccine or a VLP.

As mentioned above, the VLPs of the invention prevent or reduce at least one symptom of an infection in a subject. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of viral infection or additional symptoms, a reduced severity of viral symptoms or a suitable assays (e.g. antibody titer and/or T-cell activation assay). The objective assessment comprises both animal and human assessments.

The invention also provides assays to identify inhibitors of viral entry comprising, in at least one embodiment, genetically modified target cells expressing at least one Chikungunya viral receptor, together with any co-receptors which might be required for infection or entry. These cells are genetically modified in the sense that they express a reporter gene, such as an affinity tag, a fluorogenic protein or an enzyme able to convert substrates into fluorogenic, chromogenic or luminometric products. Coupling this type of reporter signal to an inhibition of viral infection is accomplished by arranging the expression of the reporter gene to be strongly decreased (downregulated) upon infection with the virus of interest. In principle, this can be ensured by any suitable means, but especially preferred are:

The reporter gene product itself is fused to a cellular protein which, upon infection with the virus of interest is itself downregulated. For example, the reporter gene product can be fused to the corresponding viral receptor, which in many cases is downregulated upon infection.

Thus in one aspect a compound library may be screened for the ability to inhibit the infection of cells with Chikungunya virus (CHIKV). An appropriate indicator cell line is generated that stably expresses a reporter gene. In one example, these cells are seeded in microtiter plates and incubated with CHIKV particles in presence of different compounds, e.g., antibodies, in each well. Upon infection, the fusion protein is downregulated due to the expression of the viral genes. Consequently, only cells that have not been infected with CHIKV will express the reporter gene. Thus, wells that exhibit a positive reporter signal contain compounds that inhibit infection. Variations and modifications of these assays will be apparent from the relevant sections of the description which explain individual parts of the assay in more detail. Specifically, in one embodiment, the reporter gene can be expressed when infection occurs rather than the reporter gene being downregulated upon infection. In further embodiments, the viral particles are pseudotyped viral particles comprising one or more envelope protein and, optionally, the capsid protein from CHIKV.

In another embodiment, the invention provides methods for identifying inhibitors of viral entry using a reporter gene system as exemplified herein. Briefly, the invention provides recombinant lentiviral vectors expressing a reporter gene. Cells are incubated and co-transfected with an expression vector, e.g., $Env_{37997}$, $Env_{OPY\text{-}1}$, and a reporter plasmid using a standard techniques.

Cells are plated into one day prior to infection. CHIKV Env-pseudotyped lentiviral vectors encoding the reporter gene are first titrated by serial dilution. Similar amounts of pseudotyped vectors are then incubated with the candidate inhibitors prior to adding the virus. Cells are then lysed using cell lysis buffer and the reporter gene activity is measured. Inhibitors of viral entry are identified based on the expression of the reporter gene.

Kits

The invention also provides for a pharmaceutical pack or kit comprising one or more containers filled with one or more of the ingredients of the vaccine formulations of the invention. In a preferred embodiment, the kit comprises two containers, one containing VLPs and the other containing an adjuvant. Associated with such container(s) can be a notice in the form prescribed by a governmental agency regulating the manufacture, use or sale of pharmaceuticals or biological products, which notice reflects approval by the agency of manufacture, use or sale for human administration.

The invention also provides that the VLP formulation be packaged in a hermetically sealed container such as an ampoule or sachette indicating the quantity of composition. In one embodiment, the VLP composition is supplied as a liquid, in another embodiment, as a dry sterilized lyophilized powder or water free concentrate in a hermetically sealed container and can be reconstituted, e.g., with water or saline to the appropriate concentration for administration to a subject.

The invention also features a kit comprising a VLP as described herein. The invention also features kits comprising a DNA vaccine as described herein and instructions for use.

The invention also features a kit comprising a VLP in a first container and a DNA vaccine in a second container, and instructions for use in a prime boost immunization.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 1B:
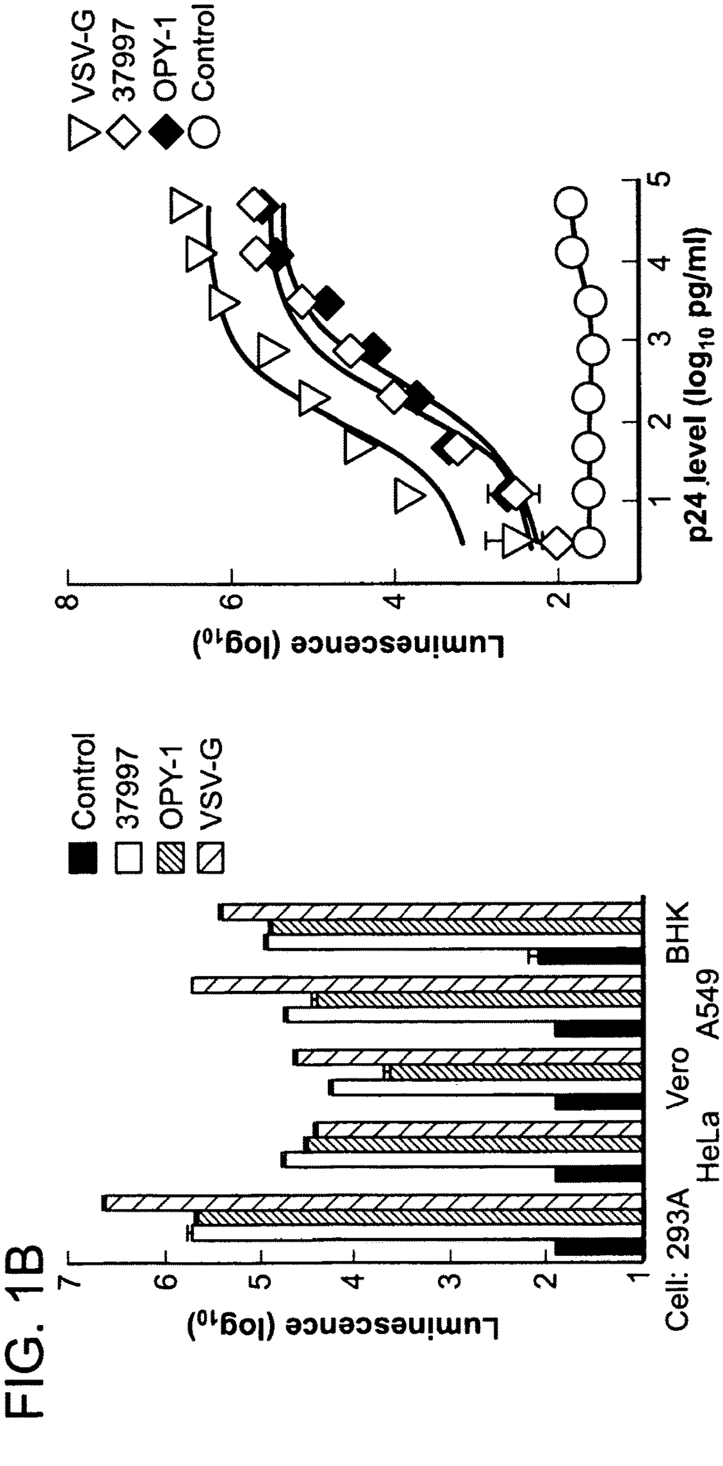
Figure 5:
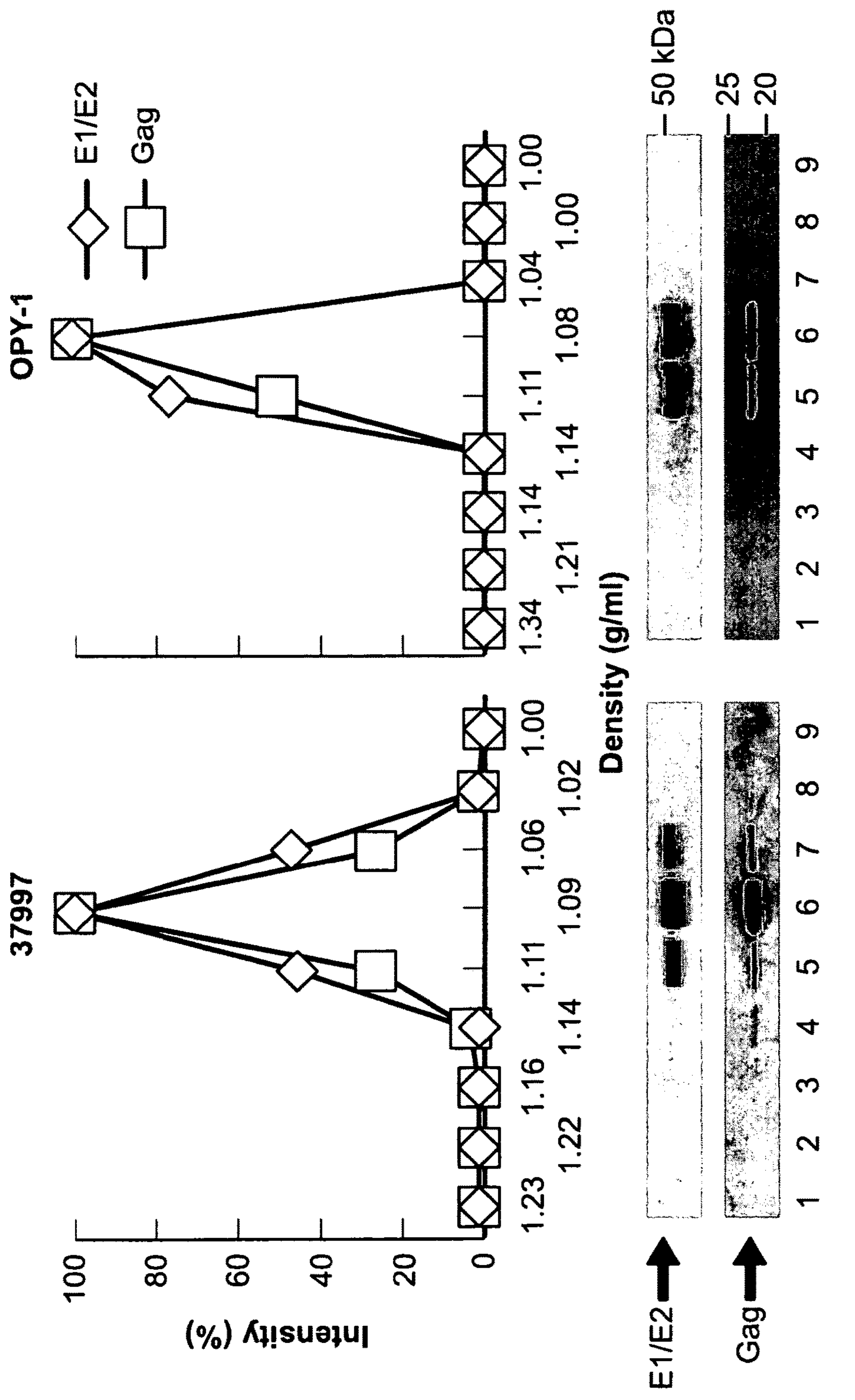
FIG. 5 shows the characterization of CHIKV E pseudotyped lentiviral vectors by buoyant density sedimentation and Western blot analysis. Plasmids encoding the indicated CHIKV Env strains were cotransfected with lentiviral expression vectors into 293T cells. Forty-eight hours after transfection, supernatants were harvested and run on sedimentation gradients as described previously. Quantification of gradient fractions is shown with the indicated strains, showing colocalization of Env with the Gag fraction of the expected buoyant density for lentiviral particles (1.08-1.1 g/ml) (upper panel). Western blot analysis of gradient fractions for CHIKV E1/E2 and Gag are shown (lower panel).
Figure 6:
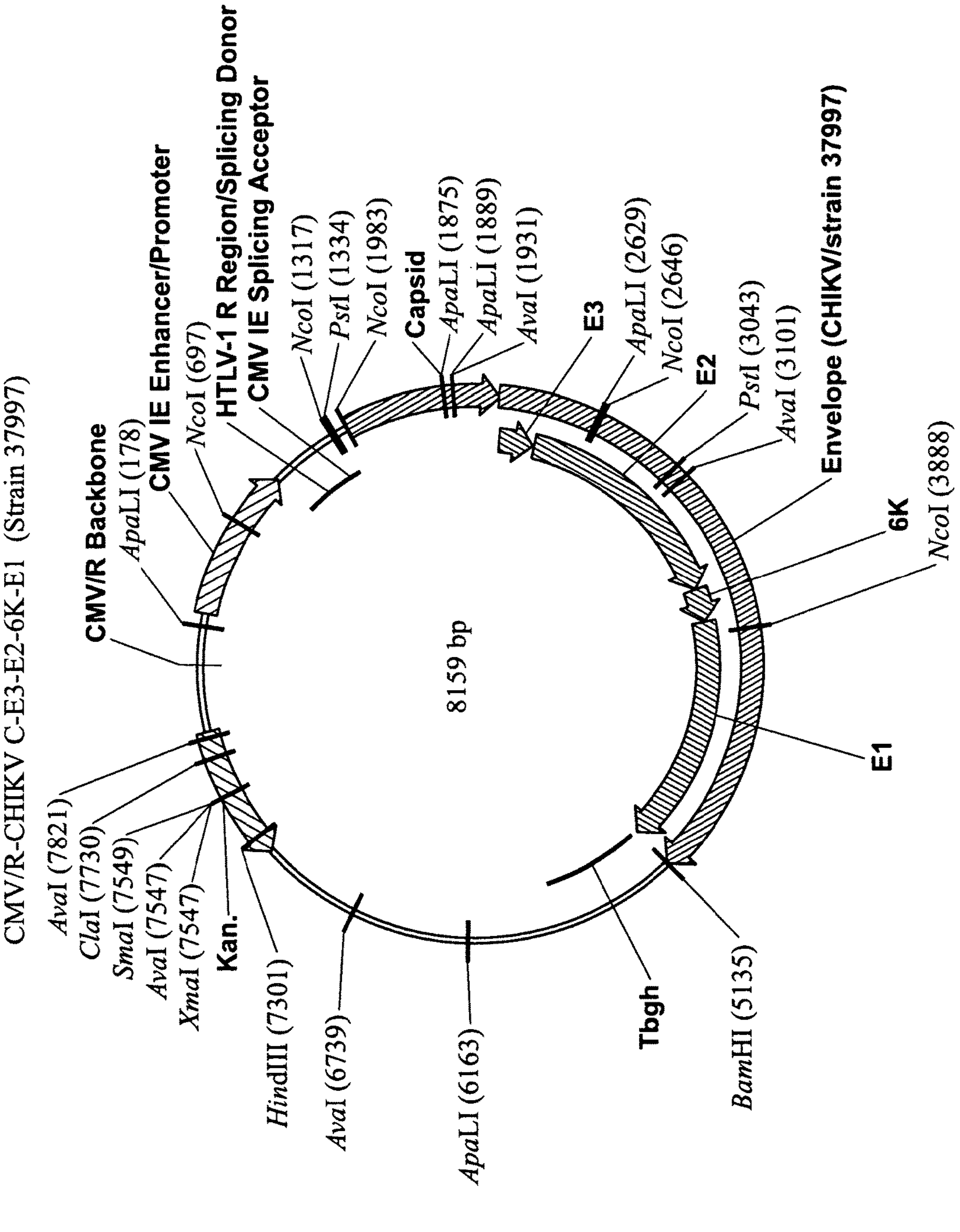
FIG. 6 shows the CMV/R-CHIKV C-E3-E2-6K-E1 plasmid (Strain 37997).
Figure 8A:
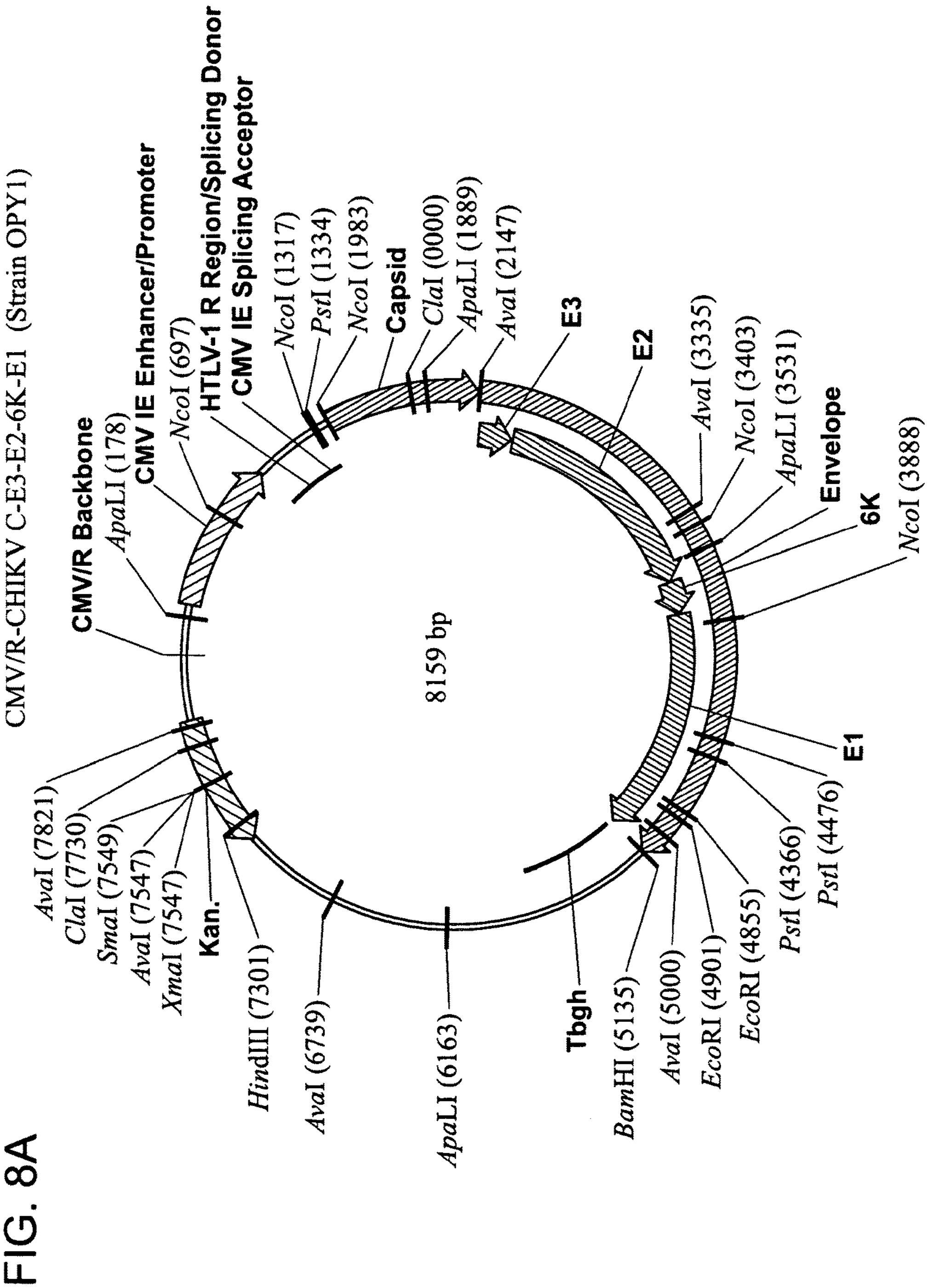
FIG. 8A shows the CMV/R-CHIKV C-E3-E2-6K-E1 plasmid (Strain OPY1).
Figure 9A:
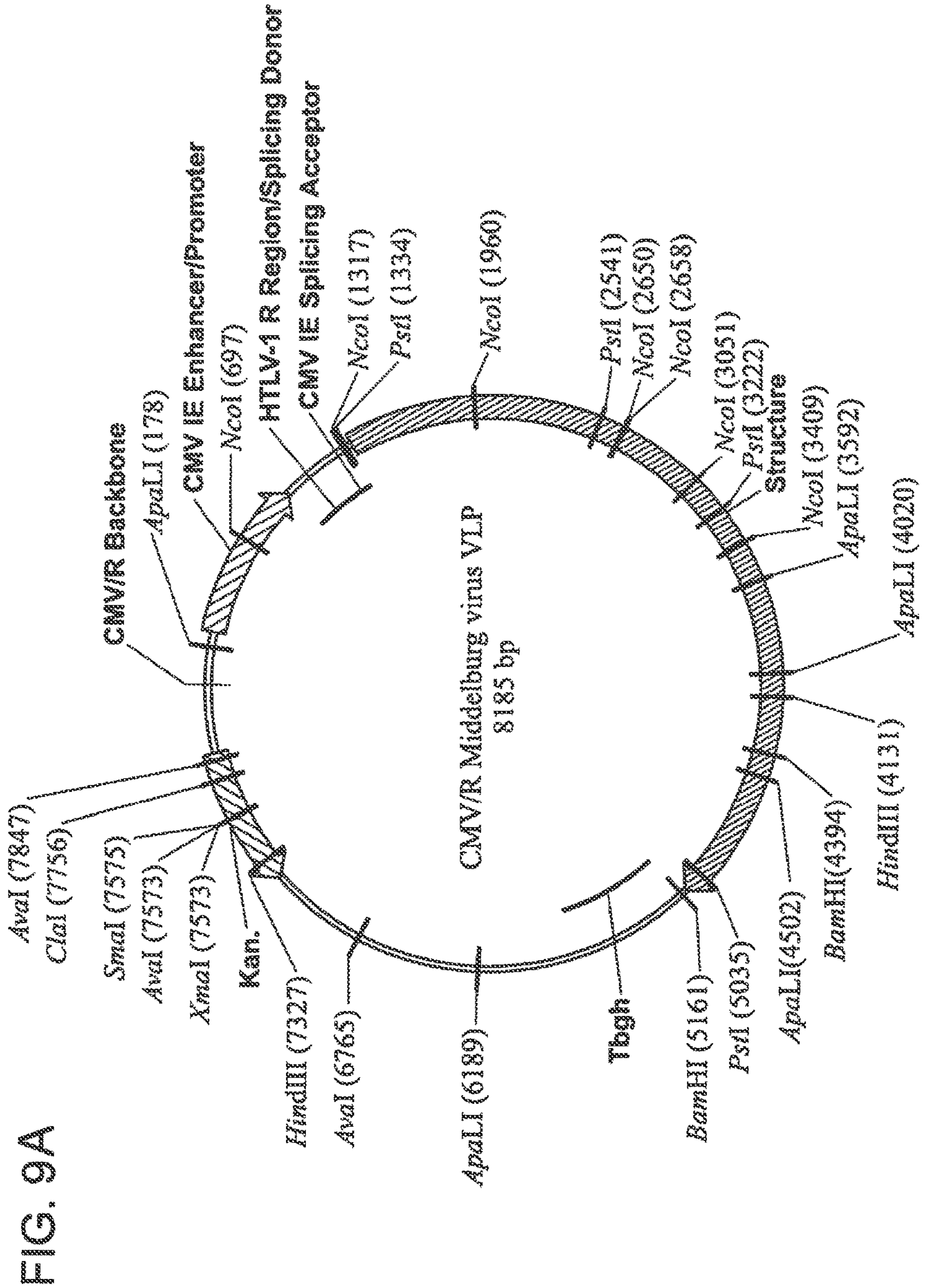
FIG. 9A shows the CMV/R-Middleburg virus VLP plasmid.
Figure 10A:
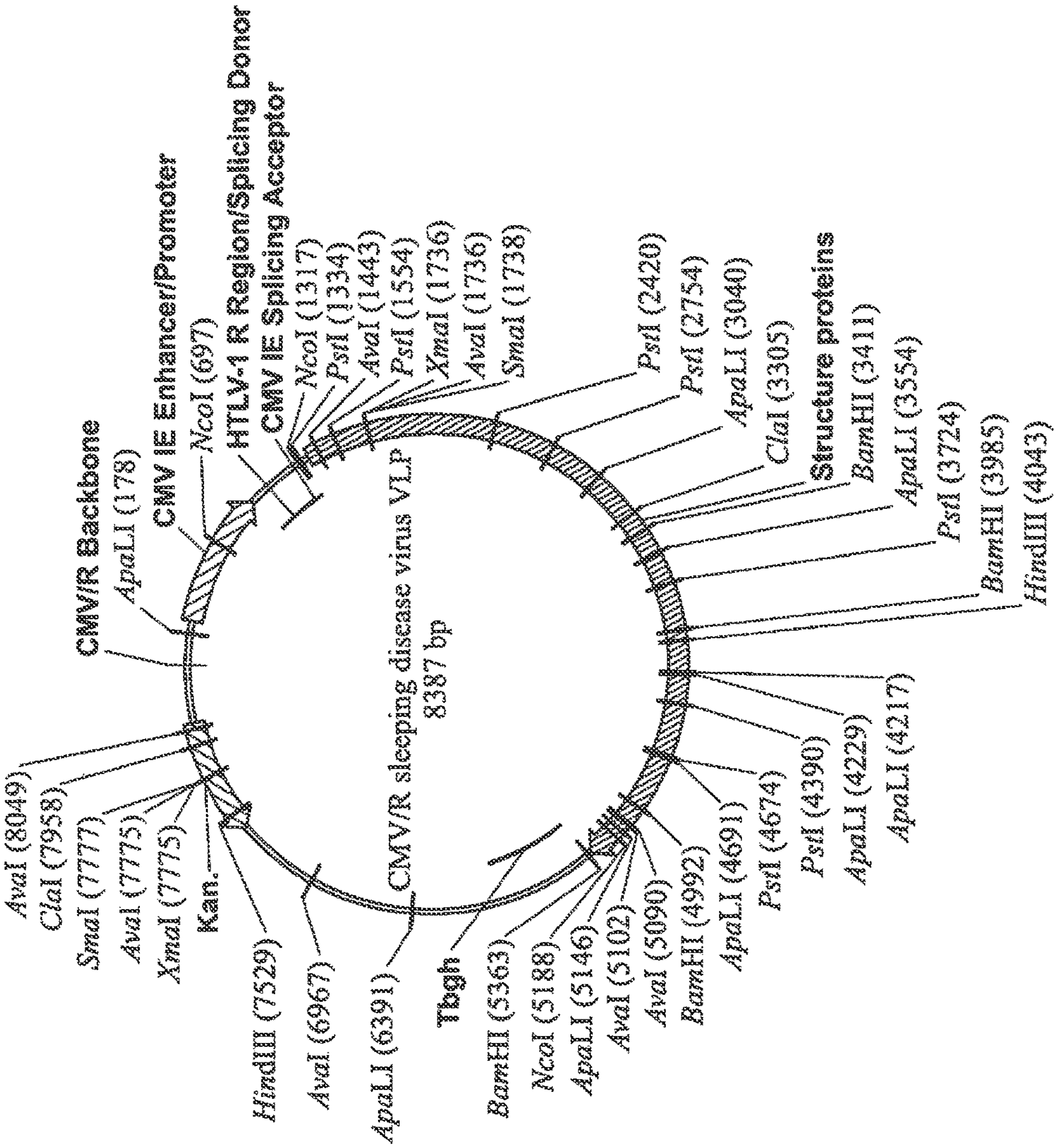
FIG. 10A shows the CMV/R-Sleeping disease virus VLP plasmid.
Figure 11A:
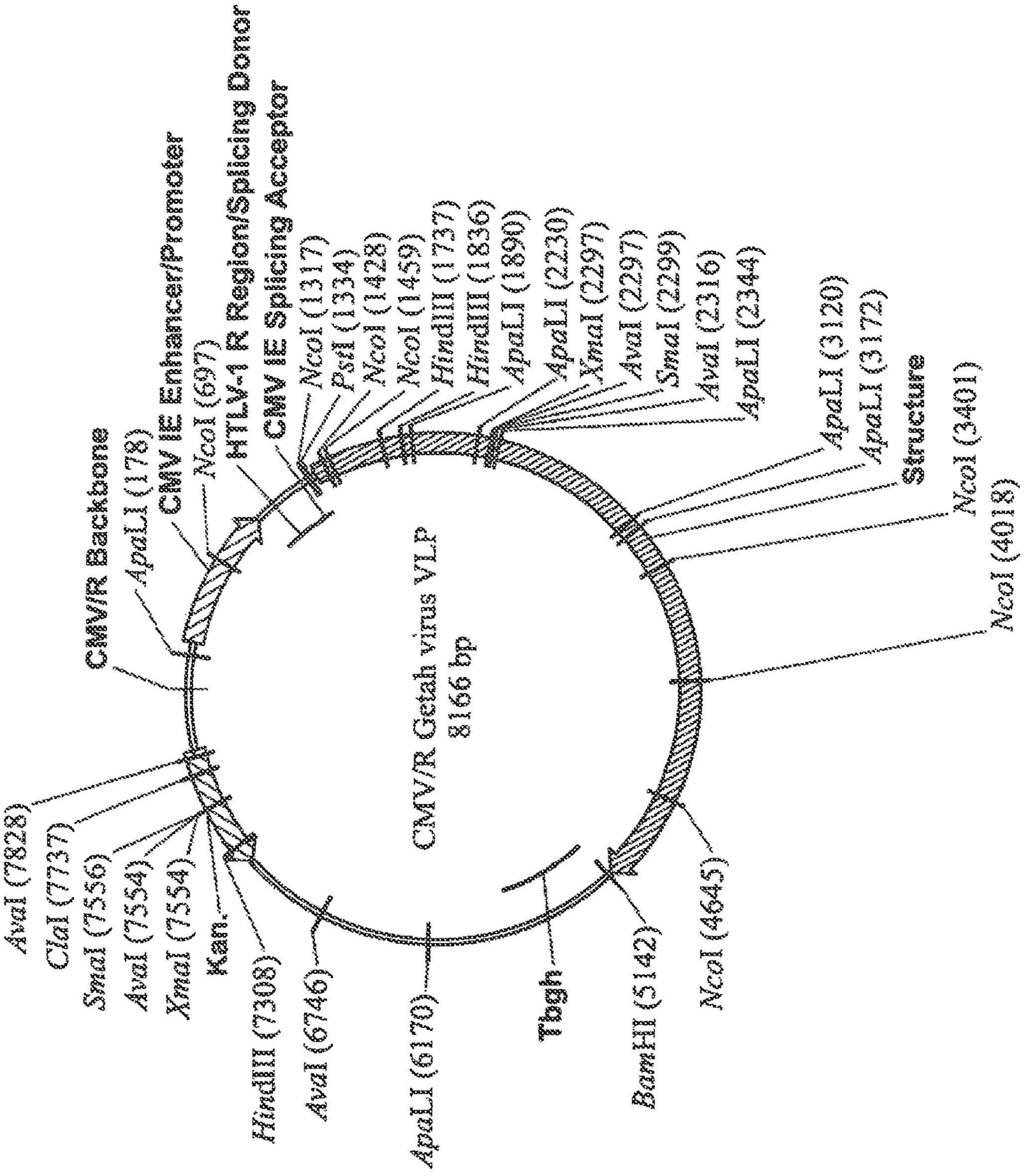
FIGS. 11 (A and B). Panel A shows the CMV/R-Getah virus VLP plasmid. Panel B shows the entire plasmid sequence (SEQ ID NO: 7).
Figure 12A:
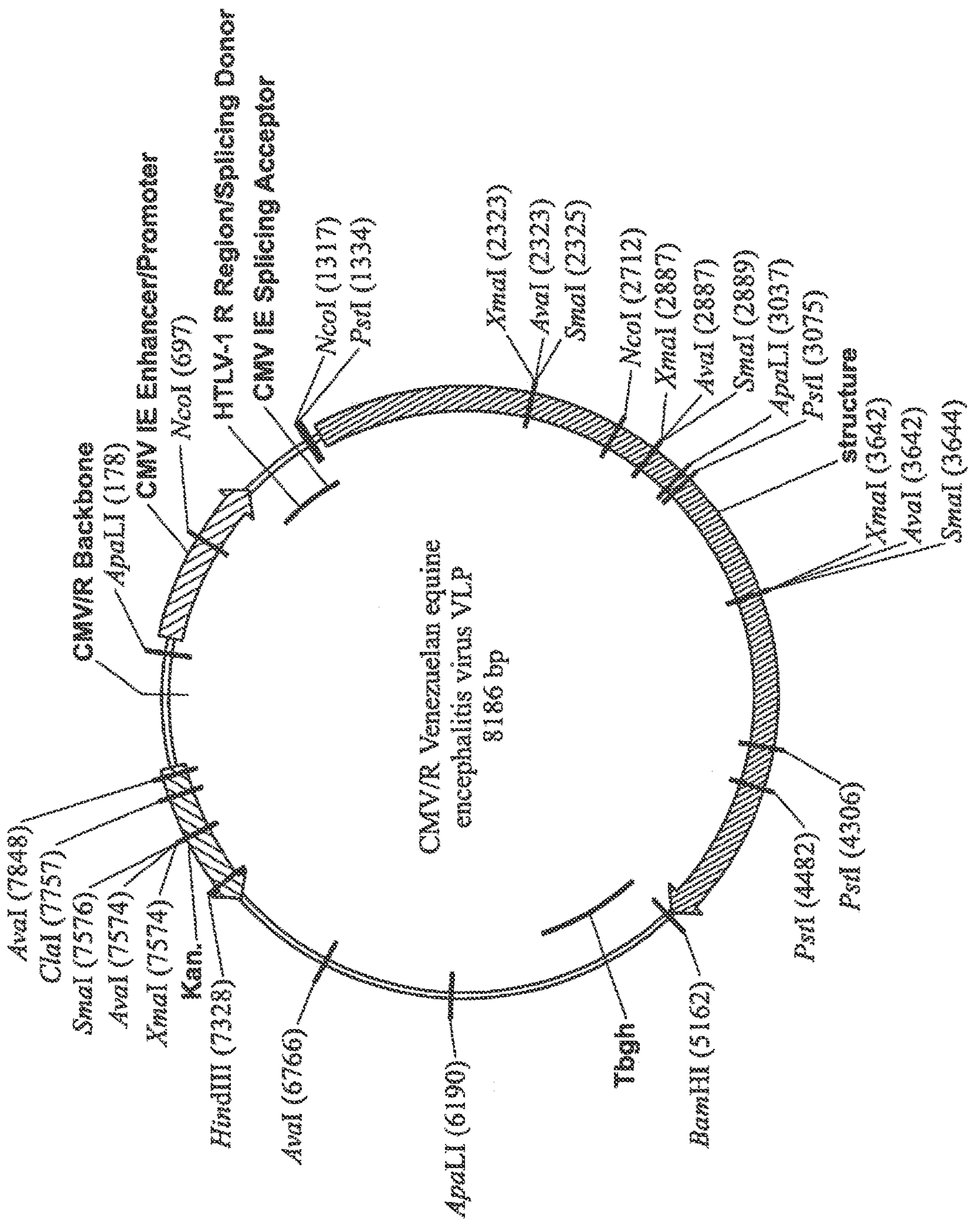
FIG. 12A shows the CMV/R-Venezuelan equine encephalitis virus VLP plasmid.
Figure 13A:
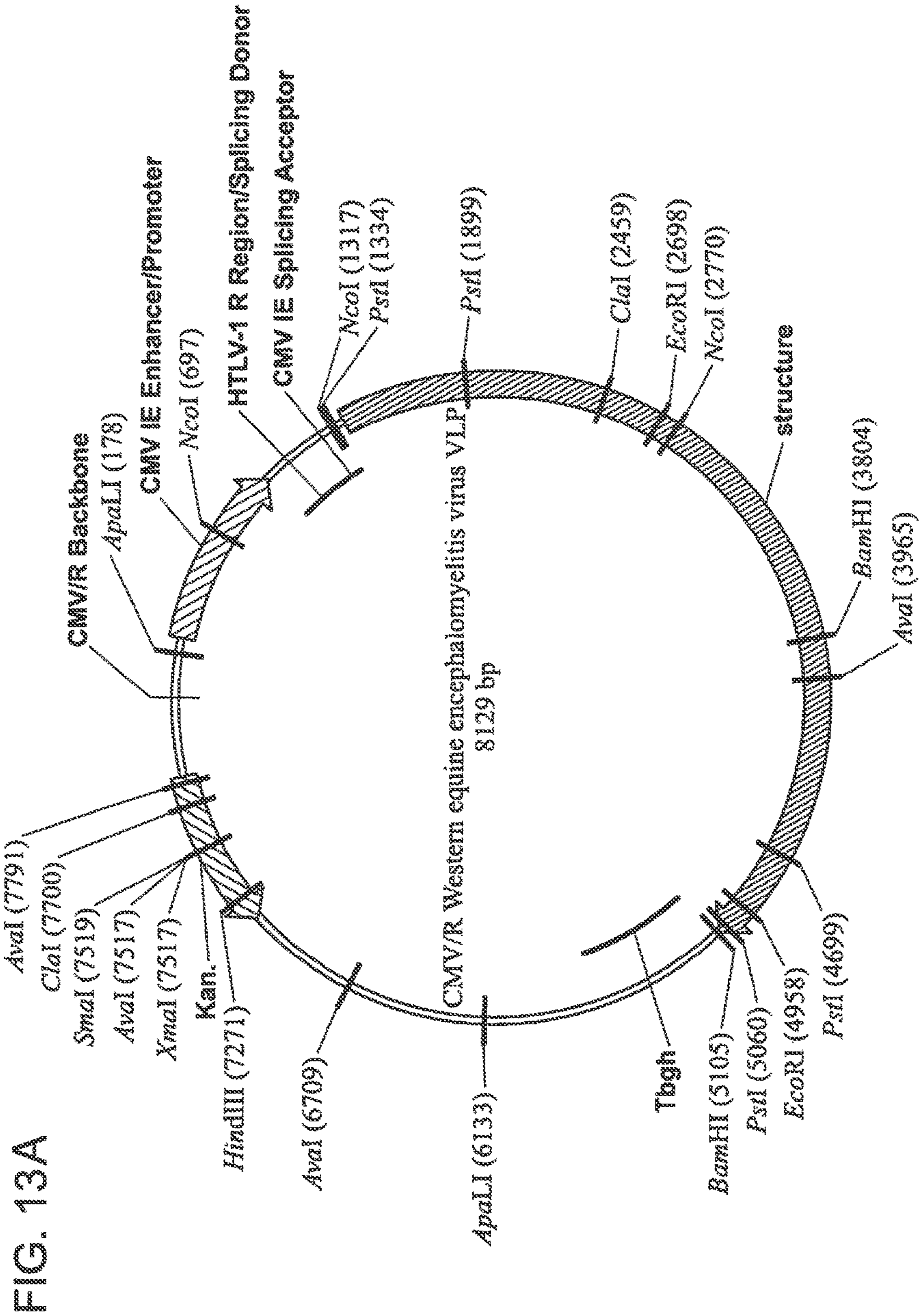
FIG. 13A shows the CMV/R-Western equine encephalitis virus VLP plasmid.
Figure 14A:
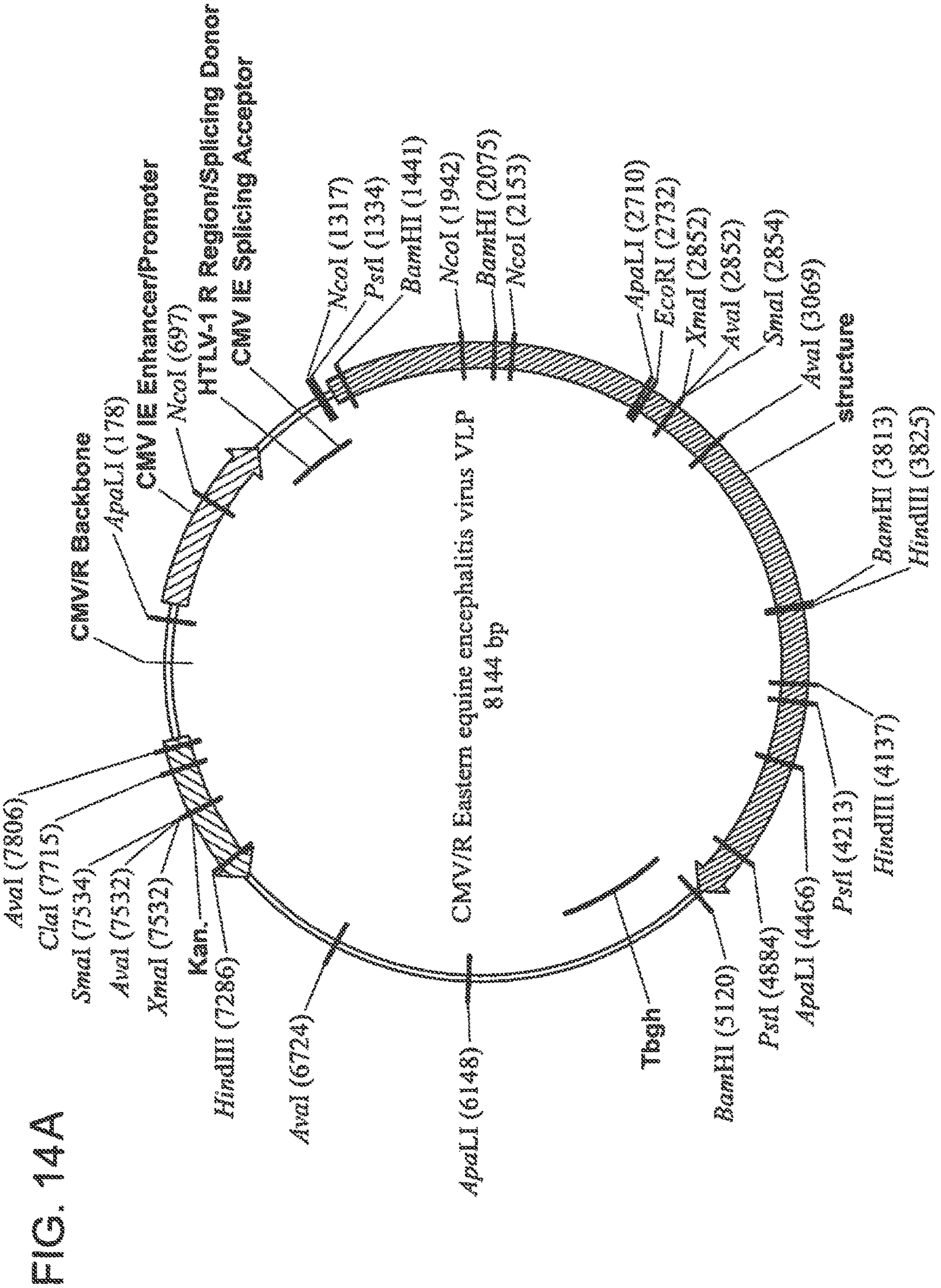
FIG. 14A shows the CMV/R-Eastern equine encephalitis virus VLP plasmid.
Figure 15A:
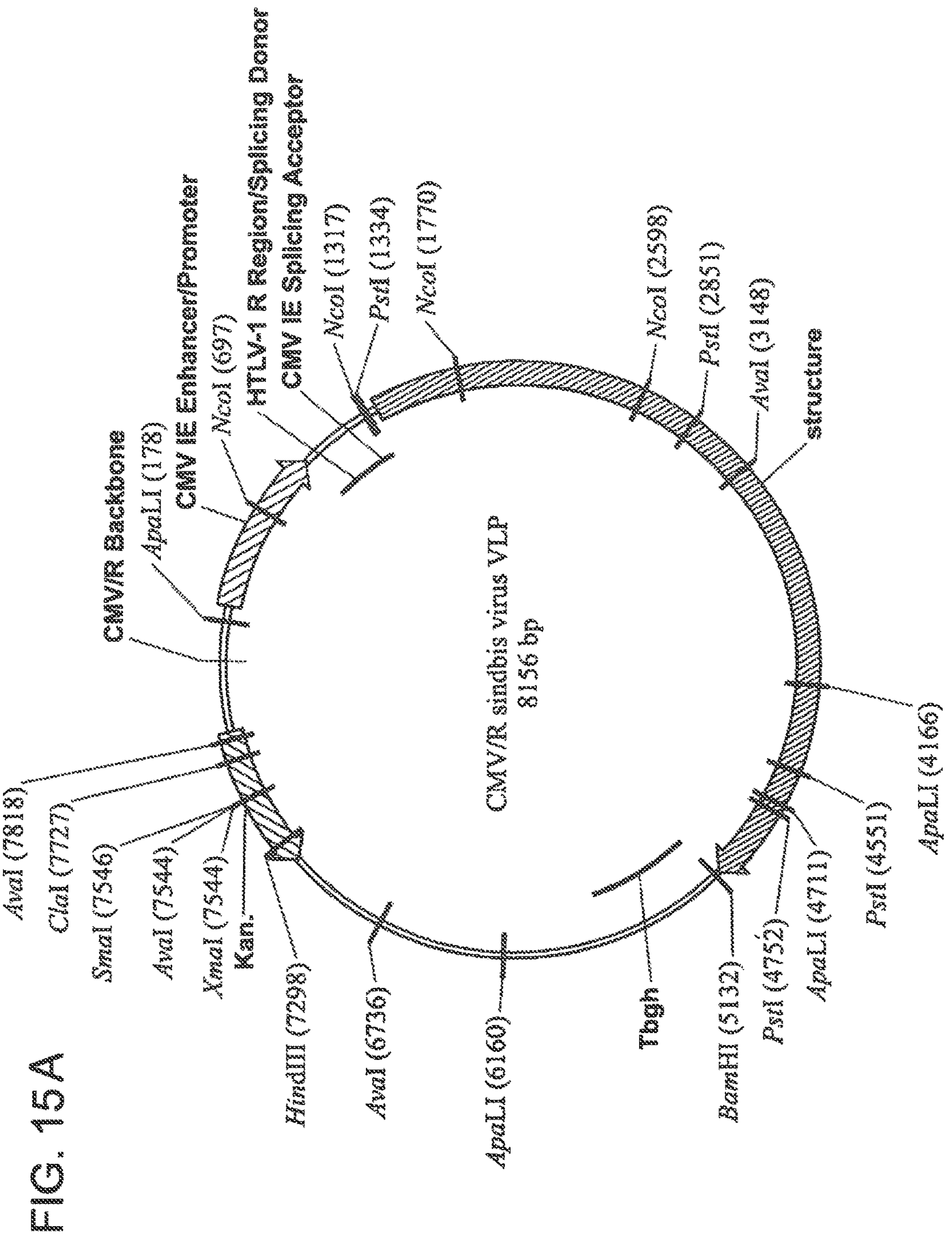
FIG. 15A shows the CMV/R-Sindbis virus VLP plasmid.
Figure 16A:
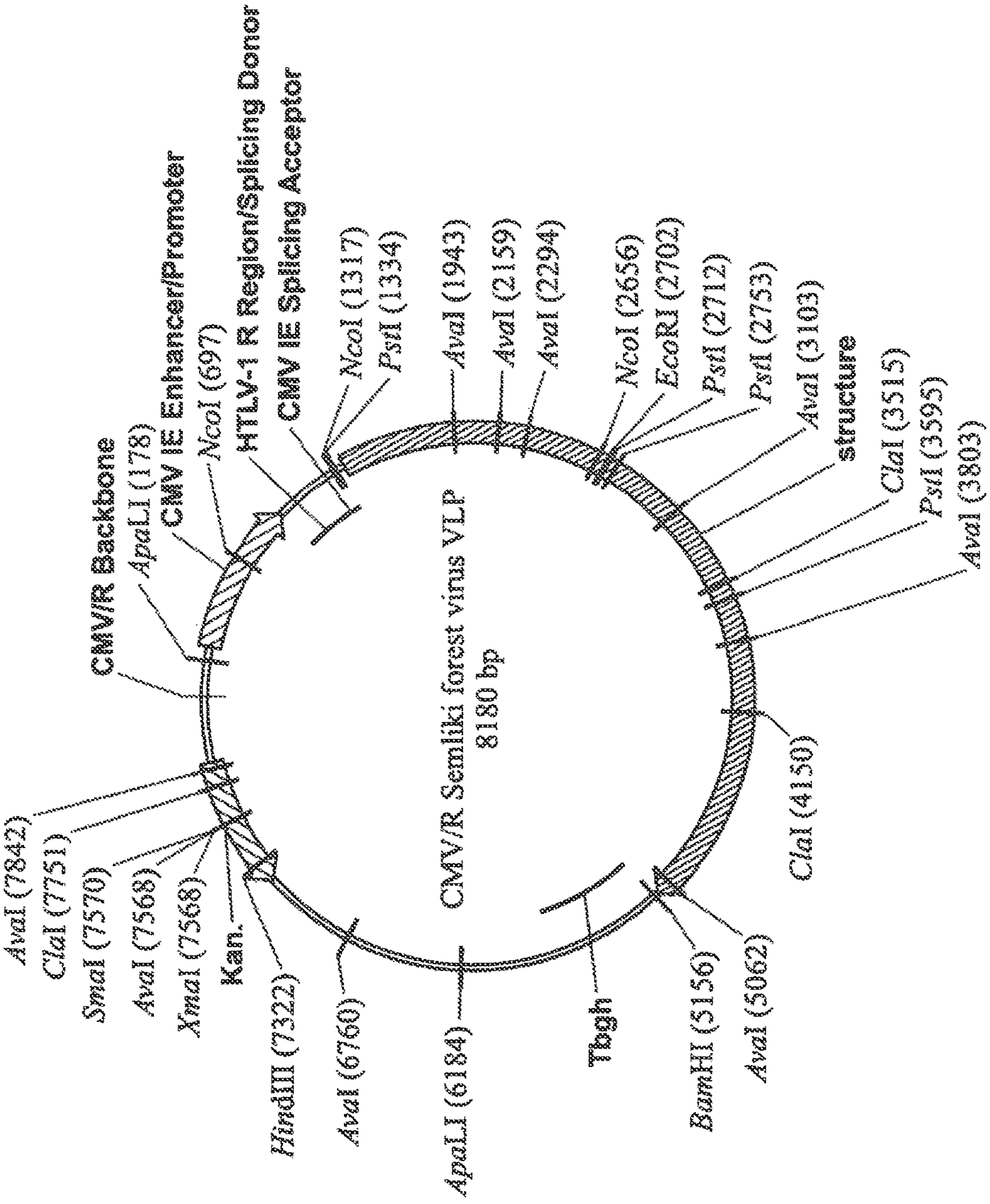
FIG. 16A shows the CMV/R-Semliki forest virus VLP plasmid.
Figure 17:
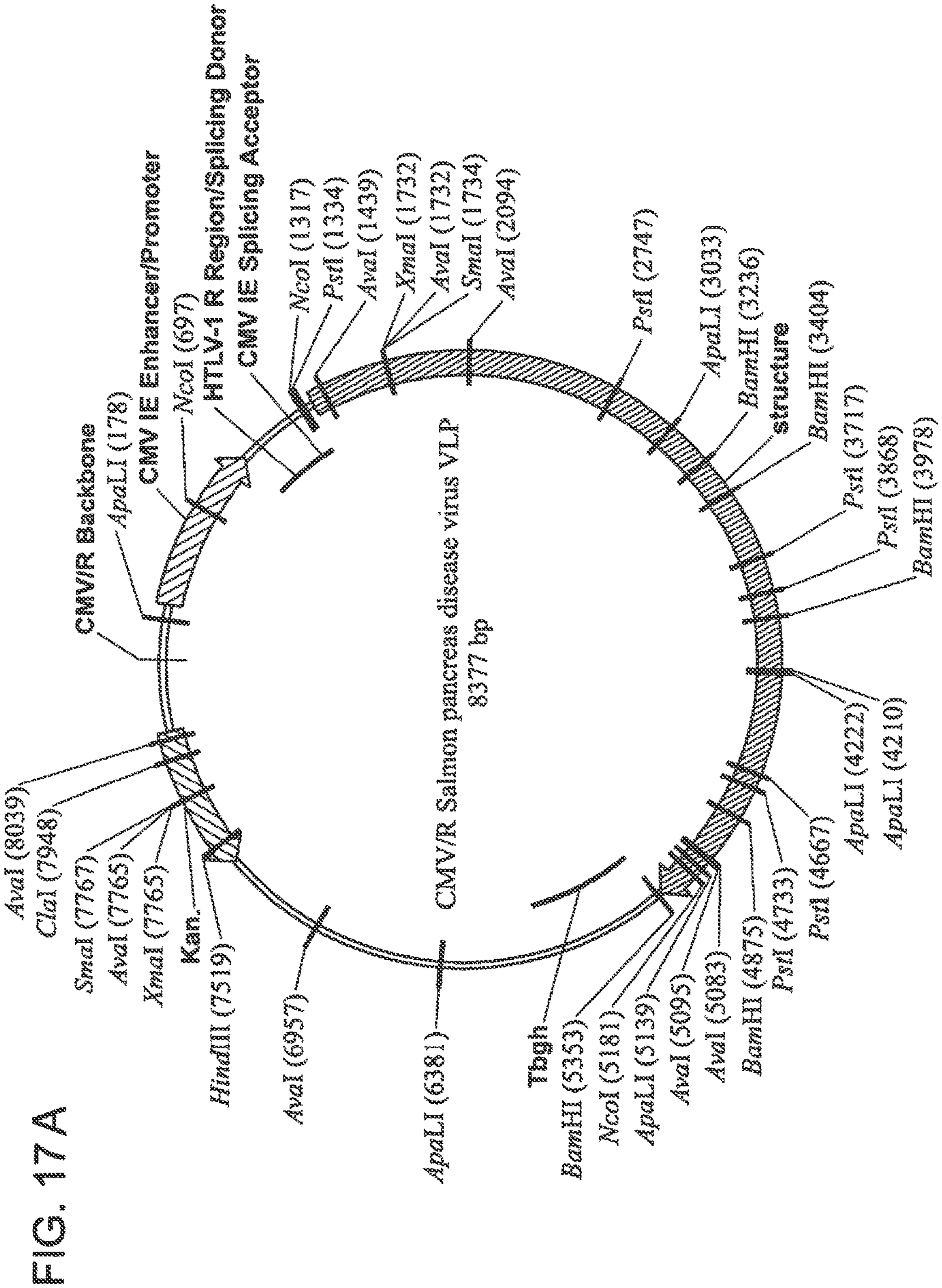
FIG. 17A shows the CMV/R-Salmon pancreas disease virus VLP plasmid.
FIG. 17B shows the entire plasmid sequence (SEQ ID NO: 13).
Figure 18A:
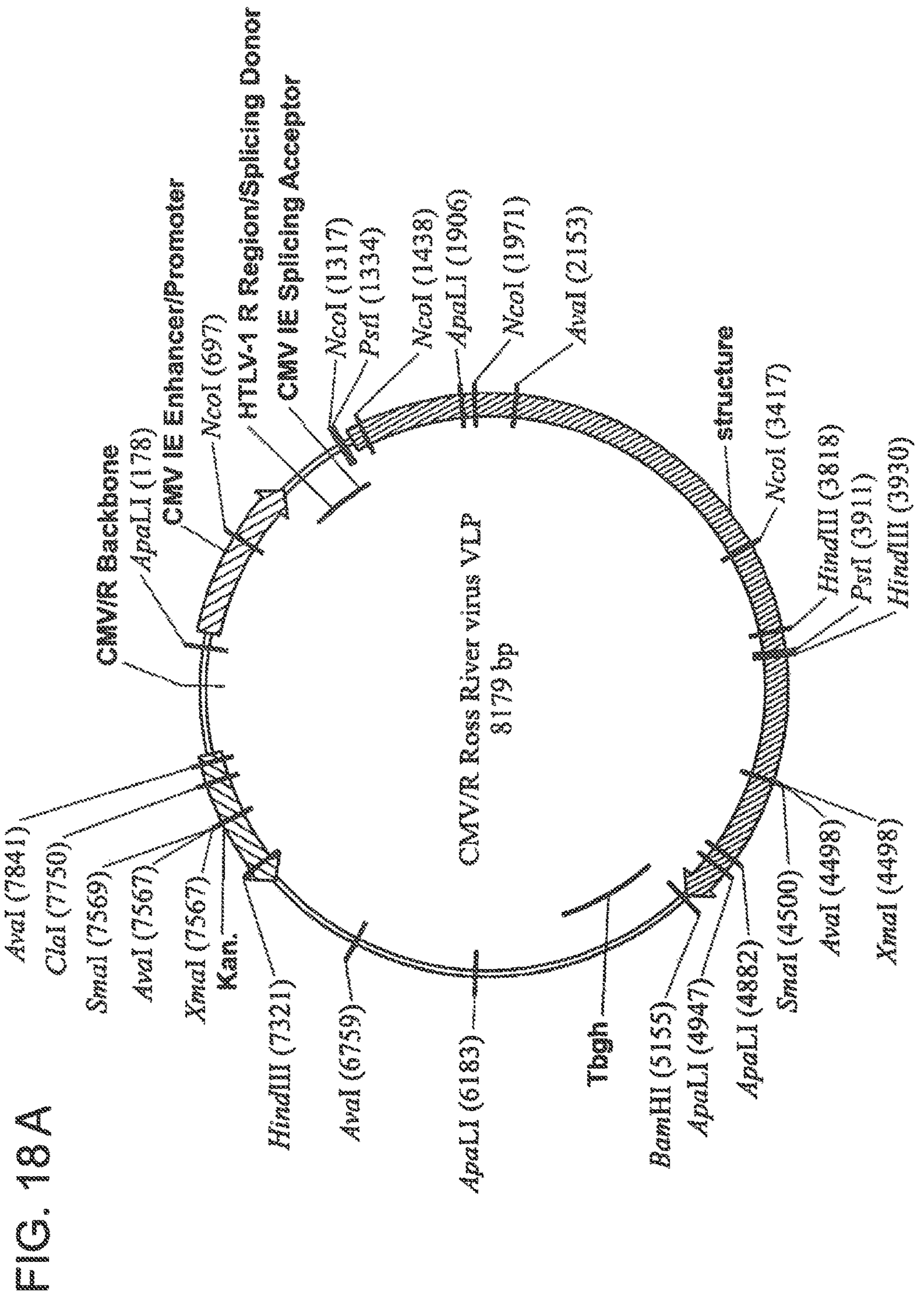
FIG. 18A shows the CMV/R-Ross River virus VLP plasmid.
Figure 19A:
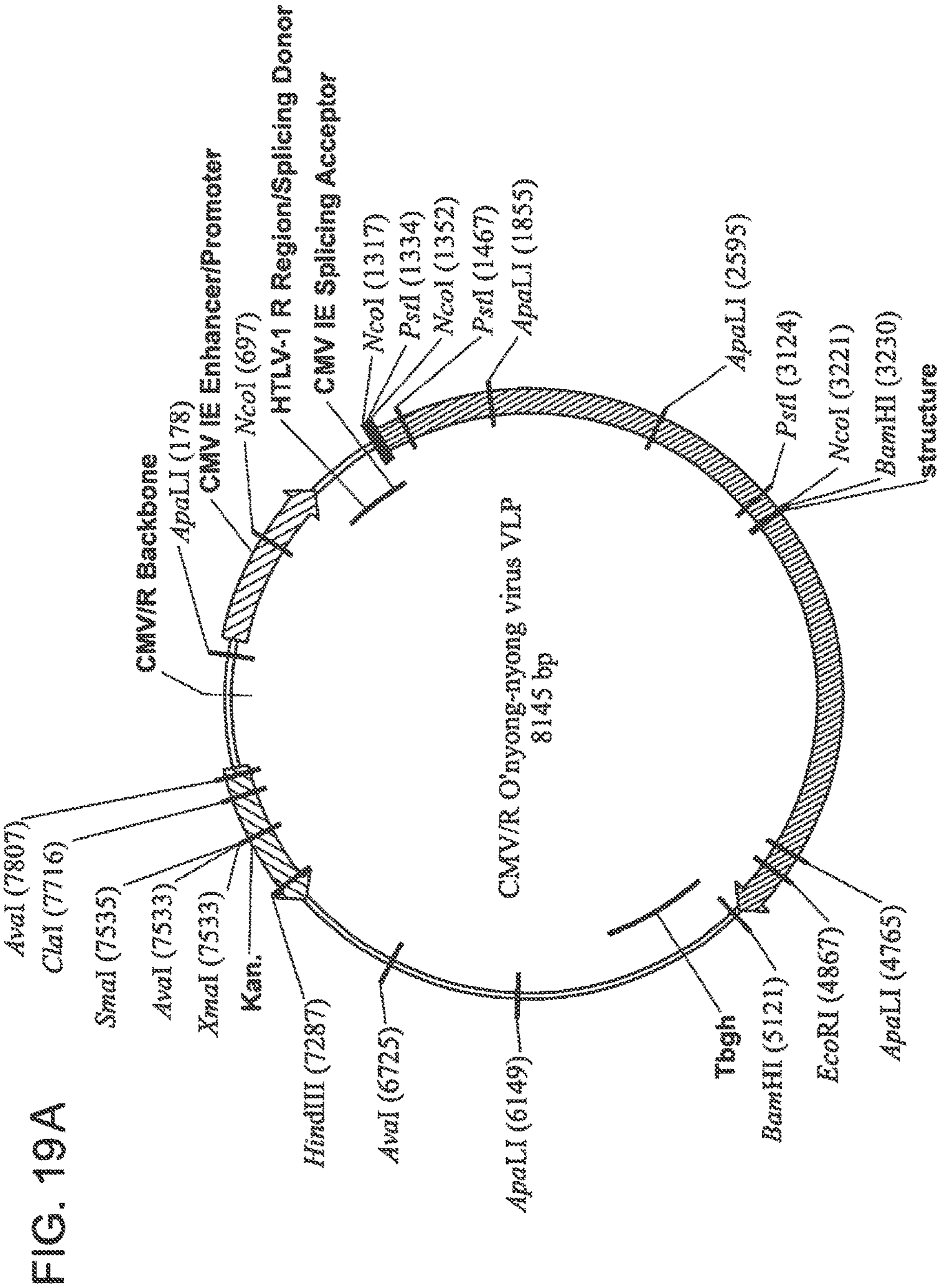
FIG. 19A shows the CMV/R-O'nyong-nyong virus VLP plasmid.
Figure 20A:
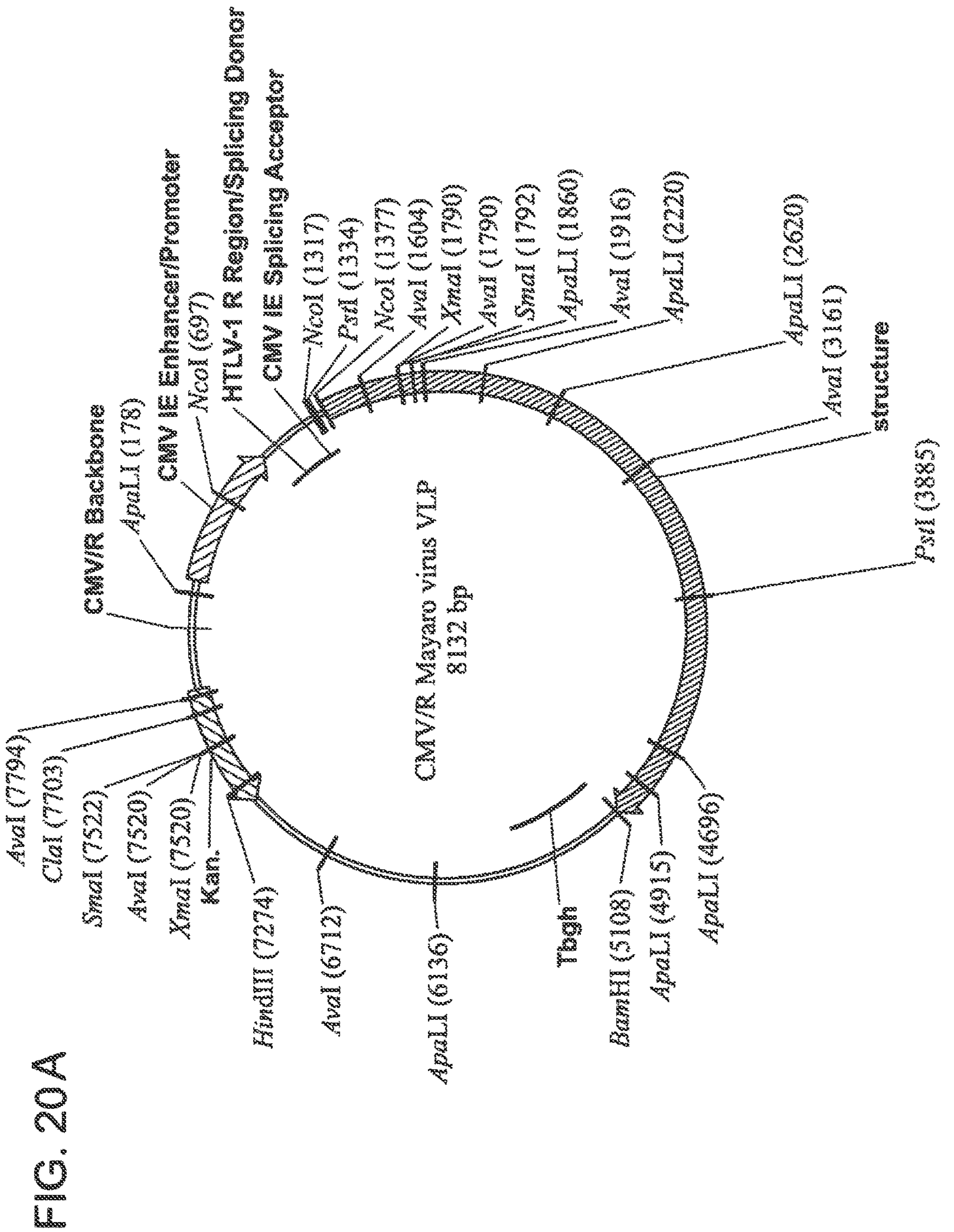
FIG. 20A shows the CMV/R-Mayaro virus VLP plasmid.
Figure 21A:
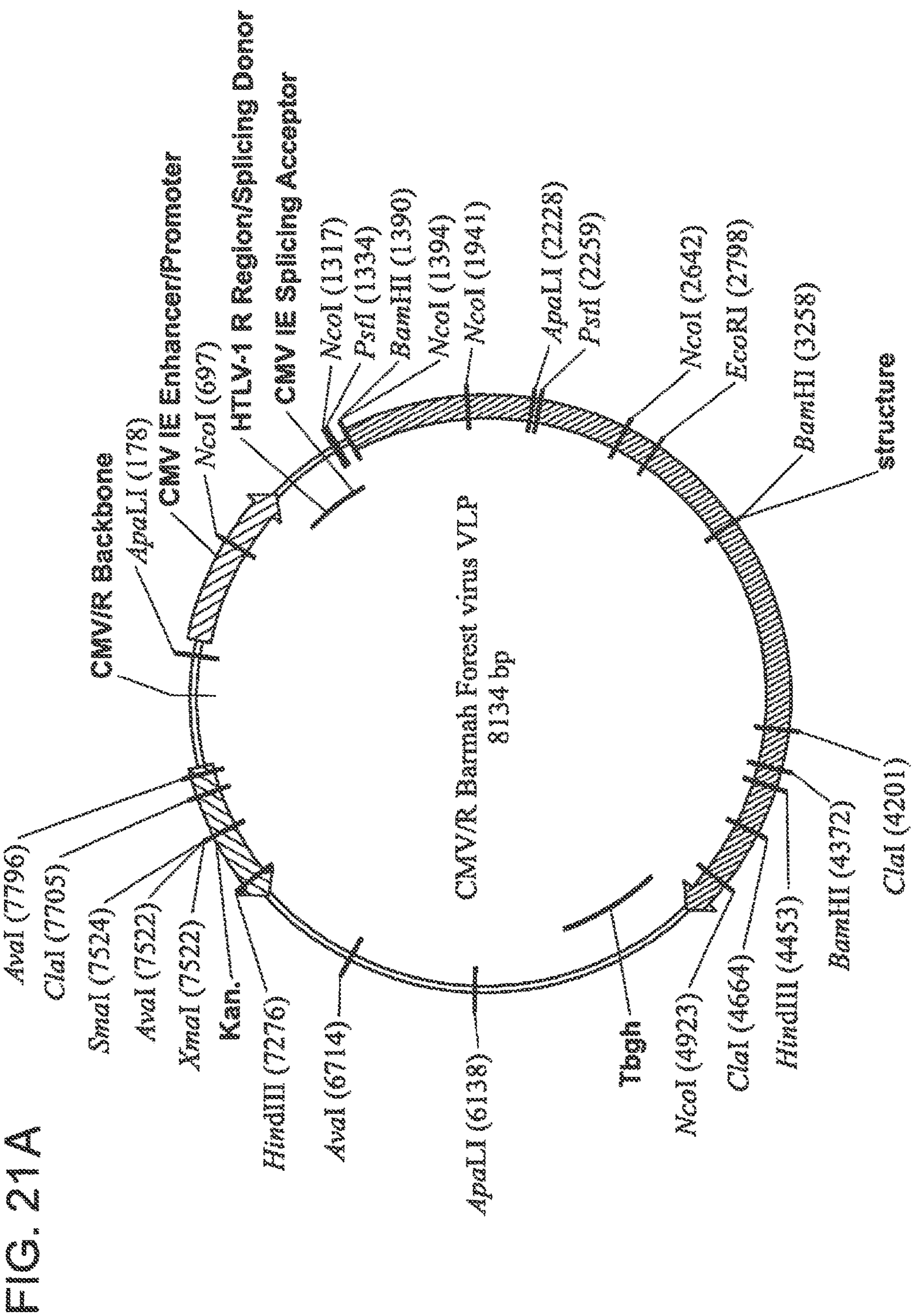
FIG. 21A shows the CMV/R-Barmah Forest virus VLP plasmid.
Figure 22:
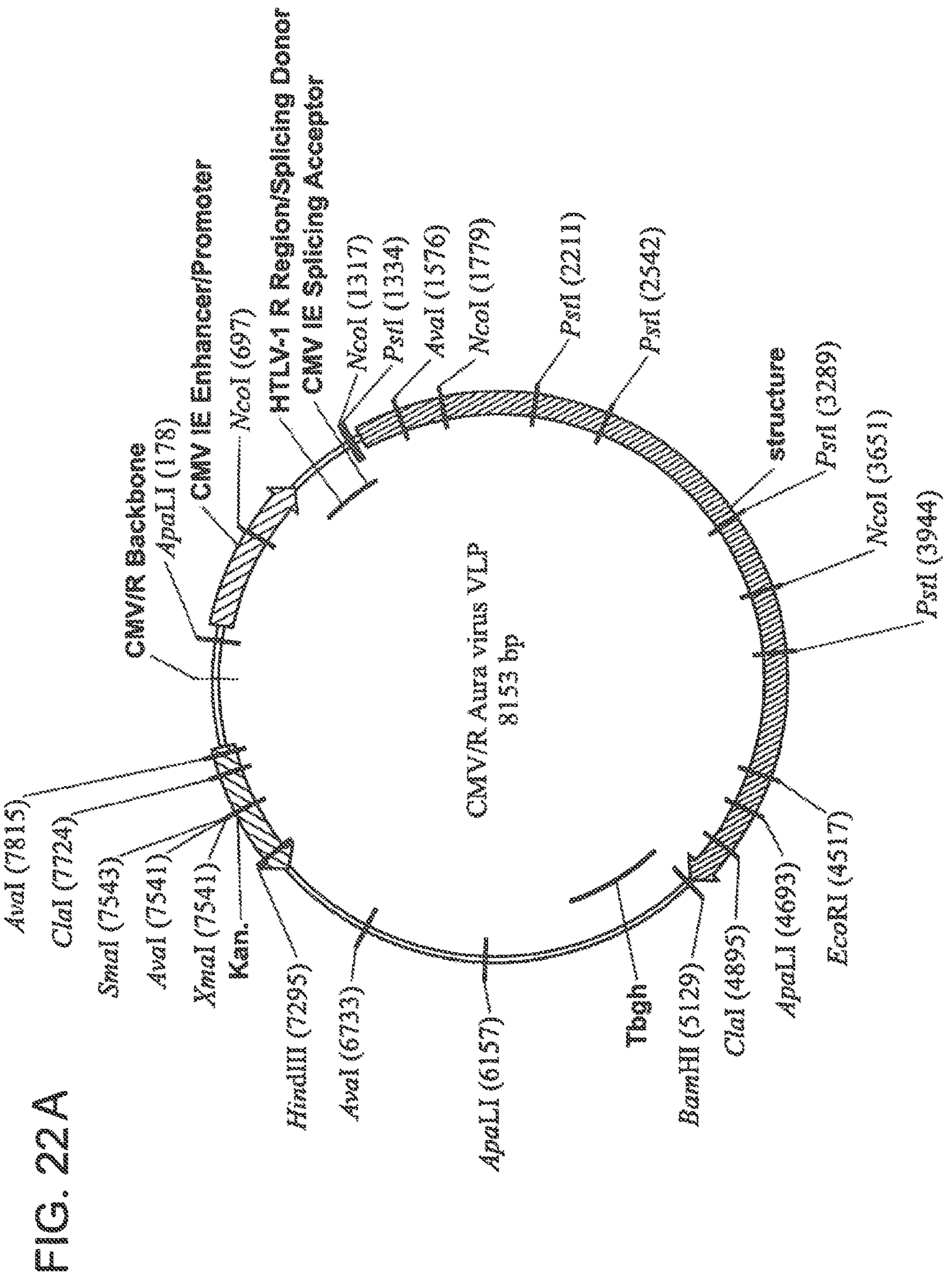
FIG. 22A shows the CMV/R-Aura virus VLP plasmid.
FIG. 22B shows the entire plasmid sequence (SEQ ID NO: 18).
Figure 23A:
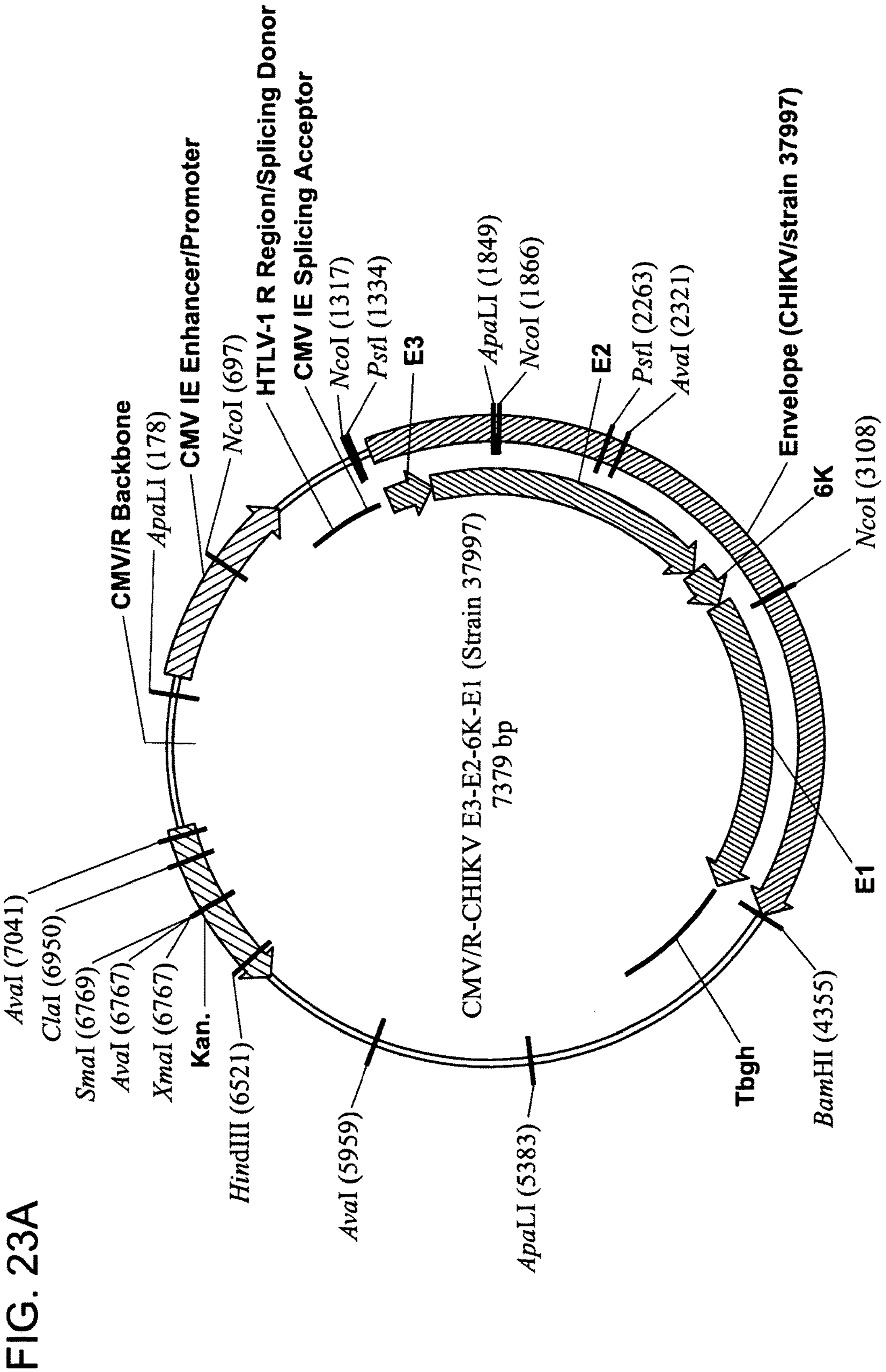
FIG. 23A shows the CMV/R-CHIKV E3-E2-6K-E1 plasmid (Strain 37997) and the sequence of the insert without the capsid (C) (SEQ ID NO:19).
Figure 23B:
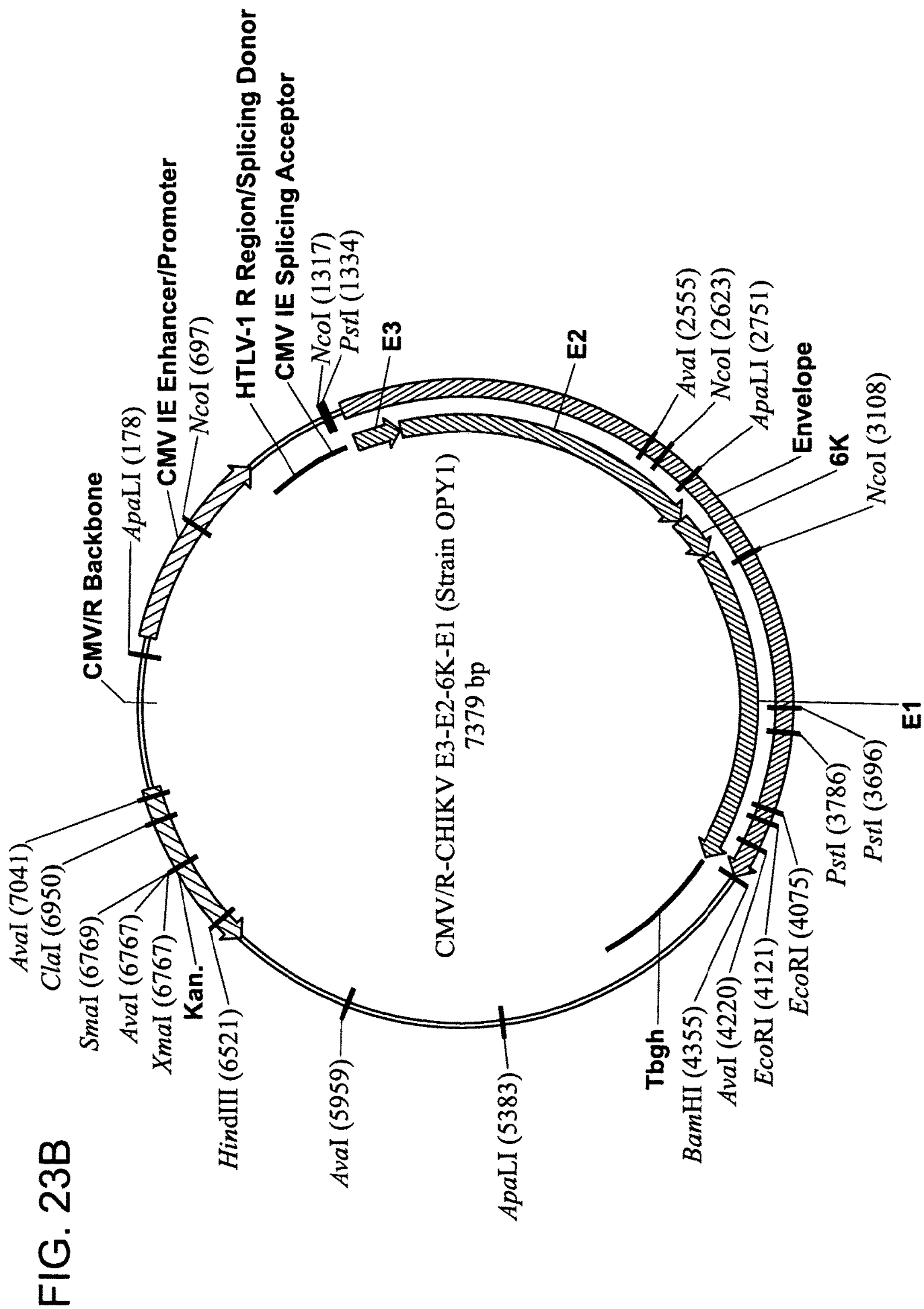
FIG. 23B shows the CMV/R-CHIKV E3-E2-6K-E1 plasmid (Strain OPY1) and the sequence of the insert without the capsid (C) (SEQ ID NO: 20).

Example 1: Lentiviral Vectors Pseudotyped with CHIKV Envelope Mediated Entry Through the Same Mechanism as Wild Type Virus To examine the mechanism and specificity of CHIKV cell entry, lentiviral vector reporters were pseudotyped with glycoproteins from different CHIKV strains that mediate entry into permissive cells. The CHIKV spike on the virion surface is formed by three E1-E2 heterodimers, where E1 glycoproteins mediate fusion and E2 glycoproteins interact with the host receptor. CHIKV E genes expressing the native polypeptide, E3-E2-6K-E1 polyprotein, for the 37997 and for LR2006 OPY-1 strains were inserted into an expression vector (E37997 and EOPY-1) (FIG. 1A, FIGS. 6, 7A, 7B, and 8A-8C). The incorporation of the two CHIKV Es into the pseudotyped lentiviral vectors was verified by buoyant density gradient sedimentation of the virus. Both CHIKV E and HIV-1 Gag had the same buoyant density as lentivirus particles (FIG. 5). The 37997 and LR2006 OPY-1 CHIKV pseudotyped lentiviral vectors infected several permissive cell lines (Sourisseau et al., *PLoS. Pathog.* 3, e89 (2007)) as measured by luciferase reporter activity, while a control devoid of CHIKV envelope proteins did not infect these cell lines (FIG. 1B, left), and infectivity was dose-dependent (FIG. 1B, right).

Figure 1C:
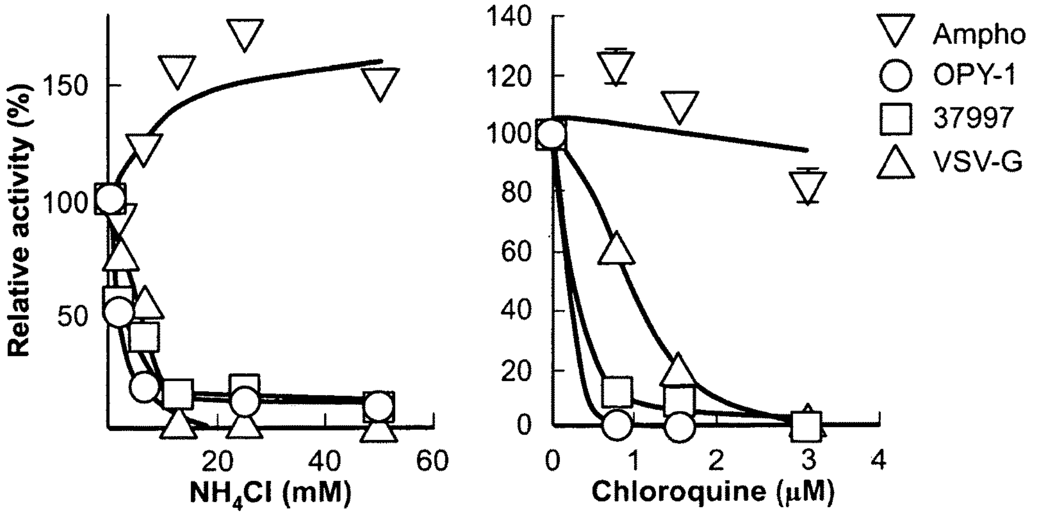
Figure 1D:
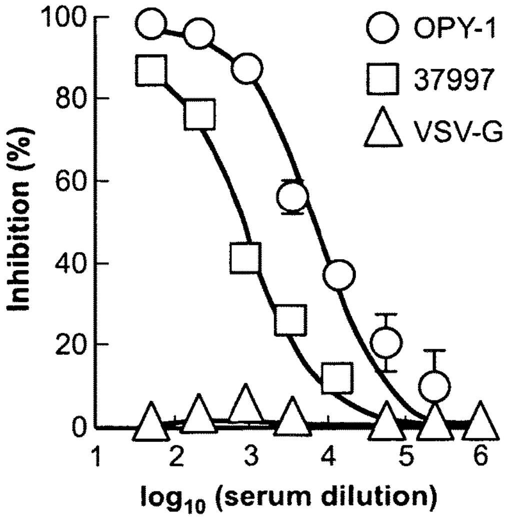

To determine whether entry occurred through the same mechanism as native virus, the pH and endosome dependence of entry was analyzed as described previously (Yang et al., *J. Virol.* 78, 5642 (2004)). CHIKV infects cells through a process of pH-dependent cell fusion. Thus, addition of ammonium chloride or chloroquine, which prevents acidification of the endosome, caused a dose-dependent reduction in CHIKV pseudotyped vector entry (FIG. 1C). Similar inhibition of entry was observed with VSV-G, known to enter in this fashion, but not with amphotropic murine leukemia virus (MuLV) glycoprotein 70, which enters in a pH-independent fashion. These findings demonstrated that lentiviral vectors pseudotyped with CHIKV envelope mediated entry through the same mechanism as wild type virus. Sera from mice injected with a CHIKV strain were next examined. Incubation of immune sera with the CHIKV pseudotyped lentiviral vector but not VSV-G pseudotyped vector inhibited entry (FIG. 1D). The specificity and potency of neutralizing antibodies could therefore be quantified without exposure to infectious virus.

Example 2: VLPs Have Morphology of Wild Type Virus

Figure 2A:
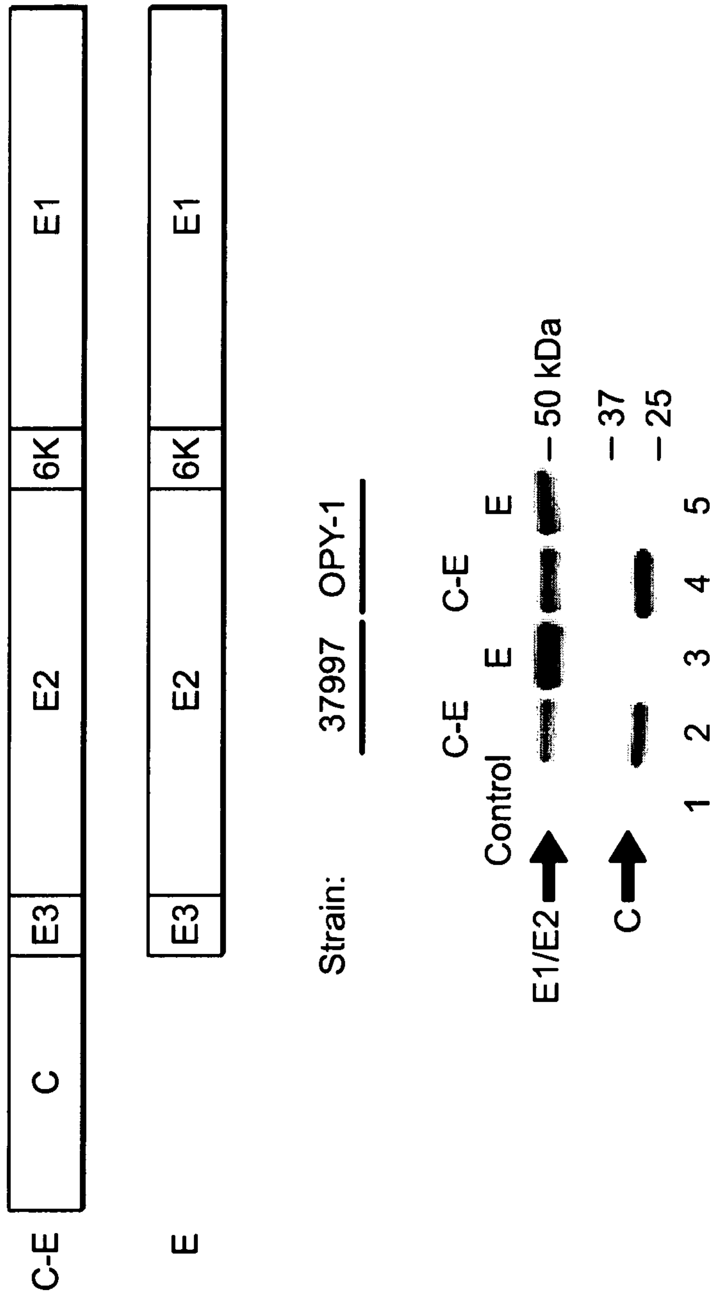
FIGS. 2A-2C show the schematic representation of plasmid expression vectors and characterization of CHIKV VLPs.
Figure 2B:
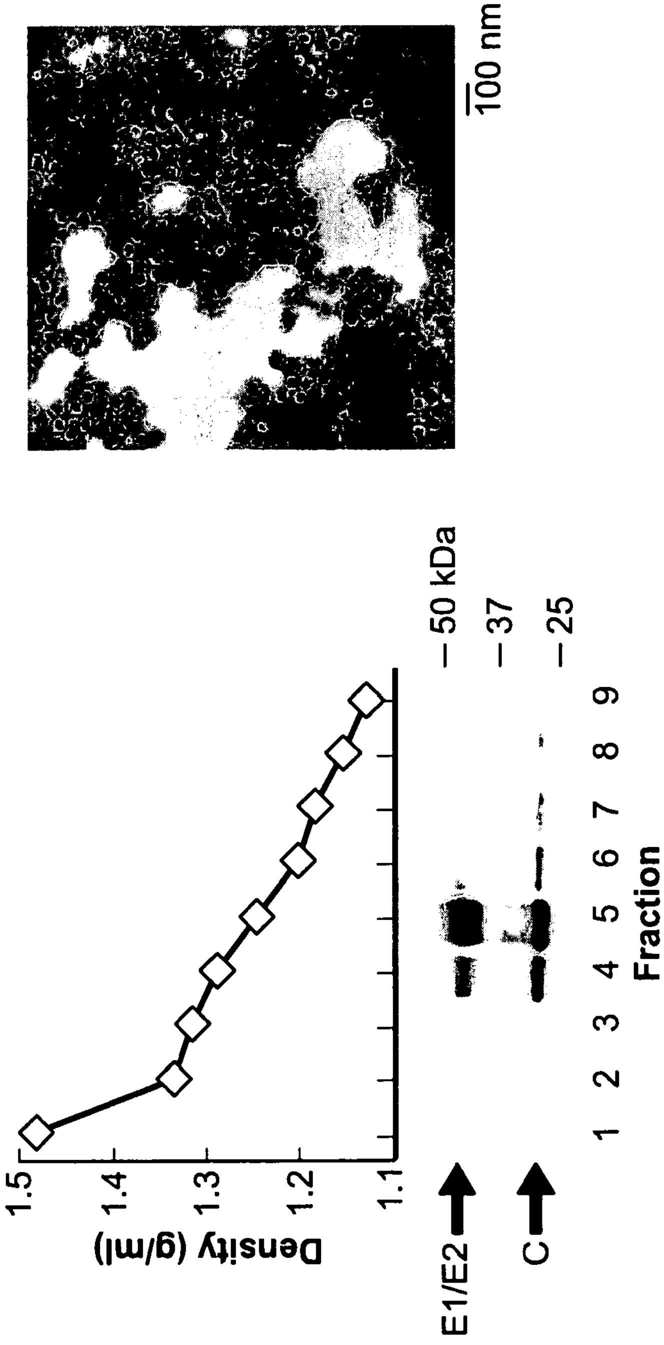

CHIKV encodes 4 nonstructural proteins, NS1, NS2, NS3 and NS4, which are involved in virus replication, and 5 structural proteins, which consist of capsid (C) and envelope proteins (E; E1, E2, E3 and 6K) that are synthesized as polyproteins and are cleaved by capsid autoproteinase and signalases (Strauss, *Microbiol. Rev.* 58, 491 (1994)). Eukaryotic expression vectors encoding C-E3-E2-6K-E1 from strains 37997 and LR2006 OPY-1 (C-E37997 and C-EOPY-1) were analyzed for their ability to give rise to VLP. The plasmids C-E37997 or C-EOPY-1 or the expression vectors described above, E37997 or EOPY-1 (FIG. 2A, upper panel), were transfected into human embryonic kidney (293T) cells, and expression was confirmed by Western blotting (FIG. 2A, lower panel). C and E1/E2 proteins were detected in the supernatant after transfection of the C-E37997 or C-EOPY-1 vector, suggesting that CHIKV VLPs had been generated. VLPs were purified by buoyant density gradient sedimentation. The yield of VLPs from strain 37797 was 10-20 mg/L, approximately 100 times higher than that from strain LR2006 OPY-1; strain 37997 was therefore chosen for further VLP characterization and development. Fractionation of clarified supernatant showed peak incorporation of E1/E2 at a density of 1.2 g/ml (FIG. 2B, left), comparable to the density of wild type CHIKV. Examination of the purified fraction from strain 37997 by electron microscopy revealed VLPs with the same morphologic appearance as wild type virus (FIG. 2B, right).

Figure 2C:
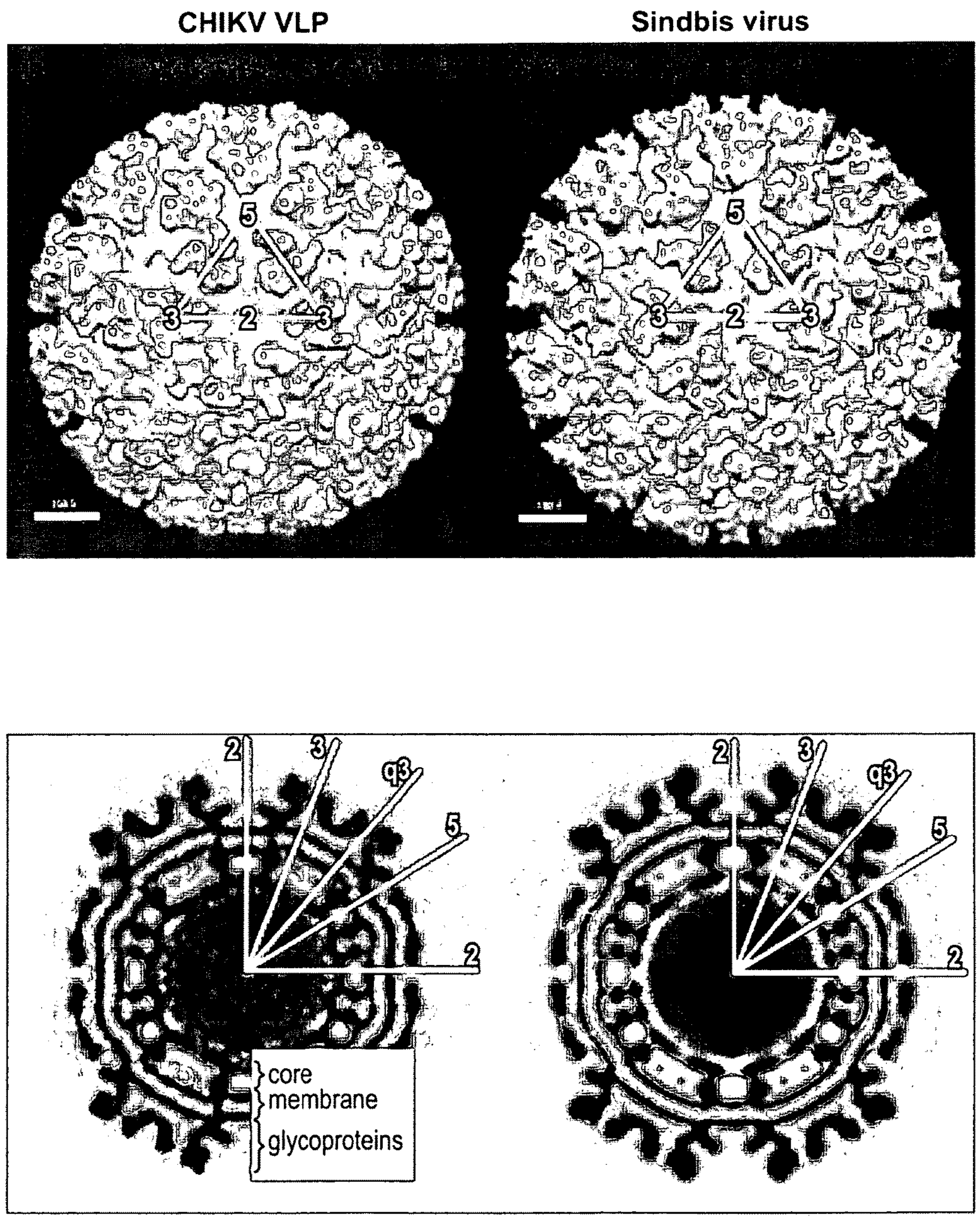

Cryoelectron microscopy and three dimensional image reconstruction assuming icosahedral symmetry showed that the VLPs had an external diameter of 65 nm and a core diameter of 40 nm (FIG. 2C, left). The potent immunogenic E1/E2 glycoproteins are organized into 240 heterodimers, assembled into 80 glycoprotein spikes arranged with T=4 quasi symmetry on the surface of the VLPs (FIG. 2C, left), closely similar to the structure of Sindbis virus (FIG. 2C, right). In addition, the organization of the nucleocapsid core is also remarkably similar to that of other alphaviruses.

Figure 3A:
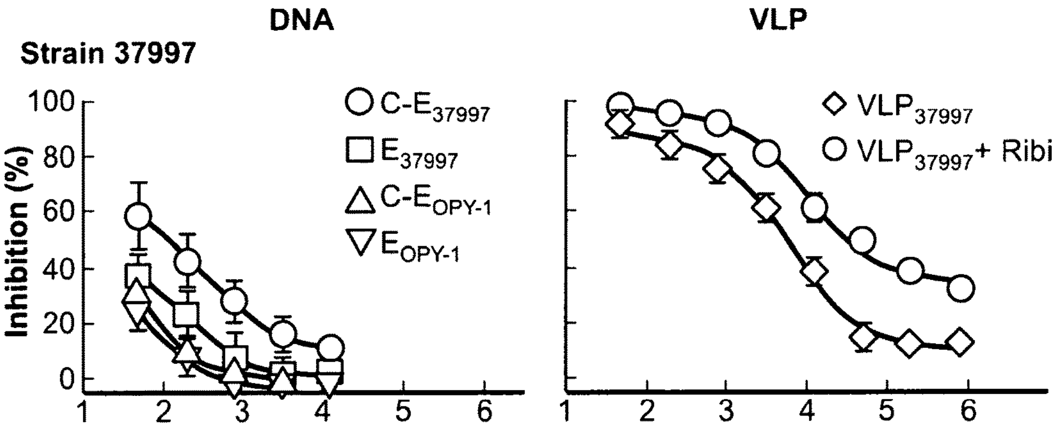
FIGS. 3A-3D are graphs showing the neutralization of CHIKV strains 37997 and LR2006 OPY-1 after DNA or VLP vaccination in mice and monkeys. Sera from immunized mice 10 days after the final immunization were tested with CHIKV strain 37997 (FIG. 3A) or LR2006 OPY-1 (FIG. 3B) E pseudotyped lentiviral vectors. Mice were immunized with the indicated DNA or $_{VLP37997}$. Each C-E or E (strain 37997 and LR2006 OPY-1, respectively) plasmid was injected at 0, 3 and 6 weeks. $_{VLP37997}$ with or without Ribi adjuvant was injected at 2 and 6 weeks. The experiment was performed in triplicate. The symbols show the average of the five mice and bars show the standard error of the mean. The curve fit was calculated by Prism software.
Figure 3B:
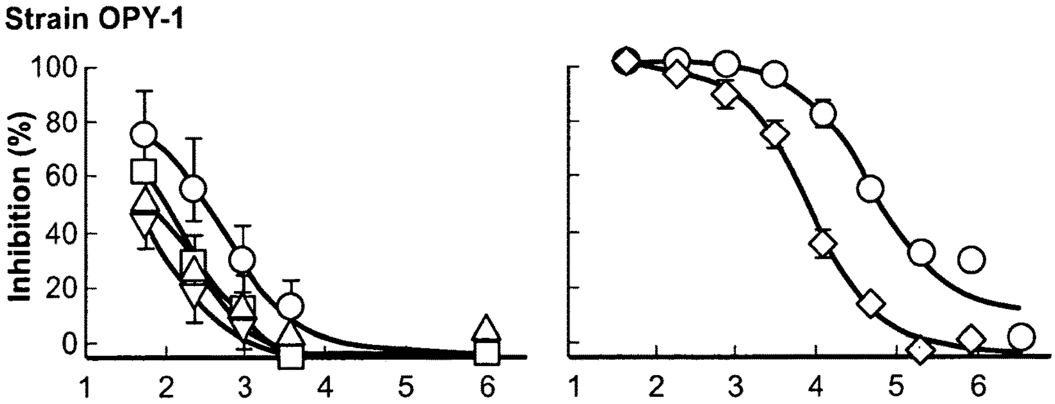

Example 3: VLPs Induced a More Potent Neutralizing Antibody Response to CHIKV than DNA Vaccines The immunogenicity of DNA and VLP vaccines was determined in mice immunized with DNA vaccines encoding C-E or E (strains 37997 and LR2006 OPY-1) or VLPs from strain 37997 (VLP37997) in the presence or absence of Ribi adjuvant. Mice injected with VLPs with adjuvant generated the highest titer neutralizing responses against both the homologous strain 37997 (FIG. 3A, right panel; IC50, 1:10,703) and the heterologous strain LR2006 OPY-1 (FIG. 3B, right panel; IC50, 1:54,600). While immunization with the plasmids encoding C-E and E from both strains elicited neutralizing responses, these responses were 100-fold lower than the VLP-immunized mice (FIG. 3A, B; left panel). These results indicate that VLPs elicited a more potent neutralizing antibody response than DNA vaccines.

Figure 3C:
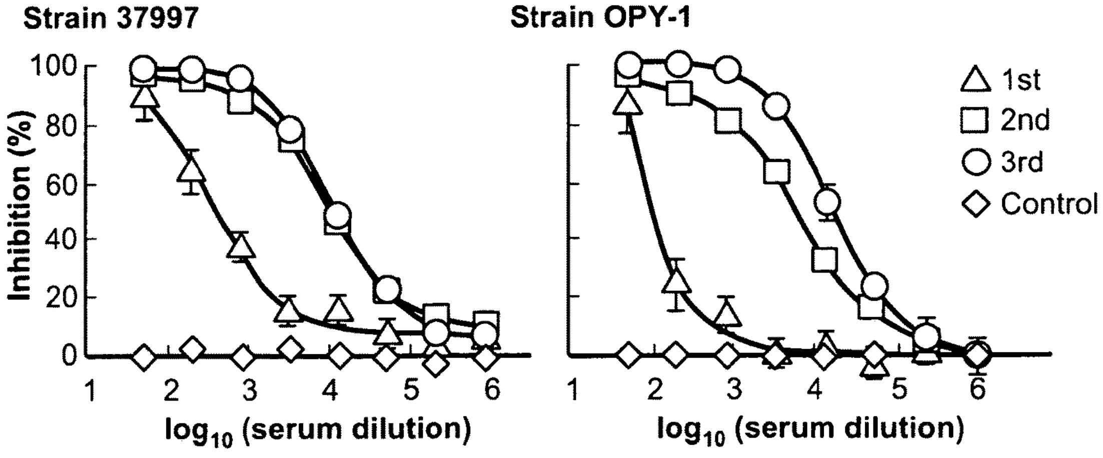
Figure 3D:
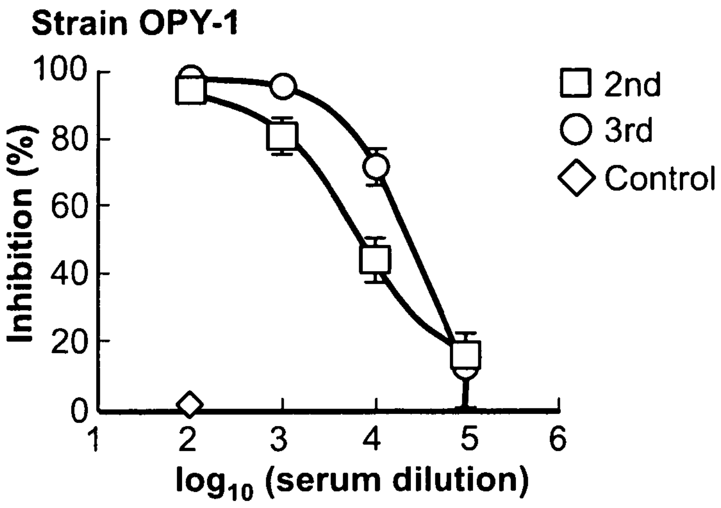

To characterize VLP-induced immune responses in a model with strong predictive value for humans, rhesus macaques were immunized with VLPs. Monkeys were injected with VLP37997 or PBS alone as a control. Sera from immunized and control monkeys were tested against CHIKV strain 37997 and LR2006 OPY-1 pseudotyped lentiviral vectors. All non-human primates (NHP) immunized with VLPs developed substantial neutralizing activity to both homologous and heterologous strains after primary immunization that increased after boosting (FIG. 3C; left panel: strain 37997, right panel: strain LR2006 OPY-1). To confirm that these antibodies neutralized infectious virus, a plaque reduction neutralization test (PRNT) was performed against the CHIKV LR2006 OPY-1. The antisera from the immunized monkeys elicited neutralizing antibody responses against LR2006 OPY-1 at titers that exceeded 1:40,000 (FIG. 3D). These data suggested that neutralizing antibodies using pseudotyped lentiviral vectors correlated with the PRNT assay, and that all immunized monkeys generated potent neutralizing antibody responses against CHIKV.

Figure 4B:
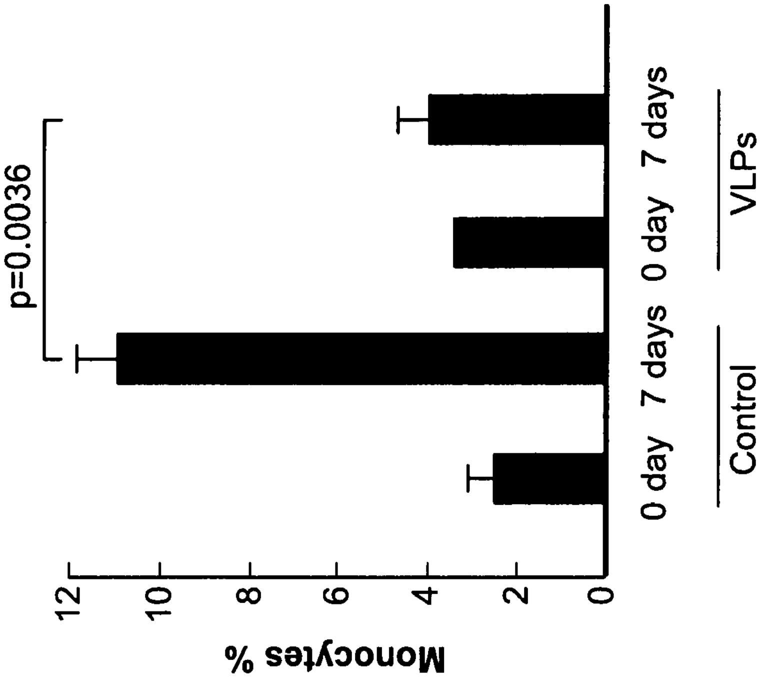
FIGS. 4A-4D are graphs showing protection against CHIKV LR2006 OPY-1 challenge in monkeys immunized with VLPs and in a CHIKV mouse model after passive transfer of purified IgG.
Figure 4A:
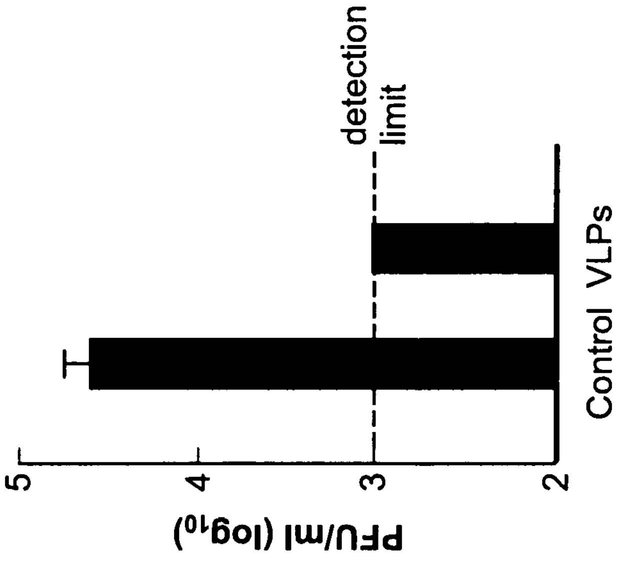
Figure 4D:
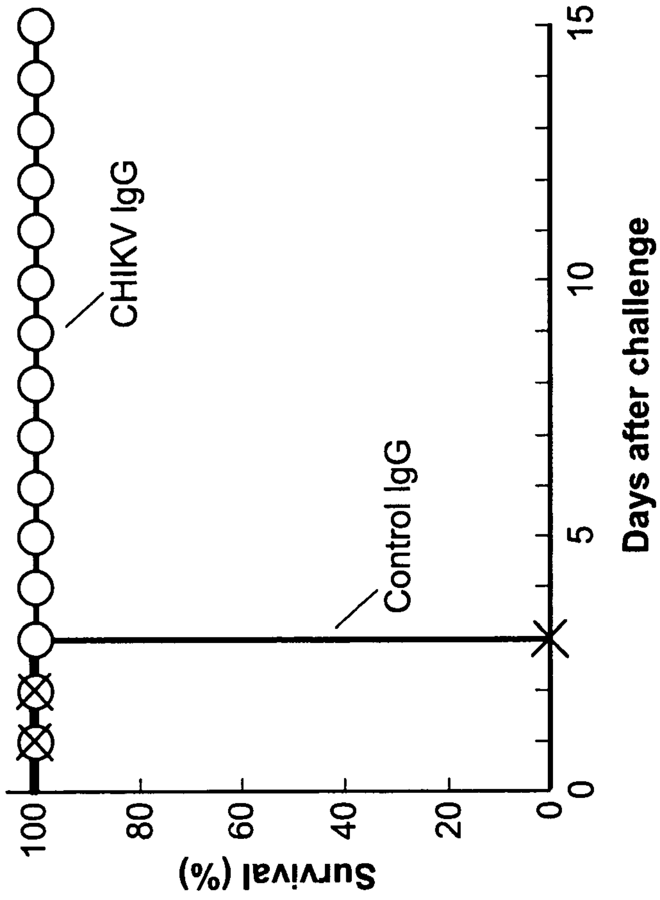

Example 4: Primate VLP Immunization Protected Against Viremia and Inflammatory Consequences of CHIKV Infection The ability of the VLP vaccine to protect against infection was determined by intravenous challenge of monkeys immunized with VLPs or controls using a high titer LR2006 OPY-1 virus stock 15 weeks after the final immunization. Similar to humans, infection in the NHP resulted in non-lethal viremia and a pro-inflammatory response as measured by an increase in monocyte counts. The control monkeys showed viremia beginning at 6 hours and lasting until 72 hours after challenge, while all of the immunized monkeys controlled the challenge virus completely (FIG. 4A). Similarly, the monocyte counts in control monkeys increased markedly relative to vaccinated monkeys by 4 days after challenge (FIG. 4B, Control vs. VLPs; p=0.0036). These data indicated that immunization protected against viremia as well as the inflammatory consequences of infection. To define the mechanism of protection in these animals, the question of whether immune IgG could protect against lethal challenge was examined using an adoptive transfer model.

Figure 4C:
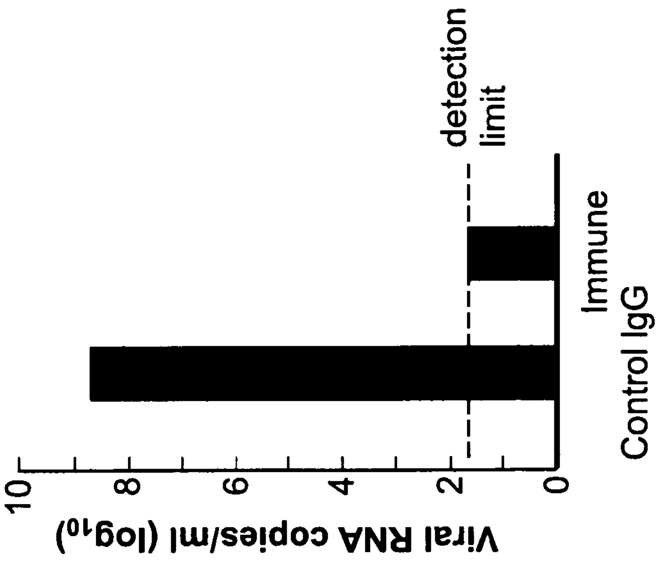

Example 5: Humoral Immune Responses Induced by CHIKV VLPs Conferred Protection Against CHIKV Infection Previous studies have shown that immunodeficient mice with defective type-I IFN signaling developed severe infection, displaying symptoms and tissue tropism analogous to humans, and providing a model to evaluate immune mechanisms of protection. Purified total IgG from immune or control monkeys was passively transferred into these mice. The recipient mice were challenged intradermally 24 hours after IgG transfer with a lethal dose of LR2006 OPY-1. Recipients of purified CHIKV immune IgG demonstrated no detectable viremia after infection and were completely protected from lethality (FIGS. 4C, D). In contrast, all mice that received purified IgG from control monkeys showed severe infection and viremia, and all died. These results indicate that humoral immune responses induced by CHIKV VLPs conferred protection against CHIKV infection.

As reported herein, VLPs and plasmid DNA vaccines against CHIKV were evaluated for their ability to elicit cross-strain neutralizing antibodies. Immunization with VLPs showed cross-strain reactivity and 100-fold higher titers than DNA vaccines, and monkeys showed protection against CHIKV infection at a dose higher than that likely to be encountered in the field. Moreover, passively transferred antibody from monkeys immunized with VLPs protected against a lethal challenge in a relevant murine model, which suggests that the humoral response is important for protection against CHIKV. The current outbreaks of CHIKV fever have occurred largely in Southern Asia and underscore the need for a human vaccine. These infections represent the spread of a virus first recognized in Kenya in 2004 before dissemination to several islands in the Indian Ocean in 2005-2006. The Reunion Island outbreak alone infected 244,000 people with an overall seroprevalence of 35%. The virus then spread to other continents, and by 2008 was reported in 37 countries with an estimated 1.4-6.5 million cases in India, Africa, Europe and Southeast Asia.

In 2009 the number of cases has continued to increase, in part because the current epidemic strain of CHIKV has adapted to a new vector, the Asian tiger mosquito, *Ae. albopictus*, which can survive in more temperate climates, including Europe and the United States. CHIKV continues to cause substantial morbidity and has resulted in significant economic losses. While there were no reports of mortality in previous chikungunya epidemics, more than 260 deaths during the latest outbreak were directly attributed to the virus. To date, there has been limited success in developing a safe and effective CHIKV vaccine. A live CHIKV vaccine candidate caused transient arthralagia in volunteers. Other efforts, which include a live attenuated vaccine, a formalin-killed vaccine, a Venezuelan equine encephalitis/CHIKV chimeric live attenuated vaccine and a consensus-based DNA vaccine (Muthumani et al., *Vaccine* 26, 5128 (2008)) have not yet proven to be both safe and effective. Although CHIKV strains vary widely, individual strains are antigenically related, so a vaccine that works against heterologous strains may be achieved (Harrison et al., *Am. J Trop. Med. Hyg.* 16, 786 (1967)). The safety and efficacy of VLP vaccines in general make them promising candidates for further study.

VLPs are known to be highly immunogenic and elicit higher titer neutralizing antibody responses than subunit vaccines based on individual proteins. Such VLPs authentically present viral spikes and other surface components in a repetitive array that effectively elicits recognition by B-cells to stimulate antibody secretion. This recognition leads to B cell signaling and MHC class II up-regulation that facilitates the generation of high titer specific antibodies. VLPs from other viruses, including hepatitis B virus (HBV) and human papillomavirus (HPV), elicit high titer neutralizing antibody responses that contribute to protective immunity in humans.

The vaccines described herein represent the first use of recombinant VLPs to prevent infection by alphaviruses. The spread of mosquito species worldwide has been aided by changes in trade, travel or global climate and may potentially cause other alphavirus outbreaks. This approach to vaccine development may prove useful for other alphaviruses of increasing concern, including Western, Eastern, and Venezuelan equine encephalitis viruses, o'nyong-nyong virus and Ross River virus.

The results reported herein were obtained using the following methods and materials.

Vector Construction

Plasmids encoding the structural polyproteins C, E1, E2, E3 and 6K (strains 37997 and LR2006 OPY-1, GenBank EU224270) (FIG. 25) and EU224268 (FIG. 24), respectively) were synthesized as previously described (Yang et al., *Science* 317,825 (2007)) (GeneArt, Regensburg, Germany). Plasmids encoding the polyproteins E3, E2, 6K, and E1 were amplified by PCR using the sense primer 5' GCTCTAGACACCATGAGCCTCGCCCTCCCG-GTCTTG 3' (SEQ ID NO:26) and antisense primer 5' TGGATCCTCATTAGTGCCTGCTAAACGACA 3' (37997) (SEQ ID NO:27) and the sense primer 5' GCTCTA-GACACCATGAGTCTTGCCATCCCAGTTATG 3' (SEQ ID NO:28) and antisense primer 5' TGGATCCTCATTAGT-GCCTGCTGAACGACA 3' (LR2006 OPY-I) (SEQ ID NO:29). XbaI and BamHI sites were inserted for cloning. Each fragment was digested with XbaVBamHI and inserted into a eukaryotic expression vector under the control of a cytomegalovirus enhancer/promoter, CMVIR (Yang et al., *Science* 317, 825 (2007)) (C-$E_{37997}$, C-$E_{OPY\text{-}1}$, $E_{37997}{}^{and}$ $E_{OPY\text{-}1}$). To confirm expression of CHIKV C and E proteins, 293T cells were transfected using a FUGENE6™ Transfection Reagent kit (Roche Diagnostics GmbH, Germany) with 3 μg of the plasmid DNAs, following the manufacturer's recommendations.

Cell Culture 293T and 293A (human embryonic kidney cells), Vero (African green monkey kidney epithelial cells), HeLa (human cervical adenocarcinoma), A549 (human lung carcinoma) and BHK (baby hamster kidney cells) were cultured in Dulbecco's modified Eagle's medium (DMEM; GIBCO BRL) containing 10% heat-inactivated fetal bovine serum (FBS) (GIBCO BRL).

Production of Pseudotyped Lentiviral Vectors

Lentiviral vectors expressing glycoproteins from different CHIKV strains were created. The recombinant lentiviral vectors expressing a luciferase reporter gene were produced as previously described (Naldini et al., *Proc. Natl. Acad. Sci. USA* 93, 11382 (1996), Yang et al., *Science* 317, 825 (2007)). Briefly, 293T cells were co-transfected with 500 ng CHIKV E plasmid from either strain $_{(E37997}$ $^{or}$ $E_{OPY-1)}$, 7 μg of a transducing vector encoding a luciferase reporter gene (pHR'CMV-luciferase plasmid), and 7 μg of a packaging plasmid expressing human immunodeficiency virus-1 (HIV-1) structural proteins (pCMVåR8.2). 2 μg of vesicular stomatitis virus glycoprotein (VSV-G), 2 μg of pNGVL-4070A amphotropic MuLV gp70 expression vector or 500 ng of empty vector served as positive and negative controls for these pseudotyped reporters respectively. After a calcium phosphate transfection (Invitrogen, Carlsbad, Calif.) overnight, the culture media was replenished with fresh media. 48 hours later, supernatants were harvested, filtered through a 0.45 μm syringe filter, stored in aliquots, and frozen at −80° C. The viruses were standardized by the amount of HIV-1 Gag p24. CHIKV pseudotyped lentiviral vectors harvested 72 h after transfection were normalized according to HIV-1 Gag p24 levels before infection, as previously described (Yang et al., *Science* 317, 825 (2007)).

Neutralization of CHIKV E Pseudotyped Lentiviral Vectors by Mouse and Monkey Antisera The neutralization assay was performed as described previously (Yang et al., *Science* 317, 825 (2007)). A total of $10^4$ 293A cells were plated into each well of a 96-well dish one day prior to infection. CHIKV E-pseudotyped lentiviral vectors encoding luciferase were first titrated by serial dilution. Similar amounts of pseudotyped lentiviral vectors (with p24 levels of approximately 50 ng/ml) were then incubated with the indicated dilutions of mouse antisera for 60 minutes at room temperature prior to adding the virus: sera solution to 293A cells ($10^4$ cells/well in a 96-well dish, 50 μl/well, in triplicate). Sera from non-immune mice or monkeys were used as a negative control. After a 24 hour incubation, cells were lysed using cell lysis buffer (Cell Signal) and the luciferase activity was measured using Microbeta® JET (PerkinElmer, Turku, Finland) following incubation with "Luciferase assay reagent" (Promega, Madison, Wis.), according to the manufacturer's protocol. Inhibition values were calculated as follows: inhibition (%)=[1−(luciferase activity (cps) in pseudotyped lentiviral vector infected cells incubated with the indicated dilutions of mouse antisera)/(luciferase activity (cps) in pseudotyped lentiviral vector infected cells incubated with the same dilutions of non-immune mouse serum)]×100. The $_{IC50}$ was calculated with Prism software (version 5).

Electron Microscopy

The morphology of the VLPs was examined by the Image Analysis Laboratory at the National Cancer Institute. VLPs were purified by Optiprep density centrifugation and were then fixed in 4% formaldehyde in PBS. Negative-stain electron microscopy for viral diagnosis has been described previously (Palmer and Martin, Electron Microscopy in Viral Diagnosis (CRC Press, Boca Raton, Fla., 1988)). Briefly, 1.0 μl of the sample was placed onto a carbon-coated Formvar-filmed copper grid (Tousimis Research Corp., Rockville, Md.) and VLPs allowed to attach. The VLPs were negatively stained by addition of 2 μl of 1% PTA solution (phosphotungstic acid, pH 7.0) (Fisher Scientific Co., Fairlawn, N.J.). The grid was then examined by electron microscope (Hitachi H7000, Tokyo, Japan) operated at 75 kV. Digital images were taken by a CCD camera (AMT, Danvers, Mass.).

Cryo-Electron Microscopy and Image Analysis

Chikungunya VLPs were flash-frozen on holey grids in liquid ethane. Images were recorded at 47K magnification with a CM300 FEG microscope with electron dose levels of approximately 20 $e^{i}$/Å$^2$. All micrographs were digitized at 6.35 μm pixel$^{il}$ using a Nikon scanner. Individual particle images were boxed using the program e2boxer in the EMAN2 package (Tang et al., *J Struct. Biol.* 157, 38 (2007)). CTF parameters were determined and phases were flipped using the CTFIT program from the EMAN package (Ludtke et al., *J Struct. Biol.* 128, 82 (1999)). An initial model was constructed in EMAN using assigned 2-, 3-, and 5-fold views and was refined in EMAN assuming icosahedral symmetry. The number of particles incorporated into the final reconstruction was 1489, giving a final resolution of 18 Å based on a 0.5 Fourier shell correlation threshold.

Buoyant Density Gradient Sedimentation Analysis and Purification of VLPs

Buoyant density gradient analysis and purification of VLPs was performed as described previously (Akahata et al., *J. Virol.* 79, 626 (2005)). Briefly, a 293-derived suspension cell line, 293F ($2.5\times10^8$ cells) (Invitrogen) was transfected with 293fectin transfection reagent (Invitrogen) and 125 μg of $_{C-E37997}$ plasmid following the manufacturer's recommendations. The supernatants were harvested 72 h after transfection and filtered through a 0.45 3 m pore size filter, then layered onto a 60% Optiprep (Iodixanol) medium (Invitrogen) and centrifuged at 50,000× g for 1.5 h with a Surespin 630 rotor (Sorvall). The supernatants were removed to leave 4 ml above the virus band and mixed to a 20% final concentration of OptiPrep. A density gradient was formed by centrifugation at 360,000× g for 3.5 hr with an NVT100 rotor (Beckman). 500 μl of each fraction was collected, weighed, and the densities of the fractions were plotted. 20 μl of each fraction was separated on a 4%-1 5% SDS-PAGE gel, transferred onto an Immobilon-P membrane, and blotted with sera from mice injected with the CHIKV strain S-27 (ATCC, VR-1241AF) and goat anti-mouse immunoglobulins linked to horseradish peroxidase (Santa Cruz Biotechnology).

Immunizations and Challenge of Mouse and Monkeys

Nineteen μg of VLPs (equivalent to approximately 10 μg of E1/E2) in 60 μl normal saline were mixed with 60 μl of Ribi solution (Sigma Adjuvant system, Sigma-Aldrich) per mouse following the manufacturer's recommendations. Female 6- to 8-week-old BALB/c mice were injected in the right and left quadriceps muscles with VLPs in normal saline or Ribi in 120 μl total volume, two times at weeks 2 and 6. For DNA vaccination groups, the mice were injected in the right and left quadriceps muscles with a total of 15 μg of purified plasmid C-$E_{37997}$, $E_{37997}$, C-$E_{OPY-1}$ $^{or}$ $E_{OPY-1}$ suspended in 100 μl of normal saline three times at weeks 0, 3 and 6. Five mice/group were injected. 10 days after the last injection, sera and spleen were collected.

In the monkey experiments, rhesus macaques (*Macaca mulatta*) weighing 3-4 kg were injected intramuscularly in the anterior quadriceps with either twenty μg of VLPs in 1 ml PBS (VLP group) or 1 ml PBS alone (control group) at weeks 0, 4 and 24. Six monkeys/group were injected. Blood was collected to measure antibody titers on days −14, 0, 10, 28, 38, 56, 70, 161 and 178. The monkeys (n=3 per group, randomly selected from each group) were challenged with $10^{10}$ PFU of CHIKV (strain LR2006 OPY-1) by intravenous injection. Blood was collected to measure viremia at 0, 6, 24, 48, 72, 96, 120 and 168 hours. The monkeys were sacrificed at 168 h after challenge. The whole blood cells were measured using a hematology analyzer (IDEXX Laboratories, Inc., Westbrook, Me.). Bleeds were EDTA-anticoagulated using 20-22 gauge needles and either syringes or vacuum tubes. The maximum blood volume removed did not exceed 20% (12 ml/kg) per month, with no more than 15% (9 ml/kg) removed during any single draw.

All animal experiments were reviewed and approved by the Animal Care and Use Committee, Vaccine Research Center (VRC), National Institute of Allergy and Infectious Diseases and performed in accordance with all relevant federal and National Institutes of Health guidelines and regulations.

Virus Preparation

CHIKV (strain LR2006 OPY-1) was prepared and the virus titers were determined as previously described (Tsetsarkin et al., PLoS. Pathog. 3, e201 (2007) and Pastorino et al., J Virol. Methods 124, 65 (2005)). Briefly, viral RNA transcribed from plasmid CHIK-LR ic was transfected into BHK-21 cells by electroporation. The supernatants from the transfected cells were aliquotted and the stock virus was titrated and tissue culture infectious dose 50% ($TCID_{50}$) endpoint titers were determined using Vero cells. To produce virus for vertebrate challenge, C6/36 (*Aedes albopictus*) cells grown to confluence in T150 flasks were infected with stock virus at a multiplicity of infection of 0.03. Supernatants were harvested at 48 hrs post-infection, aliquotted and titrated to determine $TCID_{50}$ endpoint titers on Vero cells.

Plaque Assay

Serum samples were tested for CHIKV neutralizing antibody by a standard plaque reduction neutralization test (PRNT). Briefly, monkey sera were heat inactivated at 56° C. for 30 minutes and diluted in virus diluent (PBS/5% BSA). Diluted serum samples were mixed with an equal volume of 40 PFU CHIKV (strain LR2006 OPY-1) and incubated for 1 hr at 37° C. Six-well plates of confluent Vero cells were inoculated with 200 µl of the serum-virus mixtures in duplicate and incubated at 37° C. for 1 hr. Plates were overlaid with 3 ml of medium containing 0.9% agarose (Lonza Rockland, Rockland, Me.) and incubated at 37° C. in a 5% $CO_2$ incubator for 2 days. A second overlay medium containing neutral red and 1% agarose was then added and the plates were incubated overnight before plaques were visualized and counted. The viremia in the monkeys after challenge was measured by plaque assay. Six-well plates of confluent Vero cells were inoculated with 200 µl of the serum-PBS mixtures in duplicate. The serum dilutions were 1:200, 1:400, 1:800, 1:1000, 1:10,000 and 1:100,000, since at lower dilutions toxicities were observed in the cells (detection limit 1:200 dilution=1000 PFU/ml).

Passive Transfer of Immunoglobulin and Challenge in IFNα/ßR$^{-/-}$ Mice

IFNα/ßR$^{-/-}$ mice were kindly given by Robert Seder and Daniel D. Pinschewer. IgG was purified from the serum in monkeys immunized with CHIKV VLPs or injected with PBS (control) using a HiTrap™ Protein G HP column (GE Healthcare) following the manufacturer's recommendations. IgG was further purified using a Melon Gel IgG Purification Kit (Pierce) following the manufacturer's recommendations. Purified IgG was dialyzed 3 times against PBS. 2 mg of purified IgG (from approximately 200 µl of serum) was administered intravenously into each recipient IFNα/ßR$^{-/-}$ mouse by tail vein injection 24 h before challenge. The mice were challenged with 30 PFU of CHIKV (strain LR2006 OPY-1) by intradermal injection.

Detection of CHIKV RNA by Quantitative RT-PCR

For RNA isolation, serum samples were spun down at 10,000×g for 1 hr, liquid poured off and 1 ml of RNA-STAT 60 (Isotex Diagnostics, Friendswood, Tex.) added. Samples were then incubated at RT for 5 min and resuspended in 250 µl of chloroform by vortexing. The samples were spun down at 10,000×g for 1 hr, the aqueous top-layer removed, 0.5 ml isopropanol and 10 µl tRNA (10 µg/ml) added and precipitated overnight at −20° C. Samples were spun down for 1 hr, washed with cold 75% ethanol and spun again for another hour. RNA was resuspended in 30 µl RNAse-free water. For RT-PCR, 10% RNA was added to TaqMan reagents (Applied Biosystems, Foster City, Calif.) along with primers and probe (listed below) and amplified in a 7700 Sequence Detection System (Applied Biosystems). Briefly, the sample was reverse-transcribed at 48° C. for 30 min., held at 95° C. for 10 min, then run for 30 cycles of 95° C. for 30 s and 60° C. for 1 min. The signal was compared to a standard curve of known concentrations of plasmid containing the LR2006 OPY-1 sequence starting at $10^7$ down to 1 copy/ml and multiplied by 10, giving a detection range from 40-$10^8$ copies/ml. All samples were performed in triplicate. The primers and probe were designed to bind to a highly conserved region on the E1 structural protein gene. Primer sequences: CHIKF 5' AAGCTCCGCGTCCTTTACCAAG 3' (SEQ ID NO:30) and CHIK-R 5' CCAAATTGTCCTG-GTCTTCCT3' (SEQ ID NO:31). Probe sequence: CHICK-P FAM-CCAATGTCTTCAGCCTGGACACCTTT-TAMRA (SEQ ID NO:32) as described previously (Huang et al., *J. Virol.* 78, 12557 (2004); Pastorino et al., J Virol. Methods 124, 65 (2005)).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for inducing in a subject, an immune response against Chikungunya virus (CHIKV), comprising administering to the subject a composition comprising a virus-like particle (VLP) comprising one or more structural proteins from CHIKV strain 37997, wherein the VLP does not carry genetic information encoding the VLP proteins.

2. The method of claim 1, wherein the one or more structural proteins are selected from the group consisting of CHIKV capsid (C) protein, CHIKV E3 protein, CHIKV E2 protein, CHIKV 6K protein and CHIKV E1 protein.

3. The method of claim 1, wherein the VLP comprises CHIKV envelope proteins E3, E2, 6K and E1.

4. The method of claim 1, wherein the composition comprises an adjuvant.

5. The method of claim 4, wherein the adjuvant is selected from the group consisting of Ribi, aluminum salts, muramyl peptides, bacterial cell wall components, and saponin adjuvants.

6. The method of claim 1, wherein the immune response comprises the elicitation of antibodies against homologous or heterologous strains of Chikungunya.

* * * * *

SEQUENCE LISTING

```
<160> NUMBER OF SEQ ID NOS: 33

<210> SEQ ID NO 1
<211> LENGTH: 3747
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
atggagttca tcccgacgca aactttctat aacagaaggt accaaccccg accctgggcc 60
ccacgcccta caattcaagt aattagacct agaccacgtc cacagaggca ggctgggcaa 120
ctcgcccagc tgatctccgc agtcaacaaa ttgaccatgc gcgcggtacc tcaacagaag 180
cctcgcagaa atcggaaaaa caagaagcaa aggcagaaga agcaggcgcc gcaaaacgac 240
ccaaagcaaa agaagcaacc accacaaaag aagccggctc aaaagaagaa gaaaccaggc 300
cgtagggaga gaatgtgcat gaaaattgaa aatgattgca tcttcgaagt caagcatgaa 360
ggcaaagtga tgggctacgc atgcctggtg ggggataaag taatgaaacc agcacatgtg 420
aagggaacta tcgacaatgc cgatctggct aaactggcct ttaagcggtc gtctaaatac 480
gatcttgaat gtgcacagat accggtgcac atgaagtctg atgcctcgaa gtttacccac 540
gagaaacccg aggggtacta taactggcat cacggagcag tgcagtattc aggaggccgg 600
ttcactatcc cgacgggtgc aggcaagccg ggagacagcg gcagaccgat cttcgacaac 660
aaaggacggg tggtggccat cgtcctagga ggggccaacg aaggtgcccg cacggccctc 720
tccgtggtga cgtggaacaa agacatcgtc acaaaaatta cccctgaggg agccgaagag 780
tggagcctcg ccctcccggt cttgtgcctg ttggcaaaca ctacattccc ctgctctcag 840
ccgccttgca caccctgctg ctacgaaaag gaaccggaaa gcaccttgcg catgcttgag 900
gacaacgtga tgagacccgg atactaccag ctactaaaag catcgctgac ttgctctccc 960
caccgccaaa gacgcagtac taaggacaat tttaatgtct ataaagccac aagaccatat 1020
ctagctcatt gtcctgactg cggagaaggg cattcgtgcc acagccctat cgcattggag 1080
cgcatcagaa atgaagcaac ggacggaacg ctgaaaatcc aggtctcttt gcagatcggg 1140
ataaagacag atgacagcca cgattggacc aagctgcgct atatggatag ccatacgcca 1200
gcggacgcgg agcgagccgg attgcttgta aggacttcag caccgtgcac gatcaccggg 1260
accatgggac actttattct cgcccgatgc ccgaaaggag agacgctgac agtgggattt 1320
acggacagca gaaagatcag ccacacatgc acacacccgt tccatcatga accacctgtg 1380
ataggtaggg agaggttcca ctctcgacca caacatggta aagagttacc ttgcagcacg 1440
tacgtgcaga gcaccgctgc cactgctgag gagatagagg tgcatatgcc cccagatact 1500
cctgaccgca cgctgatgac gcagcagtct ggcaacgtga agatcacagt taatgggcag 1560
acggtgcggt acaagtgcaa ctgcggtggc tcaaacgagg gactgacaac cacagacaaa 1620
gtgatcaata actgcaaaat tgatcagtgc catgctgcag tcactaatca caagaattgg 1680
caatacaact cccctttagt cccgcgcaac gctgaactcg ggaccgtaa aggaaagatc 1740 cacatcccat tcccattggc aaacgtgact tgcagagtgc caaaagcaag aaaccctaca 1800
gtaacttacg gaaaaaacca agtcaccatg ctgctgtatc ctgaccatcc gacactcttg 1860
tcttaccgta acatgggaca ggaaccaaat taccacgagg agtgggtgac acacaagaag 1920
gaggttacct tgaccgtgcc tactgagggt ctggaggtca cttggggcaa caacgaacca 1980
tacaagtact ggccgcagat gtctacgaac ggtactgctc atggtcaccc acatgagata 2040
atcttgtact attatgagct gtaccccact atgactgtag tcattgtgtc ggtggcctcg 2100
ttcgtgcttc tgtcgatggt gggcacagca gtgggaatgt gtgtgtgcgc acggcgcaga 2160

```
tgcattacac catatgaatt aacaccagga gccactgttc ccttcctgct cagcctgcta   2220

tgctgcgtca gaacgaccaa ggcggccaca tattacgagg ctgcggcata tctatggaac   2280

gaacagcagc ccctgttctg gttgcaggct cttatcccgc tggccgcctt gatcgtcctg   2340

tgcaactgtc tgaaactctt gccatgctgc tgtaagaccc tggctttttt agccgtaatg   2400

agcatcggtg cccacactgt gagcgcgtac gaacacgtaa cagtgatccc gaacacggtg   2460

ggagtaccgt ataagactct tgtcaacaga ccgggttaca gccccatggt gttggagatg   2520

gagctacaat cagtcacctt ggaaccaaca ctgtcacttg actacatcac gtgcgagtac   2580

aaaactgtca tcccctcccc gtacgtgaag tgctgtggta cagcagagtg caaggacaag   2640

agcctaccag actacagctg caaggtcttt actggagtct acccatttat gtggggcggc   2700

gcctactgct tttgcgacgc cgaaaatacg caattgagcg aggcacatgt agagaaatct   2760

gaatcttgca aaacagagtt tgcatcggcc tacagagccc acaccgcatc ggcgtcggcg   2820

aagctccgcg tcctttacca aggaaacaac attaccgtag ctgcctacgc taacggtgac   2880

catgccgtca cagtaaagga cgccaagttt gtcgtgggcc caatgtcctc cgcctggaca   2940

ccttttgaca acaaaatcgt ggtgtacaaa ggcgacgtct acaacatgga ctacccacct   3000

tttggcgcag gaagaccagg acaatttggt gacattcaaa gtcgtacacc ggaaagtaaa   3060

gacgtttatg ccaacactca gttggtacta cagaggccag cagcaggcac ggtacatgta   3120

ccatactctc aggcaccatc tggcttcaag tattggctga aggaacgagg agcatcgcta   3180

cagcacacgg caccgttcgg ttgccagatt gcgacaaacc cggtaagagc tgtaaattgc   3240

gctgtgggga acataccaat ttccatcgac ataccggatg cggcctttac tagggttgtc   3300

gatgcaccct ctgtaacgga catgtcatgc gaagtaccag cctgcactca ctcctccgac   3360

tttgggggcg tcgccatcat caaatacaca gctagcaaga aaggtaaatg tgcagtacat   3420

tcgatgacca acgccgttac cattcgagaa gccgacgtag aagtagaggg gaactcccag   3480

ctgcaaatat ccttctcaac agccctggca agcgccgagt ttcgcgtgca agtgtgctcc   3540

acacaagtac actgcgcagc cgcatgccac cctccaaagg accacatagt caattaccca   3600

gcatcacaca ccacccttgg ggtccaggat atatccacaa cggcaatgtc ttgggtgcag   3660

aagattacgg gaggagtagg attaattgtt gctgttgctg ccttaatttt aattgtggtg   3720

ctatgcgtgt cgtttagcag gcactaa                                       3747
```

<210> SEQ ID NO 2
<211> LENGTH: 8159
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420
```

```
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
accatggagt tcatcccgac gcaaactttc tataacagaa ggtaccaacc ccgaccctgg   1440
gccccacgcc ctacaattca agtaattaga cctagaccac gtccacagag gcaggctggg   1500
caactcgccc agctgatctc cgcagtcaac aaattgacca tgcgcgcggt acctcaacag   1560
aagcctcgca gaaatcggaa aaacaagaag caaaggcaga agaagcaggc gccgcaaaac   1620
gacccaaagc aaaagaagca accaccacaa aagaagccgg ctcaaaagaa gaagaaacca   1680
ggccgtaggg agagaatgtg catgaaaatt gaaaatgatt gcatcttcga agtcaagcat   1740
gaaggcaaag tgatgggcta cgcatgcctg gtgggggata aagtaatgaa accagcacat   1800
gtgaagggaa ctatcgacaa tgccgatctg gctaaactgg cctttaagcg gtcgtctaaa   1860
tacgatcttg aatgtgcaca gataccggtg cacatgaagt ctgatgcctc gaagtttacc   1920
cacgagaaac ccgaggggta ctataactgg catcacggag cagtgcagta ttcaggaggc   1980
cggttcacta tcccgacggg tgcaggcaag ccgggagaca gcggcagacc gatcttcgac   2040
aacaaaggac gggtggtggc catcgtccta ggaggggcca acgaaggtgc ccgcacggcc   2100
ctctccgtgg tgacgtggaa caaagacatc gtcacaaaaa ttacccctga gggagccgaa   2160
gagtggagcc tcgccctccc ggtcttgtgc ctgttggcaa acactacatt cccctgctct   2220
cagccgcctt gcacaccctg ctgctacgaa aaggaaccgg aaagcacctt gcgcatgctt   2280
gaggacaacg tgatgagacc cggatactac cagctactaa aagcatcgct gacttgctct   2340
ccccaccgcc aaagacgcag tactaaggac aattttaatg tctataaagc cacaagacca   2400
tatctagctc attgtcctga ctgcggagaa gggcattcgt gccacagccc tatcgcattg   2460
gagcgcatca gaaatgaagc aacggacgga acgctgaaaa tccaggtctc tttgcagatc   2520
gggataaaga cagatgacag ccacgattgg accaagctgc gctatatgga tagccatacg   2580
ccagcggacg cggagcgagc cggattgctt gtaaggactt cagcaccgtg cacgatcacc   2640
gggaccatgg gacactttat tctcgcccga tgcccgaaag gagagacgct gacagtggga   2700
tttacggaca gcagaaagat cagccacaca tgcacacacc cgttccatca tgaaccacct   2760
```

-continued gtgataggta gggagaggtt ccactctcga ccacaacatg gtaaagagtt accttgcagc 2820
acgtacgtgc agagcaccgc tgccactgct gaggagatag aggtgcatat gcccccagat 2880
actcctgacc gcacgctgat gacgcagcag tctggcaacg tgaagatcac agttaatggg 2940
cagacggtgc ggtacaagtg caactgcggt ggctcaaacg agggactgac aaccacagac 3000
aaagtgatca ataactgcaa aattgatcag tgccatgctg cagtcactaa tcacaagaat 3060
tggcaataca actccccttt agtcccgcgc aacgctgaac tcggggaccg taaaggaaag 3120
atccacatcc cattcccatt ggcaaacgtg acttgcagag tgccaaaagc aagaaaccct 3180
acagtaactt acggaaaaaa ccaagtcacc atgctgctgt atcctgacca tccgacactc 3240
ttgtcttacc gtaacatggg acaggaacca aattaccacg aggagtgggt gacacacaag 3300
aaggaggtta ccttgaccgt gcctactgag ggtctggagg tcacttgggg caacaacgaa 3360
ccatacaagt actggccgca gatgtctacg aacggtactg ctcatggtca cccacatgag 3420
ataatcttgt actattatga gctgtacccc actatgactg tagtcattgt gtcggtggcc 3480
tcgttcgtgc ttctgtcgat ggtgggcaca gcagtgggaa tgtgtgtgtg cgcacggcgc 3540
agatgcatta caccatatga attaacacca ggagccactg ttcccttcct gctcagcctg 3600
ctatgctgcg tcagaacgac caaggcggcc acatattacg aggctgcggc atatctatgg 3660
aacgaacagc agcccctgtt ctggttgcag gctcttatcc cgctggccgc cttgatcgtc 3720
ctgtgcaact gtctgaaact cttgccatgc tgctgtaaga ccctggcttt tttagccgta 3780
atgagcatcg gtgcccacac tgtgagcgcg tacgaacacg taacagtgat cccgaacacg 3840
gtgggagtac cgtataagac tcttgtcaac agaccgggtt acagccccat ggtgttggag 3900
atggagctac aatcagtcac cttggaacca acactgtcac ttgactacat cacgtgcgag 3960
tacaaaactg tcatcccctc cccgtacgtg aagtgctgtg gtacagcaga gtgcaaggac 4020
aagagcctac cagactacag ctgcaaggtc tttactggag tctacccatt tatgtggggc 4080
ggcgcctact gcttttgcga cgccgaaaat acgcaattga gcgaggcaca tgtagagaaa 4140
tctgaatctt gcaaaacaga gtttgcatcg gcctacagag cccacaccgc atcggcgtcg 4200
gcgaagctcc gcgtccttta ccaaggaaac aacattaccg tagctgccta cgctaacggt 4260
gaccatgccg tcacagtaaa ggacgccaag tttgtcgtgg gcccaatgtc ctccgcctgg 4320
acaccttttg acaacaaaat cgtggtgtac aaaggcgacg tctacaacat ggactaccca 4380
ccttttggcg caggaagacc aggacaattt ggtgacattc aaagtcgtac accggaaagt 4440
aaagacgttt atgccaacac tcagttggta ctacagaggc cagcagcagg cacggtacat 4500
gtaccatact ctcaggcacc atctggcttc aagtattggc tgaaggaacg aggagcatcg 4560
ctacagcaca cggcaccgtt cggttgccag attgcgacaa acccggtaag agctgtaaat 4620
tgcgctgtgg ggaacatacc aatttccatc gacataccgg atgcggcctt tactagggtt 4680
gtcgatgcac cctctgtaac ggacatgtca tgcgaagtac cagcctgcac tcactcctcc 4740
gactttgggg gcgtcgccat catcaaatac acagctagca agaaaggtaa atgtgcagta 4800
cattcgatga ccaacgccgt taccattcga gaagccgacg tagaagtaga ggggaactcc 4860
cagctgcaaa tatccttctc aacagccctg gcaagcgccg agtttcgcgt gcaagtgtgc 4920
tccacacaag tacactgcgc agccgcatgc caccctccaa aggaccacat agtcaattac 4980
ccagcatcac acaccaccct tggggtccag gatatatcca caacggcaat gtcttgggtg 5040
cagaagatta cgggaggagt aggattaatt gttgctgttg ctgccttaat tttaattgtg 5100
gtgctatgcg tgtcgtttag caggcactaa tgaggatcca gatctgctgt gccttctagt 5160

-continued

```
tgccagccat ctgttgtttg cccctccccc gtgccttcct tgaccctgga aggtgccact   5220
cccactgtcc tttcctaata aaatgaggaa attgcatcgc attgtctgag taggtgtcat   5280
tctattctgg ggggtggggt ggggcaggac agcaaggggg aggattggga agacaatagc   5340
aggcatgctg gggatgcggt gggctctatg ggtacccagg tgctgaagaa ttgacccggt   5400
tcctcctggg ccagaaagaa gcaggcacat ccccttctct gtgacacacc ctgtccacgc   5460
ccctggttct tagttccagc cccactcata ggacactcat agctcaggag ggctccgcct   5520
tcaatcccac ccgctaaagt acttggagcg gtctctccct ccctcatcag cccaccaaac   5580
caaacctagc ctccaagagt gggaagaaat taaagcaaga taggctatta agtgcagagg   5640
gagagaaaat gcctccaaca tgtgaggaag taatgagaga aatcatagaa ttttaaggcc   5700
atgatttaag gccatcatgg ccttaatctt ccgcttcctc gctcactgac tcgctgcgct   5760
cggtcgttcg gctgcggcga gcggtatcag ctcactcaaa ggcggtaata cggttatcca   5820
cagaatcagg ggataacgca ggaaagaaca tgtgagcaaa aggccagcaa aaggccagga   5880
accgtaaaaa ggccgcgttg ctggcgtttt tccataggct ccgcccccct gacgagcatc   5940
acaaaaatcg acgctcaagt cagaggtggc gaaacccgac aggactataa agataccagg   6000
cgtttccccc tggaagctcc ctcgtgcgct ctcctgttcc gaccctgccg cttaccggat   6060
acctgtccgc ctttctccct tcgggaagcg tggcgctttc tcatagctca cgctgtaggt   6120
atctcagttc ggtgtaggtc gttcgctcca agctgggctg tgtgcacgaa ccccccgttc   6180
agcccgaccg ctgcgcctta tccggtaact atcgtcttga gtccaacccg gtaagacacg   6240
acttatcgcc actggcagca gccactggta acaggattag cagagcgagg tatgtaggcg   6300
gtgctacaga gttcttgaag tggtggccta actacggcta cactagaaga acagtatttg   6360
gtatctgcgc tctgctgaag ccagttacct tcggaaaaag agttggtagc tcttgatccg   6420
gcaaacaaac caccgctggt agcggtggtt tttttgtttg caagcagcag attacgcgca   6480
gaaaaaaagg atctcaagaa gatcctttga tcttttctac ggggtctgac gctcagtgga   6540
acgaaaactc acgttaaggg attttggtca tgagattatc aaaaaggatc ttcacctaga   6600
tccttttaaa ttaaaaatga agttttaaat caatctaaag tatatatgag taaacttggt   6660
ctgacagtta ccaatgctta atcagtgagg cacctatctc agcgatctgt ctatttcgtt   6720
catccatagt tgcctgactc gggggggggg ggcgctgagg tctgcctcgt gaagaaggtg   6780
ttgctgactc ataccaggcc tgaatcgccc catcatccag ccagaaagtg agggagccac   6840
ggttgatgag agctttgttg taggtggacc agttggtgat tttgaacttt tgctttgcca   6900
cggaacggtc tgcgttgtcg ggaagatgcg tgatctgatc cttcaactca gcaaaagttc   6960
gatttattca acaaagccgc cgtcccgtca agtcagcgta atgctctgcc agtgttacaa   7020
ccaattaacc aattctgatt agaaaaactc atcgagcatc aaatgaaact gcaatttatt   7080
catatcagga ttatcaatac catatttttg aaaaagccgt ttctgtaatg aaggagaaaa   7140
ctcaccgagg cagttccata ggatggcaag atcctggtat cggtctgcga ttccgactcg   7200
tccaacatca atacaaccta ttaatttccc ctcgtcaaaa ataaggttat caagtgagaa   7260
atcaccatga gtgacgactg aatccggtga gaatggcaaa agcttatgca tttctttcca   7320
gacttgttca acaggccagc cattacgctc gtcatcaaaa tcactcgcat caaccaaacc   7380
gttattcatt cgtgattgcg cctgagcgag acgaaatacg cgatcgctgt taaaaggaca   7440
attacaaaca ggaatcgaat gcaaccggcg caggaacact gccagcgcat caacaatatt   7500
```

ttcacctgaa tcaggatatt cttctaatac ctggaatgct gttttcccgg ggatcgcagt 7560
ggtgagtaac catgcatcat caggagtacg gataaaatgc ttgatggtcg gaagaggcat 7620
aaattccgtc agccagttta gtctgaccat ctcatctgta acatcattgg caacgctacc 7680
tttgccatgt ttcagaaaca actctggcgc atcgggcttc ccatacaatc gatagattgt 7740
cgcacctgat tgcccgacat tatcgcgagc ccatttatac ccatataaat cagcatccat 7800
gttggaattt aatcgcggcc tcgagcaaga cgtttcccgt tgaatatggc tcataacacc 7860
ccttgtatta ctgtttatgt aagcagacag ttttattgtt catgatgata tatttttatc 7920
ttgtgcaatg taacatcaga gattttgaga cacaacgtgg ctttcccccc ccccccatta 7980
ttgaagcatt tatcagggtt attgtctcat gagcggatac atatttgaat gtatttagaa 8040
aaataaacaa ataggggttc cgcgcacatt tccccgaaaa gtgccacctg acgtctaaga 8100
aaccattatt atcatgacat taacctataa aaataggcgt atcacgaggc cctttcgtc 8159

<210> SEQ ID NO 3
<211> LENGTH: 3744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggagttca tcccaaccca aactttttac aataggaggt accagcctcg accctggact 60
ccgcgcccta ctatccaagt catcaggccc agaccgcgcc ctcagaggca agctgggcaa 120
cttgcccagc tgatctcagc agttaataaa ctgacaatgc gcgcggtacc acaacagaag 180
ccacgcagga atcggaagaa taagaagcaa aagcaaaaac aacaggcgcc acaaaacaac 240
acaaatcaaa agaagcagcc acctaaaaag aaaccggctc aaaagaaaaa gaagccgggc 300
cgcagagaga ggatgtgcat gaaaatcgaa aatgattgta ttttcgaagt caagcacgaa 360
ggtaaggtaa caggttacgc gtgcctggtg ggggacaaag taatgaaacc agcacacgta 420
aaggggacca tcgataacgc ggacctggcc aaactggcct ttaagcggtc atctaagtat 480
gaccttgaat gcgcgcagat acccgtgcac atgaagtccg acgcttcgaa gttcacccat 540
gagaaaccgg aggggtacta caactggcac cacggagcag tacagtactc aggaggccgg 600
ttcaccatcc ctacaggtgc tggcaaacca ggggacagcg gcagaccgat cttcgacaac 660
aagggacgcg tggtggccat agtcttagga ggagctaatg aaggagcccg tacagccctc 720
tcggtggtga cctggaataa agacattgtc actaaaatca cccccgaggg ggccgaagag 780
tggagtcttg ccatcccagt tatgtgcctg ttggcaaaca ccacgttccc ctgctcccag 840 ccccccttgca cgccctgctg ctacgaaaag gaaccggagg aaaccctacg catgcttgag 900
gacaacgtca tgagacctgg gtactatcag ctgctacaag catccttaac atgttctccc 960
caccgccagc gacgcagcac caaggacaac ttcaatgtct ataaagccac aagaccatac 1020
ttagctcact gtcccgactg tggagaaggg cactcgtgcc atagtcccgt agcactagaa 1080
cgcatcagaa atgaagcgac agacgggacg ctgaaaatcc aggtctcctt gcaaatcgga 1140
ataaagacgg atgacagcca cgattggacc aagctgcgtt atatggacaa ccacatgcca 1200
gcagacgcag agagggcggg gctatttgta agaacatcag caccgtgtac gattactgga 1260
acaatgggac acttcatcct ggcccgatgt ccaaaagggg aaactctgac ggtgggattc 1320
actgacagta ggaagattag tcactcatgt acgcacccat ttcaccacga ccctcctgtg 1380

-continued

```
ataggtcggg aaaaattcca ttcccgaccg cagcacggta aagagctacc ttgcagcacg   1440
tacgtgcaga gcaccgccgc aactaccgag gagatagagg tacacatgcc cccagacacc   1500
cctgatcgca cattaatgtc acaacagtcc ggcaacgtaa agatcacagt caatggccag   1560
acggtgcggt acaagtgtaa ttgcggtggc tcaaatgaag gactaacaac tacagacaaa   1620
gtgattaata actgcaaggt tgatcaatgt catgccgcgg tcaccaatca caaaaagtgg   1680
cagtataact cccctctggt cccgcgtaat gctgaacttg gggaccgaaa aggaaaaatt   1740
cacatcccgt ttccgctggc aaatgtaaca tgcagggtgc ctaaagcaag gaacccccacc   1800
gtgacgtacg ggaaaaacca agtcatcatg ctactgtatc ctgaccaccc aacactcctg   1860
tcctaccgga atatgggaga agaaccaaac tatcaagaag agtgggtgat gcataagaag   1920
gaagtcgtgc taaccgtgcc gactgaaggg ctcgaggtca cgtggggcaa caacgagccg   1980
tataagtatt ggccgcagtt atctacaaac ggtacagccc atggccaccc gcatgagata   2040
attctgtatt attatgagct gtaccccact atgactgtag tagttgtgtc agtggccacg   2100
ttcatactcc tgtcgatggt gggtatggca gcggggatgt gcatgtgtgc acgacgcaga   2160
tgcatcacac cgtatgaact gacaccagga gctaccgtcc ctttcctgct tagcctaata   2220
tgctgcatca gaacagctaa agcggccaca taccaagagg ctgcgatata cctgtggaac   2280
gagcagcaac ctttgttttg gctacaagcc cttattccgc tggcagccct gattgttcta   2340
tgcaactgtc tgagactctt accatgctgc tgtaaaacgt tggctttttt agccgtaatg   2400
agcgtcggtg cccacactgt gagcgcgtac gaacacgtaa cagtgatccc gaacacggtg   2460
ggagtaccgt ataagactct agtcaataga cctggctaca gccccatggt attggagatg   2520
gaactactgt cagtcacttt ggagccaaca ctatcgcttg attacatcac gtgcgagtac   2580
aaaaccgtca tcccgtctcc gtacgtgaag tgctgcggta cagcagagtg caaggacaaa   2640
aacctacctg actacagctg taaggtcttc accggcgtct acccatttat gtggggcggc   2700
gcctactgct tctgcgacgc tgaaaacacg cagttgagcg aagcacacgt ggagaagtcc   2760
gaatcatgca aaacagaatt tgcatcagca tacagggctc ataccgcatc tgcatcagct   2820
aagctccgcg tcctttacca aggaaataac atcactgtaa ctgcctatgc aaacggcgac   2880
catgccgtca cagttaagga cgccaaattc attgtggggc caatgtcttc agcctggaca   2940
cctttcgaca acaaaattgt ggtgtacaaa ggtgacgtct ataacatgga ctacccgccc   3000
tttggcgcag gaagaccagg acaatttggc gatatccaaa gtcgcacacc tgagagtaaa   3060
gacgtctatg ctaatacaca actggtactg cagagaccgg ctgtgggtac ggtacacgtg   3120
ccatactctc aggcaccatc tggctttaag tattggctaa aagaacgcgg ggcgtcgctg   3180
cagcacacag caccatttgg ctgccaaata gcaacaaacc cggtaagagc ggtgaactgc   3240
gccgtaggga acatgcccat ctccatcgac ataccggaag cggccttcac tagggtcgtc   3300
gacgcgccct ctttaacgga catgtcgtgc gaggtaccag cctgcaccca ttcctcagac   3360
tttgggggcg tcgccattat taaatatgca gccagcaaga aaggcaagtg tgcggtgcat   3420
tcgatgacta acgccgtcac tattcgggaa gctgagatag aagttgaagg gaattctcag   3480
ctgcaaatct ctttctcgac ggccttagcc agcgccgaat tccgcgtaca agtctgttct   3540
acacaagtac actgtgcagc cgagtgccac cccccgaagg accacatagt caactacccg   3600
gcgtcacata ccaccctcgg ggtccaggac atctccgcta cggcgatgtc atgggtgcag   3660
aagatcacgg gaggtgtggg actggttgtt gctgttgccg cactgattct aatcgtggtg   3720
ctatgcgtgt cgttcagcag gcac                                          3744
```

<210> SEQ ID NO 4
<211> LENGTH: 8159
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacac gtgtgatcag atatcgcggc cgctctagac 1380
accatggagt tcatcccaac ccaaactttt tacaatagga ggtaccagcc tcgaccctgg 1440
actccgcgcc ctactatcca agtcatcagg cccagaccgc gccctcagag gcaagctggg 1500
caacttgccc agctgatctc agcagttaat aaactgacaa tgcgcgcggt accacaacag 1560
aagccacgca ggaatcggaa gaataagaag caaaagcaaa aacaacaggc gccacaaaac 1620
aacacaaatc aaaagaagca gccacctaaa aagaaaccgg ctcaaaagaa aaagaagccg 1680
ggccgcagag agaggatgtg catgaaaatc gaaaatgatt gtattttcga agtcaagcac 1740
gaaggtaagg taacaggtta cgcgtgcctg gtgggggaca aagtaatgaa accagcacac 1800
gtaaagggga ccatcgataa cgcggacctg gccaaactgg cctttaagcg gtcatctaag 1860
tatgaccttg aatgcgcgca gatacccgtg cacatgaagt ccgacgcttc gaagttcacc 1920
catgagaaac cggaggggta ctacaactgg caccacggag cagtacagta ctcaggaggc 1980
cggttcacca tccctacagg tgctggcaaa ccaggggaca gcggcagacc gatcttcgac 2040

-continued

```
aacaagggac gcgtggtggc catagtctta ggaggagcta atgaaggagc ccgtacagcc   2100
ctctcggtgg tgacctggaa taaagacatt gtcactaaaa tcaccccga gggggccgaa    2160
gagtggagtc ttgccatccc agttatgtgc ctgttggcaa acaccacgtt cccctgctcc   2220
cagcccctt gcacgccctg ctgctacgaa aaggaaccgg aggaaaccct acgcatgctt    2280
gaggacaacg tcatgagacc tgggtactat cagctgctac aagcatcctt aacatgttct   2340
ccccaccgcc agcgacgcag caccaaggac aacttcaatg tctataaagc cacaagacca   2400
tacttagctc actgtcccga ctgtggagaa gggcactcgt gccatagtcc cgtagcacta   2460
gaacgcatca gaaatgaagc gacagacggg acgctgaaaa tccaggtctc cttgcaaatc   2520
ggaataaaga cggatgacag ccacgattgg accaagctgc gttatatgga caaccacatg   2580
ccagcagacg cagagagggc ggggctattt gtaagaacat cagcaccgtg tacgattact   2640
ggaacaatgg gacacttcat cctggcccga tgtccaaaag gggaaactct gacggtggga   2700
ttcactgaca gtaggaagat tagtcactca tgtacgcacc catttcacca cgaccctcct   2760
gtgataggtc gggaaaaatt ccattcccga ccgcagcacg gtaaagagct accttgcagc   2820
acgtacgtgc agagcaccgc cgcaactacc gaggagatag aggtacacat gcccccagac   2880
acccctgatc gcacattaat gtcacaacag tccggcaacg taaagatcac agtcaatggc   2940
cagacggtgc ggtacaagtg taattgcggt ggctcaaatg aaggactaac aactacagac   3000
aaagtgatta ataactgcaa ggttgatcaa tgtcatgccg cggtcaccaa tcacaaaaag   3060
tggcagtata actcccctct ggtcccgcgt aatgctgaac ttggggaccg aaaaggaaaa   3120
attcacatcc cgtttccgct ggcaaatgta acatgcaggg tgcctaaagc aaggaacccc   3180
accgtgacgt acgggaaaaa ccaagtcatc atgctactgt atcctgacca cccaacactc   3240
ctgtcctacc ggaatatggg agaagaacca aactatcaag aagagtgggt gatgcataag   3300
aaggaagtcg tgctaaccgt gccgactgaa gggctcgagg tcacgtgggg caacaacgag   3360
ccgtataagt attggccgca gttatctaca aacggtacag cccatggcca cccgcatgag   3420
ataattctgt attattatga gctgtacccc actatgactg tagtagttgt gtcagtggcc   3480
acgttcatac tcctgtcgat ggtgggtatg gcagcgggga tgtgcatgtg tgcacgacgc   3540
agatgcatca caccgtatga actgacacca ggagctaccg tccctttcct gcttagccta   3600
atatgctgca tcagaacagc taaagcggcc acataccaag aggctgcgat atacctgtgg   3660
aacgagcagc aacctttgtt ttggctacaa gcccttattc cgctggcagc cctgattgtt   3720
ctatgcaact gtctgagact cttaccatgc tgctgtaaaa cgttggcttt tttagccgta   3780
atgagcgtcg gtgcccacac tgtgagcgcg tacgaacacg taacagtgat cccgaacacg   3840
gtgggagtac cgtataagac tctagtcaat agacctggct acagccccat ggtattggag   3900
atggaactac tgtcagtcac tttggagcca acactatcgc ttgattacat cacgtgcgag   3960
tacaaaaccg tcatcccgtc tccgtacgtg aagtgctgcg gtacagcaga gtgcaaggac   4020
aaaaacctac ctgactacag ctgtaaggtc ttcaccggcg tctacccatt tatgtggggc   4080
ggcgcctact gcttctgcga cgctgaaaac acgcagttga gcgaagcaca cgtggagaag   4140
tccgaatcat gcaaaacaga atttgcatca gcatacaggg ctcataccgc atctgcatca   4200
gctaagctcc gcgtccttta ccaaggaaat aacatcactg taactgccta tgcaaacggc   4260
gaccatgccg tcacagttaa ggacgccaaa ttcattgtgg ggccaatgtc ttcagcctgg   4320
acacctttcg acaacaaaat tgtggtgtac aaaggtgacg tctataacat ggactacccg   4380
```

-continued

```
ccctttggcg caggaagacc aggacaattt ggcgatatcc aaagtcgcac acctgagagt   4440
aaagacgtct atgctaatac acaactggta ctgcagagac cggctgtggg tacggtacac   4500
gtgccatact ctcaggcacc atctggcttt aagtattggc taaaagaacg cggggcgtcg   4560
ctgcagcaca cagcaccatt tggctgccaa atagcaacaa acccggtaag agcggtgaac   4620
tgcgccgtag ggaacatgcc catctccatc gacataccgg aagcggcctt cactagggtc   4680
gtcgacgcgc cctctttaac ggacatgtcg tgcgaggtac cagcctgcac ccattcctca   4740
gactttgggg gcgtcgccat tattaaatat gcagccagca agaaaggcaa gtgtgcggtg   4800
cattcgatga ctaacgccgt cactattcgg gaagctgaga tagaagttga agggaattct   4860
cagctgcaaa tctctttctc gacggcctta gccagcgccg aattccgcgt acaagtctgt   4920
tctacacaag tacactgtgc agccgagtgc caccccccga aggaccacat agtcaactac   4980
ccggcgtcac ataccaccct cggggtccag gacatctccg ctacggcgat gtcatgggtg   5040
cagaagatca cgggaggtgt gggactggtt gttgctgttg ccgcactgat tctaatcgtg   5100
gtgctatgcg tgtcgttcag caggcactaa tgaggatcca gatctgctgt gccttctagt   5160
tgccagccat ctgttgtttg cccctccccc gtgccttcct tgaccctgga aggtgccact   5220
cccactgtcc tttcctaata aaatgaggaa attgcatcgc attgtctgag taggtgtcat   5280
tctattctgg ggggtggggt ggggcaggac agcaaggggg aggattggga agacaatagc   5340
aggcatgctg gggatgcggt gggctctatg ggtacccagg tgctgaagaa ttgacccggt   5400
tcctcctggg ccagaaagaa gcaggcacat ccccttctct gtgacacacc ctgtccacgc   5460
ccctggttct tagttccagc cccactcata ggacactcat agctcaggag ggctccgcct   5520
tcaatcccac ccgctaaagt acttggagcg gtctctccct ccctcatcag cccaccaaac   5580
caaacctagc ctccaagagt gggaagaaat taaagcaaga taggctatta agtgcagagg   5640
gagagaaaat gcctccaaca tgtgaggaag taatgagaga aatcatagaa ttttaaggcc   5700
atgatttaag gccatcatgg ccttaatctt ccgcttcctc gctcactgac tcgctgcgct   5760
cggtcgttcg gctgcggcga gcggtatcag ctcactcaaa ggcggtaata cggttatcca   5820
cagaatcagg ggataacgca ggaaagaaca tgtgagcaaa aggccagcaa aaggccagga   5880
accgtaaaaa ggccgcgttg ctggcgtttt tccataggct ccgcccccct gacgagcatc   5940
acaaaaatcg acgctcaagt cagaggtggc gaaacccgac aggactataa agataccagg   6000
cgtttccccc tggaagctcc ctcgtgcgct ctcctgttcc gaccctgccg cttaccggat   6060
acctgtccgc ctttctccct tcgggaagcg tggcgctttc tcatagctca cgctgtaggt   6120
atctcagttc ggtgtaggtc gttcgctcca agctgggctg tgtgcacgaa ccccccgttc   6180
agcccgaccg ctgcgcctta tccggtaact atcgtcttga gtccaacccg gtaagacacg   6240
acttatcgcc actggcagca gccactggta acaggattag cagagcgagg tatgtaggcg   6300
gtgctacaga gttcttgaag tggtggccta actacggcta cactagaaga acagtatttg   6360
gtatctgcgc tctgctgaag ccagttacct tcggaaaaag agttggtagc tcttgatccg   6420
gcaaacaaac caccgctggt agcggtggtt tttttgtttg caagcagcag attacgcgca   6480
gaaaaaaagg atctcaagaa gatcctttga tcttttctac ggggtctgac gctcagtgga   6540
acgaaaactc acgttaaggg attttggtca tgagattatc aaaaaggatc ttcacctaga   6600
tccttttaaa ttaaaaatga agttttaaat caatctaaag tatatatgag taaacttggt   6660
ctgacagtta ccaatgctta atcagtgagg cacctatctc agcgatctgt ctatttcgtt   6720
catccatagt tgcctgactc gggggggggg ggcgctgagg tctgcctcgt gaagaaggtg   6780
```

ttgctgactc ataccaggcc tgaatcgccc catcatccag ccagaaagtg agggagccac 6840
ggttgatgag agctttgttg taggtggacc agttggtgat tttgaacttt tgctttgcca 6900
cggaacggtc tgcgttgtcg ggaagatgcg tgatctgatc cttcaactca gcaaaagttc 6960
gatttattca acaaagccgc cgtcccgtca agtcagcgta atgctctgcc agtgttacaa 7020
ccaattaacc aattctgatt agaaaaactc atcgagcatc aaatgaaact gcaatttatt 7080
catatcagga ttatcaatac catatttttg aaaaagccgt ttctgtaatg aaggagaaaa 7140
ctcaccgagg cagttccata ggatggcaag atcctggtat cggtctgcga ttccgactcg 7200
tccaacatca atacaaccta ttaatttccc ctcgtcaaaa ataaggttat caagtgagaa 7260
atcaccatga gtgacgactg aatccggtga gaatggcaaa agcttatgca tttctttcca 7320
gacttgttca acaggccagc cattacgctc gtcatcaaaa tcactcgcat caaccaaacc 7380
gttattcatt cgtgattgcg cctgagcgag acgaaatacg cgatcgctgt taaaaggaca 7440
attacaaaca ggaatcgaat gcaaccggcg caggaacact gccagcgcat caacaatatt 7500
ttcacctgaa tcaggatatt cttctaatac ctggaatgct gttttcccgg ggatcgcagt 7560
ggtgagtaac catgcatcat caggagtacg gataaaatgc ttgatggtcg gaagaggcat 7620
aaattccgtc agccagttta gtctgaccat ctcatctgta acatcattgg caacgctacc 7680
tttgccatgt ttcagaaaca actctggcgc atcgggcttc ccatacaatc gatagattgt 7740
cgcacctgat tgcccgacat tatcgcgagc ccatttatac ccatataaat cagcatccat 7800
gttggaattt aatcgcggcc tcgagcaaga cgtttcccgt tgaatatggc tcataacacc 7860
ccttgtatta ctgtttatgt aagcagacag ttttattgtt catgatgata tatttttatc 7920
ttgtgcaatg taacatcaga gattttgaga cacaacgtgg ctttcccccc ccccccatta 7980
ttgaagcatt tatcagggtt attgtctcat gagcggatac atatttgaat gtatttagaa 8040
aaataaacaa ataggggttc cgcgcacatt tccccgaaaa gtgccacctg acgtctaaga 8100
aaccattatt atcatgacat taacctataa aaataggcgt atcacgaggc cctttcgtc 8159

<210> SEQ ID NO 5
<211> LENGTH: 8185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660

-continued

```
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcaa tgaattacat acctacgcag   1380
acgttctacg gccgccgatg gcgtcctcgc ccggcggccc gcccctgggt ggctccacca   1440
cccgtatact atccaccacc gccacccgtg cctgtcgacc cgcaagcgca gcaaatgcaa   1500
caacttattg ctgcggtcaa tacgctggct ataaggcaga atggcacccg aacacctgga   1560
caacaacgaa ggaaacgtca atcaaacaaa ccaaagagga aacagacacc cccgaagaaa   1620
cagaacccgg cgaaaacaaa gaacaagcag aaaccgcaac cacccaagcc taagaaacgg   1680
aaacccggca agagagaaag gaaatgcatg aagatagaga atgattgcat attcgaggtc   1740
aagctcgaag gcaaggtcac tggtacgcc tgcctggtag gagataaagt gatgaaacca   1800
gcacacgtga aaggagtcat agataaccct gaccttgcca agctagcttt taagaaatcg   1860
agcaagtatg accttgagtg tgcgcaaatt ccggtccaca tgaagtcaga tgcctcgcag   1920
ttcacccacg agaaaccaga aggacactac aactggcacc atggtgcagt acaatacctg   1980
aacggaagat ttaccatccc gacaggtgct gggaagccag gggacagcgg taggcctatc   2040
tttgacaaca agggtcgcgt agtggccatt gtgctggggg gagccaacga gggagcgagg   2100
acggctctat cggttgtcac ctggaacaaa gacatggtta cgcgcatcac cccagaagga   2160
actgaggagt ggactgccct ggtgacaact gcttgcatcc tgagcaatct gactttcgat   2220
tgcagcctgc caccatgtgc gccttgctgc tatgaaaaag acgcagaggg caccctgagg   2280
atgctggagg acaacgtcga taaccccgga tactacgatc tcctggctgc atcaacgcat   2340
tgtgacgccc cgcagcggcg tcgccgcagg gggctaactg aggactacga ggcttataaa   2400
ctcactaagc cgtacatagc ctattgctct gactgcggga acggacagtt ttgctacagc   2460
ccgatagcta ttgagagagt cagggccgag gcatcggacg gaatgctcaa gatacagatc   2520
tctgcgcaaa taggcctgca ggtggacgga gctcatgcgt ggacgaaaat cagatacatg   2580
aaagggcacg acgtggagga cacagacagg aactcactgg aggtgttcac caccggagag   2640
tgtacggtcc atggcaccat ggggcatttc atcgtagcta catgccccga aggtgactcc   2700
ttgacagtgg cgttcgttga caaacataag gtcaggcacg cttgcaggat agcatacaag   2760
catcgtgtcc ccgtattggg cagagagcac tttacggtac ggccacatca tggagtagaa   2820
ttgccatgca ccacgtacgc catgagaaca tcagtcacta ccgaagaaat agaaatgcac   2880
gtggcgcatg acgtgcccga caacaccttt ctatccaaga ccggaaataa agtgaagata   2940
acgccaaaag gaaagtctat tcgctacaac tgcacgtgtg ggtctaagga gagcggtgtc   3000
```

-continued

```
acaaagcaag acaaagaatt tgacaactgc gaagtttcgc agtgccacac catggtgacc   3060
gcccacgata agtggcagtt taactctcct tatgtcccta gggcaggctc aggcaagaaa   3120
ggaaagatcc acgtaccctt tccactgagc aactctacgt gcagagttcc gttggcgcct   3180
ttaccgaaca ccatcccggc aaagaatgga atcacactgc agttgcatcc ggtcgccccg   3240
acgctactta cctaccgcac cctcggagag aaaccagaac accacacaga atggatatca   3300
gaaagttgcg aacgtacact ccccgtacct gaggaggggt tggagtacac atggggcaat   3360
cacgcccctg tgagactgtg ggcacaactg acgactaagg gttcagccca tgggatgccg   3420
cacgaaatct tctcatatta ctatggattg taccctgcca cgacggttgc agtgtgcgtg   3480
gggctagcgt gtgtgatctt gctggctctg tccgcgtcct gctgcctgtg cgtgtcagcg   3540
agaaataagt gcttgacccc gtacgcgttg acgccaggag ccgtggtgcc gtgcactttg   3600
agcttattgt gctgcgcccc cagagccaag gccgcaacgt ttgcggagac agcggcatat   3660
ctatgggacg agaaccagac ggtgttctgg atgcaattcg caatccccgt agcatgcttt   3720
atgatagtga catattgcct gcgccacttg atgctgtgct gtaggaccgc ttcttttta    3780
gtggcagtaa gcctgggaat gggggcgacc caggcgtatg agcatagtgt aacgctcccc   3840
aacgcggtcg gatttccgta cagagcccat gtagacagac cagggttctc tccattaacg   3900
ctccatatgg aggtagtctc cactagccta gagccgacgc tcgccctgga ttacgtcact   3960
tgcgagtaca aaacggtggt gccgtcgcct aaggtcacct gttgcggcat gtcggagtgt   4020
gcacaccagc aaaaagcgga ctttcaatgt aaagtctaca ccggcgtcta ccccttttg    4080
tggggcggtg cctactgctt ttgcaattcg gaaaacactc agctgagcga agcttatgtt   4140
gagcggagcg aggtgtgcaa acacgatcac gcagcggcgt atcgcgctca tacagccgca   4200
ttgaaggcta aaatcagagt gacctacggt tccacgaacg ggacggctga ggcgtttgtc   4260
aacggagaga gcaccgcacg aattggagac ctgaaaatga tcctaggtcc catatccacc   4320
gcgtggagcc cctttgaccc aaagatcgtc gtctacaagg acgaagtcta caatcaggat   4380
tatccaccgt acggatccgg gcaaccgggt agatttgggg acttacagag caggaccacc   4440
gagagtaacg atgtgtacgc caatactgca ctgaagctgg ctcgcccatc tgccggcacg   4500
gtgcacgttc catataccca gacgccgtcc gggtttaagt attggctaaa agaaaaaggg   4560
gacgcattga accacaaggc tcctttcggc tgcatcatca agacgaaccc cgtaagggca   4620
gaaaattgtg cagtcggaaa cataccagtg tctctagaca ttcccgacgc ggcttttaca   4680
cgcatagtcg acgcaccatc gctaaccggc ctgaagtgcg aggtggcgac ttgcacgcac   4740
tcatcggact ttggaggcac tttggtggtg gagtacaaga ccgacaaagt ggggacgtgc   4800
gccgtccact cagaatccaa cacggctgtt atgcaggaga cgagtctgtc cgtgacgatg   4860
gacggccgag gtacgttgca tttctccacc gcctcagcct caccgtcctt cgtactgaaa   4920
gtgtgcagta gcaaaaccac ttgcacagca aagtgcgtgc cgccgaagga ccacgtcgtc   4980
ccttttcctg ccaaccacaa caatgttgtg ttcccggact tttccagtac tgcagtgtct   5040
tggctcaccc acactatggg cggagctact gtggtgattg ctattgggat caccatattc   5100
ttaatagtta cttgcatagc ttttagtagg cactaggcgg ccgctctaga ccaggccctg   5160
gatccagatc tgctgtgcct tctagttgcc agccatctgt tgtttgcccc tcccccgtgc   5220
cttccttgac cctggaaggt gccactccca ctgtcctttc ctaataaaat gaggaaattg   5280
catcgcattg tctgagtagg tgtcattcta ttctgggggg tggggtgggg caggacagca   5340
agggggagga ttgggaagac aatagcaggc atgctgggga tgcggtgggc tctatgggta   5400
```

```
cccaggtgct gaagaattga cccggttcct cctgggccag aaagaagcag gcacatcccc   5460
ttctctgtga cacaccctgt ccacgcccct ggttcttagt tccagcccca ctcataggac   5520
actcatagct caggagggct ccgccttcaa tcccacccgc taaagtactt ggagcggtct   5580
ctccctccct catcagccca ccaaaccaaa cctagcctcc aagagtggga agaaattaaa   5640
gcaagatagg ctattaagtg cagagggaga gaaaatgcct ccaacatgtg aggaagtaat   5700
gagagaaatc atagaatttt aaggccatga tttaaggcca tcatggcctt aatcttccgc   5760
ttcctcgctc actgactcgc tgcgctcggt cgttcggctg cggcgagcgg tatcagctca   5820
ctcaaaggcg gtaatacggt tatccacaga atcaggggat aacgcaggaa agaacatgtg   5880
agcaaaaggc cagcaaaagg ccaggaaccg taaaaaggcc gcgttgctgg cgtttttcca   5940
taggctccgc ccccctgacg agcatcacaa aaatcgacgc tcaagtcaga ggtggcgaaa   6000
cccgacagga ctataaagat accaggcgtt tccccctgga agctccctcg tgcgctctcc   6060
tgttccgacc ctgccgctta ccggatacct gtccgccttt ctcccttcgg gaagcgtggc   6120
gctttctcat agctcacgct gtaggtatct cagttcggtg taggtcgttc gctccaagct   6180
gggctgtgtg cacgaacccc ccgttcagcc cgaccgctgc gccttatccg gtaactatcg   6240
tcttgagtcc aacccggtaa gacacgactt atcgccactg gcagcagcca ctggtaacag   6300
gattagcaga gcgaggtatg taggcggtgc tacagagttc ttgaagtggt ggcctaacta   6360
cggctacact agaagaacag tatttggtat ctgcgctctg ctgaagccag ttaccttcgg   6420
aaaaagagtt ggtagctctt gatccggcaa acaaaccacc gctggtagcg gtggtttttt   6480
tgtttgcaag cagcagatta cgcgcagaaa aaaaggatct caagaagatc ctttgatctt   6540
ttctacgggg tctgacgctc agtggaacga aaactcacgt taagggattt tggtcatgag   6600
attatcaaaa aggatcttca cctagatcct tttaaattaa aaatgaagtt ttaaatcaat   6660
ctaaagtata tatgagtaaa cttggtctga cagttaccaa tgcttaatca gtgaggcacc   6720
tatctcagcg atctgtctat ttcgttcatc catagttgcc tgactcgggg gggggggcg    6780
ctgaggtctg cctcgtgaag aaggtgttgc tgactcatac caggcctgaa tcgccccatc   6840
atccagccag aaagtgaggg agccacggtt gatgagagct ttgttgtagg tggaccagtt   6900
ggtgattttg aacttttgct ttgccacgga acggtctgcg ttgtcgggaa gatgcgtgat   6960
ctgatccttc aactcagcaa aagttcgatt tattcaacaa agccgccgtc ccgtcaagtc   7020
agcgtaatgc tctgccagtg ttacaaccaa ttaaccaatt ctgattagaa aaactcatcg   7080
agcatcaaat gaaactgcaa tttattcata tcaggattat caataccata tttttgaaaa   7140
agccgtttct gtaatgaagg agaaaactca ccgaggcagt tccataggat ggcaagatcc   7200
tggtatcggt ctgcgattcc gactcgtcca acatcaatac aacctattaa tttcccctcg   7260
tcaaaaataa ggttatcaag tgagaaatca ccatgagtga cgactgaatc cggtgagaat   7320
ggcaaaagct tatgcatttc tttccagact tgttcaacag gccagccatt acgctcgtca   7380
tcaaaatcac tcgcatcaac caaaccgtta ttcattcgtg attgcgcctg agcgagacga   7440
aatacgcgat cgctgttaaa aggacaatta caaacaggaa tcgaatgcaa ccggcgcagg   7500
aacactgcca gcgcatcaac aatattttca cctgaatcag gatattcttc taatacctgg   7560
aatgctgttt tcccggggat cgcagtggtg agtaaccatg catcatcagg agtacggata   7620
aaatgcttga tggtcggaag aggcataaat tccgtcagcc agtttagtct gaccatctca   7680
tctgtaacat cattggcaac gctacctttg ccatgtttca gaaacaactc tggcgcatcg   7740
```

-continued ggcttcccat acaatcgata gattgtcgca cctgattgcc cgacattatc gcgagcccat 7800
ttatacccat ataaatcagc atccatgttg gaatttaatc gcggcctcga gcaagacgtt 7860
tcccgttgaa tatggctcat aacacccctt gtattactgt ttatgtaagc agacagtttt 7920
attgttcatg atgatatatt tttatcttgt gcaatgtaac atcagagatt ttgagacaca 7980
acgtggcttt cccccccccc ccattattga agcatttatc agggttattg tctcatgagc 8040
ggatacatat ttgaatgtat ttagaaaaat aaacaaatag gggttccgcg cacatttccc 8100
cgaaaagtgc cacctgacgt ctaagaaacc attattatca tgacattaac ctataaaaat 8160
aggcgtatca cgaggccctt tcgtc 8185

<210> SEQ ID NO 6
<211> LENGTH: 8387
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacac gtgtgatcag atatcgcggc cgccaccatg 1380
tttcccatgc aattcaccaa ctcagcctat cgccagatgg agcccatgtt cgcaccggct 1440
tctcgaggac aagtacagcc gtatcggccg cgcacaaagc gccgccaaga gccgcaagtc 1500
ggcaacgctg ctattgctgc cctcgcgaac cagatgagcg cgctccagct gcaggtggct 1560

-continued

```
ggacttgccg gccaggcaag ggtggaccgt cgtggaccga gacgtgttca gaaaaacaag   1620
cagaagaaga agaactcttc caacggagaa aaacccaagg agaagaagaa gaagcaaaaa   1680
caacaggaga agaaagggag cggcggtgaa aaagccaaga agccgcggaa ccggcccggg   1740
aaggaggtaa ggatctccgt aaagcgtgcc cgacagagca ccttccccgt gtaccatgac   1800
ggtgccatat ccggctatgc ggtgctgatt ggctcccgcg tgtttaagcc agcgcacgtg   1860
aagggtaagt tcgaccaccc cgaactggcg gacatcaagt tccaggtcgc cgaggtcatg   1920
gacctcgaag cagccgcata ccctaagtgc atgcgagacc aggcggctga accagcaacc   1980
atgatggatg gagtgtacaa tggggagtac ggcaatattc aggagtggag gacaattttg   2040
tattcgatgc gagcggcaga ggcaagccgg ggtgacagtg gcaggccatt caccgacaac   2100
tcaggaaagg ttgtcggtat cgtcctcgga ggaggacccg atggtaggcg cacacgtctc   2160
tccgtgatag gtttcgacaa gaagctgaag gccagagaga tcgcctacag cgaggccatc   2220
ccttggacac gcgcaccagc tctcctgctg ctgcctatgg tcatcgcctg cacctacaac   2280
tccaatacct ttgattgctc caaaccgtcc tgccaggatt gttgcattac tgctgaacca   2340
aagaaggcca tgactatgct gaaggacaac ctgaatgacc cgaactactg ggacctgctc   2400
attgccgtca ccacctgcag ttccgcccga aaaaagaggg ctgtgtctac gtcgcctgtc   2460
gccgtttacg acacacaaat tctcgccgcc cacgcagctg cctccccgta tagggcgtac   2520
tgccccgatt gtgacggaac tgcctgcatc tcgccgatag ctatcgacga ggtggtaagt   2580
agcggtagtg accacgtcct tcgcatccgg gtcggttctc aatcgggagt gaccgctaaa   2640
ggcggtgcgg cgggtgaaac ctctctgcga tacctgggaa gggacggtaa ggtttacgcc   2700
gcggacaaca cgcggctcgt ggtgcgcacc actgcaaagt gtgacgtgct gcaggccact   2760
ggccactaca ttctggccaa ctgcccagtg gggcagagtc tcactgttgc ggccacactg   2820
gacggtaccc ggcatcaatg caccacggtt ttcgaacatc aagtaacgga gaagttcaca   2880
agagaacgca gcaagggcca ccacctgtcc gatctgacca agaaatgcac caggttctcc   2940
accaccccga agaagtccgc gctctatctc gttgatgtgt atgatgctct gccgacttct   3000
gtagagatca gcaccgtggt gacatgcaac gaaagacagt gcacagtgag ggtgccaccc   3060
ggtaccacag tgaaattcga taagaggtgc aagaacgctg ccaaagagac cgtcaccttc   3120
accagcgact cccagacgtt tacgtgcgag gagccggtcc taacggccgc cagcatcacc   3180
cagggcaagc cgcacctcag atcgtcaatg ttgcccagcg gaggcaaaga ggtgaaagcg   3240
aggattccat tcccgttccc gccagagact gcgacttgca gagtgagcat cgccccactg   3300
ccatcgatta cctatgagga aagcgatgtt ctgctggccg gcactgcgaa ataccccgtg   3360
ctgctaacta cacggaacct tggtttccat agcaacgcca catctgaatg gatccagggt   3420
aagtacctgc gccgcatccc ggtcacgccc caagggattg aactaatgtt gggaaacaac   3480
gcaccgctgc acttctggtc atctgtcagg tacgcatctg gagacgccga cgcgtacccc   3540
tgggaacttc tggtgcacca catcaagcac catccggagt acgcgtgggc gtttgtagga   3600
gttgcatgtg gcctgctggc cgttgcagca tgcatgttcg cgtgcgcatg caacagggtg   3660
cggtactctc tgctcgccaa cacgttcaac ccgaacccac caccattgac cgcactgact   3720
gcagcattgt gctgcatacc tggggctcgc gcggatcaac cctacctgga catcattgcc   3780
tacttgtgga ccaacagcaa agtggccttc gggctgcaat gcgcggcgcc cgtggcttgc   3840
atgctcatcg ttacatacgc ccttagacat tgcagattgt gctgcaattc tttttttaggg   3900
gtaagagggt ggtcggctct gctggtcatc cttgcgtatg tacagagctg caaggcgtac   3960
```

```
gaacacaccg tggtggtccc aatggatcca agagccccgt cgtacgaggc ggtgataaac   4020
cggaatgggt atgacccccct gaagcttacc atcgcagtga actttaccgt catctcacca   4080
actacggctc tggaatactg gacctgtgca ggagtccctg tcgtcgagcc gccccatgtg   4140
ggctgctgca cgtcagtgtc ctgcccctcc gacctctcca cgctgcacgc gttcaccggc   4200
aaagccgtct ccgacgtgca ctgcgatgtg cacacgaacg tgtacccctt gttgtggggt   4260
gcggctcact gcttctgttc cactgaaaac acgcaggtca gcgctgtggc cgccaccgtt   4320
tctgagttct gtgctcagga ctcagagcgc gccgaggcgt tcagcgttca cagcagctca   4380
gtcactgcag agattctggt gacgcttggt gaagtggtga cggcggtcca cgtttacgtg   4440
gacggggtaa catcagccag ggtaccgac ctcaagatcg tggctggccc aataacaact   4500
gactactccc cgtttgaccg caaagtagtc cgtatcggcg aagaggtcta taattacgac   4560
tggcctcctt acggggctgg tcgaccaggc acattcggag acattcaagc taggtcaacc   4620
aactatgtca aacccaatga tctgtacggg gacatcggaa ttgaagtact gcagccgact   4680
aatgaccacg tgcacgtggc ttacacgtat acgacctctg ggttgctgcg ttggttgcag   4740
gacgctccga aaccactcag tgtcacagca ccgcacggtt gtaagatcag tgctaacccg   4800
ctcctggccc tcgattgtgg ggttggtgcc gtccccatgt ccatcaacat tccggacgcg   4860
aagttcaccc gcaaactaaa ggacccgaaa ccttcggccc tgaaatgcgt ggtggacagt   4920
tgcgagtacg gggtggacta cgggggcgcc gccacgatca cctacgaggg ccacgaggct   4980
gggaagtgcg ggatccattc cctgacacca ggagtccctc tgagaacatc agtggttgaa   5040
gtagttgccg gcgctaatac cgtcaaaacg accttctcct cacccacgcc cgaggttaca   5100
ctcgaggtag agatctgttc ggcaatagtg aagtgcgcca gtgagtgcac tccaccgaag   5160
gaacacgtag tcgcagccag gcctcgccat ggcagcgaca ctggaggcta catctccggg   5220
cccgcaatgc gctgggccgg aaggattgta gggaacccta gtggtcctgt ttcctcatcc   5280
ttggccgtca cctactgcgt ggtgaagaag tgccgctcta aaagaatccg gatagtcaag   5340
agctaatcta gaccaggccc tggatccaga tctgctgtgc cttctagttg ccagccatct   5400
gttgtttgcc cctcccccgt gccttccttg accctggaag gtgccactcc cactgtcctt   5460
tcctaataaa atgaggaaat tgcatcgcat tgtctgagta ggtgtcattc tattctgggg   5520
ggtggggtgg ggcaggacag caagggggag gattgggaag acaatagcag gcatgctggg   5580
gatgcggtgg gctctatggg tacccaggtg ctgaagaatt gacccggttc ctcctgggcc   5640
agaaagaagc aggcacatcc ccttctctgt gacacaccct gtccacgccc ctggttctta   5700
gttccagccc cactcatagg acactcatag ctcaggaggg ctccgccttc aatcccaccc   5760
gctaaagtac ttggagcggt ctctccctcc ctcatcagcc caccaaacca aacctagcct   5820
ccaagagtgg gaagaaatta aagcaagata ggctattaag tgcagaggga gagaaaatgc   5880
ctccaacatg tgaggaagta atgagagaaa tcatagaatt ttaaggccat gatttaaggc   5940
catcatggcc ttaatcttcc gcttcctcgc tcactgactc gctgcgctcg gtcgttcggc   6000
tgcggcgagc ggtatcagct cactcaaagg cggtaatacg gttatccaca gaatcagggg   6060
ataacgcagg aaagaacatg tgagcaaaag gccagcaaaa ggccaggaac cgtaaaaagg   6120
ccgcgttgct ggcgtttttc cataggctcc gccccctga cgagcatcac aaaaatcgac    6180
gctcaagtca gaggtggcga aacccgacag gactataaag ataccaggcg tttccccctg   6240
gaagctccct cgtgcgctct cctgttccga ccctgccgct taccggatac ctgtccgcct   6300
```

-continued

```
ttctcccttc gggaagcgtg gcgctttctc atagctcacg ctgtaggtat ctcagttcgg   6360
tgtaggtcgt tcgctccaag ctgggctgtg tgcacgaacc ccccgttcag cccgaccgct   6420
gcgccttatc cggtaactat cgtcttgagt ccaacccggt aagacacgac ttatcgccac   6480
tggcagcagc cactggtaac aggattagca gagcgaggta tgtaggcggt gctacagagt   6540
tcttgaagtg gtggcctaac tacggctaca ctagaagaac agtatttggt atctgcgctc   6600
tgctgaagcc agttaccttc ggaaaaagag ttggtagctc ttgatccggc aaacaaacca   6660
ccgctggtag cggtggtttt tttgtttgca agcagcagat tacgcgcaga aaaaaaggat   6720
ctcaagaaga tcctttgatc ttttctacgg ggtctgacgc tcagtggaac gaaaactcac   6780
gttaagggat tttggtcatg agattatcaa aaaggatctt cacctagatc cttttaaatt   6840
aaaaatgaag ttttaaatca atctaaagta tatatgagta aacttggtct gacagttacc   6900
aatgcttaat cagtgaggca cctatctcag cgatctgtct atttcgttca tccatagttg   6960
cctgactcgg gggggggggg cgctgaggtc tgcctcgtga agaaggtgtt gctgactcat   7020
accaggcctg aatcgcccca tcatccagcc agaaagtgag ggagccacgg ttgatgagag   7080
ctttgttgta ggtggaccag ttggtgattt tgaacttttg ctttgccacg gaacggtctg   7140
cgttgtcggg aagatgcgtg atctgatcct tcaactcagc aaaagttcga tttattcaac   7200
aaagccgccg tcccgtcaag tcagcgtaat gctctgccag tgttacaacc aattaaccaa   7260
ttctgattag aaaaactcat cgagcatcaa atgaaactgc aatttattca tatcaggatt   7320
atcaatacca tatttttgaa aaagccgttt ctgtaatgaa ggagaaaact caccgaggca   7380
gttccatagg atggcaagat cctggtatcg gtctgcgatt ccgactcgtc caacatcaat   7440
acaacctatt aatttcccct cgtcaaaaat aaggttatca agtgagaaat caccatgagt   7500
gacgactgaa tccggtgaga atggcaaaag cttatgcatt tctttccaga cttgttcaac   7560
aggccagcca ttacgctcgt catcaaaatc actcgcatca accaaaccgt tattcattcg   7620
tgattgcgcc tgagcgagac gaaatacgcg atcgctgtta aaaggacaat tacaaacagg   7680
aatcgaatgc aaccggcgca ggaacactgc cagcgcatca acaatatttt cacctgaatc   7740
aggatattct tctaatacct ggaatgctgt tttcccgggg atcgcagtgg tgagtaacca   7800
tgcatcatca ggagtacgga taaaatgctt gatggtcgga agaggcataa attccgtcag   7860
ccagtttagt ctgaccatct catctgtaac atcattggca acgctacctt tgccatgttt   7920
cagaaacaac tctggcgcat cgggcttccc atacaatcga tagattgtcg cacctgattg   7980
cccgacatta tcgcgagccc atttataccc atataaatca gcatccatgt tggaatttaa   8040
tcgcggcctc gagcaagacg tttcccgttg aatatggctc ataacacccc ttgtattact   8100
gtttatgtaa gcagacagtt ttattgttca tgatgatata tttttatctt gtgcaatgta   8160
acatcagaga ttttgagaca caacgtggct ttcccccccc ccccattatt gaagcattta   8220
tcagggttat tgtctcatga gcggatacat atttgaatgt atttagaaaa ataaacaaat   8280
aggggttccg cgcacatttc cccgaaaagt gccacctgac gtctaagaaa ccattattat   8340
catgacatta acctataaaa ataggcgtat cacgaggccc tttcgtc                 8387
```

<210> SEQ ID NO 7
<211> LENGTH: 8166
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcac accatgaatt acattccaac   1380
tcaaaccttt tacggacgcc gttggcgacc acgcccggcg taccgtccat ggcgggtgcc   1440
gatgcagccg gccccaccca tggtgattcc tgagctgcaa actccgatcg tccaggccca   1500
acagatgcag cagctaatca gtgcagtttc tgccctgacg accaagcaaa atggcaaagc   1560
accgaagaag ccgaagaaaa agccgcaaaa agcgaaggct aagaaaaacg aacagcaaaa   1620
gaagaacgag aacaagaaac caccgcctaa gcagaagaat ccggctaaga agaagaaacc   1680
aggaaaaagg gaacgcatgt gcatgaagat agagaatgat tgcatcttcg aggtcaagct   1740
tgacggtaag gtcacgggat acgcctgcct agtcggggat aaagtgatga agccggcaca   1800
cgtcaaaggt gtgatcgaca accccgacct agcgaagctt acctacaaga aatcgagcaa   1860
gtatgacctg gagtgcgccc agataccagt gcacatgaag tcagatgctt caaagtacac   1920
ccatgaaaaa ccagaagggc actacaattg gcatcacggt gcagtgcagt acagcggtgg   1980
caggttcaca atcccgacag gcgcaggtaa accaggagac agcggccggc cgatcttcga   2040
caacaaagga cgcgtggtgg ccattgtcct gggaggggcc aacgaaggag ccaggactgc   2100
cctatccgtc gtgacctgga ccaaagacat ggtcacacgg tacaccccag aaggaacaga   2160
agaatggtcc gccgccttga tgatgtgcgt cttagccaac gttacattcc catgctcaga   2220
gcccgcgtgt gcaccctgtt gctatgaaaa acaaccagaa cagacactga ggatgttaga   2280
ggacaacgtg gaccgcccgg gctactacga cctgctcgag gccacgatga cgtgtaacaa   2340
```

-continued

```
tagtgcacgc caccgtcgca gtgtgacgaa acacttcaac gtctacaagg ccacgaaacc   2400
gtatctagcg tattgcgcgg actgcggaga cgggcagttc tgttacagcc cggtggctat   2460
agaaaaaatt agggatgagg cttccgatgg catgataaaa atccaggtcg cagcgcaaat   2520
tggcatcaac aaaggaggaa cacacgaaca caacaaaatc aggtacatcg ccgggcatga   2580
catgaaagag gcaaaccggg actctttaca agtgcatact tccggtgtgt gcgctattcg   2640
aggcacgatg ggccacttca tcgtggccta ctgccctcca ggggacgaac taaaggtcca   2700
gttccaagat gcagaatcgc acacccaggc ctgcaaagtg cagtacaaac acgcaccggc   2760
cccagtaggc agagaaaaat tcaccgtcag gccccacttc ggtatcgaag tgccatgcac   2820
aacgtaccag ctgactaccg caccgacgga ggaagagatc gacatgcata ccccaccgga   2880
tatcccagac ataacgttgc tgtcgcagca gtcaggtaat gtaaagatca cagcaggagg   2940
aaaaaccatc agatacaact gcacgtgtgg tagtggcaac gtgggcacca ccagtagcga   3000
caagactatc aattcgtgca aaatagcaca gtgccacgct gcggtgacta accacgataa   3060
gtggcagtac acctcctcgt ttgtccctag agccgaccag ttgtctcgca aaggtaaagt   3120
gcacgtacct ttccctctga ccaactccac atgcagggtg cctgttgcac gtgcaccagg   3180
tgtcacatac ggaaagagag aactgacagt gaaactgcac ccagatcatc ccacgctgtt   3240
gacgtaccgg agtctaggag cagatccgcg cccgtatgag gagtggatag accgatacgt   3300
cgaacggacc ataccggtga ccgaagatgg gatcgagtac agatggggaa acaacccacc   3360
cgtgcgcttg tgggcccagc tgacaactga aggcaaaccc catgggtggc cgcacgagat   3420
catactctat tactatgggc tatacccagc agccaccatc gccgccgtct cagccgcggg   3480
tctcgcagtc gtactatcgc tgctggcgtc atgttacatg ttcgccactg cacgccgcaa   3540
gtgcctgacc ccatacgccc tgacccccgg agctgtcgtc ccggtaacac taggagtact   3600
atgctgcgca ccacgagcgc atgccgcgtc atttgcggaa tctatggcgt atctatggga   3660
tgagaatcaa accctgtttt ggctggagct tgcaacgccg ctcgctgcca taatcatact   3720
tgtatgctgc ctgaagaacc tgctttgctg ctgcaaaccg ctttcttttt tagtgctggt   3780
gagcctggga actcccgtcg taaaatctta cgaacacacc gcaacgatcc cgaatgtggt   3840
gggattcccg tataaggctc acattgagag gaacggcttc tccccgatga ccctacagct   3900
tgaagtactt ggaaccagct tggaacccac gctaaactta gagtacataa cctgtgaata   3960
caagacagtc gtgccatcac cttatatcaa gtgctgcggg acatcagaat gcagatccat   4020
ggagcgcccc gactatcaat gccaggtcta cacaggagtg tacccattta tgtggggcgg   4080
cgcatactgc ttctgcgaca ctgagaacac ccagctgagt gaagcatacg ttgatagatc   4140
ggacgtatgc aagcacgacc atgccgccgc ctacaaggcg catactgcgg caatgaaagc   4200
caccatccga ataagctacg ggaacctcaa tcagacaaca acggcgttcg tcaacgggga   4260
gcacacagtg accgtcggag gcagcaggtt tacttttggt ccaatctcca ctgcctggac   4320
gcctttcgac aacaagatcg tcgtctacaa gaacgacgtc tacaaccagg acttcccacc   4380
ctacgggtca ggacaaccag ggaggtttgg agacatccag agcaggacgg tagagagcaa   4440
ggacctgtat gccaacaccg ccctcaagtt gtcaagacct tcgtccggta ctgttcacgt   4500
gccttacaca cagacccctt ctggctttaa gtactggata aaagagagag gcacgtcgct   4560
gaatgacaag gctccctttg gatgcgtaat caagaccaac ccagtcagag cagaaaattg   4620
cgccgttggc aacatcccag tctccatgga catcccggac accgcgttta cgcgcgtgat   4680
```

-continued

```
tgatgcacct gccgtcacaa acctggagtg ccaagtggcg gtctgcacgc actcatcgga   4740
cttcggcggg atcgcgactc tgactttcaa aactgacaaa cccggaaaat gtgctgtcca   4800
ttctcattcg aacgtagcca ccatacagga ggcagctgtg gacatcaaaa cagatggcaa   4860
gataaccctg catttctcta cagcatcagc atccccggca ttcaaggtat ctgtgtgcag   4920
tgccaaaacg acatgcatgg cagcgtgtga gccgccgaag gaccacatcg tcccttatgg   4980
ggcgagccat aacaaccaag tttttcctga catgtctggc acggcaatga catgggtgca   5040
gcgggtagcc ggcggactcg gcgggctaac actcgccgca gtggcagtac ttatactggt   5100
gacgtgtgtg actatgcgcc gctaatctag accaggccct ggatccagat ctgctgtgcc   5160
ttctagttgc cagccatctg ttgtttgccc ctcccccgtg ccttccttga ccctggaagg   5220
tgccactccc actgtccttt cctaataaaa tgaggaaatt gcatcgcatt gtctgagtag   5280
gtgtcattct attctggggg gtggggtggg gcaggacagc aagggggagg attgggaaga   5340
caatagcagg catgctgggg atgcggtggg ctctatgggt acccaggtgc tgaagaattg   5400
acccggttcc tcctgggcca gaaagaagca ggcacatccc cttctctgtg acacaccctg   5460
tccacgcccc tggttcttag ttccagcccc actcatagga cactcatagc tcaggagggc   5520
tccgccttca atcccacccg ctaaagtact tggagcggtc tctccctccc tcatcagccc   5580
accaaaccaa acctagcctc caagagtggg aagaaattaa agcaagatag gctattaagt   5640
gcagagggag agaaaatgcc tccaacatgt gaggaagtaa tgagagaaat catagaattt   5700
taaggccatg atttaaggcc atcatggcct taatcttccg cttcctcgct cactgactcg   5760
ctgcgctcgg tcgttcggct gcggcgagcg gtatcagctc actcaaaggc ggtaatacgg   5820
ttatccacag aatcagggga taacgcagga aagaacatgt gagcaaaagg ccagcaaaag   5880
gccaggaacc gtaaaaaggc cgcgttgctg gcgtttttcc ataggctccg cccccctgac   5940
gagcatcaca aaaatcgacg ctcaagtcag aggtggcgaa acccgacagg actataaaga   6000
taccaggcgt ttccccctgg aagctccctc gtgcgctctc ctgttccgac cctgccgctt   6060
accggatacc tgtccgcctt tctcccttcg ggaagcgtgg cgctttctca tagctcacgc   6120
tgtaggtatc tcagttcggt gtaggtcgtt cgctccaagc tgggctgtgt gcacgaaccc   6180
cccgttcagc ccgaccgctg cgccttatcc ggtaactatc gtcttgagtc caacccggta   6240
agacacgact tatcgccact ggcagcagcc actggtaaca ggattagcag agcgaggtat   6300
gtaggcggtg ctacagagtt cttgaagtgg tggcctaact acggctacac tagaagaaca   6360
gtatttggta tctgcgctct gctgaagcca gttaccttcg gaaaaagagt tggtagctct   6420
tgatccggca aacaaaccac cgctggtagc ggtggttttt ttgtttgcaa gcagcagatt   6480
acgcgcagaa aaaaaggatc tcaagaagat cctttgatct tttctacggg gtctgacgct   6540
cagtggaacg aaaactcacg ttaagggatt ttggtcatga gattatcaaa aaggatcttc   6600
acctagatcc ttttaaatta aaaatgaagt tttaaatcaa tctaaagtat atatgagtaa   6660
acttggtctg acagttacca atgcttaatc agtgaggcac ctatctcagc gatctgtcta   6720
tttcgttcat ccatagttgc ctgactcggg gggggggggc gctgaggtct gcctcgtgaa   6780
gaaggtgttg ctgactcata ccaggcctga atcgccccat catccagcca gaaagtgagg   6840
gagccacggt tgatgagagc tttgttgtag gtggaccagt tggtgatttt gaacttttgc   6900
tttgccacgg aacggtctgc gttgtcggga agatgcgtga tctgatcctt caactcagca   6960
aaagttcgat ttattcaaca aagccgccgt cccgtcaagt cagcgtaatg ctctgccagt   7020
gttacaacca attaaccaat tctgattaga aaaactcatc gagcatcaaa tgaaactgca   7080
```

atttattcat atcaggatta tcaataccat atttttgaaa aagccgtttc tgtaatgaag 7140
gagaaaactc accgaggcag ttccatagga tggcaagatc ctggtatcgg tctgcgattc 7200
cgactcgtcc aacatcaata caacctatta atttcccctc gtcaaaaata aggttatcaa 7260
gtgagaaatc accatgagtg acgactgaat ccggtgagaa tggcaaaagc ttatgcattt 7320
ctttccagac ttgttcaaca ggccagccat tacgctcgtc atcaaaatca ctcgcatcaa 7380
ccaaaccgtt attcattcgt gattgcgcct gagcgagacg aaatacgcga tcgctgttaa 7440
aaggacaatt acaaacagga atcgaatgca accggcgcag gaacactgcc agcgcatcaa 7500
caatattttc acctgaatca ggatattctt ctaatacctg gaatgctgtt ttcccgggga 7560
tcgcagtggt gagtaaccat gcatcatcag gagtacggat aaaatgcttg atggtcggaa 7620
gaggcataaa ttccgtcagc cagtttagtc tgaccatctc atctgtaaca tcattggcaa 7680
cgctaccttt gccatgtttc agaaacaact ctggcgcatc gggcttccca tacaatcgat 7740
agattgtcgc acctgattgc ccgacattat cgcgagccca tttataccca tataaatcag 7800
catccatgtt ggaatttaat cgcggcctcg agcaagacgt ttcccgttga atatggctca 7860
taacacccct tgtattactg tttatgtaag cagacagttt tattgttcat gatgatatat 7920
ttttatcttg tgcaatgtaa catcagagat tttgagacac aacgtggctt tccccccccc 7980
cccattattg aagcatttat cagggttatt gtctcatgag cggatacata tttgaatgta 8040
tttagaaaaa taaacaaata ggggttccgc gcacatttcc ccgaaaagtg ccacctgacg 8100
tctaagaaac cattattatc atgacattaa cctataaaaa taggcgtatc acgaggccct 8160
ttcgtc 8166

<210> SEQ ID NO 8
<211> LENGTH: 8186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900

-continued

```
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgccaccatg   1380
ttcccgttcc aaccaatgta tccgatgcag ccaatgccct atcgtaaccc gttcgcggcc   1440
ccgcgcaggc cctggttccc cagaaccgac ccttttctgg cgatgcaggt gcaggaatta   1500
acccgctcga tggctaacct gacgttcaag caacgccggg acgcgccacc tgaggggcca   1560
cctgctaaga aacctaagag ggaggccccg caaaagcaaa aagggggagg ccaagggaag   1620
aagaagaaga accaggggaa gaagaaggcc aagacggggc cgcctaatcc gaaggcacag   1680
agtggaaaca agaagaagcc caacaagaaa ccaggcaaga gacagcgcat ggtcatgaaa   1740
ttggaatctg acaagacatt cccaattatg ctggaaggga agattaacgg ctacgcttgc   1800
gtggtcggag ggaagttatt caggccgatg cacgtggaag gcaagatcga caacgacgtt   1860
ctggccgcac ttaagacgaa gaaagcatcc aaatatgatc ttgagtatgc agatgtgcca   1920
cagaacatgc gggccgatac attcaagtac acccatgaga agccccaagg ctattacagc   1980
tggcatcatg gagcagtcca atatgaaaat gggcgtttca cggtgccaaa aggagttggg   2040
gccaagggag acagcggaag acccattctg gataatcagg gacgggtggt cgctattgtg   2100
ctgggaggtg tgaatgaagg atctaggaca gccctttcag tcgtcatgtg gaacgagaag   2160
ggagtaactg tgaagtatac tccggagaac tgcgagcaat ggtcactagt gaccactatg   2220
tgcctgctcg ccaatgtgac gttcccatgt gccgaaccac caatttgcta cgacagaaaa   2280
ccagcagaga ctttggccat gctcagcgtt aacgttgaca acccgggcta cgatgagctg   2340
ctggaagcag ctgttaagtg ccccggaaga aaaaggagat ctaccgagga gctgtttaag   2400
gagtataagc taacgcgccc ttacatggcc agatgcatca gatgtgccgt tgggagctgc   2460
catagtccaa tagcaattga ggcagtgaag agcgacgggc acgacggcta tgttagactt   2520
cagacttcct cgcagtatgg cctggattcc tctggcaact taaagggaag gactatgcgg   2580
tatgatatgc acgggaccat tgaagagata ccactacatc aagtgtcact ccacacatct   2640
cgcccgtgtc acattgtgga tgggcatggt tattttctgc ttgctaggtg cccggcaggg   2700
gactccatca ccatggaatt taagaaaggt tcagtcacac actcctgctc agtgccgtat   2760
gaagtgaaat ttaatcctgt aggcagagaa ctctacactc atccaccaga acacggagca   2820
gagcaagcgt gccaagtcta cgcgcacgat gcacagaaca gaggagctta tgtcgagatg   2880
cacctcccgg gctcagaagt ggacagcagt ttgatttcct tgagcggcag ttcagtcacc   2940
gtgacacctc ctgtcgggac tagcgccttg gtgaaatgca agtgcggcgg cacaaagatc   3000
tccgaaacca tcaacaaggc aaaacagttc agccagtgca caaagaagga gcagtgcaga   3060
gcatatcgac tgcagaatga caagtgggtg tataattctg acaaactgcc caaagcagcg   3120
ggagccaccc taaaaggaaa actacacgtc ccgttcttgc tggcagacgg caaatgcacc   3180
gtgcctctag caccggaacc tatgataacc ttcggtttcc gatcagtgtc actgaaactg   3240
```

-continued caccctaaga atcccacata tctgaccact cgccaacttg ctgatgagcc tcattacacg 3300
cacgagctca tatctgaacc agctgttagg aattttaccg tcactgaaaa ggggtgggag 3360
tttgtatggg gaaaccatcc gccgaaaagg ttttgggcac aggaaacagc acccggaaat 3420
ccacatgggc tgccacatga ggtgataact cattattacc acagataccc tatgtccacc 3480
atcctgggtt tgtcaatttg cgccgccatt gtaaccgttt ccgttgcagc gtccacctgg 3540
ctgttttgca aatccagagt ttcgtgccta actccttacc ggctaacacc taacgccagg 3600
atgccgcttt gcctggccgt gctttgctgc gcccgcactg cccgggccga gaccacctgg 3660
gagtccttgg atcacctatg gaacaataac caacagatgt tctggattca attgctgatc 3720
cctctggccg ccttgattgt agtgactcgc ctgctcaagt gcgtgtgctg tgtagtgcct 3780
tttttagtcg tggccggcgc cgcaggcgcc ggcgcctacg agcacgcgac cacgatgccg 3840
agccaagcgg gaatctcgta taacaccata gtcaacagag caggctacgc gccactccct 3900
atcagcataa caccaacaaa gatcaagctg atacccacag tgaacttgga gtacgtcacc 3960
tgccactaca aaacaggaat ggattcacca gccatcaaat gctgcggatc tcaggaatgt 4020
actccaacta acaggcctga tgaacagtgc aaagtcttca caggggttta cccgttcatg 4080
tggggaggtg catattgctt ttgcgacact gagaatactc aggtcagcaa ggcctacgta 4140
atgaaatctg acgactgcct tgcggatcat gctgaagcat acaaagcgca cacagcctca 4200
gtgcaggcgt tcctcaacat cacagtgggg gaacactcta ttgtgaccac cgtgtatgtg 4260
aatggagaaa ctcctgtgaa cttcaatggg gtcaaactaa ctgcaggtcc actttccaca 4320
gcttggacac cctttgacag aaaaatcgtg cagtatgccg ggagatcta taattacgat 4380 tttcctgagt atggggcagg acaaccagga gcatttggag acatacaatc cagaacagtc 4440
tcaagctcag atctgtatgc caataccaac ctagtgctgc agagacccaa agcaggagcg 4500
atccatgtgc catacactca ggcaccatcg ggttttgagc aatggaagaa agataaagct 4560
ccgtcattga aattcaccgc ccctttcgga tgcgaaatat atacaaaccc cattcgcgcc 4620
gaaaattgtg ctgtagggtc aattccatta gcctttgaca ttcccgacgc cttgttcacc 4680
agggtgtcag aaacaccgac actttcagcg gccgaatgca ctcttaacga gtgcgtgtat 4740
tcatccgact ttggcgggat cgccacggtc aagtattcgg ccagcaagtc aggcaagtgc 4800
gcagtccatg tgccatcagg gactgctacc ctaaaagaag cagcagtcga gctaaccgag 4860
caagggtcgg cgaccattca tttctcgacc gcaaatatcc acccggagtt caggctccaa 4920
atatgcacat catatgtcac gtgcaaaggt gattgtcacc ccccgaaaga ccacattgtg 4980
acacaccccc agtatcacgc ccaaacattt acagccgcgg tgtcaaaaac cgcgtggacg 5040
tggttaacat ccctgctggg aggatcggcc gtaattatta taattggctt agtgctggct 5100
actattgtgg ccatgtacgt gctgaccaac cagaaacata attgatctag accaggccct 5160
ggatccagat ctgctgtgcc ttctagttgc cagccatctg ttgtttgccc ctcccccgtg 5220
ccttccttga ccctggaagg tgccactccc actgtccttt cctaataaaa tgaggaaatt 5280
gcatcgcatt gtctgagtag gtgtcattct attctggggg gtggggtggg gcaggacagc 5340
aagggggagg attgggaaga caatagcagg catgctgggg atgcggtggg ctctatgggt 5400
acccaggtgc tgaagaattg acccggttcc tcctgggcca gaaagaagca ggcacatccc 5460
cttctctgtg acacaccctg tccacgcccc tggttcttag ttccagcccc actcatagga 5520
cactcatagc tcaggagggc tccgccttca atcccacccg ctaaagtact tggagcggtc 5580
tctccctccc tcatcagccc accaaaccaa acctagcctc caagagtggg aagaaattaa 5640

```
agcaagatag gctattaagt gcagagggag agaaaatgcc tccaacatgt gaggaagtaa   5700
tgagagaaat catagaattt taaggccatg atttaaggcc atcatggcct taatcttccg   5760
cttcctcgct cactgactcg ctgcgctcgg tcgttcggct gcggcgagcg gtatcagctc   5820
actcaaaggc ggtaatacgg ttatccacag aatcagggga taacgcagga aagaacatgt   5880
gagcaaaagg ccagcaaaag gccaggaacc gtaaaaaggc cgcgttgctg gcgtttttcc   5940
ataggctccg cccccctgac gagcatcaca aaaatcgacg ctcaagtcag aggtggcgaa   6000
acccgacagg actataaaga taccaggcgt ttccccctgg aagctccctc gtgcgctctc   6060
ctgttccgac cctgccgctt accggatacc tgtccgcctt tctcccttcg ggaagcgtgg   6120
cgctttctca tagctcacgc tgtaggtatc tcagttcggt gtaggtcgtt cgctccaagc   6180
tgggctgtgt gcacgaaccc cccgttcagc ccgaccgctg cgccttatcc ggtaactatc   6240
gtcttgagtc caacccggta agacacgact tatcgccact ggcagcagcc actggtaaca   6300
ggattagcag agcgaggtat gtaggcggtg ctacagagtt cttgaagtgg tggcctaact   6360
acggctacac tagaagaaca gtatttggta tctgcgctct gctgaagcca gttaccttcg   6420
gaaaaagagt tggtagctct tgatccggca aacaaaccac cgctggtagc ggtggttttt   6480
ttgtttgcaa gcagcagatt acgcgcagaa aaaaaggatc tcaagaagat cctttgatct   6540
tttctacggg gtctgacgct cagtggaacg aaaactcacg ttaagggatt ttggtcatga   6600
gattatcaaa aaggatcttc acctagatcc ttttaaatta aaaatgaagt tttaaatcaa   6660
tctaaagtat atatgagtaa acttggtctg acagttacca atgcttaatc agtgaggcac   6720
ctatctcagc gatctgtcta tttcgttcat ccatagttgc ctgactcggg ggggggggc    6780
gctgaggtct gcctcgtgaa gaaggtgttg ctgactcata ccaggcctga atcgccccat   6840
catccagcca gaaagtgagg gagccacggt tgatgagagc tttgttgtag gtggaccagt   6900
tggtgatttt gaacttttgc tttgccacgg aacggtctgc gttgtcggga agatgcgtga   6960
tctgatcctt caactcagca aaagttcgat ttattcaaca aagccgccgt cccgtcaagt   7020
cagcgtaatg ctctgccagt gttacaacca attaaccaat tctgattaga aaaactcatc   7080
gagcatcaaa tgaaactgca atttattcat atcaggatta tcaataccat atttttgaaa   7140
aagccgtttc tgtaatgaag gagaaaactc accgaggcag ttccatagga tggcaagatc   7200
ctggtatcgg tctgcgattc cgactcgtcc aacatcaata caacctatta atttcccctc   7260
gtcaaaaata aggttatcaa gtgagaaatc accatgagtg acgactgaat ccggtgagaa   7320
tggcaaaagc ttatgcattt ctttccagac ttgttcaaca ggccagccat tacgctcgtc   7380
atcaaaatca ctcgcatcaa ccaaaccgtt attcattcgt gattgcgcct gagcgagacg   7440
aaatacgcga tcgctgttaa aaggacaatt acaaacagga atcgaatgca accggcgcag   7500
gaacactgcc agcgcatcaa caatattttc acctgaatca ggatattctt ctaatacctg   7560
gaatgctgtt ttcccgggga tcgcagtggt gagtaaccat gcatcatcag gagtacggat   7620
aaaatgcttg atggtcggaa gaggcataaa ttccgtcagc cagtttagtc tgaccatctc   7680
atctgtaaca tcattggcaa cgctaccttt gccatgtttc agaaacaact ctggcgcatc   7740
gggcttccca tacaatcgat agattgtcgc acctgattgc ccgacattat cgcgagccca   7800
tttataccca tataaatcag catccatgtt ggaatttaat cgcggcctcg agcaagacgt   7860
ttcccgttga atatggctca taacacccct tgtattactg tttatgtaag cagacagttt   7920
tattgttcat gatgatatat ttttatcttg tgcaatgtaa catcagagat tttgagacac   7980
```

-continued

```
aacgtggctt tccccccccc cccattattg aagcatttat cagggttatt gtctcatgag   8040

cggatacata tttgaatgta tttagaaaaa taaacaaata ggggttccgc gcacatttcc   8100

ccgaaaagtg ccacctgacg tctaagaaac cattattatc atgacattaa cctataaaaa   8160

taggcgtatc acgaggccct ttcgtc                                        8186
```

<210> SEQ ID NO 9
<211> LENGTH: 8129
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctcca tcggctcgca tctctccttc acgcgcccgc   1020

cgccctacct gaggccgcca tccacgccgg ttgagtcgcg ttctgccgcc tcccgcctgt   1080

ggtgcctcct gaactgcgtc cgccgtctag gtaagtttaa agctcaggtc gagaccgggc   1140

ctttgtccgg cgctcccttg gagcctacct agactcagcc ggctctccac gctttgcctg   1200

accctgcttg ctcaactcta gttaacggtg gagggcagtg tagtctgagc agtactcgtt   1260

gctgccgcgc gcgccaccag acataatagc tgacagacta acagactgtt cctttccatg   1320

ggtcttttct gcagtcaccg tcgtcgacac gtgtgatcag atatcgcggc cgccaccatg   1380

tttccatacc ctcagctgaa ctttccacca gtttacccta caaatccgat ggcttaccga   1440

gatccaaacc ctcctaggcg ccgctggagg ccgtttcggc ccccgctggc tgctcaaatc   1500

gaagatctta ggaggtcgat agtcaacttg actttcaaac aacgatcacc taatccgccg   1560

ccaggtccac cgccaaagaa gaagaagagt gctcctaagc caaaacctac tcagcctaaa   1620

aagaagaagc agcaagccaa gaggacgaaa cgcaagccta aaccagggaa acgacaacgt   1680

atgtgtatga agttggagtc ggacaagaca tttccgatca tgctgaacgg ccaagtgaat   1740

ggatatgcct gcgttgtcgg aggaaggctg atgaaaccac tccacgttga aggaaaaatt   1800
```

-continued

```
gataatgagc aattagcggc cgtgaaattg aagaaggcta gcatgtacga cttggagtac   1860
ggcgacgttc cccagaacat gaaatcagac acgctgcagt acaccagcga caaaccaccg   1920
ggcttctaca actggcacca cggcgcagtc cagtatgaga atgggagatt taccgtaccg   1980
agaggagtgg gcgggaaagg cgacagcgga agaccgatcc tggacaacag aggcagagtt   2040
gtggctattg ttctaggagg tgcaaatgag ggcacgcgta cggcgctttc agtggtcact   2100
tggaaccaga aaggggtgac cattagggat acccccgaag gttctgaacc gtggtcacta   2160
gttacagcgc tatgcgtgct ttcgaatgtc acgttcccat gcgacaaacc acccgtgtgc   2220
tattcactga cgccagaacg aacactcgac gtgctcgaag agaacgtcga caatccaaat   2280
tacgacacgc tgctggagaa cgtcttgaaa tgtccatcac gccggcccaa acgaagcatt   2340
accgatgact tcacactgac cagtccctac ctggggttct gcccgtattg cagacactca   2400
acgccgtgtt tcagcccaat aaaaattgag aacgtgtggg acgaatctga tgatggatcg   2460
attagaatcc aggtctcggc acaattcggc tacaatcagg caggcactgc ggatgtcacc   2520
aaattccgtt acatgtcttt cgaccacgac catgacatca aggaagacag tatggagaaa   2580
atagctatca gcacatctgg accctgccgt cgtcttggcc acaaagggta cttcctgtta   2640
gctcaatgtc ctccaggtga cagtgtaacc gtcagtatca cgagcggagc atctgagaat   2700
tcatgcaccg tggagaaaaa gatcaggagg aagtttgtcg gtagagagga gtacttgttc   2760
ccacccgtcc atggaaagct ggtaaagtgc cacgtttacg atcacttgaa ggagacgtct   2820
gccgggtaca taaccatgca caggccaggc ccacacgcgt ataagtccta tctggaggaa   2880
gcgtcaggcg aagtgtacat taaaccacct tctggcaaga acgtcaccta cgaatgtaag   2940
tgtggcgact acagcacagg tatcgtgagc acgcgaacga agatgaacgg ctgcactaaa   3000
gcaaaacagt gcattgccta caagagcgac caaacgaaat gggtcttcaa ctcgccggat   3060
cttattaggc acacagacca ctcagtgcaa ggtaaattgc acattccatt ccgcttgaca   3120
ccgacagtct gcccggttcc gttagctcac acgcctacag tcacgaagtg gttcaaaggc   3180
atcaccctcc acctgactgc aatgcgacca acattgctga caacgagaaa attggggctg   3240
cgagcagacg caacagcaga atggattaca gggtctacat ccaggaattt ttctgtgggg   3300
cgagaagggc tggagtacgt atggggtaac catgaaccag tcagagtctg ggcccaggag   3360
tcggcaccag gcgacccaca tggatggccg catgagatca tcatccacta ttatcatcgg   3420
catccagtct acactgtcat tgtgctgtgt ggtgtcgctc ttgctatcct ggtaggcact   3480
gcatcatcag cagcttgcat cgccaaagca agaagagact gcctgacgcc atacgcgctt   3540
gcaccgaacg caacggtacc cacagcatta gcggttttgt gctgcattcg gccaaccaac   3600
gctgaaacat ttggagaaac tttgaaccat ctgtggttta acaaccaacc gtttctctgg   3660
gcacagttgt gcattcctct ggcagcgctt gttattctgt tccgctgctt ttcatgctgc   3720
atgccttttt tattggttgc aggcgtctgc ctggggaagg tagacgcctt cgaacatgcg   3780
accactgtgc caaatgttcc ggggatcccg tataaggcgt tggtcgaacg cgcaggttac   3840
gcgccactta acctggagat cacggtcgtc tcatcggaat taacaccttc aactaacaag   3900
gagtacgtga cctgcaaatt ccacacagtc attccttcac cacaagttaa atgctgcggg   3960
tccctcgagt gcaaggcatc ctcaaaggcg gattacacat gccgcgtttt tggcggtgtg   4020
taccctttca tgtggggagg cgcacaatgc ttctgtgaca gtgagaacac acaactgagt   4080
gaggcgtacg tcgagttcgc tccagactgc actatagatc acgcagtcgc actaaaagtt   4140
cacacagctg ctctgaaagt cggcctgcgt atagtatacg gcaacaccac cgcgcacctg   4200
```

-continued

```
gatacgtttg tcaatggcgt cacgccaggt tcctcacggg acctgaaggt catagcaggg   4260
ccgatatcag ccgctttttc accctttgac cataaggtcg tcatcagaaa ggggcttgtt   4320
tacaactacg acttccctga gtatggagct atgaaaccag gagcgttcgg cgatattcaa   4380
gcatcctcgc ttgatgctac agacatagta gcccgcactg acatacggct gctgaagcct   4440
tctgtcaaga acatccacgt cccctacacc caagcagtat cagggtatga aatgtggaag   4500
aacaactcag gacgacccct gcaagaaaca gcaccatttg gatgtaaaat tgaagtggag   4560
cctctgcgag cgtctaactg tgcttacggg cacatcccta tctcgattga catccctgat   4620
gcagcttttg tgagatcatc agaatcacca acaattttag aagttagctg cacagtagca   4680
gactgcattt attctgcaga ctttggtggt tctctaacat tacagtacaa agctgacagg   4740
gagggacatt gtccagttca ctcccactcc acgacagctg ttttgaagga agcgaccaca   4800
catgtgactg ccgtaggcag cataacacta cattttagca catcgagccc acaagcaaat   4860
tttatagttt cgctatgcgg caagaagtcc acctgcaatg ctgaatgtaa accaccggcc   4920
gaccacataa ttggagaacc acataaagtc gaccaagaat tccaggcggc agtttccaaa   4980
acatcttgga actggctgct tgcactgttt gggggagcat catccctcat tgttgtagga   5040
cttatagtgt tggtctgcag ctctatgctt ataaacacac gtagatgatc tagaccaggc   5100
cctggatcca gatctgctgt gccttctagt tgccagccat ctgttgtttg cccctccccc   5160
gtgccttcct tgaccctgga aggtgccact cccactgtcc tttcctaata aaatgaggaa   5220
attgcatcgc attgtctgag taggtgtcat tctattctgg ggggtggggt ggggcaggac   5280
agcaaggggg aggattggga agacaatagc aggcatgctg gggatgcggt gggctctatg   5340
ggtacccagg tgctgaagaa ttgacccggt tcctcctggg ccagaaagaa gcaggcacat   5400
ccccttctct gtgacacacc ctgtccacgc ccctggttct tagttccagc cccactcata   5460
ggacactcat agctcaggag ggctccgcct tcaatcccac ccgctaaagt acttggagcg   5520
gtctctccct ccctcatcag cccaccaaac caaacctagc ctccaagagt gggaagaaat   5580
taaagcaaga taggctatta agtgcagagg gagagaaaat gcctccaaca tgtgaggaag   5640
taatgagaga aatcatagaa ttttaaggcc atgatttaag gccatcatgg ccttaatctt   5700
ccgcttcctc gctcactgac tcgctgcgct cggtcgttcg gctgcggcga gcggtatcag   5760
ctcactcaaa ggcggtaata cggttatcca cagaatcagg ggataacgca ggaaagaaca   5820
tgtgagcaaa aggccagcaa aaggccagga accgtaaaaa ggccgcgttg ctggcgtttt   5880
tccataggct ccgcccccct gacgagcatc acaaaaatcg acgctcaagt cagaggtggc   5940
gaaacccgac aggactataa agataccagg cgtttccccc tggaagctcc ctcgtgcgct   6000
ctcctgttcc gaccctgccg cttaccggat acctgtccgc ctttctccct tcgggaagcg   6060
tggcgctttc tcatagctca cgctgtaggt atctcagttc ggtgtaggtc gttcgctcca   6120
agctgggctg tgtgcacgaa ccccccgttc agcccgaccg ctgcgcctta tccggtaact   6180
atcgtcttga gtccaacccg gtaagacacg acttatcgcc actggcagca gccactggta   6240
acaggattag cagagcgagg tatgtaggcg gtgctacaga gttcttgaag tggtggccta   6300
actacggcta cactagaaga acagtatttg gtatctgcgc tctgctgaag ccagttacct   6360
tcggaaaaag agttggtagc tcttgatccg gcaaacaaac caccgctggt agcggtggtt   6420
tttttgtttg caagcagcag attacgcgca gaaaaaaagg atctcaagaa gatcctttga   6480
tcttttctac ggggtctgac gctcagtgga acgaaaactc acgttaaggg attttggtca   6540
```

tgagattatc aaaaaggatc ttcacctaga tccttttaaa ttaaaaatga agttttaaat 6600
caatctaaag tatatatgag taaacttggt ctgacagtta ccaatgctta atcagtgagg 6660
cacctatctc agcgatctgt ctatttcgtt catccatagt tgcctgactc gggggggggg 6720
ggcgctgagg tctgcctcgt gaagaaggtg ttgctgactc ataccaggcc tgaatcgccc 6780
catcatccag ccagaaagtg agggagccac ggttgatgag agctttgttg taggtggacc 6840
agttggtgat tttgaacttt tgctttgcca cggaacggtc tgcgttgtcg ggaagatgcg 6900
tgatctgatc cttcaactca gcaaaagttc gatttattca acaaagccgc cgtcccgtca 6960
agtcagcgta atgctctgcc agtgttacaa ccaattaacc aattctgatt agaaaaactc 7020
atcgagcatc aaatgaaact gcaatttatt catatcagga ttatcaatac catatttttg 7080
aaaaagccgt ttctgtaatg aaggagaaaa ctcaccgagg cagttccata ggatggcaag 7140
atcctggtat cggtctgcga ttccgactcg tccaacatca atacaaccta ttaatttccc 7200
ctcgtcaaaa ataaggttat caagtgagaa atcaccatga gtgacgactg aatccggtga 7260
gaatggcaaa agcttatgca tttctttcca gacttgttca acaggccagc cattacgctc 7320
gtcatcaaaa tcactcgcat caaccaaacc gttattcatt cgtgattgcg cctgagcgag 7380
acgaaatacg cgatcgctgt taaaaggaca attacaaaca ggaatcgaat gcaaccggcg 7440
caggaacact gccagcgcat caacaatatt ttcacctgaa tcaggatatt cttctaatac 7500
ctggaatgct gttttcccgg ggatcgcagt ggtgagtaac catgcatcat caggagtacg 7560
gataaaatgc ttgatggtcg gaagaggcat aaattccgtc agccagttta gtctgaccat 7620
ctcatctgta acatcattgg caacgctacc tttgccatgt ttcagaaaca actctggcgc 7680
atcgggcttc ccatacaatc gatagattgt cgcacctgat tgcccgacat tatcgcgagc 7740
ccatttatac ccatataaat cagcatccat gttggaattt aatcgcggcc tcgagcaaga 7800
cgtttcccgt tgaatatggc tcataacacc ccttgtatta ctgtttatgt aagcagacag 7860
ttttattgtt catgatgata tatttttatc ttgtgcaatg taacatcaga gattttgaga 7920
cacaacgtgg ctttcccccc ccccccatta ttgaagcatt tatcagggtt attgtctcat 7980
gagcggatac atatttgaat gtatttagaa aaataaacaa ataggggttc cgcgcacatt 8040
tccccgaaaa gtgccacctg acgtctaaga aaccattatt atcatgacat taacctataa 8100
aaataggcgt atcacgaggc cctttcgtc 8129

<210> SEQ ID NO 10
<211> LENGTH: 8144
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420

-continued

```
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgccaccatg   1380
ttcccatacc ctacacttaa ctacccgcct atggcgccga ttaacccgat ggcttaccgg   1440
gatcctaatc cgcctaggcg caggtggcgg ccctttaggc caccacttgc agctcaaatt   1500
gaggacctga gacgttccat cgctaacctg actttgaaac aacgagcacc taaccctcca   1560
gcaggaccgc ccgccaaacg caagaagcct gcgccaagcc taagcctgcg caggaaaaag   1620
aagcgaccac caccacctgc caagaaacaa aaacgtaaac ctaaaccagg caaacgacag   1680
cgaatgtgta tgaagctaga gtcagataaa acgtttccaa tcatgttgaa cggacaggtg   1740
aatggttacg cgtgcgtcgt gggtggacga gtgttcaaac cgctgcacgt agaaggcaga   1800
atagacaatg agcaactggc cgccatcaag ctgaagaagg ccagcatata tgaccttgag   1860
tatggtgatg tgccacaatg catgaaatca gataccctcc agtacaccag tgacaagcct   1920
cctggctttt ataactggca ccatggagct gtacagtatg agaacaatag gttcaccgta   1980
ccacgggggg tcggtggaaa gggtgacagc gggagaccta ttcttgacaa caaaggtaga   2040
gtcgtcgcaa ttgtcctggg tggagtcaac gaaggatcca ggacggctct atcagtggtg   2100
acatggaacc aaaaaggggt tacagtcaaa gatacaccag aggggtcaga gccatggtcg   2160
cttgccactg tcatgtgcgt cctggccaat atcacgtttc catgtgatca accaccctgc   2220
atgccatgct gttatgaaaa gaatccacac gaaacactca ccatgttgga acagaattac   2280
gacagccgag cctatgatca gctgctcgat gccgctgtga aatgtaatgc taggagaacc   2340
aggagagatt tggacactca tttcacccag tataagctgg cacgcccgta tattgctgat   2400
tgccctaact gtgggcatag tcggtgcgac agccctatag ctatagaaga agtcagaggg   2460
gatgcgcacg caggagtcat ccgcatccag acatcagcta tgttcggtct gaagacggat   2520
ggagttgatt tggcctacat gagtttcatg aacggcaaaa cgcagaaatc aataaagatc   2580
gacaacctgc atgtgcgcac ctcagcccct tgttccctcg tgtcgcacca cggctattac   2640
atcctggctc aatgcccacc aggggacacg gttacagttg ggtttcacga cgggcctaac   2700
cgccatacgt gcacagttgc ccataaggta gaattcaggc cagtgggtag agagaaatac   2760
cgtcacccac ctgaacatgg agttgaatta ccatgcaacc gttacaccca caagcgtgca   2820
```

-continued

```
gaccaaggac actacgttga gatgcatcaa cccgggctag ttgccgacca ctctctcctt   2880
agcatccaca gtgccaaggt gaaaattacg gtaccgagcg gcgcccaagt gaaatactac   2940
tgcaagtgcc cagacgtacg agagggaact accagcagcg actatacaac cacctgcacg   3000
gatgtcaaac aatgcagggc ttacctgatt gacaacaaaa aatgggtgta caactctgga   3060
agactgcctc gaggagaggg cgacactttt aaaggaaaac ttcatgtgcc ctttgtgcct   3120
gttaaggcca agtgcatcgc cacgctggca ccagagcctc tagttgagca caaacaccgc   3180
accctgattt tacacctgta cccggaccac ccgaccttgc tgacgaccag gtcacttgga   3240
agtgatgcaa atccaactcg acaatggatt gagcgaccaa caactgtcaa tttcacagtc   3300
accggagaag ggttggagta tacctgggga aaccatccac caaaaagagt atgggctcaa   3360
gagtcaggag aagggaatcc acatggatgg ccgcacgaag tggtagtcta ttactacaac   3420
agatacccat taaccacaat tatcgggtta tgcacctgtg tggctatcat catggtctct   3480
tgtgtcacat ccgtgtggct cctttgcagg actcgcaatc tttgcataac cccgtataaa   3540
ctagccccga acgctcaagt cccaatactc ctggcgttac tttgctgcat taagccgacg   3600
agggcagatg acaccttgca agtgctgaat tacctgtgga acaacaatca aaactttttc   3660
tggatgcaga cgcttatccc acttgcagcg cttattgtat gcatgcgcat gctgcgctgc   3720
ttattttgct gtgggccggc ttttttactt gtctgcggcg ccttgggcgc cgcagcgtac   3780
gaacacacag cagtgatgcc gaacaaggtg gggatcccgt acaaagcttt agtcgaacgc   3840
ccaggttatg cacccgttca cctacagata cagctggtta ataccaggat aattccatca   3900
actaacctgg agtacatcac ctgcaagtat aagacaaaag tgccttctcc agtagtgaaa   3960
tgctgcggtg ccactcaatg tacctccaaa ccccatcctg actatcagtg tcaggtgttt   4020
acaggtgttt acccattcat gtggggagga gcctactgct tctgcgacac tgaaaacacc   4080
cagatgagcg aggcgtatgt agagcgctcg gaagagtgct ctattgacca cgcaaaagct   4140
tataaagtac acacaggcac tgttcaggca atggtgaaca taacttatgg gagcgtcagc   4200
tggagatctg cagatgttta cgtcaatggt gaaactcccg cgaaaatagg agatgccaaa   4260
ctcatcatag gtccactgtc atctgcgtgg tccccattcg ataacaaggt ggtggttcat   4320
gggcatgaag tgtataatta cgactttcct gagtacggca ccggcaaagc aggctctttt   4380
ggagacctgc aatcacgcac atcaaccagc aacgatctgt acgcaaacac caacttgaag   4440
ctacaacgac cccaggctgg tatcgtgcac acacctttca cccaggcgcc ctccggcttc   4500
gaacgatgga aaagggacaa aggggcaccg ttgaacgacg tagccccgtt tggctgttcg   4560
attgccctgg agccgctccg tgcagaaaat tgtgcagtgg gaagcatccc tatatctata   4620
gatataccccg atgcggcttt taccagaata tctgaaacac cgacagtctc agacctggaa   4680
tgcaaaatta cggagtgtac ttatgcctcc gatttcggtg gtatagccac cgttgcctac   4740
aaatccagta aagcaggaaa ctgtccaatt cattctccat caggtgttgc agttattaaa   4800
gagaatgacg tcactcttgc tgagagcgga tcatttacat tccacttctc cactgcaaac   4860
atccatcctg cttttaagct gcaggtctgc actagtgcag ttacctgcaa aggagattgt   4920
aagccaccga aagaccacat cgtcgattat ccagcacaac atactgaatc ctttacgtcg   4980
gcgatatccg ccactgcgtg gtcgtggcta aaagtgctgg taggaggaac atcagcattt   5040
atcgttctgg ggcttattgc tacagcagtg gttgccctag ttctgttctt ccatagacat   5100
taatctagac caggccctgg atccagatct gctgtgcctt ctagttgcca gccatctgtt   5160
```

-continued

```
gtttgcccct cccccgtgcc ttccttgacc ctggaaggtg ccactcccac tgtcctttcc   5220
taataaaatg aggaaattgc atcgcattgt ctgagtaggt gtcattctat tctggggggt   5280
ggggtggggc aggacagcaa gggggaggat tgggaagaca atagcaggca tgctggggat   5340
gcggtgggct ctatgggtac ccaggtgctg aagaattgac ccggttcctc ctgggccaga   5400
aagaagcagg cacatcccct tctctgtgac acaccctgtc cacgcccctg gttcttagtt   5460
ccagccccac tcataggaca ctcatagctc aggagggctc cgccttcaat cccacccgct   5520
aaagtacttg gagcggtctc tccctccctc atcagcccac caaaccaaac ctagcctcca   5580
agagtgggaa gaaattaaag caagataggc tattaagtgc agagggagag aaaatgcctc   5640
caacatgtga ggaagtaatg agagaaatca tagaatttta aggccatgat ttaaggccat   5700
catggcctta atcttccgct tcctcgctca ctgactcgct gcgctcggtc gttcggctgc   5760
ggcgagcggt atcagctcac tcaaaggcgg taatacggtt atccacagaa tcaggggata   5820
acgcaggaaa gaacatgtga gcaaaaggcc agcaaaaggc caggaaccgt aaaaaggccg   5880
cgttgctggc gtttttccat aggctccgcc cccctgacga gcatcacaaa aatcgacgct   5940
caagtcagag gtggcgaaac ccgacaggac tataaagata ccaggcgttt ccccctggaa   6000
gctccctcgt gcgctctcct gttccgaccc tgccgcttac cggatacctg tccgcctttc   6060
tcccttcggg aagcgtggcg ctttctcata gctcacgctg taggtatctc agttcggtgt   6120
aggtcgttcg ctccaagctg ggctgtgtgc acgaaccccc cgttcagccc gaccgctgcg   6180
ccttatccgg taactatcgt cttgagtcca acccggtaag acacgactta tcgccactgg   6240
cagcagccac tggtaacagg attagcagag cgaggtatgt aggcggtgct acagagttct   6300
tgaagtggtg gcctaactac ggctacacta gaagaacagt atttggtatc tgcgctctgc   6360
tgaagccagt taccttcgga aaaagagttg gtagctcttg atccggcaaa caaaccaccg   6420
ctggtagcgg tggttttttt gtttgcaagc agcagattac gcgcagaaaa aaaggatctc   6480
aagaagatcc tttgatcttt tctacggggt ctgacgctca gtggaacgaa aactcacgtt   6540
aagggatttt ggtcatgaga ttatcaaaaa ggatcttcac ctagatcctt ttaaattaaa   6600
aatgaagttt taaatcaatc taaagtatat atgagtaaac ttggtctgac agttaccaat   6660
gcttaatcag tgaggcacct atctcagcga tctgtctatt tcgttcatcc atagttgcct   6720
gactcggggg gggggggcgc tgaggtctgc ctcgtgaaga aggtgttgct gactcatacc   6780
aggcctgaat cgccccatca tccagccaga aagtgaggga gccacggttg atgagagctt   6840
tgttgtaggt ggaccagttg gtgattttga acttttgctt tgccacggaa cggtctgcgt   6900
tgtcgggaag atgcgtgatc tgatccttca actcagcaaa agttcgattt attcaacaaa   6960
gccgccgtcc cgtcaagtca gcgtaatgct ctgccagtgt tacaaccaat taaccaattc   7020
tgattagaaa aactcatcga gcatcaaatg aaactgcaat ttattcatat caggattatc   7080
aataccatat ttttgaaaaa gccgtttctg taatgaagga gaaaactcac cgaggcagtt   7140
ccataggatg gcaagatcct ggtatcggtc tgcgattccg actcgtccaa catcaataca   7200
acctattaat ttcccctcgt caaaaataag gttatcaagt gagaaatcac catgagtgac   7260
gactgaatcc ggtgagaatg gcaaaagctt atgcatttct ttccagactt gttcaacagg   7320
ccagccatta cgctcgtcat caaaatcact cgcatcaacc aaaccgttat tcattcgtga   7380
ttgcgcctga gcgagacgaa atacgcgatc gctgttaaaa ggacaattac aaacaggaat   7440
cgaatgcaac cggcgcagga acactgccag cgcatcaaca atattttcac ctgaatcagg   7500
atattcttct aatacctgga atgctgtttt cccggggatc gcagtggtga gtaaccatgc   7560
```

-continued

```
atcatcagga gtacggataa aatgcttgat ggtcggaaga ggcataaatt ccgtcagcca   7620

gtttagtctg accatctcat ctgtaacatc attggcaacg ctacctttgc catgtttcag   7680

aaacaactct ggcgcatcgg gcttcccata caatcgatag attgtcgcac ctgattgccc   7740

gacattatcg cgagcccatt tatacccata taaatcagca tccatgttgg aatttaatcg   7800

cggcctcgag caagacgttt cccgttgaat atggctcata acaccccttg tattactgtt   7860

tatgtaagca gacagtttta ttgttcatga tgatatattt ttatcttgtg caatgtaaca   7920

tcagagattt tgagacacaa cgtggctttc cccccccccc cattattgaa gcatttatca   7980

gggttattgt ctcatgagcg gatacatatt tgaatgtatt tagaaaaata aacaaatagg   8040

ggttccgcgc acatttcccc gaaaagtgcc acctgacgtc taagaaacca ttattatcat   8100

gacattaacc tataaaaata ggcgtatcac gaggcccttt cgtc                    8144
```

<210> SEQ ID NO 11
<211> LENGTH: 8156
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctcca tcggctcgca tctctccttc acgcgcccgc   1020

cgccctacct gaggccgcca tccacgccgg ttgagtcgcg ttctgccgcc tcccgcctgt   1080

ggtgcctcct gaactgcgtc cgccgtctag gtaagtttaa agctcaggtc gagaccgggc   1140

ctttgtccgg cgctcccttg gagcctacct agactcagcc ggctctccac gctttgcctg   1200

accctgcttg ctcaactcta gttaacggtg gagggcagtg tagtctgagc agtactcgtt   1260

gctgccgcgc gcgccaccag acataatagc tgacagacta acagactgtt cctttccatg   1320

ggtcttttct gcagtcaccg tcgtcgacac gtgtgatcag atatcgcggc cgccaccatg   1380

aatagaggat tctttaacat gctcggccgc cgccccttcc cggcccccac tgccatgtgg   1440
```

-continued

```
aggccgcgga gaaggaggca ggcggccccg atgcctgccc gcaacgggct ggcttctcaa   1500
atccagcaac tgaccacagc cgtcagtgcc ctagtcattg gacaggcaac tagacctcaa   1560
cccccacgtc cacgcccgcc accgcgccag aagaagcagg cgcccaagca accaccgaag   1620
ccgaagaaac caaaaacgca ggagaagaag aagaagcaac ctgcaaaacc caaacccgga   1680
aagagacagc gcatggcact taagttggag gccgacagat tgttcgacgt caagaacgag   1740
gacggagatg tcatcgggca cgcactggcc atggaaggaa aggtaatgaa acctctgcac   1800
gtgaaaggaa ccatcgacca ccctgtgcta tcaaagctca aatttaccaa gtcgtcagca   1860
tacgacatgg agttcgcaca gttgccagtc aacatgagaa gtgaggcatt cacctacacc   1920
agtgaacacc ccgaaggatt ctataactgg caccacggag cggtgcagta tagtggaggt   1980
agatttacca tccctcgcgg agtaggaggc agaggagaca gcggtcgtcc gatcatggat   2040
aactccggtc gggttgtcgc gatagtcctc ggtggcgctg atgaaggaac acgaactgcc   2100
ctttcggtcg tcacctggaa tagtaaaggg aagacaatta agacgacccc ggaagggaca   2160
gaagagtggt ccgcagcacc actggtcacg gcaatgtgtt tgctcggaaa tgtgagcttc   2220
ccatgcgacc gcccgcccac atgctatacc cgcgaacctt ccagagccct cgacatcctt   2280
gaagagaacg tgaaccatga ggcctacgat accctgctca atgccatatt gcggtgcgga   2340
tcgtctggca gaagcaaaag aagcgtcatt gacgacttta ccctgaccag cccctacttg   2400
ggcacatgct cgtactgcca ccatactgta ccgtgcttca gccctgttaa gatcgagcag   2460
gtctgggacg aagcggacga taacaccata cgcatacaga cttccgccca gtttggatac   2520
gaccaaagcg gagcagcaag cgcaaacaag taccgctaca tgtcgcttaa gcaggatcac   2580
accgttaaag aaggcaccat ggatgacatc aagattagca cctcaggacc gtgtagaagg   2640
cttagctaca aaggatactt tctcctcgca aaatgccctc caggggacag cgtaacggtt   2700
agcatagtga gtagcaactc agcaacgtca tgtacactgg cccgcaagat aaaaccaaaa   2760
ttcgtgggac gggaaaaata tgatctacct cccgttcacg gtaaaaaaat tccttgcaca   2820
gtgtacgacc gtctgaaaga aacaactgca ggctacatca ctatgcacag gccgagaccg   2880
cacgcttata catcctacct ggaagaatca tcagggaaag tttacgcaaa gccgccatct   2940
gggaagaaca ttacgtatga gtgcaagtgc ggcgactaca agaccggaac cgtttcgacc   3000
cgcaccgaaa tcactggttg caccgccatc aagcagtgcg tcgcctataa gagcgaccaa   3060
acgaagtggg tcttcaactc accggacttg atcagacatg acgaccacac ggcccaaggg   3120
aaattgcatt tgcctttcaa gttgatcccg agtacctgca tggtccctgt tgcccacgcg   3180
ccgaatgtaa tacatggctt taaacacatc agcctccaat tagatacaga ccacttgaca   3240
ttgctcacca ccaggagact aggggcaaac ccggaaccaa ccactgaatg gatcgtcgga   3300
aagacggtca gaaacttcac cgtcgaccga gatggcctgg aatacatatg gggaaatcat   3360
gagccagtga gggtctatgc ccaagagtca gcaccaggag accctcacgg atggccacac   3420
gaaatagtac agcattacta ccatcgccat cctgtgtaca ccatcttagc cgtcgcatca   3480
gctaccgtgg cgatgatgat tggcgtaact gttgcagtgt tatgtgcctg taaagcgcgc   3540
cgtgagtgcc tgacgccata cgccctggcc ccaaacgccg taatcccaac ttcgctggca   3600
ctcttgtgct gcgttaggtc ggccaatgct gaaacgttca ccgagaccat gagttacttg   3660
tggtcgaaca gtcagccgtt cttctgggtc cagttgtgca tacctttggc cgctttcatc   3720
gttctaatgc gctgctgctc ctgctgcctg cctttttttag tggttgccgg cgcctacctg   3780
```

-continued

```
gcgaaggtag acgcctacga acatgcgacc actgttccaa atgtgccaca gataccgtat   3840
aaggcacttg ttgaaagggc agggtatgcc ccgctcaatt tggagatcac tgtcatgtcc   3900
tcggaggttt tgccttccac caaccaagag tacattacct gcaaattcac cactgtggtc   3960
ccctccccaa aaatcaaatg ctgcggctcc ttggaatgtc agccggccgc tcatgcagac   4020
tatacctgca aggtcttcgg aggggtctac ccctttatgt ggggaggagc gcaatgtttt   4080
tgcgacagtg agaacagcca gatgagtgag gcgtacgtcg aattgtcagc agattgcgcg   4140
tctgaccacg cgcaggcgat taaggtgcac actgccgcga tgaaagtagg actgcgtatt   4200
gtgtacggga acactaccag tttcctagat gtgtacgtga acggagtcac accaggaacg   4260
tctaaagact tgaaagtcat agctggacca atttcagcat cgtttacgcc attcgatcat   4320
aaggtcgtta tccatcgcgg cctggtgtac aactatgact tcccggaata tggagcgatg   4380
aaaccaggag cgtttggaga cattcaagct acctccttga ctagcaagga tctcatcgcc   4440
agcacagaca ttaggctact caagccttcc gccaagaacg tgcatgtccc gtacacgcag   4500
gcctcatcag gatttgagat gtggaaaaac aactcaggcc gcccactgca ggaaaccgca   4560
cctttcgggt gtaagattgc agtaaatccg ctccgagcgg tggactgttc atacgggaac   4620
attcccattt ctattgacat cccgaacgct gcctttatca ggacatcaga tgcaccactg   4680
gtctcaacag tcaaatgtga agtcagtgag tgcacttatt cagcagactt cggcgggatg   4740
gccaccctgc agtatgtatc cgaccgcgaa ggtcaatgcc ccgtacattc gcattcgagc   4800
acagcaactc tccaagagtc gacagtacat gtcctggaga aaggagcggt gacagtacac   4860
tttagcaccg cgagtccaca ggcgaacttt atcgtatcgc tgtgtgggaa gaagacaaca   4920
tgcaatgcag aatgtaaacc accagctgac catatcgtga gcaccccgca caaaaatgac   4980
caagaatttc aagccgccat ctcaaaaaca tcatggagtt ggctgtttgc ccttttcggc   5040
ggcgcctcgt cgctattaat tataggactt atgatttttg cttgcagcat gatgctgact   5100
agcacacgaa gatgatctag accaggccct ggatccagat ctgctgtgcc ttctagttgc   5160
cagccatctg ttgtttgccc ctcccccgtg ccttccttga ccctggaagg tgccactccc   5220
actgtccttt cctaataaaa tgaggaaatt gcatcgcatt gtctgagtag gtgtcattct   5280
attctggggg gtggggtggg gcaggacagc aagggggagg attgggaaga caatagcagg   5340
catgctgggg atgcggtggg ctctatgggt acccaggtgc tgaagaattg acccggttcc   5400
tcctgggcca gaaagaagca ggcacatccc cttctctgtg acacaccctg tccacgcccc   5460
tggttcttag ttccagcccc actcatagga cactcatagc tcaggagggc tccgccttca   5520
atcccacccg ctaaagtact tggagcggtc tctccctccc tcatcagccc accaaaccaa   5580
acctagcctc caagagtggg aagaaattaa agcaagatag gctattaagt gcagagggag   5640
agaaaatgcc tccaacatgt gaggaagtaa tgagagaaat catagaattt taaggccatg   5700
atttaaggcc atcatggcct taatcttccg cttcctcgct cactgactcg ctgcgctcgg   5760
tcgttcggct gcggcgagcg gtatcagctc actcaaaggc ggtaatacgg ttatccacag   5820
aatcagggga taacgcagga aagaacatgt gagcaaaagg ccagcaaaag gccaggaacc   5880
gtaaaaaggc cgcgttgctg gcgtttttcc ataggctccg cccccctgac gagcatcaca   5940
aaaatcgacg ctcaagtcag aggtggcgaa acccgacagg actataaaga taccaggcgt   6000
ttccccctgg aagctccctc gtgcgctctc ctgttccgac cctgccgctt accggatacc   6060
tgtccgcctt tctcccttcg ggaagcgtgg cgctttctca tagctcacgc tgtaggtatc   6120
tcagttcggt gtaggtcgtt cgctccaagc tgggctgtgt gcacgaaccc cccgttcagc   6180
```

ccgaccgctg cgccttatcc ggtaactatc gtcttgagtc caacccggta agacacgact 6240
tatcgccact ggcagcagcc actggtaaca ggattagcag agcgaggtat gtaggcggtg 6300
ctacagagtt cttgaagtgg tggcctaact acggctacac tagaagaaca gtatttggta 6360
tctgcgctct gctgaagcca gttaccttcg gaaaaagagt tggtagctct tgatccggca 6420
aacaaaccac cgctggtagc ggtggttttt ttgtttgcaa gcagcagatt acgcgcagaa 6480
aaaaaggatc tcaagaagat cctttgatct tttctacggg gtctgacgct cagtggaacg 6540
aaaactcacg ttaagggatt ttggtcatga gattatcaaa aaggatcttc acctagatcc 6600
ttttaaatta aaaatgaagt tttaaatcaa tctaaagtat atatgagtaa acttggtctg 6660
acagttacca atgcttaatc agtgaggcac ctatctcagc gatctgtcta tttcgttcat 6720
ccatagttgc ctgactcggg gggggggggc gctgaggtct gcctcgtgaa gaaggtgttg 6780
ctgactcata ccaggcctga atcgccccat catccagcca gaaagtgagg gagccacggt 6840
tgatgagagc tttgttgtag gtggaccagt tggtgatttt gaacttttgc tttgccacgg 6900
aacggtctgc gttgtcggga agatgcgtga tctgatcctt caactcagca aaagttcgat 6960
ttattcaaca aagccgccgt cccgtcaagt cagcgtaatg ctctgccagt gttacaacca 7020
attaaccaat tctgattaga aaaactcatc gagcatcaaa tgaaactgca atttattcat 7080
atcaggatta tcaataccat atttttgaaa aagccgtttc tgtaatgaag gagaaaactc 7140
accgaggcag ttccatagga tggcaagatc ctggtatcgg tctgcgattc cgactcgtcc 7200
aacatcaata caacctatta atttcccctc gtcaaaaata aggttatcaa gtgagaaatc 7260
accatgagtg acgactgaat ccggtgagaa tggcaaaagc ttatgcattt ctttccagac 7320
ttgttcaaca ggccagccat tacgctcgtc atcaaaatca ctcgcatcaa ccaaaccgtt 7380
attcattcgt gattgcgcct gagcgagacg aaatacgcga tcgctgttaa aaggacaatt 7440
acaaacagga atcgaatgca accggcgcag gaacactgcc agcgcatcaa caatattttc 7500
acctgaatca ggatattctt ctaatacctg gaatgctgtt ttcccgggga tcgcagtggt 7560
gagtaaccat gcatcatcag gagtacggat aaaatgcttg atggtcggaa gaggcataaa 7620
ttccgtcagc cagtttagtc tgaccatctc atctgtaaca tcattggcaa cgctaccttt 7680
gccatgtttc agaaacaact ctggcgcatc gggcttccca tacaatcgat agattgtcgc 7740
acctgattgc ccgacattat cgcgagccca tttataccca tataaatcag catccatgtt 7800
ggaatttaat cgcggcctcg agcaagacgt ttcccgttga atatggctca taacacccct 7860
tgtattactg tttatgtaag cagacagttt tattgttcat gatgatatat ttttatcttg 7920
tgcaatgtaa catcagagat tttgagacac aacgtggctt tccccccccc cccattattg 7980
aagcatttat cagggttatt gtctcatgag cggatacata tttgaatgta tttagaaaaa 8040
taaacaaata ggggttccgc gcacatttcc ccgaaaagtg ccacctgacg tctaagaaac 8100
cattattatc atgacattaa cctataaaaa taggcgtatc acgaggccct ttcgtc 8156

<210> SEQ ID NO 12
<211> LENGTH: 8180
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacac gtgtgatcag atatcgcggc cgccaccatg 1380
aattacatcc ctacgcaaac gttttacggc cgccggtggc gcccgcgccc ggcggcccgt 1440
ccttggccgt tgcaggccac tccggtggct cccgtcgtcc ccgacttcca ggcccagcag 1500
atgcagcaac tcatcagcgc cgtaaatgcg ctgacaatga gacagaacgc aattgctcct 1560
gctaggcctc ccaaaccaaa gaagaagaag acaaccaaac caaagccgaa aacgcagccc 1620
aagaagatca acggaaaaac gcagcagcaa aagaagaaag acaagcaagc cgacaagaag 1680
aagaagaaac ccggaaaaag agaaagaatg tgcatgaaga ttgaaaatga ctgtatcttc 1740
gaagtcaaac acgaaggaaa ggtcactggg tacgcctgcc tggtgggcga caaagtcatg 1800
aaacctgccc acgtgaaagg agtcatcgac aacgcggacc tggcaaagct agctttcaag 1860
aaatcgagca agtatgacct tgagtgtgcc cagataccag ttcacatgag gtcggatgcc 1920
tcaaagtaca cgcatgagaa gcccgaggga cactataact ggcaccacgg ggctgttcag 1980
tacagcggag gtaggttcac tataccgaca ggagcgggca aaccgggaga cagtggccgg 2040
cccatctttg acaacaaggg gagggtagtc gctatcgtcc tgggcggggc caacgagggc 2100
tcacgcacag cactgtcggt ggtcacctgg aacaaagata tggtgactag agtgaccccc 2160
gaggggtccg aagagtggtc cgccccgctg attactgcca tgtgtgtcct tgccaatgct 2220
accttcccgt gcttccagcc cccgtgtgta ccttgctgct atgaaaacaa cgcagaggcc 2280
acactacgga tgctcgagga taacgtggat aggccagggt actacgacct ccttcaggca 2340
gccttgacgt gccgaaacgg aacaagacac cggcgcagcg tgtcgcaaca cttcaacgtg 2400

-continued

```
tataaggcta cacgccctta catcgcgtac tgcgccgact gcggagcagg gcactcgtgt   2460
catagccccg tagcaattga agcggtcagg tccgaagcta ccgacgggat gctgaagatt   2520
cagttctcgg cacaaattgg catagataag agtgacaatc atgactacac gaagataagg   2580
tacgcagacg ggcacgccat tgagaatgcc gtccggtcat ctttgaaggt agccacctcc   2640
ggagactgtt tcgtccatgg cacaatggga catttcatac tggcaaagtg cccaccgggt   2700
gaattcctgc aggtctcgat ccaggacacc agaaacgcgg tccgtgcctg cagaatacaa   2760
tatcatcatg accctcaacc ggtgggtaga gaaaaattta caattagacc acactatgga   2820
aaagagatcc cttgcaccac ttatcaacag accacagcgg agaccgtgga ggaaatcgac   2880
atgcatatgc cgccagatac gccggacagg acgttgctat cacagcaatc tggcaatgta   2940
aagatcacag tcggaggaaa gaaggtgaaa tacaactgca cctgtggaac cggaaacgtt   3000
ggcactacta attcggacat gacgatcaac acgtgtctaa tagagcagtg ccacgtctca   3060
gtgacggacc ataagaaatg gcagttcaac tcacctttcg tcccgagagc cgacgaaccg   3120
gctagaaaag gcaaagtcca tatcccattc ccgttggaca acatcacatg cagagttcca   3180
atggcgcgcg aaccaaccgt catccacggc aaaagagaag tgacactgca ccttcaccca   3240
gatcatccca cgctcttttc ctaccgcaca ctgggtgagg acccgcagta tcacgaggaa   3300
tgggtgacag cggcggtgga acggaccata cccgtaccag tggacgggat ggagtaccac   3360
tggggaaaca acgacccagt gaggctttgg tctcaactca ccactgaagg gaaaccgcac   3420
ggctggccgc atcagatcgt acagtactac tatgggcttt acccggccgc tacagtatcc   3480
gcggtcgtcg ggatgagctt actggcgttg atatcgatct tcgcgtcgtg ctacatgctg   3540
gttgcggccc gcagtaagtg cttgacccct tatgctttaa caccaggagc tgcagttccg   3600
tggacgctgg ggatactctg ctgcgccccg cgggcgcacg cagctagtgt ggcagagact   3660
atggcctact tgtgggacca aaaccaagcg ttgttctggt tggagtttgc ggcccctgtt   3720
gcctgcatcc tcatcatcac gtattgcctc agaaacgtgc tgtgttgctg taagagcctt   3780
tctttttag tgctactgag cctcggggca accgccagag cttacgaaca ttcgacagta   3840
atgccgaacg tggtggggtt cccgtataag gctcacattg aaaggccagg atatagcccc   3900
ctcactttgc agatgcaggt tgttgaaacc agcctcgaac caacccttaa tttggaatac   3960
ataacctgtg agtacaagac ggtcgtcccg tcgccgtacg tgaagtgctg cggcgcctca   4020
gagtgctcca ctaaagagaa gcctgactac caatgcaagg tttacacagg cgtgtacccg   4080
ttcatgtggg gaggggcata ttgcttctgc gactcagaaa acacgcaact cagcgaggcg   4140
tacgtcgatc gatcggacgt atgcaggcat gatcacgcat ctgcttacaa agcccataca   4200
gcatcgctga aggccaaagt gagggttatg tacggcaacg taaaccagac tgtggatgtt   4260
tacgtgaacg gagaccatgc cgtcacgata gggggtactc agttcatatt cgggccgctg   4320
tcatcggcct ggaccccgtt cgacaacaag atagtcgtgt acaaagacga agtgttcaat   4380
caggacttcc cgccgtacgg atctgggcaa ccagggcgct tcggcgacat ccaaagcaga   4440
acagtggaga gtaacgacct gtacgcgaac acggcactga agctggcacg cccttcaccc   4500
ggcatggtcc atgtaccgta cacacagaca ccttcagggt tcaaatattg gctaaaggaa   4560
aaagggacag ccctaaatac gaaggctcct tttggctgcc aaatcaaaac gaaccctgtc   4620
agggccatga actgcgccgt gggaaacatc cctgtctcca tgaatttgcc tgacagcgcc   4680
tttacccgca ttgtcgaggc gccgaccatc attgacctga cttgcacagt ggctacctgt   4740
acgcactcct cggatttcgg cggcgtcttg acactgacgt acaagaccaa caagaacggg   4800
```

-continued gactgctctg tacactcgca ctctaacgta gctactctac aggaggccac agcaaaagtg 4860
aagacagcag gtaaggtgac cttacacttc tccacggcaa gcgcatcacc ttcttttgtg 4920
gtgtcgctat gcagtgctag ggccacctgt tcagcgtcgt gtgagccccc gaaagaccac 4980
atagtcccat atgcggctag ccacagtaac gtagtgtttc cagacatgtc gggcaccgca 5040
ctatcatggg tgcagaaaat ctcgggtggt ctgggggcct tcgcaatcgg cgctatcctg 5100
gtgctggttg tggtcacttg cattgggctc cgcagataat ctagaccagg ccctggatcc 5160
agatctgctg tgccttctag ttgccagcca tctgttgttt gcccctcccc cgtgccttcc 5220
ttgaccctgg aaggtgccac tcccactgtc ctttcctaat aaaatgagga aattgcatcg 5280
cattgtctga gtaggtgtca ttctattctg gggggtgggg tggggcagga cagcaagggg 5340
gaggattggg aagacaatag caggcatgct ggggatgcgg tgggctctat gggtacccag 5400
gtgctgaaga attgacccgg ttcctcctgg gccagaaaga agcaggcaca tccccttctc 5460
tgtgacacac cctgtccacg cccctggttc ttagttccag ccccactcat aggacactca 5520
tagctcagga gggctccgcc ttcaatccca cccgctaaag tacttggagc ggtctctccc 5580
tccctcatca gcccaccaaa ccaaacctag cctccaagag tgggaagaaa ttaaagcaag 5640
ataggctatt aagtgcagag ggagagaaaa tgcctccaac atgtgaggaa gtaatgagag 5700
aaatcataga attttaaggc catgatttaa ggccatcatg gccttaatct tccgcttcct 5760
cgctcactga ctcgctgcgc tcggtcgttc ggctgcggcg agcggtatca gctcactcaa 5820
aggcggtaat acggttatcc acagaatcag gggataacgc aggaaagaac atgtgagcaa 5880
aaggccagca aaaggccagg aaccgtaaaa aggccgcgtt gctggcgttt ttccataggc 5940
tccgcccccc tgacgagcat cacaaaaatc gacgctcaag tcagaggtgg cgaaacccga 6000
caggactata aagataccag gcgtttcccc ctggaagctc cctcgtgcgc tctcctgttc 6060
cgaccctgcc gcttaccgga tacctgtccg cctttctccc ttcgggaagc gtggcgcttt 6120
ctcatagctc acgctgtagg tatctcagtt cggtgtaggt cgttcgctcc aagctgggct 6180
gtgtgcacga accccccgtt cagcccgacc gctgcgcctt atccggtaac tatcgtcttg 6240
agtccaaccc ggtaagacac gacttatcgc cactggcagc agccactggt aacaggatta 6300
gcagagcgag gtatgtaggc ggtgctacag agttcttgaa gtggtggcct aactacggct 6360
acactagaag aacagtattt ggtatctgcg ctctgctgaa gccagttacc ttcggaaaaa 6420
gagttggtag ctcttgatcc ggcaaacaaa ccaccgctgg tagcggtggt ttttttgttt 6480
gcaagcagca gattacgcgc agaaaaaaag gatctcaaga agatcctttg atcttttcta 6540
cggggtctga cgctcagtgg aacgaaaact cacgttaagg gattttggtc atgagattat 6600
caaaaaggat cttcacctag atccttttaa attaaaaatg aagttttaaa tcaatctaaa 6660
gtatatatga gtaaacttgg tctgacagtt accaatgctt aatcagtgag gcacctatct 6720
cagcgatctg tctatttcgt tcatccatag ttgcctgact cggggggggg gggcgctgag 6780
gtctgcctcg tgaagaaggt gttgctgact cataccaggc ctgaatcgcc ccatcatcca 6840
gccagaaagt gagggagcca cggttgatga gagctttgtt gtaggtggac cagttggtga 6900
ttttgaactt ttgctttgcc acggaacggt ctgcgttgtc gggaagatgc gtgatctgat 6960
ccttcaactc agcaaaagtt cgatttattc aacaaagccg ccgtcccgtc aagtcagcgt 7020
aatgctctgc cagtgttaca accaattaac caattctgat tagaaaaact catcgagcat 7080
caaatgaaac tgcaatttat tcatatcagg attatcaata ccatattttt gaaaaagccg 7140
tttctgtaat gaaggagaaa actcaccgag gcagttccat aggatggcaa gatcctggta 7200
tcggtctgcg attccgactc gtccaacatc aatacaacct attaatttcc cctcgtcaaa 7260
aataaggtta tcaagtgaga aatcaccatg agtgacgact gaatccggtg agaatggcaa 7320
aagcttatgc atttctttcc agacttgttc aacaggccag ccattacgct cgtcatcaaa 7380
atcactcgca tcaaccaaac cgttattcat tcgtgattgc gcctgagcga gacgaaatac 7440
gcgatcgctg ttaaaaggac aattacaaac aggaatcgaa tgcaaccggc gcaggaacac 7500
tgccagcgca tcaacaatat tttcacctga atcaggatat tcttctaata cctggaatgc 7560
tgttttcccg gggatcgcag tggtgagtaa ccatgcatca tcaggagtac ggataaaatg 7620
cttgatggtc ggaagaggca taaattccgt cagccagttt agtctgacca tctcatctgt 7680
aacatcattg gcaacgctac ctttgccatg tttcagaaac aactctggcg catcgggctt 7740
cccatacaat cgatagattg tcgcacctga ttgcccgaca ttatcgcgag cccatttata 7800
cccatataaa tcagcatcca tgttggaatt taatcgcggc ctcgagcaag acgtttcccg 7860
ttgaatatgg ctcataacac cccttgtatt actgtttatg taagcagaca gttttattgt 7920
tcatgatgat atatttttat cttgtgcaat gtaacatcag agattttgag acacaacgtg 7980
gctttccccc cccccccatt attgaagcat ttatcagggt tattgtctca tgagcggata 8040
catatttgaa tgtatttaga aaaataaaca aataggggtt ccgcgcacat ttccccgaaa 8100
agtgccacct gacgtctaag aaaccattat tatcatgaca ttaacctata aaaataggcg 8160
tatcacgagg ccctttcgtc 8180

<210> SEQ ID NO 13
<211> LENGTH: 8377
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960

-continued

```
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgcatgtttc   1380
ccatgcaatt caccaactca gcctatcgcc agatggagcc catgtttgca ccgggttccc   1440
gaggacaagt acagccgtac cggccgcgca ctaagcgccg ccaggagccg caagtcggca   1500
acgccgccat tactgccctc gcgaaccaga tgagtgcgct ccagttgcag gtagctggac   1560
ttgccggcca ggcaagggtg gaccgccgtg ggccaagacg tgttcagaag aacaagcaga   1620
agaagaagaa ctcttccaac ggagaaaaac ccaaagagaa gaagaagaag caaaaacaac   1680
aggagaagaa gggaagcggt ggcgaaaaag tcaagaagac taggaaccga cccgggaagg   1740
aggtaaggat ctccgtaaag tgtgcccgac agagcacctt ccccgtgtac cacgaaggtg   1800
ctatatccgg ctacgctgtg ctgattggat ctcgcgtatt caagccggca cacgtgaagg   1860
gtaagatcga ccaccctgaa ctggcagaca tcaagttcca ggtcgccgag gacatggacc   1920
tcgaagcagc tgcgtacccg aagagcatgc gagaccaagc ggctgaacca gcgaccatga   1980
tggacagagt gtacaactgg gagtatggca ctatcagagt ggaggataat gtcataatcg   2040
acgcaagcgg taggggcaag ccgggtgaca gtggcagggc catcaccgac aactcgggaa   2100
aggttgttgg tattgtcctc ggaggaggac ccgatggcag gcgcacacgc ctctccgtga   2160
taggtttcga caagaagatg aaggctaggg agatcgccta cagtgatgcc ataccttgga   2220
cacgcgctcc ggccctcctg ctgctgccta tggttattgt ctgcacctac aattccaaca   2280
ccttcgattg ctccaaaccg tcctgccagg actgctgcat tactgctgaa ccagagaagg   2340
ccatgaccat gctgaaggac aatctgaacg acccgaacta ctgggaccta ctcattgctg   2400
tcaccacctg tggctccgcc cggagaaaga gggctgtgtc tacgtcgcct gccgcctttt   2460
acgacacaca gatcctcgcc gcccacgcag ctgcctcccc atacagggcg tactgccccg   2520
attgtgacgg aacagcgtgt atctcgccga tagccatcga cgaggtggtg agcagtggca   2580
gcgaccacgt cctccgcatg cgggttggtt ctcaatcggg agtgaccgct aagggtggtg   2640
cggcgggtga aacctctctg cgatacctgg gaagggacgg gaaggttcac gccgcagaca   2700
acacgcgact cgtggtgcgc acgactgcaa agtgcgacgt gctgcaggcc actggccact   2760
acatcctggc caactgccca gtggggcaga gcctaaccgt tgcggccaca ctggatggca   2820
cccggcatca atgcaccacg gttttcgaac accaagtaac ggagaagttc accagagaac   2880
gcagcaaggg ccaccatctg tccgacatga ccaagaaatg caccagattt tccactacac   2940
caaaaaagtc cgccctctac ctcgttgatg tgtatgacgc tctgccgatt tctgtagaga   3000
ttagcaccgt cgtaacatgc agcgacagcc agtgcacagt gagggtgcca cctggtacca   3060
cagtgaaatt cgacaagaaa tgcaagagcg ctgactcggc aaccgtcact ttcaccagcg   3120
actcccagac gtttacgtgt gaggagccag tcctaacggc tgccagtatc acccagggca   3180
agccacacct cagatcggca atgttgccta gcggaggcaa ggaagtgaaa gcaaggatcc   3240
cgttcccgtt cccgccggaa accgcaactt gcagagtgag tgtagcccca ctgccgtcga   3300
tcacctacga ggaaagcgat gtcctgctag ccggtaccgc aaaataccct gtgctgctaa   3360
```

-continued

```
ccacacggaa ccttggtttc catagcaacg ccacatccga atggatccag ggcaagtacc   3420
tgcgccgcat cccggtcacg cctcaaggga tcgagctaac atggggaaac aacgcgccga   3480
tgcacttttg gtcatccgtc aggtacgcat ccggggacgc tgatgcgtac ccctgggaac   3540
ttctggtgta ccacaccaag caccatccag agtacgcgtg ggcgtttgta ggagttgcat   3600
gcggcctgct ggctatcgca gcgtgcatgt ttgcgtgcgc atgcagcagg gtgcggtact   3660
ctctggtcgc caacacgttc aactcgaacc caccaccatt gaccgcactg actgcagcac   3720
tgtgttgcat accaggggct cgcgcggacc aaccctactt ggacatcatt gcctacttgt   3780
ggaccaacag caaagtggcc ttcgggctac aatttgcggc gcccgtggcc tgtgtgctca   3840
tcattacata cgcccttagg cactgcagat tgtgctgcaa gtctttttta ggggtaagag   3900
ggtggtcagc cctgctggtc atccttgcgt atgtacagag ctgcaagagc tacgaacaca   3960
ccgtggtggt cccaatggat ccaagagccc cgtcgtacga agcagtgata aaccggaatg   4020
ggtatgatcc attgaagctg accatctcag tgaatttcac cgtcatctca ccaactacgg   4080
ctctggaata ttggacctgc gcaggagtcc ccatcgtcga gccgccccat gtgggctgct   4140
gcacgtcggt gtcctgcccc tctgacctct ctacgctgca tgcgtttact ggcaaagctg   4200
tctccgacgt gcactgcgat gtgcacacaa acgtgtaccc cttgttgtgg ggcgcggctc   4260
actgcttctg ttccaccgag aatacacagg tcagcgctgt ggcagccacc gtttctgagt   4320
tctgtgccca ggactcagag cgtgccgaag cgttcagcgt acacagcagc tcagtcaccg   4380
ctgaggtcct ggtgacgctt ggtgaagtgg tgacggcagt ccacgtttac gtggacgggg   4440
taacatcagc caggggcact gacctcaaga tcgtggctgg accaataaca accgactact   4500
ccccattcga tcgcaaagta gtccgcatcg gcgaagaggt ctataactat gactggcctc   4560
cttacggggc tggccgacca ggcacattcg gagacattca agctaggtca accaactatg   4620
tcaaacccaa cgatctgtat ggggacatcg gaattgaagt actgcagccg actaacgacc   4680
acgtacatgt ggcttacacg tatacgacct ctgggttact gcgttggctg caggacgctc   4740
cgaaaccact cagtgtcaca gcaccgcacg gttgtaagat cagtgccaat ccgctcctgg   4800
ccctcgattg tggggttggt gccgtcccca tgtccatcaa cattccggac gcgaagttta   4860
cccgcaaatt aaaggatccg aaaccatcgg ccctgaaatg cgtggtggac agctgcgagt   4920
acggggtgga ctacgggggc gccgccacga tcacctacga gggccacgag gccgggaagt   4980
gcgggattca ttccctgaca ccaggagtcc ccctgagaac atcggtggtt gaagtggttg   5040
ctggcgccaa taccgtcaaa acgaccttct cctcacccac gcccgaggtt gcactcgagg   5100
tagagatctg ttcggcaata gtgaagtgcg ctggtgagtg cactccaccg aaggaacatg   5160
tggtcgcaac caggcctcgc catggcagcg accctggagg ctacatctcc gggcccgcaa   5220
tgcgctgggc cggagggatt gtagggaccc tagtggtcct gttccttatc cttgccgtca   5280
tctactgcgt ggtgaagaag tgccgctcca aaagaatccg gatagtcaag agctaatcta   5340
gaccaggccc tggatccaga tctgctgtgc cttctagttg ccagccatct gttgtttgcc   5400
cctcccccgt gccttccttg accctggaag gtgccactcc cactgtcctt tcctaataaa   5460
atgaggaaat tgcatcgcat tgtctgagta ggtgtcattc tattctgggg ggtggggtgg   5520
ggcaggacag caagggggag gattgggaag acaatagcag gcatgctggg gatgcggtgg   5580
gctctatggg tacccaggtg ctgaagaatt gacccggttc ctcctgggcc agaaagaagc   5640
aggcacatcc ccttctctgt gacacaccct gtccacgccc ctggttctta gttccagccc   5700
```

-continued

```
cactcatagg acactcatag ctcaggaggg ctccgccttc aatcccaccc gctaaagtac   5760
ttggagcggt ctctccctcc ctcatcagcc caccaaacca aacctagcct ccaagagtgg   5820
gaagaaatta aagcaagata ggctattaag tgcagaggga gagaaaatgc ctccaacatg   5880
tgaggaagta atgagagaaa tcatagaatt ttaaggccat gatttaaggc catcatggcc   5940
ttaatcttcc gcttcctcgc tcactgactc gctgcgctcg gtcgttcggc tgcggcgagc   6000
ggtatcagct cactcaaagg cggtaatacg gttatccaca gaatcagggg ataacgcagg   6060
aaagaacatg tgagcaaaag gccagcaaaa ggccaggaac cgtaaaaagg ccgcgttgct   6120
ggcgtttttc cataggctcc gcccccctga cgagcatcac aaaaatcgac gctcaagtca   6180
gaggtggcga aacccgacag gactataaag ataccaggcg tttccccctg gaagctccct   6240
cgtgcgctct cctgttccga ccctgccgct taccggatac ctgtccgcct ttctcccttc   6300
gggaagcgtg gcgctttctc atagctcacg ctgtaggtat ctcagttcgg tgtaggtcgt   6360
tcgctccaag ctgggctgtg tgcacgaacc ccccgttcag cccgaccgct gcgccttatc   6420
cggtaactat cgtcttgagt ccaacccggt aagacacgac ttatcgccac tggcagcagc   6480
cactggtaac aggattagca gagcgaggta tgtaggcggt gctacagagt tcttgaagtg   6540
gtggcctaac tacggctaca ctagaagaac agtatttggt atctgcgctc tgctgaagcc   6600
agttaccttc ggaaaaagag ttggtagctc ttgatccggc aaacaaacca ccgctggtag   6660
cggtggtttt tttgtttgca agcagcagat tacgcgcaga aaaaaaggat ctcaagaaga   6720
tcctttgatc ttttctacgg ggtctgacgc tcagtggaac gaaaactcac gttaagggat   6780
tttggtcatg agattatcaa aaaggatctt cacctagatc cttttaaatt aaaaatgaag   6840
ttttaaatca atctaaagta tatatgagta aacttggtct gacagttacc aatgcttaat   6900
cagtgaggca cctatctcag cgatctgtct atttcgttca tccatagttg cctgactcgg   6960
gggggggggg cgctgaggtc tgcctcgtga agaaggtgtt gctgactcat accaggcctg   7020
aatcgcccca tcatccagcc agaaagtgag ggagccacgg ttgatgagag ctttgttgta   7080
ggtggaccag ttggtgattt tgaacttttg ctttgccacg gaacggtctg cgttgtcggg   7140
aagatgcgtg atctgatcct tcaactcagc aaaagttcga tttattcaac aaagccgccg   7200
tcccgtcaag tcagcgtaat gctctgccag tgttacaacc aattaaccaa ttctgattag   7260
aaaaactcat cgagcatcaa atgaaactgc aatttattca tatcaggatt atcaatacca   7320
tatttttgaa aaagccgttt ctgtaatgaa ggagaaaact caccgaggca gttccatagg   7380
atggcaagat cctggtatcg gtctgcgatt ccgactcgtc caacatcaat acaacctatt   7440
aatttcccct cgtcaaaaat aaggttatca agtgagaaat caccatgagt gacgactgaa   7500
tccggtgaga atggcaaaag cttatgcatt tctttccaga cttgttcaac aggccagcca   7560
ttacgctcgt catcaaaatc actcgcatca accaaaccgt tattcattcg tgattgcgcc   7620
tgagcgagac gaaatacgcg atcgctgtta aaaggacaat tacaaacagg aatcgaatgc   7680
aaccggcgca ggaacactgc cagcgcatca acaatatttt cacctgaatc aggatattct   7740
tctaatacct ggaatgctgt tttcccgggg atcgcagtgg tgagtaacca tgcatcatca   7800
ggagtacgga taaaatgctt gatggtcgga agaggcataa attccgtcag ccagtttagt   7860
ctgaccatct catctgtaac atcattggca acgctacctt tgccatgttt cagaaacaac   7920
tctggcgcat cgggcttccc atacaatcga tagattgtcg cacctgattg cccgacatta   7980
tcgcgagccc atttataccc atataaatca gcatccatgt tggaatttaa tcgcggcctc   8040
gagcaagacg tttcccgttg aatatggctc ataacacccc ttgtattact gtttatgtaa   8100
```

gcagacagtt ttattgttca tgatgatata tttttatctt gtgcaatgta acatcagaga 8160
ttttgagaca caacgtggct ttcccccccc ccccattatt gaagcattta tcagggttat 8220
tgtctcatga gcggatacat atttgaatgt atttagaaaa ataaacaaat aggggttccg 8280
cgcacatttc cccgaaaagt gccacctgac gtctaagaaa ccattattat catgacatta 8340
acctataaaa ataggcgtat cacgaggccc tttcgtc 8377

<210> SEQ ID NO 14
<211> LENGTH: 8179
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1645)..(1646)
<223> OTHER INFORMATION: a, c, t, g, unknown or other
<220> FEATURE:
<221> NAME/KEY: modified_base
<222> LOCATION: (1993)..(1994)
<223> OTHER INFORMATION: a, c, t, g, unknown or other
<220> FEATURE:
<221> NAME/KEY: modified_base
<222> LOCATION: (2072)..(2072)
<223> OTHER INFORMATION: a, c, t, g, unknown or other
<220> FEATURE:
<221> NAME/KEY: modified_base
<222> LOCATION: (2426)..(2427)
<223> OTHER INFORMATION: a, c, t, g, unknown or other
<220> FEATURE:
<221> NAME/KEY: modified_base
<222> LOCATION: (2713)..(2713)
<223> OTHER INFORMATION: a, c, t, g, unknown or other
<220> FEATURE:
<221> NAME/KEY: modified_base
<222> LOCATION: (3081)..(3081)
<223> OTHER INFORMATION: a, c, t, g, unknown or other
<220> FEATURE:
<221> NAME/KEY: modified_base
<222> LOCATION: (3253)..(3253)
<223> OTHER INFORMATION: a, c, t, g, unknown or other
<220> FEATURE:
<221> NAME/KEY: modified_base
<222> LOCATION: (3618)..(3620)
<223> OTHER INFORMATION: a, c, t, g, unknown or other
<220> FEATURE:
<221> NAME/KEY: modified_base
<222> LOCATION: (3706)..(3722)
<223> OTHER INFORMATION: a, c, t, g, unknown or other
<220> FEATURE:
<221> NAME/KEY: modified_base
<222> LOCATION: (3888)..(3890)
<223> OTHER INFORMATION: a, c, t, g, unknown or other
<220> FEATURE:
<221> NAME/KEY: modified_base
<222> LOCATION: (3926)..(3927)
<223> OTHER INFORMATION: a, c, t, g, unknown or other
<220> FEATURE:
<221> NAME/KEY: modified_base
<222> LOCATION: (4415)..(4415)
<223> OTHER INFORMATION: a, c, t, g, unknown or other
<220> FEATURE:
<221> NAME/KEY: modified_base
<222> LOCATION: (4761)..(4763)
<223> OTHER INFORMATION: a, c, t, g, unknown or other
<220> FEATURE:
<221> NAME/KEY: modified_base
<222> LOCATION: (4893)..(4897)
<223> OTHER INFORMATION: a, c, t, g, unknown or other

<400> SEQUENCE: 14
tcgcgcgttt cggtgatgac ggtgaaaacc tctgacacat gcagctcccg gagacggtca 60

```
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgcatgaatt   1380
acataccaac ccagactttt tacggacgcc gttggcggcc tcgcccggcg ttccgtccat   1440
ggcaggtgcc gatgcagccg acacctacta tggttacacc catgctgcaa gcaccggacc   1500
tacaggctca acagatgcaa caactgatca gcgcagtctc tgcactaacc accaaacaga   1560
atgtaaaagc accaaaaggg caacggaaac agaaacagca gaaaccaaag gaaaagaagg   1620
aaaaacagaa gaaaaagccg acgcnnaaga agaagcagca gcagaaacca aaaccacagg   1680
ctaagaagaa gaaaccaggg agaagagaaa gaatgtgcat gaagatcgag aatgactgca   1740
tattcgaggt caaactggac ggcaaggtta ccggctatgc gtgcctagtc ggagataagg   1800
tcatgaagcc ggctcacgtt aaaggcacaa ttgataaccc agaccttgcg aagttgactt   1860
acaagaaatc cagtaagtat gacctcgaat gcgcccagat cccagtgcac atgaagtccg   1920
acgcctccaa gtacacacat gaaaagcccg aaggtcatta caattggcac catggagcag   1980
tgcagtacag cgnnggaagg tttaccatcc ccacaggcgc cggcaaacca ggagatagcg   2040
gtaggcctat ttttgacaac aaagggcgag tngtggccat cgtgttaggc ggggccaacg   2100
aaggtgcccg cactgcgctg tctgtggtga cgtggacaaa agacatggtc actcgggtaa   2160
cgccagaagg aaccgaagag tggtctgccg cgctgatgat gtgtatcctt gccaacacct   2220
ctttcccatg ctcgtcacct ccctgctacc cctgctgcta cgaaaaacag ccagaacaga   2280
cactgcggat gctggaagac aacgtgaata gacctgggta ctatgagtta ctggaagcgt   2340
ccatgacatg cagaaacaga tcacgccacc gccgcagtgt aatagagcac ttcaatgtgt   2400
```

-continued

```
ataaggctac tagaccgtac ttagcnnact gcgctgactg cggggacggg tacttctgct   2460
atagcccggt tgctatcgag aagatccgag atgaggcgtc tgatggcatg ctcaagatcc   2520
aagtctccgc ccaaataggt ctggacaagg caggtaccca cgcccacacg aagatgcgat   2580
atatggctgg tcatgatgtt caggaatcta agagagattc cttgagggtg tatacgtccg   2640
cagcgtgctc tatacatggg acgatgggac acttcatcgt cgcacactgt ccaccaggcg   2700
actacctcaa ggnttcgttc gaggacgcaa attcacacgt gaaggcatgt aaggtccaat   2760
acaagcacga cccattgccg gtgggtagag agaagtttgt ggttagacca cactttggcg   2820
tagagctgcc atgcacctca taccagctga caacggctcc caccgacgag gagattgaca   2880
tgcatacacc gccagatata ccggatcgca ccctgctatc acagacggcg ggcaacgtca   2940
aaataacagc aggcggcagg actatcaggt acaattgtac ctgcggccgt gacaacgtag   3000
gcactaccag tactgacaag accatcaaca catgcaagat agaccaatgc catgctgccg   3060
ttaccagcca tgacaaatgg naatttacct ctccatttgt tcccagggct gatcagacag   3120
ccaggaaagg caaagtgcat gttccattcc ctttgactaa cgtcacctgc cgagtgccgt   3180
tggcacgagc gccggatgtc acctatggta agaaggaggt gaccctaaga ttacacccag   3240
atcatccgac gcncttctcc tataggagtt taggagccgt accgcacccg tacgaggaat   3300
gggttgacaa gttctctgag cgcatcatcc cagtgacgga agaagggatt gagtaccagt   3360
ggggtaacaa cccgccggtc cgcctgtggg cgcaactgac gactgagggt aaacccccatg   3420
gctggccaca tgaaatcatt cagtactatt atggactata ccccgccgcc actattgccg   3480
cagtatccgg ggcgagtctg atggccctcc taactctagc ggccacatgc tgcatgctgg   3540
ccaccgcgag gagaaagtgc ctaacaccgt acgctttgac gccaggagcg gtggtaccgt   3600
tgacattggg gctgcttnnn tgcgcaccga gggcgaacgc agcatcattt gctgagacta   3660
tggcctatct gtgggacgag aacaaaaccc tcttttggat ggaatnnnnn nnnnnnnnnn   3720
nngcgcttgc tttgctggca tgctgtatca aaagcctgat ctgctgttgt aagccatttt   3780
ctttttttagt gttactgagc ctgggagcct ccgcaaaagc ttatgagcac acagccacaa   3840
ttccgaacgt ggtggggttc ccgtataagg ctcacattga aaggaatnnn ttctcgccca   3900
tgactctgca gcttgaagtg gtgganncaa gcttggaacc cacacttaac ctggagtaca   3960
ttacctgcga atacaagacg gtggtccctt cgccatttat caaatgttgc ggaacatcag   4020
aatgctcatc taaagagcag ccagactacc aatgcaaggt gtacacgggt gtataccctt   4080
tcatgtgggg tggagcttac tgtttctgcg actccgagaa cacgcagctt agcgaggcct   4140
atgtcgacag gtcagacgtt tgcaaacatg atcatgcatt ggcctacaag gcacacacgg   4200
cctctctaaa agcaacaatc aggatcagct acggcaccat caaccagacc accgaggcct   4260
tcgtcaatgg agaacacgcg gtcaacgtgg gcggaagcaa gttcatcttt ggaccgatct   4320
caacagcttg gtcaccgttc gacaataaaa ttgtcgtgta taaagatgat gtctacaacc   4380
aggacttccc accctacgga tcaggccagc cgggnagatt cggagacatc cagagcagga   4440
cagtggagag caaagacttg tatgctaata cggccctaaa actctcaaga ccatcacccg   4500
gggttgtgca tgtgccatac acgcagacac catccggatt taagtattgg ctgaaggaga   4560
aaggatcttc attgaataca aaggcccctt ttggctgcaa gataaagacc aatccagtca   4620
gagctatgga ttgtgcagtt ggcagtatac ctgtgtcgat ggacatacct gacagtgcat   4680
tcacacgagt ggtagatgcc ccggctgtaa cagacctgag ctgccaggta gctgtctgta   4740
cacactcctc cgatttcgga nnngttgcca cattgtctta caagacggac aaacccggca   4800
```

agtgcgccgt tcactcacat tccaacgtcg caacgttgca agaggcgacg gtggatgtca 4860
aggaggatgg caaggtcaca gtgcactttt ctnnnnngtc cgcctccccg gcattcaaag 4920
tgtccgtctg tgacgcaaaa acaacgtgca cggcggcgtg cgagcctccg aaagaccaca 4980
tcgtccctta tggggcgagc cataacaacc aggtctttcc ggacatgtca ggaactgcga 5040
tgacgtgggt acagaggatg gccagtgggt taggtgggct ggccctcatc gcggtggttg 5100
tgctggtctt ggtaacctgc ataacaatgc gtcggtaatc tagaccaggc cctggatcca 5160
gatctgctgt gccttctagt tgccagccat ctgttgtttg cccctccccc gtgccttcct 5220
tgaccctgga aggtgccact cccactgtcc tttcctaata aaatgaggaa attgcatcgc 5280
attgtctgag taggtgtcat tctattctgg ggggtggggt ggggcaggac agcaaggggg 5340
aggattggga agacaatagc aggcatgctg gggatgcggt gggctctatg ggtacccagg 5400
tgctgaagaa ttgacccggt tcctcctggg ccagaaagaa gcaggcacat ccccttctct 5460
gtgacacacc ctgtccacgc ccctggttct tagttccagc cccactcata ggacactcat 5520
agctcaggag ggctccgcct tcaatcccac ccgctaaagt acttggagcg gtctctccct 5580
ccctcatcag cccaccaaac caaacctagc ctccaagagt gggaagaaat taaagcaaga 5640
taggctatta agtgcagagg gagagaaaat gcctccaaca tgtgaggaag taatgagaga 5700
aatcatagaa ttttaaggcc atgatttaag gccatcatgg ccttaatctt ccgcttcctc 5760
gctcactgac tcgctgcgct cggtcgttcg gctgcggcga gcggtatcag ctcactcaaa 5820
ggcggtaata cggttatcca cagaatcagg ggataacgca ggaaagaaca tgtgagcaaa 5880
aggccagcaa aaggccagga accgtaaaaa ggccgcgttg ctggcgtttt tccataggct 5940
ccgcccccct gacgagcatc acaaaaatcg acgctcaagt cagaggtggc gaaacccgac 6000
aggactataa agataccagg cgtttccccc tggaagctcc ctcgtgcgct ctcctgttcc 6060
gaccctgccg cttaccggat acctgtccgc ctttctccct tcgggaagcg tggcgctttc 6120
tcatagctca cgctgtaggt atctcagttc ggtgtaggtc gttcgctcca agctgggctg 6180
tgtgcacgaa ccccccgttc agcccgaccg ctgcgcctta tccggtaact atcgtcttga 6240
gtccaacccg gtaagacacg acttatcgcc actggcagca gccactggta acaggattag 6300
cagagcgagg tatgtaggcg gtgctacaga gttcttgaag tggtggccta actacggcta 6360
cactagaaga acagtatttg gtatctgcgc tctgctgaag ccagttacct tcggaaaaag 6420
agttggtagc tcttgatccg gcaaacaaac caccgctggt agcggtggtt tttttgtttg 6480
caagcagcag attacgcgca gaaaaaaagg atctcaagaa gatcctttga tcttttctac 6540
ggggtctgac gctcagtgga acgaaaactc acgttaaggg attttggtca tgagattatc 6600
aaaaaggatc ttcacctaga tccttttaaa ttaaaaatga agttttaaat caatctaaag 6660
tatatatgag taaacttggt ctgacagtta ccaatgctta atcagtgagg cacctatctc 6720
agcgatctgt ctatttcgtt catccatagt tgcctgactc gggggggggg ggcgctgagg 6780
tctgcctcgt gaagaaggtg ttgctgactc ataccaggcc tgaatcgccc catcatccag 6840
ccagaaagtg agggagccac ggttgatgag agctttgttg taggtggacc agttggtgat 6900
tttgaacttt tgctttgcca cggaacggtc tgcgttgtcg ggaagatgcg tgatctgatc 6960
cttcaactca gcaaaagttc gatttattca acaaagccgc cgtcccgtca agtcagcgta 7020
atgctctgcc agtgttacaa ccaattaacc aattctgatt agaaaaactc atcgagcatc 7080
aaatgaaact gcaatttatt catatcagga ttatcaatac catatttttg aaaaagccgt 7140
ttctgtaatg aaggagaaaa ctcaccgagg cagttccata ggatggcaag atcctggtat 7200
cggtctgcga ttccgactcg tccaacatca atacaaccta ttaatttccc ctcgtcaaaa 7260
ataaggttat caagtgagaa atcaccatga gtgacgactg aatccggtga gaatggcaaa 7320
agcttatgca tttctttcca gacttgttca acaggccagc cattacgctc gtcatcaaaa 7380
tcactcgcat caaccaaacc gttattcatt cgtgattgcg cctgagcgag acgaaatacg 7440
cgatcgctgt taaaaggaca attacaaaca ggaatcgaat gcaaccggcg caggaacact 7500
gccagcgcat caacaatatt ttcacctgaa tcaggatatt cttctaatac ctggaatgct 7560
gttttcccgg ggatcgcagt ggtgagtaac catgcatcat caggagtacg gataaaatgc 7620
ttgatggtcg gaagaggcat aaattccgtc agccagttta gtctgaccat ctcatctgta 7680
acatcattgg caacgctacc tttgccatgt ttcagaaaca actctggcgc atcgggcttc 7740
ccatacaatc gatagattgt cgcacctgat tgcccgacat tatcgcgagc ccatttatac 7800
ccatataaat cagcatccat gttggaattt aatcgcggcc tcgagcaaga cgtttcccgt 7860
tgaatatggc tcataacacc ccttgtatta ctgtttatgt aagcagacag ttttattgtt 7920
catgatgata tatttttatc ttgtgcaatg taacatcaga gattttgaga cacaacgtgg 7980
ctttcccccc ccccccatta ttgaagcatt tatcagggtt attgtctcat gagcggatac 8040
atatttgaat gtatttagaa aaataaacaa ataggggttc cgcgcacatt tccccgaaaa 8100
gtgccacctg acgtctaaga aaccattatt atcatgacat taacctataa aaataggcgt 8160
atcacgaggc cctttcgtc 8179

<210> SEQ ID NO 15
<211> LENGTH: 8145
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960

-continued tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacca ccatggagtt cataccagca caaacttact 1380
acaatagaag ataccagcct agaccctgga ctcaacgccc tactatccag gtgatcaggc 1440
caaaaccacg ccgaagaagg cctgcaggac aactcgcaca actgatatcc gcagtcagca 1500
gactagcact gcgtacagtt ccccagaaac cacgccggac ccgaaaaatt aagaagcaaa 1560
agcaagtaaa gcaagaacaa cagagtacta cgaaccagaa gaaaaaggcg ccgaaacaaa 1620
agcagaccca aaagaaaaag agaccaggac gaagggaaag gatgtgcatg aagattgaaa 1680
atgactgcat cttcgaagtc agacatgaag gaaaagtaac ggggtatgca tgcctagtag 1740
gtgataaggt aatgaaacca gcacacgtga aaggaactat tgacaacgca gacctagcga 1800
agttggcgtt caaaagatca tccaaatatg atctagagtg cgcacagata ccagtgcaca 1860
tgaaatcgga cgcctcaaag ttcacccatg aaaaaccaga aggctattac aactggcatc 1920
acggagcagt acagtattct ggagggaggt tcacgatccc tacaggcgca ggaaagcctg 1980
gggacagcgg aagaccaatc tttgacaaca aggggcgtgt cgtggctatt gttctaggcg 2040
gagcaaacga aggaaccagg acagcactat ctgtagtgac ttggaataaa gacatagtca 2100
caaaaatcac accagagggg tcagttgaat ggagccttgc cctccctgtc atgtgcctgt 2160
tggcaaatac aaccttccca tgttcccaac cgccttgcgc gccgtgctgc tacgaaaaga 2220
aaccggaaga aaccttgaga atgctggagg acaacgtcat gcaaccagga tattaccagt 2280
tactcgattc agcattggcc tgctcacaac gtcgtcaaaa acgtaatgca agagaaaact 2340
tcaatgtcta caaagtcact aggccgtact tagcccactg tcctgactgc ggggagggac 2400
actcatgcca cagcccaata gcattagaac ggatcagaag tgaggcaaca gatggtacct 2460
tgaaaatcca ggtatctctg caaatcggaa taaagacaga cgacagccac gattggacga 2520
agctacggta tatggatagc catacacctg tggatgcaga ccgatccggg ttgtttgtca 2580
gaacgtcagc accgtgcacc atcacgggaa cgatgggaca tttcatacta gcacgctgtc 2640
cgaaaggaga gacgctgacg gtaggatttg tagacagtag aaggatcagt cacacgtgca 2700
tgcacccgtt ccgccacgag ccaccgctga tagggagaga gaagtttcac tcccgcccgc 2760
agcatggcaa agaactacct tgcagtacat acgtccatac cacagcggca actgctgagg 2820
aaatagaagt gcatatgccg ccagataccc ctgactacac gctgatgaca cagcaagcgg 2880
gaaacgttaa gatcacagtt gacggccaga cggtacgata caagtgcaaa tgtgacggct 2940
ccaatgaagg attaataacc gctgacaaag tcataaataa ctgcaaagta gaccaatgcc 3000
acacagcggt tacaaaccac aagaaatggc aatacaattc accgctgacc ccgcggaact 3060
ccgaacaagg agatagaaaa ggtaagatcc atatcccatt tccactggtg aacacaacct 3120
gcagggtacc aaaagcaaga aatccgactg tcacatacgg taaaaacaga gtcactctgc 3180
tgttacatcc agaccaccca acactccttt cgtaccgcgc catgggaagg atcccggatt 3240
accatgaaga gtggataaca aacaagaagg aaataagtat cacagtacca gcagaaggct 3300
tagaggttac gtggggtaat aatgacccat acaaatattg gccccaactg tctacaaatg 3360

```
gtactgcgca cgggcaccca catgaaataa tcctctatta ctatgagctg tacccaacta   3420
ccacaattgc tgtactagct gctgcttcta tcgtaataac atctttggta ggtctatcat   3480
taggcatgtg catatgcgcg agacgcaggt gcatcacgcc atatgagctg actccaggag   3540
ctaccatccc attcctccta ggtgtactat gctgtgccag gactgcaaaa gcagcatcgt   3600
actacgaagc tgcaacatac ctctggaatg agcaacaacc attattttgg ttacagcttc   3660
taatccctct gtcagctgca attgttgtgt gtaattgcct aaaacttttta ccatgctgct   3720
gcaaaacatt gactttttta gccgtcatga gcatcggtgc ccgcactgtg accgcgtacg   3780
agcacgcaac agtgatcccg aacacggtgg gagtaccgtg taagactctt gttagcagac   3840
cagggtacag ccctatggtc ttagaaatgg agctacagtc ggtcactctg gaaccagcat   3900
tatccttgga ttacattacg tgtgagtata aaacaatcac accgtccccg tacgtaaaat   3960
gctgtggtac agctgaatgt aaggccaaga acctgccaga ttataactgc aaagtattca   4020
caggcgtcta cccatttatg tggggaggag catactgctt ctgtgacgca gagaacacac   4080
agctcagcga ggcacacgtt gagaaatcag aatcatgcaa aactgagttt gcatcagcct   4140
acagagccca cacagcttca gtatcagcta aactacgtgt cttttaccaa gggaataata   4200
tcaccgtgtc tgcatacgcc aatggtgatc atgcagttac ggtggaagac gcgaagtttg   4260
tcatcggtcc actatcgtcc gcctggtcac catttgataa taagatcgtg gtgtacaaag   4320
gcgaagtcta caatatggac tatccacctt tcggcgcagg gaggccagga cagttcggtg   4380
acatccagag ccgcacgcca gacagcaagg acgtctatgc gaatacgcag ttaatactgc   4440
aaagaccagc ggcaggagca atacacgtgc cttactccca ggcaccttcg ggctttaagt   4500
actggctcaa ggaaaaaggg gcatcattgc agcatactgc accatttggc tgtcagatag   4560
caacaaaccc ggtaagagca gtgaactgtg cagtgggcaa cataccagtc tccattgaca   4620
tcccagatgc agctttcacc agggtcactg acgctccttc catcacagac atgtcctgcg   4680
aagtagcttc gtgtacccat tcatctgatt ttggaggtgc cgcagtcata aagtacacag   4740
ctagtaaaaa aggaaaatgc gccgtgcact ctgtaacaaa tgcggtcact atccgcgaac   4800
ctaacgtaga tgtcaaggga acagcacaat tgcaaattgc cttctcgacc gcactagcta   4860
gtgcggaatt caaggtgcag atctgctcca cactggtaca ctgctcagcg acgtgccatc   4920
ctcctaaaga ccatatagtc aattacccgt cacctcacac cacactagga gtgcaggaca   4980
tttcaacgac agctatgtct tgggtccaga agattacagg aggagtggga ctcgtggttg   5040
ctatagctgc tttgatctta attatagttc tctgcgtatc atttagcaga cactaagcgg   5100
ccgctctaga ccaggccctg gatccagatc tgctgtgcct tctagttgcc agccatctgt   5160
tgtttgcccc tcccccgtgc cttccttgac cctggaaggt gccactccca ctgtcctttc   5220
ctaataaaat gaggaaattg catcgcattg tctgagtagg tgtcattcta ttctgggggg   5280
tggggtgggg caggacagca agggggagga ttgggaagac aatagcaggc atgctgggga   5340
tgcggtgggc tctatgggta cccaggtgct gaagaattga cccggttcct cctgggccag   5400
aaagaagcag gcacatcccc ttctctgtga cacaccctgt ccacgcccct ggttcttagt   5460
tccagcccca ctcataggac actcatagct caggagggct ccgccttcaa tcccacccgc   5520
taaagtactt ggagcggtct ctccctccct catcagccca ccaaaccaaa cctagcctcc   5580
aagagtggga agaaattaaa gcaagatagg ctattaagtg cagagggaga gaaaatgcct   5640
ccaacatgtg aggaagtaat gagagaaatc atagaatttt aaggccatga tttaaggcca   5700
```

-continued

```
tcatggcctt aatcttccgc ttcctcgctc actgactcgc tgcgctcggt cgttcggctg   5760
cggcgagcgg tatcagctca ctcaaaggcg gtaatacggt tatccacaga atcaggggat   5820
aacgcaggaa agaacatgtg agcaaaaggc cagcaaaagg ccaggaaccg taaaaaggcc   5880
gcgttgctgg cgtttttcca taggctccgc ccccctgacg agcatcacaa aaatcgacgc   5940
tcaagtcaga ggtggcgaaa cccgacagga ctataaagat accaggcgtt tccccctgga   6000
agctccctcg tgcgctctcc tgttccgacc ctgccgctta ccggatacct gtccgccttt   6060
ctcccttcgg gaagcgtggc gctttctcat agctcacgct gtaggtatct cagttcggtg   6120
taggtcgttc gctccaagct gggctgtgtg cacgaacccc ccgttcagcc cgaccgctgc   6180
gccttatccg gtaactatcg tcttgagtcc aacccggtaa gacacgactt atcgccactg   6240
gcagcagcca ctggtaacag gattagcaga gcgaggtatg taggcggtgc tacagagttc   6300
ttgaagtggt ggcctaacta cggctacact agaagaacag tatttggtat ctgcgctctg   6360
ctgaagccag ttaccttcgg aaaaagagtt ggtagctctt gatccggcaa acaaaccacc   6420
gctggtagcg gtggtttttt tgtttgcaag cagcagatta cgcgcagaaa aaaaggatct   6480
caagaagatc ctttgatctt ttctacgggg tctgacgctc agtggaacga aaactcacgt   6540
taagggattt tggtcatgag attatcaaaa aggatcttca cctagatcct tttaaattaa   6600
aaatgaagtt ttaaatcaat ctaaagtata tatgagtaaa cttggtctga cagttaccaa   6660
tgcttaatca gtgaggcacc tatctcagcg atctgtctat ttcgttcatc catagttgcc   6720
tgactcgggg ggggggggcg ctgaggtctg cctcgtgaag aaggtgttgc tgactcatac   6780
caggcctgaa tcgccccatc atccagccag aaagtgaggg agccacggtt gatgagagct   6840
ttgttgtagg tggaccagtt ggtgattttg aacttttgct ttgccacgga acggtctgcg   6900
ttgtcgggaa gatgcgtgat ctgatccttc aactcagcaa aagttcgatt tattcaacaa   6960
agccgccgtc ccgtcaagtc agcgtaatgc tctgccagtg ttacaaccaa ttaaccaatt   7020
ctgattagaa aaactcatcg agcatcaaat gaaactgcaa tttattcata tcaggattat   7080
caataccata tttttgaaaa agccgtttct gtaatgaagg agaaaactca ccgaggcagt   7140
tccataggat ggcaagatcc tggtatcggt ctgcgattcc gactcgtcca acatcaatac   7200
aacctattaa tttcccctcg tcaaaaataa ggttatcaag tgagaaatca ccatgagtga   7260
cgactgaatc cggtgagaat ggcaaaagct tatgcatttc tttccagact tgttcaacag   7320
gccagccatt acgctcgtca tcaaaatcac tcgcatcaac caaaccgtta ttcattcgtg   7380
attgcgcctg agcgagacga aatacgcgat cgctgttaaa aggacaatta caaacaggaa   7440
tcgaatgcaa ccggcgcagg aacactgcca gcgcatcaac aatattttca cctgaatcag   7500
gatattcttc taatacctgg aatgctgttt tcccggggat cgcagtggtg agtaaccatg   7560
catcatcagg agtacggata aaatgcttga tggtcggaag aggcataaat tccgtcagcc   7620
agtttagtct gaccatctca tctgtaacat cattggcaac gctacctttg ccatgtttca   7680
gaaacaactc tggcgcatcg ggcttcccat acaatcgata gattgtcgca cctgattgcc   7740
cgacattatc gcgagcccat ttatacccat ataaatcagc atccatgttg gaatttaatc   7800
gcggcctcga gcaagacgtt tcccgttgaa tatggctcat aacacccctt gtattactgt   7860
ttatgtaagc agacagtttt attgttcatg atgatatatt tttatcttgt gcaatgtaac   7920
atcagagatt ttgagacaca acgtggcttt cccccccccc ccattattga agcatttatc   7980
agggttattg tctcatgagc ggatacatat ttgaatgtat ttagaaaaat aaacaaatag   8040
gggttccgcg cacatttccc cgaaaagtgc cacctgacgt ctaagaaacc attattatca   8100
```

tgacattaac ctataaaaat aggcgtatca cgaggccctt tcgtc 8145

<210> SEQ ID NO 16
<211> LENGTH: 8132
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacac gtgtgatcag atatcgcggc cgccaccatg 1380
gacttcctac caactcaagt gttctatggc agacgctgga gaccacgaat gccgccacgc 1440
ccttggagac cacgcatgcc tacaatgcag agaccagacc aacaggcccg acaaatgcag 1500
caattgattg cagcggttag cacgcttgcc ctgaggcaga atgcagccgc ccctcagcgt 1560
ggaaagaaga agcagccacg cagaaagaaa ccaaaaccgc agcccgagaa accaaagaag 1620
caagaacaga agccgaagca aaagaaggcc cctaaacgaa agccagggag aagagaacgc 1680
atgtgcatga agattgagca tgattgcatc ttcgaggtta agcacgaagg taaagtcacg 1740
ggttacgcct gccttgtcgg tgacaaggta atgaagccag cacacgttcc cggggtgata 1800
gacaatgcag atcttgcacg cctgtcgtac aagaaatcca gtaagtacga tctggaatgt 1860
gcacaaatac ccgtggctat gaagtcagat gcttcgaagt acacccatga gaaacccgag 1920
ggtcattaca actggcacta cggcgccgtc cagtacacgg gaggaagatt cacggtgccc 1980

-continued acaggagtgg gtaagcctgg cgacagcggt cggcccatct ttgacaacaa agggccggtt 2040
gtcgcaatag tgctgggagg agccaacgaa ggtaccagaa ccgccctttc cgttgtgaca 2100
tggaataaag acatggtcac gaagattaca cctgaaggca ctgtggagtg ggcagcctcg 2160
acagtgacag ccatgtgtct tttgacaaat atatccttcc catgtttcca accgagctgt 2220
gcaccgtgct gctatgaaaa ggggcctgag ccgacgctga ggatgctgga ggagaacgta 2280
aattcagaag gatattacga cctgctgcac gctgccgtgt actgtagaaa cagttcaagg 2340
tcgaagagaa gcactgcaaa tcattttaat gcgtataagt tgacccgtcc atatgtggct 2400
tactgcgcag actgcggtat gggtcattct tgccacagcc cagccatgat cgaaaatatt 2460
caggcggatg caacagatgg cacgctaaaa attcagtttg cttcccaaat tggcctgacc 2520
aaaacggaca cgcacgatca cacaaagatt agatatgctg aaggacacga cattgcagag 2580
gctgccagat caacccttaa ggtacacagt agcagtgagt gcacggtaac cggcacaatg 2640
ggacacttta tcctggccaa atgtccacct ggcgaacgaa tcagtgtctc atttgttgat 2700
tcgaaaaacg aacaccggac ctgccggata gcctaccacc atgaacagag gttaataggg 2760
cgagaaagat tcacggtgcg accgcatcat ggaattgagc taccttgcac cacttatcaa 2820
ttgactaccg ccgaaacctc tgaagaaatt gatatgcaca tgccgccgga cattccggat 2880
agaactatcc tttcccaaca atcaggaaat gttaagataa cggtgaatgg acgaaccgtc 2940
aggtacagct cttcttgcgg ttcccaagcc gtcgggacaa caaccacaga caagaccatt 3000
aatagctgta ccgttgacaa atgtcaggct tacgtcacga gccacacaaa atggcaattc 3060
aattcacctt ttgtcccacg tcggatgcaa gcagagcgca agggcaaagt gcatatcccc 3120
tttcccctta ttaacaccac ctgccgtgta ccgctggctc ccgaggccct tgttaggagc 3180
ggtaaacgcg aagctacact ttcattgcac cctatccacc ccacattgct aagttacaga 3240
acatttggag cggagcgggt ctttgacgag cagtggatca ccgcccagac ggaggtaacg 3300
atcccggtac ctgtggaggg agtggagtac cagtggggca accataaacc tcaacgtttt 3360
gtggtcgcac tgacgactga aggcaaagca catggatggc ctcatgaaat tattgaatac 3420
tactacggac tgcatcctac gacaaccatt gtcgtggtga ttcgtgtctc agtggtggtg 3480
cttctgtcat tcgccgcctc ggtctacatg tgcgtggtag cacgaaccaa atgtctgaca 3540
ccatatgcac tcacgccggg agctgttgtt cctgttacca ttggggtgct gtgttgcgca 3600
ccgaaagcac atgcagccag tttcgcagaa ggtatggcct atctgtggga taacaatcag 3660
tcgatgttct ggatggagct gaccggacca ttggccctcc ttattctggc tacatgctgc 3720
gcccgatcac tgctttcctg ctgcaagggg tctttttag tcgcaatgag catcgggagt 3780
gccgttgcca gtgcttacga gcacacggca attattccga accaagtggg attcccgtat 3840
aaggctcatg ttgcgcgtga aggttacagt cctttgaccc tgcagatgca ggtgatagag 3900
accagccttg agccaacact caacctggag tatatcactt gcgattacaa aacaaaagtt 3960
ccatcaccat acgtaaagtg ctgcggcacg gcagaatgcc gcacacagga caagcctgag 4020
tacaaatgtg cagtgttcac aggtgtgtat ccttttatgt ggggaggtgc atactgtttt 4080
tgtgattcgg agaacacaca gatgagcgaa gcctacgtgg agcgcgctga cgtgtgtaaa 4140
cacgaccacg cagctgccta ccgtgcccac accgcatccc ttagagcaaa aattaaggtg 4200
acatacggta ctgtgaacca gacagttgag gcgtatgtga acggtgacca tgccgtaacg 4260
attgccggaa caaaatttat ttttgggcca gtgtcaacgc cttggacacc gttcgataca 4320

-continued

```
aaaattctgg tttacaaagg ggagttatac aatcaggact tcccacggta tggtgccggg   4380
cagcctggaa gatttgggga cattcagagc cggacgctgg atagtcgaga cctatatgcc   4440
aacacgggcc tcaagctggc acgaccggca gccggcaaca ttcacgtccc ctatacccag   4500
actccatctg gctttaaaac atggcaaaaa gacagggact caccgcttaa cgccaaggcg   4560
ccttttggat gcataatcca gacaaatccg gtccgagcca tgaactgcgc cgtcggcaac   4620
atacccgttt cgatggatat cgccgacagc gccttcacaa gattgaccga cgcgcctgta   4680
atctctgagt tgacgtgcac tgtgtctaca tgcacgcact catcggattt tggcgggatc   4740
gctgtacttt cctacaaggt ggaaaaatca ggcaggtgcg acatccattc acattcaaac   4800
gtcgcggtac tccaggaagt ttccatcgag acagaaggtc gatcagtgat ccacttctca   4860
accgcatcag cctccccttc cttcgtagtt tctgtttgta gttcgcgtgc tacgtgcaca   4920
gcgaaatgtg aaccaccgaa agaccacgtt gttacatatc cagcaaatca taacggggta   4980
actttgccag acttatctag cactgccatg acgtgggcac aacatcttgc cggcggagtt   5040
gggttgctga tagctctggc cgtgctaatt ctggtaatag ttacttgtgt gactttgaga   5100
aggtaaggat ccagatctgc tgtgccttct agttgccagc catctgttgt ttgcccctcc   5160
cccgtgcctt ccttgaccct ggaaggtgcc actcccactg tcctttccta ataaaatgag   5220
gaaattgcat cgcattgtct gagtaggtgt cattctattc tggggggtgg ggtggggcag   5280
gacagcaagg gggaggattg ggaagacaat agcaggcatg ctggggatgc ggtgggctct   5340
atgggtaccc aggtgctgaa gaattgaccc ggttcctcct gggccagaaa gaagcaggca   5400
catccccttc tctgtgacac accctgtcca cgcccctggt tcttagttcc agccccactc   5460
ataggacact catagctcag gagggctccg ccttcaatcc cacccgctaa agtacttgga   5520
gcggtctctc cctccctcat cagcccacca aaccaaacct agcctccaag agtgggaaga   5580
aattaaagca agataggcta ttaagtgcag agggagagaa aatgcctcca acatgtgagg   5640
aagtaatgag agaaatcata gaattttaag gccatgattt aaggccatca tggccttaat   5700
cttccgcttc ctcgctcact gactcgctgc gctcggtcgt tcggctgcgg cgagcggtat   5760
cagctcactc aaaggcggta atacggttat ccacagaatc aggggataac gcaggaaaga   5820
acatgtgagc aaaaggccag caaaaggcca ggaaccgtaa aaaggccgcg ttgctggcgt   5880
ttttccatag gctccgcccc cctgacgagc atcacaaaaa tcgacgctca agtcagaggt   5940
ggcgaaaccc gacaggacta taaagatacc aggcgtttcc ccctggaagc tccctcgtgc   6000
gctctcctgt tccgaccctg ccgcttaccg gatacctgtc cgcctttctc ccttcgggaa   6060
gcgtggcgct ttctcatagc tcacgctgta ggtatctcag ttcggtgtag gtcgttcgct   6120
ccaagctggg ctgtgtgcac gaaccccccg ttcagcccga ccgctgcgcc ttatccggta   6180
actatcgtct tgagtccaac ccggtaagac acgacttatc gccactggca gcagccactg   6240
gtaacaggat tagcagagcg aggtatgtag gcggtgctac agagttcttg aagtggtggc   6300
ctaactacgg ctacactaga agaacagtat ttggtatctg cgctctgctg aagccagtta   6360
ccttcggaaa aagagttggt agctcttgat ccggcaaaca aaccaccgct ggtagcggtg   6420
gtttttttgt ttgcaagcag cagattacgc gcagaaaaaa aggatctcaa gaagatcctt   6480
tgatcttttc tacggggtct gacgctcagt ggaacgaaaa ctcacgttaa gggattttgg   6540
tcatgagatt atcaaaaagg atcttcacct agatcctttt aaattaaaaa tgaagtttta   6600
aatcaatcta aagtatatat gagtaaactt ggtctgacag ttaccaatgc ttaatcagtg   6660
aggcacctat ctcagcgatc tgtctatttc gttcatccat agttgcctga ctcggggggg   6720
```

-continued gggggcgctg aggtctgcct cgtgaagaag gtgttgctga ctcataccag gcctgaatcg 6780
ccccatcatc cagccagaaa gtgagggagc cacggttgat gagagctttg ttgtaggtgg 6840
accagttggt gattttgaac ttttgctttg ccacggaacg gtctgcgttg tcgggaagat 6900
gcgtgatctg atccttcaac tcagcaaaag ttcgatttat tcaacaaagc cgccgtcccg 6960
tcaagtcagc gtaatgctct gccagtgtta caaccaatta accaattctg attagaaaaa 7020
ctcatcgagc atcaaatgaa actgcaattt attcatatca ggattatcaa taccatattt 7080
ttgaaaaagc cgtttctgta atgaaggaga aaactcaccg aggcagttcc ataggatggc 7140
aagatcctgg tatcggtctg cgattccgac tcgtccaaca tcaatacaac ctattaattt 7200
cccctcgtca aaaataaggt tatcaagtga gaaatcacca tgagtgacga ctgaatccgg 7260
tgagaatggc aaaagcttat gcatttcttt ccagacttgt tcaacaggcc agccattacg 7320
ctcgtcatca aaatcactcg catcaaccaa accgttattc attcgtgatt gcgcctgagc 7380
gagacgaaat acgcgatcgc tgttaaaagg acaattacaa acaggaatcg aatgcaaccg 7440
gcgcaggaac actgccagcg catcaacaat attttcacct gaatcaggat attcttctaa 7500
tacctggaat gctgttttcc cggggatcgc agtggtgagt aaccatgcat catcaggagt 7560
acggataaaa tgcttgatgg tcggaagagg cataaattcc gtcagccagt ttagtctgac 7620
catctcatct gtaacatcat tggcaacgct acctttgcca tgtttcagaa acaactctgg 7680
cgcatcgggc ttcccataca atcgatagat tgtcgcacct gattgcccga cattatcgcg 7740
agcccattta tacccatata aatcagcatc catgttggaa tttaatcgcg gcctcgagca 7800
agacgtttcc cgttgaatat ggctcataac accccttgta ttactgttta tgtaagcaga 7860
cagttttatt gttcatgatg atatattttt atcttgtgca atgtaacatc agagattttg 7920
agacacaacg tggctttccc cccccccca ttattgaagc atttatcagg gttattgtct 7980
catgagcgga tacatatttg aatgtattta gaaaaataaa caaatagggg ttccgcgcac 8040
atttccccga aaagtgccac ctgacgtcta agaaaccatt attatcatga cattaaccta 8100
taaaaatagg cgtatcacga ggccctttcg tc 8132

<210> SEQ ID NO 17
<211> LENGTH: 8134
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (2169)..(2169)
<223> OTHER INFORMATION: a, c, t, g, unknown or other

<400> SEQUENCE: 17
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480

-continued

```
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
caggccctgg atccatggat ttcatcccca cccaaacctt ctatggtaga cgatggagac   1440
cagcaccagt ccagagatac ataccccaac cccaaccacc agcgcctcca cgccgtagga   1500
gaggaccatc tcaactccaa cagcttgtgg ctgcattggg cgcactagct ctacaaccca   1560
agcagaaaca aaaaagagca cagaagaagc ccaagaagac accaccacca aaaccaaaaa   1620
agacccagaa gcctaagaaa ccaacccaaa agaagaagtc caaacccggc aaacgtatgc   1680
gtaactgcat gaagatcgag aatgactgca tctttccggt gatgctcgat ggaaaggtta   1740
acggctacgc ttgcttagtg ggggataaag tcatgaaacc agctcatgtg aagggcacga   1800
tcgacaatcc agaactagcc aaattgacat tcaagaaatc tagcaagtat gatctagaat   1860
gtgctcaagt gccggtatgc atgaaatcag acgcatccaa gttcacccat gagaaaccag   1920
aaggacatta caactggcac catggggcag tgcaatttag caatggtagg tttaccattc   1980
cgacgggctc tggcaaacct ggagacagtg gtaggcctat ttttgacaat accggcaagg   2040
tagtagccat agtgctggga ggtgcaaatg aaggggcccg gacagcccta tccgtggtca   2100
cctggaataa ggatatggtg acccgcataa cacctgaaga atcagtggag tggtcggcgg   2160
ccgcactgna tataacagca ctatgtgtcc tccagaactt atcgttcccg tgtgatgcac   2220
caccatgtgc accatgctgt tacgaaaaag accctgcagg gaccctaaga ttgctgtctg   2280
accactacta ccaccccaag tattatgaat tacttgactc gacgatgcac tgcccacaag   2340
gaaggagacc taagaggtct gttgcgcatt tcgaagccta caaggctacg agaccgtata   2400
tagggtggtg cgcagattgt ggactggcag gatcatgccc atcccctgtg agcatcgagc   2460
acgtctggag tgatgccgac gacggcgtac tgaagatcca agtgtccatg cagatcggta   2520
tagctaaaag caatactatt aaccacgcta agatacgtta catgggtgcc aatggagtac   2580
aggaggctga acgctctacc ctaagtgtat ccacaacagc accatgtgac atcttggcga   2640
ccatgggcca tttcatcttg gcccgctgcc gacccggcag tcaagttgaa gtatcactaa   2700
gcaccgatcc aaagctgcta tgccgtacac cattctccca caagcccagg tttattggca   2760
atgaaaagtc cccagcaccc accgggcaca agacccgaat tccctgcaaa acttactccc   2820
```

-continued

```
atcagacaga cttaacgaga gaagagatta caatgcatgt accgccggat gtccccatcc   2880
aagggctagt gtccaataca ggtaagtcgt actcattaga cccaaagacg aagaccatca   2940
agtacaaatg cacttgcggc gagactgtaa aagaaggtac tgctacgaac aaaatcacac   3000
tgttcaattg tgacaccgcc ccaaagtgta ttacatatgc agtggataac acagtgtggc   3060
agtacaactc ccaatacgtg cccaggtccg aagttacgga ggtgaaagga aagatccatg   3120
tgcctttccc tctgaccgac agcacgtgtg cagtcagcgt agcacctgaa ccgcaagtga   3180
catacagact gggggaagtg gagttccact tccaccctat gtaccccacc ctcttctcca   3240
ttaggagcct cggaaaggat ccgagccaca gtcaagaatg gatagataca cccatgagca   3300
agacaatcca agttggggca gaaggcgtgg agtatgtctg gggaaacaac aacccggtac   3360
gactatgggc acagaagagc tcatcgagca gcgcgcatgg taaccctatt agcatagtct   3420
cacattacta tgacctgtac ccttactgga ccatcacagt actagcgagt ctaggcttgc   3480
taatagtgat tagttccggt ttttcatgct tttgtgttc agtcgctcga accaaatgcc   3540
ttacacccta tcaattagca ccaggcgccc aattacccac atttatagca ctcctttgct   3600
gcgctaagtc tgcacgcgca gacactttag atgatttttc ctacctgtgg accaacaacc   3660
aagccatgtt ttggctccaa ctggcatctc cggttgcagc gttcttgtgc ttatcctatt   3720
gctgtagaaa tctagcatgc tgtatgaaga ttttttttagg gataagcggc ctgtgtgtaa   3780
ttgccacgca ggcctacgag cactcaacca cgatgccgaa tcaggtggga ataccgttta   3840
aagccttgat agagcgacca ggttacgcag gcctcccgct atctttagta gtgattaagt   3900
cagaattagt cccctcatta gttcaggatt atattacctg caactacaag actgtggtcc   3960
cgtctccgta cattaaatgt tgcggaggcg ctgagtgttc acacaaaaat gaagcggact   4020
ataagtgctc ggtgttcaca ggcgtgtacc cgtttatgtg ggaggcgcc tactgcttct   4080
gtgacaccga aaacagtcag atgagtgaag tatacgtaac cagaggagaa tcatgcgagg   4140
ctgaccatgc catcgcttat caggtacaca cagcatcgct taaggcacaa gtaatgatat   4200
cgattggaga actgaaccaa accgtcgacg tgtttgtcaa cggagacagt ccagccagaa   4260
tccaacaatc aaagttcata cttgggccga tatccagtgc ctggtctcct tttgatcaca   4320
aggtgatcgt atacagggat gaggtgtaca atgaagacta cgcaccgtac ggatccggcc   4380
aagcaggcag gttcggagac atccaaagta gaactgttaa cagcactgat gtctatgcca   4440
acaccaattt gaagcttaaa agaccggctt caggcaatgt tcatgtacca tacacgcaaa   4500
ccccttcggg tttctcgtac tggaaaaaag agaagggagt accattgaat cgaaacgccc   4560
cttttggctg tatcatcaaa gtcaatccag tacgtgctga aaactgcgta tatggcaaca   4620
taccgatcag tatggatatt gcggacgcgc acttcacaag gatcgatgaa tccccgtctg   4680
tgtccttgaa ggcgtgtgaa gtgcagtcct gcacttattc atcggatttt ggcggagtag   4740
cgagcatttc ctacacatct aataaggtag gtaagtgtgc catccacagc cactcgaact   4800
ccgcaacgat gaaggattct gtgcaggatg tccaggaaag cggcgccttg tcgcttttct   4860
ttgcgacttc ctctgtcgag ccgaacttcg tggtccaagt gtgtaacgcg cggatcactt   4920
gccatggtaa gtgtgaacca ccgaaagacc acatcgtacc atacgcagcc aaacacaacg   4980
acgccgagtt tccatccatc tctactacag cttggcaatg gttggcacac accacctcag   5040
ggccactcac catacttgtg gtagctatta tagtcgttgt tgtagtatcc attgtagtat   5100
gtgcaagaca ctagagatct gctgtgcctt ctagttgcca gccatctgtt gtttgcccct   5160
cccccgtgcc ttccttgacc ctggaaggtg ccactcccac tgtcctttcc taataaaatg   5220
```

-continued

```
aggaaattgc atcgcattgt ctgagtaggt gtcattctat tctggggggt ggggtggggc   5280
aggacagcaa gggggaggat tgggaagaca atagcaggca tgctggggat gcggtgggct   5340
ctatgggtac ccaggtgctg aagaattgac ccggttcctc ctgggccaga aagaagcagg   5400
cacatcccct tctctgtgac acaccctgtc cacgcccctg gttcttagtt ccagccccac   5460
tcataggaca ctcatagctc aggagggctc cgccttcaat cccacccgct aaagtacttg   5520
gagcggtctc tccctccctc atcagcccac caaaccaaac ctagcctcca agagtgggaa   5580
gaaattaaag caagataggc tattaagtgc agagggagag aaaatgcctc caacatgtga   5640
ggaagtaatg agagaaatca tagaatttta aggccatgat ttaaggccat catggcctta   5700
atcttccgct tcctcgctca ctgactcgct gcgctcggtc gttcggctgc ggcgagcggt   5760
atcagctcac tcaaaggcgg taatacggtt atccacagaa tcaggggata acgcaggaaa   5820
gaacatgtga gcaaaaggcc agcaaaaggc caggaaccgt aaaaaggccg cgttgctggc   5880
gtttttccat aggctccgcc cccctgacga gcatcacaaa aatcgacgct caagtcagag   5940
gtggcgaaac ccgacaggac tataaagata ccaggcgttt ccccctggaa gctccctcgt   6000
gcgctctcct gttccgaccc tgccgcttac cggatacctg tccgcctttc tcccttcggg   6060
aagcgtggcg ctttctcata gctcacgctg taggtatctc agttcggtgt aggtcgttcg   6120
ctccaagctg ggctgtgtgc acgaaccccc cgttcagccc gaccgctgcg ccttatccgg   6180
taactatcgt cttgagtcca acccggtaag acacgactta tcgccactgg cagcagccac   6240
tggtaacagg attagcagag cgaggtatgt aggcggtgct acagagttct tgaagtggtg   6300
gcctaactac ggctacacta gaagaacagt atttggtatc tgcgctctgc tgaagccagt   6360
taccttcgga aaaagagttg gtagctcttg atccggcaaa caaaccaccg ctggtagcgg   6420
tggttttttt gtttgcaagc agcagattac gcgcagaaaa aaaggatctc aagaagatcc   6480
tttgatcttt tctacggggt ctgacgctca gtggaacgaa aactcacgtt aagggatttt   6540
ggtcatgaga ttatcaaaaa ggatcttcac ctagatcctt ttaaattaaa aatgaagttt   6600
taaatcaatc taaagtatat atgagtaaac ttggtctgac agttaccaat gcttaatcag   6660
tgaggcacct atctcagcga tctgtctatt tcgttcatcc atagttgcct gactcggggg   6720
gggggggcgc tgaggtctgc ctcgtgaaga aggtgttgct gactcatacc aggcctgaat   6780
cgccccatca tccagccaga aagtgaggga gccacggttg atgagagctt tgttgtaggt   6840
ggaccagttg gtgattttga acttttgctt tgccacggaa cggtctgcgt tgtcgggaag   6900
atgcgtgatc tgatccttca actcagcaaa agttcgattt attcaacaaa gccgccgtcc   6960
cgtcaagtca gcgtaatgct ctgccagtgt tacaaccaat taaccaattc tgattagaaa   7020
aactcatcga gcatcaaatg aaactgcaat ttattcatat caggattatc aataccatat   7080
ttttgaaaaa gccgtttctg taatgaagga gaaaactcac cgaggcagtt ccataggatg   7140
gcaagatcct ggtatcggtc tgcgattccg actcgtccaa catcaataca acctattaat   7200
ttcccctcgt caaaaataag gttatcaagt gagaaatcac catgagtgac gactgaatcc   7260
ggtgagaatg gcaaaagctt atgcatttct ttccagactt gttcaacagg ccagccatta   7320
cgctcgtcat caaaatcact cgcatcaacc aaaccgttat tcattcgtga ttgcgcctga   7380
gcgagacgaa atacgcgatc gctgttaaaa ggacaattac aaacaggaat cgaatgcaac   7440
cggcgcagga acactgccag cgcatcaaca atattttcac ctgaatcagg atattcttct   7500
aatacctgga atgctgtttt cccggggatc gcagtggtga gtaaccatgc atcatcagga   7560
```

-continued

```
gtacggataa aatgcttgat ggtcggaaga ggcataaatt ccgtcagcca gtttagtctg   7620

accatctcat ctgtaacatc attggcaacg ctacctttgc catgtttcag aaacaactct   7680

ggcgcatcgg gcttcccata caatcgatag attgtcgcac ctgattgccc gacattatcg   7740

cgagcccatt tatacccata taaatcagca tccatgttgg aatttaatcg cggcctcgag   7800

caagacgttt cccgttgaat atggctcata acaccccttg tattactgtt tatgtaagca   7860

gacagtttta ttgttcatga tgatatattt ttatcttgtg caatgtaaca tcagagattt   7920

tgagacacaa cgtggctttc cccccccccc cattattgaa gcatttatca gggttattgt   7980

ctcatgagcg gatacatatt tgaatgtatt tagaaaaata aacaaatagg ggttccgcgc   8040

acatttcccc gaaaagtgcc acctgacgtc taagaaacca ttattatcat gacattaacc   8100

tataaaaata ggcgtatcac gaggcccttt cgtc                               8134
```

<210> SEQ ID NO 18
<211> LENGTH: 8153
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctcca tcggctcgca tctctccttc acgcgcccgc   1020

cgccctacct gaggccgcca tccacgccgg ttgagtcgcg ttctgccgcc tcccgcctgt   1080

ggtgcctcct gaactgcgtc cgccgtctag gtaagtttaa agctcaggtc gagaccgggc   1140

ctttgtccgg cgctcccttg gagcctacct agactcagcc ggctctccac gctttgcctg   1200

accctgcttg ctcaactcta gttaacggtg gagggcagtg tagtctgagc agtactcgtt   1260

gctgccgcgc gcgccaccag acataatagc tgacagacta acagactgtt cctttccatg   1320

ggtcttttct gcagtcaccg tcgtcgacac gtgtgatcag atatcgcggc cgccaccatg   1380

aactctgtct tttacaatcc gtttggccga ggtgcctacg ctcaacctcc aatagcatgg   1440
```

-continued aggccaagac gtagggctgc acctgcgcct cgaccatccg ggttgactac ccagatccaa 1500
cagctcacta gggctgttag agctttggtg ctggacaatg ctacacgtcg ccagcgcccg 1560
gctcctcgca cgcgcccgag gaagccgaag actcaaaaac ctaagccgaa gaagcaaaac 1620
cagaaaccac cacaacagca gaagaaaggg aaaaatcagc cccaacaacc gaagaaaccg 1680
aagcccggta aacgacagcg taccgccctg aaatttgaag ccgaccgcac atttgtcggg 1740
aagaatgaag acggcaagat tatgggatac gccgttgcca tggaagggaa agtgataaaa 1800
ccactacatg taaaaggaac cattgaccac ccggccctag cgaaacttaa attcactaaa 1860
tcttcttctt acgacatgga gtttgctaaa ctaccgaccg aaatgaaaag cgacgcattc 1920
gggtatacaa cggaacaccc cgaagtattt tacaactggc atcacggagc tgtccaattt 1980
tccggcggaa ggttcaccat ccctacagga gtcggaggcc ccggagatag cggaaggcct 2040
atactggata actccggaaa agtggtagcc atagtcctag gaggagctaa tgaagtgcca 2100
ggaacggcac tttctgttgt cacctggaat aagaagggag ccgctattaa aaccacccac 2160
gaagatactg tagagtggtc gcgggctatt accgctatgt gcatcctgca gaacgtcaca 2220
ttcccatgtg accgaccgcc aacttgctat aatcgtaatc ctgacttgac cctaaccatg 2280
ttggaaacaa atgtcaatca cccttcgtac gacgttctgc tggacgctgc tctgaggtgc 2340
cccacgagac ggcacgtcag atcaacgccc accgatgact tcactctcac agcaccgtac 2400
ctcggcttgt gtcacagatg taagacgatg gaaccatgct acagccctat aaaaatcgaa 2460
aaagtgtggg atgatgccga tgacggagtt ctccgtatac aagtaagtgc ccagttaggg 2520
tacaacaggg cgggcactgc agctagcgcc cgactccggt tcatgggcgg aggagtgcct 2580
ccggaaatcc aggagggagc aattgcagat tttaaggtct tcacgtccaa accatgttta 2640
cacctatcac ataaaggata ctttgtcatt gtcaagtgcc ctcctggtga tagtattaca 2700
acatcattga aagtgcatgg ctcggatcaa acctgcacaa ttccaatgcg agtaggttac 2760
aagttcgtag gcagggaaaa atatactctg ccaccaatgc atgggacaca aataccttgc 2820
cttacctacg aaaggacacg agagaaaagt gcaggatacg tgaccatgca tcgtcccgga 2880
caacaatcca taaccatgct gatggaagag agcggagggg aggtgtacgt acaaccgacc 2940
agtgggcgaa acgtcaccta cgagtgtaaa tgcggagact ttaaaactgg gactgtcact 3000
gcgcgcacta aaatagacgg ctgtacagaa aggaaacaat gcattgcgat ttctgccgac 3060
cacgtcaaat gggtgtttaa ctcccctgac ttgatcaggc ataccgacca cacagcccaa 3120
gggaagttgc atataccatt cccgctacag caggctcaat gtacagtacc actggcgcac 3180
cttccaggcg ttaagcatgc ttatcgcagt atgtctctga cactgcacgc tgagcatcct 3240
acattgctta ctacccgcca tcttggagaa aatcctcagc ccactgcaga atggattgtc 3300
gggagtgtaa ctcgaaactt ctccataacc atacaagggt tcgagtatac ttggggaaat 3360
cagaaaccgg tccgagtgta cgcgcaggaa tcggcacctg gcaatcctca tggctggcca 3420
catgaaatcg tacgccatta ctaccacctc tatcccttct acaccgttac agtgctgagc 3480
ggcatgggac tggccatatg cgctggctta gtgatcagta ttttatgctg ctgcaaagca 3540
agaagggatt gcctaacacc ttaccaactg gccccgaacg ctaccgtacc atttctggta 3600
acattgtgtt gctgtttcca acggacttca gcggatgaat ttaccgatac catggggtac 3660
ctatggcaac acagtcaaac aatgttctgg atacaattgg tcataccttt agcagcagtg 3720
ataactttgg ttagatgttg ctcctgctgt ctaccttttt tattggttgc cagtcctcct 3780
aacaaagcgg acgcctacga acatacgatc actgtcccaa atgcgccgtt gaactcgtat 3840

-continued

```
aaagcactag tggaacggcc tgggtatgcc cccttgaatc ttgaagtcat ggtcatgaac   3900
acccagatca taccatcggt taaacgtgaa tacattacct gcaggtacca caccgttgtt   3960
ccttcaccgc agattaaatg ttgcggaact gtcgaatgcc cgaaaggtga aaaagcagac   4020
tatacctgca aggtgttcac tggtgtgtac ccatttctgt ggggaggagc acagtgtttt   4080
tgcgactccg aaaacagtca gcttagcgac aagtacgtcg aactgtcaac agattgcgcc   4140
acagaccatg ccgaggcggt cagagtacac acggcttcgg tgaaatcaca gctccgaata   4200
acctacggga actccacagc acaagtagac gtatttgtca acggtgtgac tccagccagg   4260
agcaaagaca tgaaattgat agccggccca ttatctacta cattttcccc gtttgataat   4320
aaggtcatta tatatcatgg gaaagtctat aactatgact tcccggaatt tggggccgga   4380
acacctggag ctttcggaga tgtccaagcg tcatccacca ccggatcaga tctattagca   4440
aacacagcaa ttcatttgca gaggccggaa gccagaaaca tacacgtccc gtacacccaa   4500
gctccaagcg ggttcgaatt ctggaagaat aacagcggtc agcctttatc tgacactgcc   4560
cctttcggat gcaaagtcaa tgtcaacccg ctacgtgcag acaagtgtgc cgtgggatca   4620
ctcccgatat ccgtggatat accggacgct gcatttacac gcgtatccga gcccctgcca   4680
tcactgctta agtgcaccgt tactagttgc acatactcta cagactatgg cggagtgctc   4740
gtgttgacat acgagtcgga tcgcgcgggg caatgcgctg tacactcgca ttcatcaaca   4800
gcggtactgc gagacccatc ggtatacgtc gagcaaaaag gggagactac acttaaattt   4860
agtacgcgtt ccttgcaggc agacttcgag gtatcgatgt gcggaacgag aaccacttgc   4920
catgcccaat gtcaaccacc aacggaacac gtaatgaaca gaccccagaa gtcgactcca   4980
gacttctcct cagcgatatc caaaacatca tggaactgga ttacagcgct tatgggggga   5040
atttccagta tagctgctat agccgcaatt gtgctggtca tagcattagt atttacagca   5100
caacacagat gatctagacc aggccctgga tccagatctg ctgtgccttc tagttgccag   5160
ccatctgttg tttgcccctc ccccgtgcct tccttgaccc tggaaggtgc cactcccact   5220
gtcctttcct aataaaatga ggaaattgca tcgcattgtc tgagtaggtg tcattctatt   5280
ctggggggtg gggtggggca ggacagcaag ggggaggatt gggaagacaa tagcaggcat   5340
gctggggatg cggtgggctc tatgggtacc caggtgctga agaattgacc cggttcctcc   5400
tgggccagaa agaagcaggc acatcccctt ctctgtgaca caccctgtcc acgcccctgg   5460
ttcttagttc cagccccact cataggacac tcatagctca ggagggctcc gccttcaatc   5520
ccacccgcta aagtacttgg agcggtctct ccctccctca tcagcccacc aaaccaaacc   5580
tagcctccaa gagtgggaag aaattaaagc aagataggct attaagtgca gagggagaga   5640
aaatgcctcc aacatgtgag gaagtaatga gagaaatcat agaattttaa ggccatgatt   5700
taaggccatc atggccttaa tcttccgctt cctcgctcac tgactcgctg cgctcggtcg   5760
ttcggctgcg gcgagcggta tcagctcact caaaggcggt aatacggtta tccacagaat   5820
caggggataa cgcaggaaag aacatgtgag caaaaggcca gcaaaaggcc aggaaccgta   5880
aaaaggccgc gttgctggcg tttttccata ggctccgccc ccctgacgag catcacaaaa   5940
atcgacgctc aagtcagagg tggcgaaacc cgacaggact ataaagatac caggcgtttc   6000
cccctggaag ctccctcgtg cgctctcctg ttccgaccct gccgcttacc ggatacctgt   6060
ccgcctttct cccttcggga agcgtggcgc tttctcatag ctcacgctgt aggtatctca   6120
gttcggtgta ggtcgttcgc tccaagctgg gctgtgtgca cgaacccccc gttcagcccg   6180
```

accgctgcgc cttatccggt aactatcgtc ttgagtccaa cccggtaaga cacgacttat 6240
cgccactggc agcagccact ggtaacagga ttagcagagc gaggtatgta ggcggtgcta 6300
cagagttctt gaagtggtgg cctaactacg gctacactag aagaacagta tttggtatct 6360
gcgctctgct gaagccagtt accttcggaa aaagagttgg tagctcttga tccggcaaac 6420
aaaccaccgc tggtagcggt ggtttttttg tttgcaagca gcagattacg cgcagaaaaa 6480
aaggatctca agaagatcct ttgatctttt ctacggggtc tgacgctcag tggaacgaaa 6540
actcacgtta agggattttg gtcatgagat tatcaaaaag gatcttcacc tagatccttt 6600
taaattaaaa atgaagtttt aaatcaatct aaagtatata tgagtaaact tggtctgaca 6660
gttaccaatg cttaatcagt gaggcaccta tctcagcgat ctgtctattt cgttcatcca 6720
tagttgcctg actcgggggg ggggggcgct gaggtctgcc tcgtgaagaa ggtgttgctg 6780
actcatacca ggcctgaatc gccccatcat ccagccagaa agtgagggag ccacggttga 6840
tgagagcttt gttgtaggtg gaccagttgg tgattttgaa cttttgcttt gccacggaac 6900
ggtctgcgtt gtcgggaaga tgcgtgatct gatccttcaa ctcagcaaaa gttcgattta 6960
ttcaacaaag ccgccgtccc gtcaagtcag cgtaatgctc tgccagtgtt acaaccaatt 7020
aaccaattct gattagaaaa actcatcgag catcaaatga aactgcaatt tattcatatc 7080
aggattatca ataccatatt tttgaaaaag ccgtttctgt aatgaaggag aaaactcacc 7140
gaggcagttc cataggatgg caagatcctg gtatcggtct gcgattccga ctcgtccaac 7200
atcaatacaa cctattaatt tcccctcgtc aaaaataagg ttatcaagtg agaaatcacc 7260
atgagtgacg actgaatccg gtgagaatgg caaaagctta tgcatttctt tccagacttg 7320
ttcaacaggc cagccattac gctcgtcatc aaaatcactc gcatcaacca aaccgttatt 7380
cattcgtgat tgcgcctgag cgagacgaaa tacgcgatcg ctgttaaaag gacaattaca 7440
aacaggaatc gaatgcaacc ggcgcaggaa cactgccagc gcatcaacaa tattttcacc 7500
tgaatcagga tattcttcta atacctggaa tgctgttttc ccggggatcg cagtggtgag 7560
taaccatgca tcatcaggag tacggataaa atgcttgatg gtcggaagag gcataaattc 7620
cgtcagccag tttagtctga ccatctcatc tgtaacatca ttggcaacgc tacctttgcc 7680
atgtttcaga aacaactctg gcgcatcggg cttcccatac aatcgataga ttgtcgcacc 7740
tgattgcccg acattatcgc gagcccattt atacccatat aaatcagcat ccatgttgga 7800
atttaatcgc ggcctcgagc aagacgtttc ccgttgaata tggctcataa caccccttgt 7860
attactgttt atgtaagcag acagttttat tgttcatgat gatatatttt tatcttgtgc 7920
aatgtaacat cagagatttt gagacacaac gtggctttcc cccccccccc attattgaag 7980
catttatcag ggttattgtc tcatgagcgg atacatattt gaatgtattt agaaaaataa 8040
acaaataggg gttccgcgca catttccccg aaaagtgcca cctgacgtct aagaaaccat 8100
tattatcatg acattaacct ataaaaatag gcgtatcacg aggccctttc gtc 8153

<210> SEQ ID NO 19
<211> LENGTH: 2964
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19
atgagcctcg ccctcccggt cttgtgcctg ttggcaaaca ctacattccc ctgctctcag 60

-continued

```
ccgccttgca caccctgctg ctacgaaaag gaaccggaaa gcaccttgcg catgcttgag    120
gacaacgtga tgagacccgg atactaccag ctactaaaag catcgctgac ttgctctccc    180
caccgccaaa gacgcagtac taaggacaat tttaatgtct ataaagccac aagaccatat    240
ctagctcatt gtcctgactg cggagaaggg cattcgtgcc acagccctat cgcattggag    300
cgcatcagaa atgaagcaac ggacggaacg ctgaaaatcc aggtctcttt gcagatcggg    360
ataaagacag atgacagcca cgattggacc aagctgcgct atatggatag ccatacgcca    420
gcggacgcgg agcgagccgg attgcttgta aggacttcag caccgtgcac gatcaccggg    480
accatgggac actttattct cgcccgatgc ccgaaaggag agacgctgac agtgggattt    540
acggacagca gaaagatcag ccacacatgc acacacccgt tccatcatga accacctgtg    600
ataggtaggg agaggttcca ctctcgacca caacatggta aagagttacc ttgcagcacg    660
tacgtgcaga gcaccgctgc cactgctgag gagatagagg tgcatatgcc cccagatact    720
cctgaccgca cgctgatgac gcagcagtct ggcaacgtga agatcacagt taatgggcag    780
acggtgcggt acaagtgcaa ctgcggtggc tcaaacgagg gactgacaac cacagacaaa    840
gtgatcaata actgcaaaat tgatcagtgc catgctgcag tcactaatca caagaattgg    900
caatacaact cccctttagt cccgcgcaac gctgaactcg ggaccgtaa aggaaagatc    960
cacatcccat tcccattggc aaacgtgact tgcagagtgc caaaagcaag aaaccctaca   1020
gtaacttacg gaaaaaacca agtcaccatg ctgctgtatc ctgaccatcc gacactcttg   1080
tcttaccgta acatgggaca ggaaccaaat taccacgagg agtgggtgac acacaagaag   1140
gaggttacct tgaccgtgcc tactgagggt ctggaggtca cttggggcaa caacgaacca   1200
tacaagtact ggccgcagat gtctacgaac ggtactgctc atggtcaccc acatgagata   1260
atcttgtact attatgagct gtaccccact atgactgtag tcattgtgtc ggtggcctcg   1320
ttcgtgcttc tgtcgatggt gggcacagca gtgggaatgt gtgtgtgcgc acggcgcaga   1380
tgcattacac catatgaatt aacaccagga gccactgttc ccttcctgct cagcctgcta   1440
tgctgcgtca gaacgaccaa ggcggccaca tattacgagg ctgcggcata tctatggaac   1500
gaacagcagc ccctgttctg gttgcaggct cttatcccgc tggccgcctt gatcgtcctg   1560
tgcaactgtc tgaaactctt gccatgctgc tgtaagaccc tggctttttt agccgtaatg   1620
agcatcggtg cccacactgt gagcgcgtac gaacacgtaa cagtgatccc gaacacggtg   1680
ggagtaccgt ataagactct tgtcaacaga ccgggttaca gccccatggt gttggagatg   1740
gagctacaat cagtcacctt ggaaccaaca ctgtcacttg actacatcac gtgcgagtac   1800
aaaactgtca tcccctcccc gtacgtgaag tgctgtggta cagcagagtg caaggacaag   1860
agcctaccag actacagctg caaggtcttt actggagtct acccatttat gtggggcggc   1920
gcctactgct tttgcgacgc cgaaaatacg caattgagcg aggcacatgt agagaaatct   1980
gaatcttgca aaacagagtt tgcatcggcc tacagagccc acaccgcatc ggcgtcggcg   2040
aagctccgcg tcctttacca aggaaacaac attaccgtag ctgcctacgc taacggtgac   2100
catgccgtca cagtaaagga cgccaagttt gtcgtgggcc caatgtcctc cgcctggaca   2160
ccttttgaca acaaaatcgt ggtgtacaaa ggcgacgtct acaacatgga ctacccacct   2220
tttggcgcag gaagaccagg acaatttggt gacattcaaa gtcgtacacc ggaaagtaaa   2280
gacgtttatg ccaacactca gttggtacta cagaggccag cagcaggcac ggtacatgta   2340
ccatactctc aggcaccatc tggcttcaag tattggctga aggaacgagg agcatcgcta   2400
cagcacacgg caccgttcgg ttgccagatt gcgacaaacc cggtaagagc tgtaaattgc   2460
```

-continued gctgtgggga acataccaat ttccatcgac ataccggatg cggcctttac tagggttgtc 2520
gatgcaccct ctgtaacgga catgtcatgc gaagtaccag cctgcactca ctcctccgac 2580
tttgggggcg tcgccatcat caaatacaca gctagcaaga aaggtaaatg tgcagtacat 2640
tcgatgacca acgccgttac cattcgagaa gccgacgtag aagtagaggg gaactcccag 2700
ctgcaaatat ccttctcaac agccctggca agcgccgagt ttcgcgtgca agtgtgctcc 2760
acacaagtac actgcgcagc cgcatgccac cctccaaagg accacatagt caattaccca 2820
gcatcacaca ccacccttgg ggtccaggat atatccacaa cggcaatgtc ttgggtgcag 2880
aagattacgg gaggagtagg attaattgtt gctgttgctg ccttaatttt aattgtggtg 2940
ctatgcgtgt cgtttagcag gcac 2964

<210> SEQ ID NO 20
<211> LENGTH: 2964
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20
atgagtcttg ccatcccagt tatgtgcctg ttggcaaaca ccacgttccc ctgctcccag 60 ccccccttgca cgccctgctg ctacgaaaag gaaccggagg aaaccctacg catgcttgag 120
gacaacgtca tgagacctgg gtactatcag ctgctacaag catccttaac atgttctccc 180
caccgccagc gacgcagcac caaggacaac ttcaatgtct ataaagccac aagaccatac 240
ttagctcact gtcccgactg tggagaaggg cactcgtgcc atagtcccgt agcactagaa 300
cgcatcagaa atgaagcgac agacgggacg ctgaaaatcc aggtctcctt gcaaatcgga 360
ataaagacgg atgacagcca cgattggacc aagctgcgtt atatggacaa ccacatgcca 420
gcagacgcag agagggcggg gctatttgta agaacatcag caccgtgtac gattactgga 480
acaatgggac acttcatcct ggcccgatgt ccaaaagggg aaactctgac ggtgggattc 540
actgacagta ggaagattag tcactcatgt acgcacccat ttcaccacga ccctcctgtg 600
ataggtcggg aaaaattcca ttcccgaccg cagcacggta aagagctacc ttgcagcacg 660
tacgtgcaga gcaccgccgc aactaccgag gagatagagg tacacatgcc cccagacacc 720
cctgatcgca cattaatgtc acaacagtcc ggcaacgtaa agatcacagt caatggccag 780
acggtgcggt acaagtgtaa ttgcggtggc tcaaatgaag gactaacaac tacagacaaa 840
gtgattaata actgcaaggt tgatcaatgt catgccgcgg tcaccaatca caaaaagtgg 900
cagtataact cccctctggt cccgcgtaat gctgaacttg gggaccgaaa aggaaaaatt 960
cacatcccgt ttccgctggc aaatgtaaca tgcagggtgc ctaaagcaag gaaccccacc 1020
gtgacgtacg ggaaaaacca agtcatcatg ctactgtatc ctgaccaccc aacactcctg 1080
tcctaccgga atatgggaga agaaccaaac tatcaagaag agtgggtgat gcataagaag 1140
gaagtcgtgc taaccgtgcc gactgaaggg ctcgaggtca cgtggggcaa caacgagccg 1200
tataagtatt ggccgcagtt atctacaaac ggtacagccc atggccaccc gcatgagata 1260
attctgtatt attatgagct gtaccccact atgactgtag tagttgtgtc agtggccacg 1320
ttcatactcc tgtcgatggt gggtatggca gcggggatgt gcatgtgtgc acgacgcaga 1380
tgcatcacac cgtatgaact gacaccagga gctaccgtcc ctttcctgct tagcctaata 1440
tgctgcatca gaacagctaa agcggccaca taccaagagg ctgcgatata cctgtggaac 1500

```
gagcagcaac ctttgttttg gctacaagcc cttattccgc tggcagccct gattgttcta   1560

tgcaactgtc tgagactctt accatgctgc tgtaaaacgt tggctttttt agccgtaatg   1620

agcgtcggtg cccacactgt gagcgcgtac gaacacgtaa cagtgatccc gaacacggtg   1680

ggagtaccgt ataagactct agtcaataga cctggctaca gccccatggt attggagatg   1740

gaactactgt cagtcacttt ggagccaaca ctatcgcttg attacatcac gtgcgagtac   1800

aaaaccgtca tcccgtctcc gtacgtgaag tgctgcggta cagcagagtg caaggacaaa   1860

aacctacctg actacagctg taaggtcttc accggcgtct acccatttat gtggggcggc   1920

gcctactgct tctgcgacgc tgaaaacacg cagttgagcg aagcacacgt ggagaagtcc   1980

gaatcatgca aaacagaatt tgcatcagca tacagggctc ataccgcatc tgcatcagct   2040

aagctccgcg tcctttacca aggaaataac atcactgtaa ctgcctatgc aaacggcgac   2100

catgccgtca cagttaagga cgccaaattc attgtggggc caatgtcttc agcctggaca   2160

cctttcgaca acaaaattgt ggtgtacaaa ggtgacgtct ataacatgga ctacccgccc   2220

tttggcgcag gaagaccagg acaatttggc gatatccaaa gtcgcacacc tgagagtaaa   2280

gacgtctatg ctaatacaca actggtactg cagagaccgg ctgtgggtac ggtacacgtg   2340

ccatactctc aggcaccatc tggctttaag tattggctaa aagaacgcgg ggcgtcgctg   2400

cagcacacag caccatttgg ctgccaaata gcaacaaacc cggtaagagc ggtgaactgc   2460

gccgtaggga acatgcccat ctccatcgac ataccggaag cggccttcac tagggtcgtc   2520

gacgcgccct ctttaacgga catgtcgtgc gaggtaccag cctgcaccca ttcctcagac   2580

tttgggggcg tcgccattat taaatatgca gccagcaaga aaggcaagtg tgcggtgcat   2640

tcgatgacta acgccgtcac tattcgggaa gctgagatag aagttgaagg gaattctcag   2700

ctgcaaatct ctttctcgac ggccttagcc agcgccgaat tccgcgtaca agtctgttct   2760

acacaagtac actgtgcagc cgagtgccac cccccgaagg accacatagt caactacccg   2820

gcgtcacata ccaccctcgg ggtccaggac atctccgcta cggcgatgtc atgggtgcag   2880

aagatcacgg gaggtgtggg actggttgtt gctgttgccg cactgattct aatcgtggtg   2940

ctatgcgtgt cgttcagcag gcac                                          2964
```

<210> SEQ ID NO 21
<211> LENGTH: 783
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
atggagttca tcccgacgca aactttctat aacagaaggt accaaccccg accctgggcc     60

ccacgcccta caattcaagt aattagacct agaccacgtc cacagaggca ggctgggcaa    120

ctcgcccagc tgatctccgc agtcaacaaa ttgaccatgc gcgcggtacc tcaacagaag    180

cctcgcagaa atcggaaaaa caagaagcaa aggcagaaga agcaggcgcc gcaaaacgac    240

ccaaagcaaa agaagcaacc accacaaaag aagccggctc aaaagaagaa gaaaccaggc    300

cgtagggaga gaatgtgcat gaaaattgaa aatgattgca tcttcgaagt caagcatgaa    360

ggcaaagtga tgggctacgc atgcctggtg ggggataaag taatgaaacc agcacatgtg    420

aagggaacta tcgacaatgc cgatctggct aaactggcct ttaagcggtc gtctaaatac    480

gatcttgaat gtgcacagat accggtgcac atgaagtctg atgcctcgaa gtttacccac    540
```

gagaaacccg aggggtacta taactggcat cacggagcag tgcagtattc aggaggccgg 600
ttcactatcc cgacgggtgc aggcaagccg ggagacagcg gcagaccgat cttcgacaac 660
aaaggacggg tggtggccat cgtcctagga ggggccaacg aaggtgcccg cacggccctc 720
tccgtggtga cgtggaacaa agacatcgtc acaaaaatta cccctgaggg agccgaagag 780
tgg 783

<210> SEQ ID NO 22
<211> LENGTH: 783
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22
atggagttca tcccaaccca aactttttac aataggaggt accagcctcg accctggact 60
ccgcgcccta ctatccaagt catcaggccc agaccgcgcc ctcagaggca agctgggcaa 120
cttgcccagc tgatctcagc agttaataaa ctgacaatgc gcgcggtacc acaacagaag 180
ccacgcagga atcggaagaa taagaagcaa aagcaaaaac aacaggcgcc acaaaacaac 240
acaaatcaaa agaagcagcc acctaaaaag aaaccggctc aaaagaaaaa gaagccgggc 300
cgcagagaga ggatgtgcat gaaaatcgaa aatgattgta ttttcgaagt caagcacgaa 360
ggtaaggtaa caggttacgc gtgcctggtg ggggacaaag taatgaaacc agcacacgta 420
aaggggacca tcgataacgc ggacctggcc aaactggcct ttaagcggtc atctaagtat 480
gaccttgaat gcgcgcagat acccgtgcac atgaagtccg acgcttcgaa gttcacccat 540
gagaaaccgg aggggtacta caactggcac cacggagcag tacagtactc aggaggccgg 600
ttcaccatcc ctacaggtgc tggcaaacca ggggacagcg gcagaccgat cttcgacaac 660
aagggacgcg tggtggccat agtcttagga ggagctaatg aaggagcccg tacagccctc 720
tcggtggtga cctggaataa agacattgtc actaaaatca cccccgaggg ggccgaagag 780
tgg 783

<210> SEQ ID NO 23
<211> LENGTH: 13756
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23
atggctgcgt gagacacacg tagcctacca gtttcttact gctctactct gcaaagcaag 60
agattaataa cccatcatgg atcctgtgta cgtggacata gacgctgaca gcgccttttt 120
gaaggccctg caacgtgcgt accccatgtt tgaggtggaa ccaaggcagg tcacaccgaa 180
tgaccatgct aatgctagag cgttctcgca tctagctata aaactaatag agcaggaaat 240
tgaccccgac tcaaccatcc tggatatcgg cagtgcgcca gcaaggagga tgatgtcgga 300
caggaagtac cactgcgtct gcccgatgcg cagtgcggaa gatcccgaga gactcgccaa 360
ttatgcgaga aagctagcat ctgccgcagg aaaagtcctg gacagaaaca tctctggaaa 420
gatcggggac ttacaagcag taatggccgt gccagacacg gagacgccaa cattctgctt 480
acacacagac gtctcatgta gacagagagc agacgtcgct atataccaag acgtctatgc 540

-continued

```
tgtacacgca cccacgtcgc tataccacca ggcgattaaa ggggtccgag tggcgtactg    600
ggttgggttc gacacaaccc cgttcatgta caatgccatg gcgggtgcct acccctcata    660
ctcgacaaac tgggcagatg agcaggtact gaaggctaag aacataggat tatgttcaac    720
agacctgacg gaaggtagac gaggcaagtt gtctattatg agagggaaaa agctaaaacc    780
gtgcgaccgt gtgctgttct cagtagggtc aacgctctac ccggaaagcc gcaagctact    840
taagagctgg cacctgccat cggtgttcca tttaaagggc aaactcagct tcacatgccg    900
ctgtgataca gtggtttcgt gtgagggcta cgtcgttaag agaataacga tgagcccagg    960
cctttatgga aaaaccacag ggtatgcggt aacccaccac gcagacggat tcctgatgtg   1020
caagactacc gacacggttg acggcgaaag aatgtcattc tcggtgtgca catacgtgcc   1080
ggcgaccatt tgtgatcaaa tgaccggcat ccttgctaca gaagtcacgc cggaggatgc   1140
acagaagctg ttggtggggc tgaaccagag aatagtggtt aacggcagaa cgcaacggaa   1200
tacgaacacc atgaaaaatt atctgcttcc cgtggtcgcc caagccttca gtaagtgggc   1260
aaaggagtgc cggaaagaca tggaagatga aaaactcctg gggggtcagag aaagaacact   1320
gacctgctgc tgtctatggg cattcaagaa gcagaaaaca cacacggtct acaagaggcc   1380
tgatacccag tcaattcaga aggttcaggc cgagtttgac agctttgtgg taccgagtct   1440
gtggtcgtcc gggttgtcaa tccctttgag gactagaatc aaatggttgt taagcaaggt   1500
gccaaaaacc gacctgatcc catacagcgg agacgcccga gaagcccggg acgcagaaaa   1560
agaagcagag gaagaacgag aagcagaact gactcgcgaa gccctaccac ctctacaggc   1620
agcacaggaa gatgttcagg tcgaaatcga cgtggaacag cttgaggaca gagcgggcgc   1680
aggaataata gagactccga gaggagctat caaagttact gcccaaccaa cagaccacgt   1740
cgtgggagag tacctggtac tctccccgca gaccgtacta cgtagccaga agctcagtct   1800
gattcacgct ttggcggagc aagtgaagac gtgcacgcac aacggacgag cagggaggta   1860
tgcggtcgaa gcgtacgacg gccgagtcct agtgccctca ggctatgcaa tctcgcctga   1920
agacttccag agtctaagcg aaagcgcaac gatggtgtat aacgaaagag agttcgtaaa   1980
cagaaagcta caccatattg cgatgcacgg accagccctg aacaccgacg aagagtcgta   2040
tgagctggtg agggcagaga ggacagaaca cgagtacgtc tacgacgtgg atcagagaag   2100
atgctgtaag aaggaagaag ccgcaggact ggtactggtg ggcgacttga ctaatccgcc   2160
ctaccacgaa ttcgcatatg aagggctaaa aatccgccct gcctgcccat acaaaattgc   2220
agtcatagga gtcttcggag taccgggatc tggcaagtca gctattatca agaacctagt   2280
taccaggcag gacctggtga ctagcggaaa gaaagaaaac tgccaagaaa tcaccaccga   2340
cgtgatgaga cagagaggtc tagagatatc tgcacgtacg gttgactcgc tgctcttgaa   2400
tggatgcaac agaccagtcg acgtgttgta cgtagacgag gcgtttgcgt gccactctgg   2460
aacgctactt gctttgatcg ccttggtgag accaaggcag aaagttgtac tttgtggtga   2520
cccgaagcag tgcggcttct tcaatatgat gcagatgaaa gtcaactata atcacaacat   2580
ctgcacccaa gtgtaccaca aaagtatctc caggcggtgt acactgcctg tgaccgccat   2640
tgtgtcatcg ttgcattacg aaggcaaaat gcgcactacg aatgagtaca acaagccgat   2700
tgtagtggac actacaggct caacaaaacc tgaccctgga gacctcgtgt taacgtgctt   2760
cagagggtgg gttaaacaac tgcaaattga ctatcgtgga tacgaggtca tgacagcagc   2820
cgcatcccaa gggttaacca gaaaaggagt ttacgcagtt agacaaaaag ttaatgaaaa   2880
cccgctctat gcatcaacgt cagagcacgt caacgtactc ctaacgcgta cggaaggtaa   2940
```

-continued

```
actggtatgg aagacacttt ccggcgaccc gtggataaag acgctgcaga acccaccgaa   3000
aggaaacttc aaagcaacta ttaaggagtg ggaggtggag catgcatcaa taatggcggg   3060
catctgcagt caccaaatga ccttcgatac attccaaaat aaagccaacg tttgttgggc   3120
taagagcttg gtccctatcc tcgaaacagc ggggataaaa ctaaatgata ggcagtggtc   3180
tcagataatt caagccttca aagaagacaa agcatactca cctgaagtag ccctgaatga   3240
aatatgtacg cgcatgtatg ggtggatct agacagcggg ctattttcta aaccgttggt   3300
gtctgtgtat tacgcggata accactggga taataggcct ggagggaaaa tgttcggatt   3360
taaccccgag gcagcatcca ttctagaaag aaagtatcca ttcacaaaag ggaagtggaa   3420
catcaacaag cagatctgcg tgactaccag gaggatagaa gactttaacc ctaccaccaa   3480
catcataccg gccaacagga gactaccaca ctcattagtg gccgaacacc gcccagtaaa   3540
aggggaaaga atggaatggc tggttaacaa gataaacggc caccacgtgc tcctggtcag   3600
tggctataac cttgcactgc ctactaagag agtcacttgg gtagcgccgt taggtgtccg   3660
cggagcggac tacacataca acctagagtt gggtctgcca gcaacgcttg gtaggtatga   3720
cctagtggtc ataaacatcc acacaccttt tcgcatacac cattaccaac agtgcgtcga   3780
ccacgcaatg aaactgcaaa tgctcggggg tgactcattg agactgctca aaccgggcgg   3840
ctctctattg atcagagcat atggttacgc agatagaacc agtgaacgag tcatctgcgt   3900
attgggacgc aagtttagat cgtctagagc gttgaaacca ccatgtgtca ccagcaacac   3960
tgagatgttt ttcctattca gcaactttga caatggcaga aggaatttca caactcatgt   4020
catgaacaat caactgaatg cagccttcgt aggacaggtc acccgagcag gatgtgcacc   4080
gtcgtaccgg gtaaaacgca tggacatcgc gaagaacgat gaagagtgcg tagtcaacgc   4140
cgctaaccct cgcgggttac cgggtggcgg tgtttgcaag gcagtataca aaaaatggcc   4200
ggagtccttt aagaacagtg caacaccagt gggaaccgca aaaacagtta tgtgcggtac   4260
gtatccagta atccacgctg ttggaccaaa cttctctaat tattcggagt ctgaagggga   4320
ccgggaattg gcagctgcct atcgagaagt cgcaaaggaa gtaactaggc tgggagtaaa   4380
tagtgtagct atacctctcc tctccacagg tgtatactca ggagggaaag acaggctgac   4440
ccagtcactg aaccacctct ttacagccat ggactcgacg gatgcagacg tggtcatcta   4500
ctgccgcgac aaagaatggg agaagaaaat atctgaggcc atacagatgc ggacccaagt   4560
agagctgctg gatgagcaca tctccataga ctgcgatatt gttcgcgtgc accctgacag   4620
cagcttggca ggcagaaaag gatacagcac cacggaaggc gcactgtact catatctaga   4680
agggacccgt tttcatcaga cggctgtgga tatggcggag atacatacta tgtggccaaa   4740
gcaaacagag gccaatgagc aagtctgcct atatgccctg gggggaaagta ttgaatcgat   4800
caggcagaaa tgcccggtgg atgatgcaga cgcatcatct ccccccaaaa ctgtcccgtg   4860
cctttgccgt tacgctatga ctccagaacg cgtcacccgg cttcgcatga accacgtcac   4920
aagcataatt gtgtgttctt cgtttcccct cccaaagtac aaaatagaag gagtgcaaaa   4980
agtcaaatgc tctaaggtaa tgctatttga ccacaacgtg ccatcgcgcg taagtccaag   5040
ggaatataga tcttcccagg agtctgcaca ggaggcgagt acaatcacgt cactgacgca   5100
tagtcaattc gacctaagcg ttgatggcga gatactgccc gtcccgtcag acctggatgc   5160
tgacgcccca gccctagaac cagcactaga cgacggggcg acacacacgc tgccatccac   5220
aaccggaaac cttgcggccg tgtctgattg ggtaatgagc accgtacctg tcgcgccgcc   5280
```

-continued

```
cagaagaagg cgagggagaa acctgactgt gacatgtgac gagagagaag ggaatataac   5340
acccatggct agcgtccgat tctttagggc agagctgtgt ccggtcgtac aagaaacagc   5400
ggagacgcgt gacacagcaa tgtctcttca ggcaccaccg agtaccgcca cggaaccgaa   5460
tcatccgccg atctccttcg gagcatcaag cgagacgttc cccattacat ttggggactt   5520
caacgaagga gaaatcgaaa gcttgtcttc tgagctacta actttcggag acttcttacc   5580
aggagaagtg gatgacttga cagacagcga ctggtccacg tgctcagaca cggacgacga   5640
gttaagacta gacagggcag gtgggtatat attctcgtcg gacaccggtc caggtcattt   5700
acaacagaag tcagtacgcc agtcagtgct gccggtgaac accctggagg aagtccacga   5760
ggagaagtgt tacccaccta agctggatga agcaaaggag caactattac ttaagaaact   5820
ccaggagagt gcatccatgg ccaacagaag caggtatcag tcgcgcaaag tagaaaacat   5880
gaaagcagca atcatccaga gactaaagag aggctgtaga ctatacttaa tgtcagagac   5940
cccaaaagtc cctacttacc ggactacata tccggcgcct gtgtactcgc ctccgatcaa   6000
cgtccgattg tccaatcccg agtccgcagt ggcagcatgc aatgagttct tagctagaaa   6060
ctatccaact gtctcatcat accaaattac cgacgagtat gatgcatatc tagacatggt   6120
ggacgggtcg gagagttgcc tggaccgagc gacattcaat ccgtcaaaac tcaggagcta   6180
cccgaaacag cacgcttacc acgcgccctc catcagaagc gctgtaccgt ccccattcca   6240
gaacacacta cagaatgtac tggcagcagc cacgaaaaga aactgcaacg tcacacagat   6300
gagggaatta cccactttgg actcagcagt attcaacgtg gagtgtttca aaaaattcgc   6360
atgcaaccaa gaatactggg aagaatttgc tgccagccct attaggataa caactgagaa   6420
tttagcaacc tatgttacta aactaaaagg gccaaaagca gcagcgctat tcgcaaaaac   6480
ccataatcta ctgccactac aggaagtacc aatggatagg ttcacagtag atatgaaaag   6540
ggacgtaaag gtgactcctg gtacaaagca tacagaggaa agacctaagg tgcaggttat   6600
acaggcggct gaacccttgg cgacagcata cctatgtggg attcacagag agctggttag   6660
gaggctgaac gccgtcctcc tacccaatgt acatacacta tttgacatgt ctgccgagga   6720
tttcgatgcc atcatagccg cacactttaa gccaggagac actgttttgg aaacggacat   6780
agcctccttt gataagagcc aagatgattc acttgcgctt actgctttga tgctgttaga   6840
ggatttaggg gtggatcact ccctgctgga cttgatagag gctgctttcg gagagatttc   6900
cagctgtcac ctaccgacag gtacgcgctt caagttcggc gccatgatga aatcaggtat   6960
gttcctaact ctgttcgtca acacattgtt aaacatcacc atcgccagcc gagtgctgga   7020
agatcgtctg acaaaatccg cgtgcgcggc cttcatcggc gacgacaaca taatacatgg   7080
agtcgtctcc gatgaattga tggcagccag atgtgccact tggatgaaca tggaagtgaa   7140
gatcatagat gcagttgtat ccttgaaagc cccttacttt tgtggagggt ttatactgca   7200
cgatactgtg acaggaacag cttgcagagt ggcagacccg ctaaaaaggc tttttaaact   7260
gggcaaaccg ctagcggcag gtgacgaaca agatgaagat agaagacgag cgctggctga   7320
cgaagtgatc agatggcaac gaacagggct aattgatgag ctggagaaag cggtatactc   7380
taggtacgaa gtgcagggta tatcagttgt ggtaatgtcc atggccacct ttgcaagctc   7440
cagatccaac ttcgagaagc tcagaggacc cgtcataact ttgtacggcg gtcctaaata   7500
ggtacgcact acagctacct attttgcaga agccgacagc aagtatctaa acactaatca   7560
gctacaatgg agttcatccc aacccaaact tttacaata ggaggtacca gcctcgaccc   7620
tggactccgc gccctactat ccaagtcatc aggcccagac cgcgccctca gaggcaagct   7680
```

-continued gggcaacttg cccagctgat ctcagcagtt aataaactga caatgcgcgc ggtaccacaa 7740
cagaagccac gcaggaatcg gaagaataag aagcaaaagc aaaaacaaca ggcgccacaa 7800
aacaacacaa atcaaaagaa gcagccacct aaaaagaaac cggctcaaaa gaaaaagaag 7860
ccgggccgca gagagaggat gtgcatgaaa atcgaaaatg attgtatttt cgaagtcaag 7920
cacgaaggta aggtaacagg ttacgcgtgc ctggtggggg acaaagtaat gaaaccagca 7980
cacgtaaagg ggaccatcga taacgcggac ctggccaaac tggcctttaa gcggtcatct 8040
aagtatgacc ttgaatgcgc gcagataccc gtgcacatga agtccgacgc ttcgaagttc 8100
acccatgaga aaccggaggg gtactacaac tggcaccacg gagcagtaca gtactcagga 8160
ggccggttca ccatccctac aggtgctggc aaaccagggg acagcggcag accgatcttc 8220
gacaacaagg gacgcgtggt ggccatagtc ttaggaggag ctaatgaagg agcccgtaca 8280
gccctctcgg tggtgacctg gaataaagac attgtcacta aaatcacccc cgagggggcc 8340
gaagagtgga gtcttgccat cccagttatg tgcctgttgg caaacaccac gttcccctgc 8400
tcccagcccc cttgcacgcc ctgctgctac gaaaaggaac cggaggaaac cctacgcatg 8460
cttgaggaca acgtcatgag acctgggtac tatcagctgc tacaagcatc cttaacatgt 8520
tctccccacc gccagcgacg cagcaccaag gacaacttca atgtctataa agccacaaga 8580
ccatacttag ctcactgtcc cgactgtgga gaagggcact cgtgccatag tcccgtagca 8640
ctagaacgca tcagaaatga agcgacagac gggacgctga aatccaggt ctccttgcaa 8700 atcggaataa agacggatga cagccacgat tggaccaagc tgcgttatat ggacaaccac 8760
atgccagcag acgcagagag ggcggggcta tttgtaagaa catcagcacc gtgtacgatt 8820
actggaacaa tgggacactt catcctggcc cgatgtccaa aaggggaaac tctgacggtg 8880
ggattcactg acagtaggaa gattagtcac tcatgtacgc acccatttca ccacgaccct 8940
cctgtgatag gtcgggaaaa attccattcc cgaccgcagc acggtaaaga gctaccttgc 9000
agcacgtacg tgcagagcac cgccgcaact accgaggaga tagaggtaca catgcccca 9060 gacacccctg atcgcacatt aatgtcacaa cagtccggca acgtaaagat cacagtcaat 9120
ggccagacgg tgcggtacaa gtgtaattgc ggtggctcaa atgaaggact aacaactaca 9180
gacaaagtga ttaataactg caaggttgat caatgtcatg ccgcggtcac caatcacaaa 9240
aagtggcagt ataactcccc tctggtcccg cgtaatgctg aacttgggga ccgaaaagga 9300
aaaattcaca tcccgtttcc gctggcaaat gtaacatgca gggtgcctaa agcaaggaac 9360
cccaccgtga cgtacgggaa aaaccaagtc atcatgctac tgtatcctga ccacccaaca 9420
ctcctgtcct accggaatat gggagaagaa ccaaactatc aagaagagtg ggtgatgcat 9480
aagaaggaag tcgtgctaac cgtgccgact gaagggctcg aggtcacgtg ggcaacaac 9540 gagccgtata agtattggcc gcagttatct acaaacggta cagcccatgg ccacccgcat 9600
gagataattc tgtattatta tgagctgtac cccactatga ctgtagtagt tgtgtcagtg 9660
gccacgttca tactcctgtc gatggtgggt atggcagcgg ggatgtgcat gtgtgcacga 9720
cgcagatgca tcacaccgta tgaactgaca ccaggagcta ccgtcccttt cctgcttagc 9780
ctaatatgct gcatcagaac agctaaagcg gccacatacc aagaggctgc gatatacctg 9840
tggaacgagc agcaaccttt gttttggcta caagccctta ttccgctggc agccctgatt 9900
gttctatgca actgtctgag actcttacca tgctgctgta aaacgttggc ttttttagcc 9960
gtaatgagcg tcggtgccca cactgtgagc gcgtacgaac acgtaacagt gatcccgaac 10020

-continued

```
acggtgggag taccgtataa gactctagtc aatagacctg gctacagccc catggtattg  10080
gagatggaac tactgtcagt cactttggag ccaacactat cgcttgatta catcacgtgc  10140
gagtacaaaa ccgtcatccc gtctccgtac gtgaagtgct gcggtacagc agagtgcaag  10200
gacaaaaacc tacctgacta cagctgtaag gtcttcaccg gcgtctaccc atttatgtgg  10260
ggcggcgcct actgcttctg cgacgctgaa aacacgcagt tgagcgaagc acacgtggag  10320
aagtccgaat catgcaaaac agaatttgca tcagcataca gggctcatac cgcatctgca  10380
tcagctaagc tccgcgtcct ttaccaagga aataacatca ctgtaactgc ctatgcaaac  10440
ggcgaccatg ccgtcacagt taaggacgcc aaattcattg tggggccaat gtcttcagcc  10500
tggacacctt tcgacaacaa aattgtggtg tacaaaggtg acgtctataa catggactac  10560
ccgccctttg gcgcaggaag accaggacaa tttggcgata tccaaagtcg cacacctgag  10620
agtaaagacg tctatgctaa tacacaactg gtactgcaga gaccggctgt gggtacggta  10680
cacgtgccat actctcaggc accatctggc tttaagtatt ggctaaaaga acgcggggcg  10740
tcgctgcagc acacagcacc atttggctgc caaatagcaa caaacccggt aagagcggtg  10800
aactgcgccg tagggaacat gcccatctcc atcgacatac cggaagcggc cttcactagg  10860
gtcgtcgacg cgccctcttt aacggacatg tcgtgcgagg taccagcctg cacccattcc  10920
tcagactttg ggggcgtcgc cattattaaa tatgcagcca gcaagaaagg caagtgtgcg  10980
gtgcattcga tgactaacgc cgtcactatt cgggaagctg agatagaagt tgaagggaat  11040
tctcagctgc aaatctcttt ctcgacggcc ttagccagcg ccgaattccg cgtacaagtc  11100
tgttctacac aagtacactg tgcagccgag tgccaccccc cgaaggacca catagtcaac  11160
tacccggcgt cacataccac cctcggggtc caggacatct ccgctacggc gatgtcatgg  11220
gtgcagaaga tcacgggagg tgtgggactg gttgttgctg ttgccgcact gattctaatc  11280
gtggtgctat gcgtgtcgtt cagcaggcac taacttgaca attaagtatg aaggtatatg  11340
tgtcccctaa gagacacact gtacatagca aataatctat agatcaaagg gctacgcaac  11400
ccctgaatag taacaaaata caaaatcact aaaaattata aaaacagaaa aatacataaa  11460
taggtatacg tgtcccctaa gagacacatt gtatgtaggt gataagtata gatcaaaggg  11520
ccgaataacc cctgaatagt aacaaaatat gaaaatcaat aaaaatcata aaatagaaaa  11580
accataaaca gaagtagttc aaagggctat aaaacccctg aatagtaaca aaacataaaa  11640
ttaataaaaa tcaaatgaat accataattg gcaaacggaa gagatgtagg tacttaagct  11700
tcctaaaagc agccgaactc actttgagaa gtaggcatag cataccgaac tcttccacga  11760
ttctccgaac ccacagggac gtaggagatg ttattttgtt tttaatattt caaaaaaaaa  11820
aaaaaaaaaa aaaaaaaaaa aaaaaaaaaa agcggccgct taattaatcg aggggaatta  11880
attcttgaag acgaaagggc caggtggcac ttttcgggga aatgtgcgcg gaacccctat  11940
ttgtttattt ttctaaatac attcaaatat gtatccgctc atgagacaat aaccctgata  12000
aatgcttcaa taatattgaa aaaggaagag tatgagtatt caacatttcc gtgtcgccct  12060
tattcccttt tttgcggcat tttgccttcc tgtttttgct cacccagaaa cgctggtgaa  12120
agtaaaagat gctgaagatc agttgggtgc acgagtgggt tacatcgaac tggatctcaa  12180
cagcggtaag atccttgaga gttttcgccc cgaagaacgt tttccaatga tgagcacttt  12240
taaagttctg ctatgtggcg cggtattatc ccgtgttgac gccgggcaag agcaactcgg  12300
tcgccgcata cactattctc agaatgactt ggttgagtac tcaccagtca cagaaaagca  12360
tcttacggat ggcatgacag taagagaatt atgcagtgct gccataacca tgagtgataa  12420
```

cactgcggcc aacttacttc tgacaacgat cggaggaccg aaggagctaa ccgctttttt 12480
gcacaacatg ggggatcatg taactcgcct tgatcgttgg gaaccggagc tgaatgaagc 12540
cataccaaac gacgagcgtg acaccacgat gcctgtagca atggcaacaa cgttgcgcaa 12600
actattaact ggcgaactac ttactctagc ttcccggcaa caattaatag actggatgga 12660
ggcggataaa gttgcaggac cacttctgcg ctcggccctt ccggctggct ggtttattgc 12720
tgataaatct ggagccggtg agcgtgggtc tcgcggtatc attgcagcac tggggccaga 12780
tggtaagccc tcccgtatcg tagttatcta cacgacgggg agtcaggcaa ctatggatga 12840
acgaaataga cagatcgctg agataggtgc ctcactgatt aagcattggt aactgtcaga 12900
ccaagtttac tcatatatac tttagattga tttaaaactt catttttaat ttaaaaggat 12960
ctaggtgaag atcctttttg ataatctcat gaccaaaatc ccttaacgtg agttttcgtt 13020
ccactgagcg tcagaccccg tagaaaagat caaaggatct tcttgagatc cttttttct 13080 gcgcgtaatc tgctgcttgc aaacaaaaaa accaccgcta ccagcggtgg tttgtttgcc 13140
ggatcaagag ctaccaactc tttttccgaa ggtaactggc ttcagcagag cgcagatacc 13200
aaatactgtc cttctagtgt agccgtagtt aggccaccac ttcaagaact ctgtagcacc 13260
gcctacatac ctcgctctgc taatcctgtt accagtggct gctgccagtg gcgataagtc 13320
gtgtcttacc gggttggact caagacgata gttaccggat aaggcgcagc ggtcgggctg 13380
aacggggggt tcgtgcacac agcccagctt ggagcgaacg acctacaccg aactgagata 13440
cctacagcgt gagcattgag aaagcgccac gcttcccgaa gggagaaagg cggacaggta 13500
tccggtaagc ggcagggtcg gaacaggaga gcgcacgagg gagcttccag ggggaaacgc 13560
ctggtatctt tatagtcctg tcgggtttcg ccacctctga cttgagcgtc gatttttgtg 13620
atgctcgtca ggggggcgga gcctatggaa aaacgccagc aacgcgagct cgtatggaca 13680
tattgtcgtt agaacgcggc tacaattaat acataacctt atgtatcata cacaatcgat 13740
ttaggtgaca ctatag 13756

<210> SEQ ID NO 24
<211> LENGTH: 1248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Met Glu Phe Ile Pro Thr Gln Thr Phe Tyr Asn Arg Arg Tyr Gln Pro
1 5 10 15

Arg Pro Trp Thr Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Lys Gln Lys Gln Gln Ala Pro Gln Asn Asn
65 70 75 80

Thr Asn Gln Lys Lys Gln Pro Pro Lys Lys Lys Pro Ala Gln Lys Lys
85 90 95

Lys Lys Pro Gly Arg Arg Glu Arg Met Cys Met Lys Ile Glu Asn Asp
100 105 110

-continued

```
Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
    290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
```

```
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
    610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Val Val Ser Val Ala Thr Phe Ile Leu Leu
    690                 695                 700

Ser Met Val Gly Met Ala Ala Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Thr Ala Tyr Ala Asn Gly Asp
945                 950                 955                 960
```

His Ala Val Thr Val Lys Asp Ala Lys Phe Ile Val Gly Pro Met Ser
965 970 975

Ser Ala Trp Thr Pro Phe Asp Asn Lys Ile Val Val Tyr Lys Gly Asp
980 985 990

Val Tyr Asn Met Asp Tyr Pro Pro Phe Gly Ala Gly Arg Pro Gly Gln
995 1000 1005

Phe Gly Asp Ile Gln Ser Arg Thr Pro Glu Ser Lys Asp Val Tyr
1010 1015 1020

Ala Asn Thr Gln Leu Val Leu Gln Arg Pro Ala Val Gly Thr Val
1025 1030 1035

His Val Pro Tyr Ser Gln Ala Pro Ser Gly Phe Lys Tyr Trp Leu
1040 1045 1050

Lys Glu Arg Gly Ala Ser Leu Gln His Thr Ala Pro Phe Gly Cys
1055 1060 1065

Gln Ile Ala Thr Asn Pro Val Arg Ala Val Asn Cys Ala Val Gly
1070 1075 1080

Asn Met Pro Ile Ser Ile Asp Ile Pro Glu Ala Ala Phe Thr Arg
1085 1090 1095

Val Val Asp Ala Pro Ser Leu Thr Asp Met Ser Cys Glu Val Pro
1100 1105 1110

Ala Cys Thr His Ser Ser Asp Phe Gly Gly Val Ala Ile Ile Lys
1115 1120 1125

Tyr Ala Ala Ser Lys Lys Gly Lys Cys Ala Val His Ser Met Thr
1130 1135 1140

Asn Ala Val Thr Ile Arg Glu Ala Glu Ile Glu Val Glu Gly Asn
1145 1150 1155

Ser Gln Leu Gln Ile Ser Phe Ser Thr Ala Leu Ala Ser Ala Glu
1160 1165 1170

Phe Arg Val Gln Val Cys Ser Thr Gln Val His Cys Ala Ala Glu
1175 1180 1185

Cys His Pro Pro Lys Asp His Ile Val Asn Tyr Pro Ala Ser His
1190 1195 1200

Thr Thr Leu Gly Val Gln Asp Ile Ser Ala Thr Ala Met Ser Trp
1205 1210 1215

Val Gln Lys Ile Thr Gly Gly Val Gly Leu Val Val Ala Val Ala
1220 1225 1230

Ala Leu Ile Leu Ile Val Val Leu Cys Val Ser Phe Ser Arg His
1235 1240 1245

<210> SEQ ID NO 25
<211> LENGTH: 1248
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

Met Glu Phe Ile Pro Thr Gln Thr Phe Tyr Asn Arg Arg Tyr Gln Pro
1 5 10 15

Arg Pro Trp Ala Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn

-continued

```
    50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480
```

-continued

```
Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Ile Asp Gln Cys His Ala Ala Val Thr Asn His Lys Asn Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Thr Met Leu Leu Tyr Pro Asp His Pro Thr Leu Leu Ser Tyr Arg Asn
    610                 615                 620

Met Gly Gln Glu Pro Asn Tyr His Glu Glu Trp Val Thr His Lys Lys
625                 630                 635                 640

Glu Val Thr Leu Thr Val Pro Thr Glu Gly Leu Glu Val Thr Trp Gly
                645                 650                 655

Asn Asn Glu Pro Tyr Lys Tyr Trp Pro Gln Met Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Ile Val Ser Val Ala Ser Phe Val Leu Leu
    690                 695                 700

Ser Met Val Gly Thr Ala Val Gly Met Cys Val Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Leu Cys Cys Val Arg Thr Thr Lys Ala Ala Thr Tyr Tyr
            740                 745                 750

Glu Ala Ala Ala Tyr Leu Trp Asn Glu Gln Gln Pro Leu Phe Trp Leu
        755                 760                 765

Gln Ala Leu Ile Pro Leu Ala Ala Leu Ile Val Leu Cys Asn Cys Leu
    770                 775                 780

Lys Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Gln Ser Val Thr Leu Glu
        835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Ser Leu Pro Asp Tyr Ser Cys Lys Val Phe Thr Gly Val Tyr Pro Phe
                885                 890                 895
```

-continued

```
Met Trp Gly Gly Ala Tyr Cys Phe Cys Asp Ala Glu Asn Thr Gln Leu
            900                 905                 910

Ser Glu Ala His Val Glu Lys Ser Glu Ser Cys Lys Thr Glu Phe Ala
        915                 920                 925

Ser Ala Tyr Arg Ala His Thr Ala Ser Ala Ser Ala Lys Leu Arg Val
    930                 935                 940

Leu Tyr Gln Gly Asn Asn Ile Thr Val Ala Ala Tyr Ala Asn Gly Asp
945                 950                 955                 960

His Ala Val Thr Val Lys Asp Ala Lys Phe Val Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro  Phe Gly Ala Gly Arg  Pro Gly Gln
        995                 1000                 1005

Phe Gly  Asp Ile Gln Ser Arg  Thr Pro Glu Ser Lys  Asp Val Tyr
    1010                 1015                 1020

Ala Asn  Thr Gln Leu Val Leu  Gln Arg Pro Ala Ala  Gly Thr Val
    1025                 1030                 1035

His Val  Pro Tyr Ser Gln Ala  Pro Ser Gly Phe Lys  Tyr Trp Leu
    1040                 1045                 1050

Lys Glu  Arg Gly Ala Ser Leu  Gln His Thr Ala Pro  Phe Gly Cys
    1055                 1060                 1065

Gln Ile  Ala Thr Asn Pro Val  Arg Ala Val Asn Cys  Ala Val Gly
    1070                 1075                 1080

Asn Ile  Pro Ile Ser Ile Asp  Ile Pro Asp Ala Ala  Phe Thr Arg
    1085                 1090                 1095

Val Val  Asp Ala Pro Ser Val  Thr Asp Met Ser Cys  Glu Val Pro
    1100                 1105                 1110

Ala Cys  Thr His Ser Ser Asp  Phe Gly Gly Val Ala  Ile Ile Lys
    1115                 1120                 1125

Tyr Thr  Ala Ser Lys Lys Gly  Lys Cys Ala Val His  Ser Met Thr
    1130                 1135                 1140

Asn Ala  Val Thr Ile Arg Glu  Ala Asp Val Glu Val  Glu Gly Asn
    1145                 1150                 1155

Ser Gln  Leu Gln Ile Ser Phe  Ser Thr Ala Leu Ala  Ser Ala Glu
    1160                 1165                 1170

Phe Arg  Val Gln Val Cys Ser  Thr Gln Val His Cys  Ala Ala Ala
    1175                 1180                 1185

Cys His  Pro Pro Lys Asp His  Ile Val Asn Tyr Pro  Ala Ser His
    1190                 1195                 1200

Thr Thr  Leu Gly Val Gln Asp  Ile Ser Thr Thr Ala  Met Ser Trp
    1205                 1210                 1215

Val Gln  Lys Ile Thr Gly Gly  Val Gly Leu Ile Val  Ala Val Ala
    1220                 1225                 1230

Ala Leu  Ile Leu Ile Val Val  Leu Cys Val Ser Phe  Ser Arg His
    1235                 1240                 1245
```

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
gctctagaca ccatgagcct cgccctcccg gtcttg 36

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tggatcctca ttagtgcctg ctaaacgaca 30

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
gctctagaca ccatgagtct tgccatccca gttatg 36

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
tggatcctca ttagtgcctg ctgaacgaca 30

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
aagctccgcg tcctttacca ag 22

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ccaaattgtc ctggtcttcc t 21

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 32
ccaatgtctt cagcctggac accttt 26

<210> SEQ ID NO 33
<211> LENGTH: 13826
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atggctgcgt gagacacacg tagcctacca gtttcttact gctctactct gcttagcaag 60
agacttgaga acccatcatg gatcccgtgt acgtggacat agacgccgac agcgcctttt 120
taaaggccct gcagcgtgcg taccccatgt ttgaggtgga accaaggcag gtcacaccga 180
atgaccatgc caatgctaga gcattctcgc atctagctat aaaactaata gagcaggaaa 240
ttgatcccga ctcaaccatc ctggacatag gcagcgcgcc agcaaggagg atgatgtcgg 300
ataggaagta ccactgcgtt tgccctatgc gcagcgcaga agaccctgag agactcgcca 360
actacgcgag aaaactagca tctgccgcag gaaaagtctt ggacagaaac atctccgaaa 420
aaattggaga tctacaagca gtaatggctg taccagacgc agaaacgccc acattctgct 480
tgcacactga cgtctcatgt agacaaaggg cggacgtcgc tatataccag gatgtctacg 540
ccgtgcatgc accaacatcg ctgtaccacc aggcgattaa aggagtccgt gtagcatact 600
ggatagggtt tgatacaacc ccgttcatgt ataatgccat ggcaggtgca taccccctcgt 660 actcgacaaa ctgggcagat gagcaggtgc tgaaggcaaa gaacatagga ttatgttcaa 720
cagacctgac ggaaggtaga cgaggtaaat tgtctatcat gagaggaaaa aagatgaagc 780
catgtgaccg cgtactgttc tcagtcgggt caacgcttta cccggagagc cgtaagcttc 840
ttaagagttg gcacttacct tcagtgttcc atctaaaagg gaagctcagc ttcacgtgcc 900
gctgtgatac agtggtttcg tgtgaaggct atgtcgttaa gagaataacg attagcccgg 960
gcctctacgg taaaaccaca gggtacgcag taacccacca tgcagacgga ttcctaatgt 1020
gcaaaacaac cgatacggta gatggcgaga gagtgtcatt ttcggtatgc acgtacgtac 1080
ccgcaaccat ttgtgatcaa atgacaggta ttcttgccac ggaggttaca ccggaggatg 1140
cacagaagct gctggtggga ctgaaccaga ggatagtggt caatggcaga acgcagagga 1200
acacgaacac aatgaagaat tacttgcttc ctgtagttgc ccaagccctc agtaagtggg 1260
caaaggaatg ccggaaagat atggaagatg aaaaactttt gggcatcaga gaaaggacac 1320
tgacatgctg ctgcctttgg gcgttcaaga agcagaagac acacacggtc tacaagaggc 1380
ctgacactca gtcaattcag aaagtcccag ccgaatttga cagctttgtg gtaccaagtc 1440
tgtggtcatc tggactgtcg atcccgctac ggaccagaat caagtggctg ctaagcaaag 1500
tgccaaagac tgatttgatc ccttacagcg gtgacgccaa agaagcccgc gacgctgaaa 1560
aagaagcaga agaagaacga gaagcggagc taactcgcga ggcactacca ccactacagg 1620
cggcacagga cgacgtccag gtcgaaattg acgtggaaca gctcgaagac agagctgggg 1680
caggaataat tgaaactcca agaggagcta tcaaagtcac tgcccaacca acagaccacg 1740
tcgtgggaga gtacttggta ctttccccgc agaccgtgtt acgaagccag aagctcagcc 1800
tgatccacgc attggcggaa caagtgaaga catgcacaca cagcggacgg gcaggaaggt 1860
acgcggtcga agcatatgac ggcagaatcc ttgtgccctc aggctatgca atatcacctg 1920
aagacttcca gagcctgagc gaaagtgcga cgatggtgta caacgaaagg gagttcgtaa 1980

-continued

```
ataggaaatt acaccatatc gcgttgcacg gaccagccct gaacactgac gaggagtcgt   2040
acgagctggt aagggcagaa aggacagagc atgagtacgt ctatgatgtg gaccaaagaa   2100
ggtgctgcaa gaaagaggag gcagccgggc tggtactggt cggcgacttg accaacccgc   2160
cctaccatga gttcgcatat gaagggctga gaatccgccc cgcctgccca tacaagaccg   2220
cagtaatagg ggtctttgga gtgccaggat ccggcaaatc agcaatcatt aagaacctag   2280
ttaccaggca agacctagtg accagtggaa agaaagaaaa ctgccaagaa atctccaccg   2340
acgtgatgcg acagaggaac ctggagatat ctgcacgcac ggtcgactca ctgctcttga   2400
acggatgcaa tagaccagtc gacgtgttgt acgtcgacga agcttttgcg tgccattctg   2460
gcacgctact tgctctgata gccttggtga gaccgaggca gaaagtcgtg ctatgcggtg   2520
atccgaaaca gtgcggcttc ttcaatatga tgcagatgaa agttaactac aaccataaca   2580
tctgcaccca agtgtaccat aaaagtattt ccaggcggtg tacactgcct gtgactgcca   2640
ttgtgtcctc gttgcattac gaaggcaaaa tgcgcacaac aaatgagtac aacaagccaa   2700
ttgtagtgga tactacaggc tcgacaaaac ccgaccccgg agaccttgtg ctaacatgtt   2760
tcagagggtg ggttaagcaa ctgcaaattg actatcgtgg acacgaggtc atgacagcag   2820
ctgcatctca ggggctaacc agaaaagggg tctatgccgt caggcaaaaa gttaatgaaa   2880
acccccttta cgcatcaaca tcagagcacg tgaacgtgct actgacgcgt acggaaggca   2940
aactagtatg gaagacactt tctggagacc catggataaa gacactgcag aacccgccga   3000
aaggaaattt taaagcaaca attaaggaat gggaagtgga acatgcttca ataatggcgg   3060
gtatctgtaa ccaccaagtg acctttgaca cgttccagaa taaagccaat gtctgctggg   3120
cgaagagctt agtccccatc ctagaaacag cagggataaa attaaacgac aggcagtggt   3180
cccagataat ccaggctttt aaagaagaca gagcatactc acccgaggtg gccctgaatg   3240
agatatgcac gcgcatgtac ggggtagacc tggacagcgg actgttctct aaaccactgg   3300
tgtccgtgca tcatgcggat aatcactggg acaacaggcc gggagggaag atgttcggat   3360
tcaaccccga agcggcgtcc atactggaga ggaaataccc gtttacaaaa gggaagtgga   3420
ataccaacaa gcaaatctgt gtgactacta ggaggattga agattttaac ccgaacacca   3480
acattatacc tgccaacagg agattaccgc attcattggt ggccgaacat cgcccggtaa   3540
aaggggagag gatggaatgg ttggtcaaca aaataaatgg ccaccatgtg ctcctggtca   3600
gcggctacaa cctcgttctg cccactaaga gagtcacctg ggtggcgccg ctgggcattc   3660
ggggagctga ctacacatac aacctagagt taggcctacc agcaacgctc ggtagatatg   3720
acctagtgat tataaacatc cacacaccct ttcgcataca tcattaccaa cagtgcgtgg   3780
atcacgcaat gaagctgcag atgctcggag gagactccct gagactgctc aagccgggtg   3840
gttcattact gatcagggca tacggctacg cagacagaac aagcgaacga gtagtctgcg   3900
tattgggacg caagtttcga tcatccagag cgttgaaacc gccgtgcgtc actagcaaca   3960
ccgagatgtt tttcttgttc agcaactttg ataacggcag aaggaacttt acgacgcacg   4020
taatgaacaa ccagctgaat gctgcttttg ttggtcaggc cacccgagca gggtgcgcac   4080
cgtcgtaccg ggttaaacgc atggacatcg caaagaacga tgaagagtgt gtagtcaacg   4140
ccgccaaccc tcgtgggcta ccaggcgatg gcgtctgtaa agcagtatac aaaaaatggc   4200
cggagtcctt caagaacagt gcaacaccag tgggaaccgc aaagacagtc atgtgcggta   4260
catacccggt aatccatgca gtaggaccta atttctcaaa ttactctgag tccgaaggag   4320
accgggaatt ggcagctgct taccgagaag tcgctaagga ggtgactaga ctaggagtaa   4380
```

acagcgtagc tataccgctc ctttccaccg gtgtgtactc tggagggaaa gacaggctga 4440
ctcagtcact aaaccacctt tttacagcat tagactcaac tgatgcagat gtggttatct 4500
actgccgcga caaggagtgg gagaagaaaa tagctgaggc catacaaatg aggacccaag 4560
tggaattact agacgaacac atctctgtag actgcgatat catccgagtg caccctgaca 4620
gcagtttggc aggtagaaaa gggtacagca ctacagaagg ttcactgtac tcctacttgg 4680
aagggacacg gttccatcag acggcagtgg acatggcaga agtatacacc atgtggccaa 4740
agcagacgga ggctaatgaa caagtttgct tgtacgcatt gggggaaagt atagaatcaa 4800
tcaggcaaaa gtgcccagtg gatgacgcag atgcatcgtc gcccccaaaa accgtcccgt 4860
gcctctgccg ttatgccatg acacccgaac gagtcaccag gcttcgtatg aaccatgtca 4920
caagcataat agtatgctca tcattccccc ttccaaagta taaaatagaa ggagtgcaga 4980
aagtcaagtg ttctaaagtg atgctgttcg accataacgt gccatcacgc gttagtccaa 5040
gggaatataa atcgcctcag gagaccgcac aagaagtaag ttcgaccacg tcactgacgc 5100
acagccaatt cgaccttagc gttgacggtg aggaactgcc cgctccgtct gacttggaag 5160
ctgacgctcc gattccggaa ccaacaccag acgacagagc ggtacttact ttgcctccca 5220
cgattgataa tttttcggct gtgtcagact gggtaatgaa taccgcgcca gtcgcaccac 5280
ccagaagaag acgtgggaaa aacttgaatg tcacctgcga cgagagagaa gggaacgtac 5340
ttcccatggc tagcgttcgg ttcttcagag cggatctgca ctccatcgta caggaaacgg 5400
cagagatacg cgatacggcc gcgtccctcc aggcgcccct gagtgtcgct acagaaccga 5460
atcaactgcc gatctcattt ggagcaccaa acgagacttt ccccataacg ttcggggatt 5520
ttgatgaagg ggagattgaa agcttgtcct ctgagttact gacctttggg gacttctcgc 5580
cgggcgaagt ggatgacctg acagacagcg actggtccac gtgttcagac acggacgacg 5640
aattatgact agatagggca ggtgggtaca tattctcatc tgacaccggc cccggccacc 5700
tgcaacagag gtctgtccgt cagacagtac tgccggtaaa taccttggag gaagttcagg 5760
aggagaaatg ttacccacct aagttggatg aagtgaaaga gcagttgtta cttaagaaac 5820
tccaggaaag tgcgtccatg gctaacagaa gcaggtacca atcccgcaaa gtagagaaca 5880
tgaaagcaac aatagtccaa aggctgaagg gtggttgcaa actttattta atgtcggaga 5940
ccccgaaagt tcctacctac cgaactacat atccggcacc agtgtactca cccccaatca 6000
atatccgact gtccaacccc gagtctgctg tggcagcgtg caatgagttc ctagcaagga 6060
actatccgac agttgcgtcg taccaaatca ccgatgagta cgatgcatac ctagacatgg 6120
tggacgggtc ggaaagttgc cttgaccggg cgacgttcaa cccatcaaag cttagaagtt 6180
atccaaaaca gcactcctac catgcaccca caatcagaag tgccgtacct tccccgttcc 6240
agaacacgct gcagaacgta ctggctgctg ccacgaaaag aaattgcaac gtcacacaga 6300
tgagagaact gcctactttg gattcagcgg tatttaatgt tgagtgcttt aaaaaatttg 6360
cgtgcaatca agaatactgg aaggaatttg ccgccagccc tattaggata acgactgaga 6420
acttgacaac ttatgtcaca aaactaaaag gaccaaaagc agcagcactg tttgccaaga 6480
cacataacct gctaccactg caggaggtgc cgatggacag gtttactgta gacatgaaaa 6540
gggacgtgaa ggtgactccg gggacgaagc acactgagga aagacctaaa gtgcaggtca 6600
tacaggcagc cgaacctttg gcaacagcat atctgtgtgg gatccacaga gagttggtca 6660
gaaggctgaa tgcagtcctt ctacctaatg tacacacgct gtttgacatg tctgccgagg 6720

-continued

```
actttgacgc cattattgcc gcgcacttca agccggggga cgccgtattg gaaaccgata   6780
tagcctcctt tgacaagagc caagacgact cattggcgct cactgctcta atgttgctag   6840
aggatttggg ggtggatcat cccctgttgg acttgataga ggctgccttc ggggagatct   6900
ccagctgcca cctaccgacg ggcacccgtt ttaagttcgg cgccatgatg aagtctggta   6960
tgttcctaac cctgttcgtc aacacactgc taaacatcac catagccagc cgagtgctgg   7020
aggaccgctt gacaaggtct gcgtgcgcgg ccttcatcgg cgacgacaat ataatacatg   7080
gggttgtctc tgacgaactg atggcagcaa ggtgtgctac atggatgaac atggaagtga   7140
agatcataga tgcggtcgtg tctcagaaag ccccgtactt ctgcggaggg tttatactgt   7200
atgacacagt agcaggcacg gcctgcagag tggcagaccc gctaaagcgg ctgttcaagc   7260
tgggcaaacc gctggcagcg ggagatgaac aagacgacga cagaagacgt gcactggctg   7320
acgaagtggt tagatggcaa cgaacaggac taactgatga gctagaaaaa gcggtacact   7380
ccaggtatga agtgcagggc atatctgtcg tggtaatgtc tatggccacc tttgcaagct   7440
ctagatctaa ctttgagaag ctcagaggac ccgtcgtaac cctgtacggt ggtcctaaat   7500
aggtacgcac tacagctacc tatttcgtca gaaaccaatc gcagctactt gcatacctac   7560
cagctacaat ggagttcatc ccgacgcaaa ctttctataa cagaaggtac caaccccgac   7620
cctgggcccc acgccctaca attcaagtaa ttagacctag accacgtcca cagaggcagg   7680
ctgggcaact cgcccagctg atctccgcag tcaacaaatt gaccatgcgc gcggtacctc   7740
aacagaagcc tcgcagaaat cggaaaaaca agaagcaaag gcagaagaag caggcgccgc   7800
aaaacgaccc aaagcaaaag aagcaaccac cacaaaagaa gccggctcaa aagaagaaga   7860
aaccaggccg tagggagaga atgtgcatga aaattgaaaa tgattgcatc ttcgaagtca   7920
agcatgaagg caaagtgatg ggctacgcat gcctggtggg ggataaagta atgaaaccag   7980
cacatgtgaa gggaactatc gacaatgccg atctggctaa actggccttt aagcggtcgt   8040
ctaaatacga tcttgaatgt gcacagatac cggtgcacat gaagtctgat gcctcgaagt   8100
ttacccacga gaaacccgag ggtactata actggcatca cggagcagtg cagtattcag    8160
gaggccggtt cactatcccg acgggtgcag gcaagccggg agacagcggc agaccgatct   8220
tcgacaacaa aggacgggtg gtggccatcg tcctaggagg ggccaacgaa ggtgcccgca   8280
cggccctctc cgtggtgacg tggaacaaag acatcgtcac aaaaattacc cctgagggag   8340
ccgaagagtg gagcctcgcc ctcccggtct tgtgcctgtt ggcaaacact acattcccct   8400
gctctcagcc gccttgcaca ccctgctgct acgaaaagga accggaaagc accttgcgca   8460
tgcttgagga caacgtgatg agacccggat actaccagct actaaaagca tcgctgactt   8520
gctctcccca ccgccaaaga cgcagtacta aggacaattt taatgtctat aaagccacaa   8580
gaccatatct agctcattgt cctgactgcg gagaagggca ttcgtgccac agccctatcg   8640
cattggagcg catcagaaat gaagcaacgg acggaacgct gaaaatccag gtctctttgc   8700
agatcgggat aaagacagat gacagccacg attggaccaa gctgcgctat atggatagcc   8760
atacgccagc ggacgcggag cgagccggat tgcttgtaag gacttcagca ccgtgcacga   8820
tcaccgggac catgggacac tttattctcg cccgatgccc gaaaggagag acgctgacag   8880
tgggatttac ggacagcaga aagatcagcc acacatgcac acacccgttc catcatgaac   8940
cacctgtgat aggtagggag aggttccact ctcgaccaca acatggtaaa gagttacctt   9000
gcagcacgta cgtgcagagc accgctgcca ctgctgagga gatagaggtg catatgcccc   9060
cagatactcc tgaccgcacg ctgatgacgc agcagtctgg caacgtgaag atcacagtta   9120
```

```
atgggcagac ggtgcggtac aagtgcaact gcggtggctc aaacgaggga ctgacaacca   9180
cagacaaagt gatcaataac tgcaaaattg atcagtgcca tgctgcagtc actaatcaca   9240
agaattggca atacaactcc cctttagtcc cgcgcaacgc tgaactcggg gaccgtaaag   9300
gaaagatcca catcccattc ccattggcaa acgtgacttg cagagtgcca aaagcaagaa   9360
accctacagt aacttacgga aaaaaccaag tcaccatgct gctgtatcct gaccatccga   9420
cactcttgtc ttaccgtaac atgggacagg aaccaaatta ccacgaggag tgggtgacac   9480
acaagaagga ggttaccttg accgtgccta ctgagggtct ggaggtcact tggggcaaca   9540
acgaaccata caagtactgg ccgcagatgt ctacgaacgg tactgctcat ggtcacccac   9600
atgagataat cttgtactat tatgagctgt accccactat gactgtagtc attgtgtcgg   9660
tggcctcgtt cgtgcttctg tcgatggtgg gcacagcagt gggaatgtgt gtgtgcgcac   9720
ggcgcagatg cattacacca tatgaattaa caccaggagc cactgttccc ttcctgctca   9780
gcctgctatg ctgcgtcaga acgaccaagg cggccacata ttacgaggct gcggcatatc   9840
tatggaacga acagcagccc ctgttctggt tgcaggctct tatcccgctg gccgccttga   9900
tcgtcctgtg caactgtctg aaactcttgc catgctgctg taagaccctg gctttttttag   9960
ccgtaatgag catcggtgcc cacactgtga gcgcgtacga acacgtaaca gtgatcccga  10020
acacggtggg agtaccgtat aagactcttg tcaacagacc gggttacagc cccatggtgt  10080
tggagatgga gctacaatca gtcaccttgg aaccaacact gtcacttgac tacatcacgt  10140
gcgagtacaa aactgtcatc ccctccccgt acgtgaagtg ctgtggtaca gcagagtgca  10200
aggacaagag cctaccagac tacagctgca aggtctttac tggagtctac ccatttatgt  10260
ggggcggcgc ctactgcttt tgcgacgccg aaaatacgca attgagcgag gcacatgtag  10320
agaaatctga atcttgcaaa acagagtttg catcggccta cagagcccac accgcatcgg  10380
cgtcggcgaa gctccgcgtc ctttaccaag gaaacaacat taccgtagct gcctacgcta  10440
acggtgacca tgccgtcaca gtaaaggacg ccaagtttgt cgtgggccca atgtcctccg  10500
cctggacacc ttttgacaac aaaatcgtgg tgtacaaagg cgacgtctac aacatggact  10560
acccaccttt tggcgcagga agaccaggac aatttggtga cattcaaagt cgtacaccgg  10620
aaagtaaaga cgtttatgcc aacactcagt tggtactaca gaggccagca gcaggcacgg  10680
tacatgtacc atactctcag gcaccatctg gcttcaagta ttggctgaag gaacgaggag  10740
catcgctaca gcacacggca ccgttcggtt gccagattgc gacaaacccg gtaagagctg  10800
taaattgcgc tgtggggaac ataccaattt ccatcgacat accggatgcg gcctttacta  10860
gggttgtcga tgcaccctct gtaacggaca tgtcatgcga agtaccagcc tgcactcact  10920
cctccgactt tgggggcgtc gccatcatca aatacacagc tagcaagaaa ggtaaatgtg  10980
cagtacattc gatgaccaac gccgttacca ttcgagaagc cgacgtagaa gtagaggggga  11040
actcccagct gcaaatatcc ttctcaacag ccctggcaag cgccgagttt cgcgtgcaag  11100
tgtgctccac acaagtacac tgcgcagccg catgccaccc tccaaaggac cacatagtca  11160
attacccagc atcacacacc acccttgggg tccaggatat atccacaacg gcaatgtctt  11220
gggtgcagaa gattacggga ggagtaggat taattgttgc tgttgctgcc ttaattttaa  11280
ttgtggtgct atgcgtgtcg tttagcaggc actaaaccga tgataaggca cgaaataact  11340
aaatagcaaa agtagaaagt acataaccag gtatatgtgc cccttaagag gcacaatata  11400
tatagctaag cactattaga tcaaagggct atacaacccc tgaatagtaa caaaacacaa  11460
```

-continued aaaccaataa aaatcataaa aagaaaaatc tcataaacag gtataagtgt cccctaagag 11520
acacattgta tgtaggtagt aagtatagat caaagggcta tattaacccc tgaatagtaa 11580
caaaacacaa aaacaataaa aactacaaaa tagaaaatct ataaacaaaa gtagttcaaa 11640
gggctacaaa acccctgaat agtaacaaaa cataaaatgt aataaaaatt aagtgtgtac 11700
ccaaaagagg tacagtaaga atcagtgaat atcacaattg gcaacgagaa gagacgtagg 11760
tatttaagct tcctaaaagc agccgaactc actttgagac gtaggcatag cataccgaac 11820
tcttccacta ttctccgaac ccacagggac gtaggagatg ttattttgtt tttaatattt 11880
caaaaaaaaa aaaaaaaaaa aaaaaaaaaa aaaaaaaaaa agcggccgct taattaatcg 11940
aggggaatta attcttgaag acgaaagggc caggtggcac ttttcgggga aatgtgcgcg 12000
gaacccctat ttgtttattt ttctaaatac attcaaatat gtatccgctc atgagacaat 12060
aaccctgata aatgcttcaa taatattgaa aaaggaagag tatgagtatt caacatttcc 12120
gtgtcgccct tattcccttt tttgcggcat tttgccttcc tgtttttgct cacccagaaa 12180
cgctggtgaa agtaaaagat gctgaagatc agttgggtgc acgagtgggt tacatcgaac 12240
tggatctcaa cagcggtaag atccttgaga gttttcgccc cgaagaacgt tttccaatga 12300
tgagcacttt taaagttctg ctatgtggcg cggtattatc ccgtgttgac gccgggcaag 12360
agcaactcgg tcgccgcata cactattctc agaatgactt ggttgagtac tcaccagtca 12420
cagaaaagca tcttacggat ggcatgacag taagagaatt atgcagtgct gccataacca 12480
tgagtgataa cactgcggcc aacttacttc tgacaacgat cggaggaccg aaggagctaa 12540
ccgctttttt gcacaacatg ggggatcatg taactcgcct tgatcgttgg gaaccggagc 12600
tgaatgaagc cataccaaac gacgagcgtg acaccacgat gcctgtagca atggcaacaa 12660
cgttgcgcaa actattaact ggcgaactac ttactctagc ttcccggcaa caattaatag 12720
actggatgga ggcggataaa gttgcaggac cacttctgcg ctcggccctt ccggctggct 12780
ggtttattgc tgataaatct ggagccggtg agcgtgggtc tcgcggtatc attgcagcac 12840
tggggccaga tggtaagccc tcccgtatcg tagttatcta cacgacgggg agtcaggcaa 12900
ctatggatga acgaaataga cagatcgctg agataggtgc ctcactgatt aagcattggt 12960
aactgtcaga ccaagtttac tcatatatac tttagattga tttaaaactt catttttaat 13020
ttaaaaggat ctaggtgaag atcctttttg ataatctcat gaccaaaatc ccttaacgtg 13080
agttttcgtt ccactgagcg tcagaccccg tagaaaagat caaaggatct tcttgagatc 13140 cttttttttct gcgcgtaatc tgctgcttgc aaacaaaaaa accaccgcta ccagcggtgg 13200
tttgtttgcc ggatcaagag ctaccaactc tttttccgaa ggtaactggc ttcagcagag 13260
cgcagatacc aaatactgtc cttctagtgt agccgtagtt aggccaccac ttcaagaact 13320
ctgtagcacc gcctacatac ctcgctctgc taatcctgtt accagtggct gctgccagtg 13380
gcgataagtc gtgtcttacc gggttggact caagacgata gttaccggat aaggcgcagc 13440
ggtcgggctg aacggggggt tcgtgcacac agcccagctt ggagcgaacg acctacaccg 13500
aactgagata cctacagcgt gagcattgag aaagcgccac gcttcccgaa gggagaaagg 13560
cggacaggta tccggtaagc ggcagggtcg gaacaggaga gcgcacgagg gagcttccag 13620

-continued

```
ggggaaacgc ctggtatctt tatagtcctg tcgggtttcg ccacctctga cttgagcgtc  13680

gatttttgtg atgctcgtca ggggggcgga gcctatggaa aaacgccagc aacgcgagct  13740

cgtatggaca tattgtcgtt agaacgcggc tacaattaat acataacctt atgtatcata  13800

cacaatcgat ttaggtgaca ctatag                                       13826
```

UNITED STATES PATENT AND TRADEMARK OFFICE
CERTIFICATE OF CORRECTION

PATENT NO. : 10,369,208 B2
APPLICATION NO. : 15/145483
DATED : August 6, 2019
INVENTOR(S) : Gary J. Nabel, Wataru Akahata and Srinivas Rao It is certified that error appears in the above-identified patent and that said Letters Patent is hereby corrected as shown below:

On the Title Page

Item (62), please correct the PCT application number listed as "PCT/EP/2009/006294" to read, --PCT/US2009/006294--.

Signed and Sealed this
Twelfth Day of November, 2019

Andrei Iancu
*Director of the United States Patent and Trademark Office*